US009127067B2

(12) United States Patent
Brown et al.

(10) Patent No.: US 9,127,067 B2
(45) Date of Patent: Sep. 8, 2015

(54) METHODS OF TREATMENT USING CHEMOKINE RECEPTOR BINDING POLYPEPTIDES

(71) Applicants: Michelle Bradley, Horsham (GB); Steven John Charlton, Horsham (GB); Karen Cromie, Merelbeke (BE); Bruno Dombrecht, Heusden (BE); Soren Steffensen, Zwijnaarde (BE); Gino Anselmus Van Heeke, Upper Beeding (GB)

(72) Inventors: Zarin Brown, Reigate (GB); Michelle Bradley, Horsham (GB); Steven John Charlton, Horsham (GB); Karen Cromie, Merelbeke (BE); Bruno Dombrecht, Heusden (BE); Soren Steffensen, Zwijnaarde (BE); Gino Anselmus Van Heeke, Upper Beeding (GB)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 14/065,679

(22) Filed: Oct. 29, 2013

(65) Prior Publication Data

US 2014/0050736 A1 Feb. 20, 2014

Related U.S. Application Data

(62) Division of application No. 13/290,175, filed on Nov. 7, 2011, now Pat. No. 8,591,896.

(60) Provisional application No. 61/411,083, filed on Nov. 8, 2010.

(51) Int. Cl.
*A61K 39/395* (2006.01)
*C07K 16/28* (2006.01)
*C07K 16/46* (2006.01)

(52) U.S. Cl.
CPC ......... *C07K 16/2866* (2013.01); *C07K 2317/31* (2013.01); *C07K 2317/569* (2013.01); *C07K 2317/626* (2013.01); *C07K 2317/76* (2013.01)

(58) Field of Classification Search
None
See application file for complete search history.

(56) References Cited

U.S. PATENT DOCUMENTS 5,116,964 A 5/1992 Capon et al.
5,440,021 A 8/1995 Chuntharapei et al.

FOREIGN PATENT DOCUMENTS

| | | | |
|---|---|---|---|
| JP | 2005-527189 | A | 9/2005 |
| WO | 92/17497 | A1 | 10/1992 |
| WO | 9306229 | A1 | 4/1993 |
| WO | 9507934 | A2 | 3/1995 |
| WO | 0172830 | A2 | 10/2001 |
| WO | 02/072788 | A2 | 9/2002 |
| WO | 2004041170 | A2 | 5/2004 |
| WO | 2004058797 | A2 | 7/2004 |
| WO | 2004/081026 | A2 | 9/2004 |
| WO | 2005103702 | A2 | 11/2005 |
| WO | 2007005605 | A2 | 1/2007 |
| WO | 2007024715 | A2 | 3/2007 |
| WO | 2008003319 | A1 | 1/2008 |
| WO | 2008028044 | A2 | 3/2008 |
| WO | 2008/074839 | A2 | 6/2008 |
| WO | 2009/138519 | A1 | 11/2009 |
| WO | 2010/043650 | A2 | 4/2010 |
| WO | 2010/070145 | A2 | 6/2010 |
| WO | 2010/096941 | A | 9/2010 |

OTHER PUBLICATIONS

Lazaar et al, British Journal of Clinical Pharmacology, 2011, vol. 72, No. 2, pp. 282-293.*
Brummell et al. Biochemistry, 1993; vol. 32, pp. 1180-1187.*
Kobayashi et al. Protein Engineering; 1999; vol. 12, pp. 879-844.*
Brorson et al. (J. Immunology, 1999, vol. 163, pp. 6694-6701.*
Coleman et al, Research in Immunology, 1994; vol. 145, pp. 33-36.*
Strieter et al., Current Drug Targets—Inflammation & Allergy, 2005; vol. 4, pp. 299-203.*
Belperio et al., Journal of Clinical Investigation; 2005; vol. 115, No. 5, pp. 1150-1162.*
Londhe et al., Pediatric Research, 2005; vol. 58, No. 5, pp. 919-926.*
Muyldermans, Serge, "Single domain camel antibodies: current status," Reviews in Molecular Biotechnology, 74(4):277-302 (Jun. 1, 2001).
Holliger and Hudson, "Engineered antibody fragments and the rise of single domains," Nature Biotechnology 23(9):1126-1136 (Sep. 2005).
Gabellini et al., "Functional activity of CXCL8 receptors, CXCR1 and CXCR2, on human malignant melanoma progression," European Journal of Cancer 45(14):2618-2627 (Sep. 1, 2009).
Raimondo et al., "CXC-Chmokine/CXCR2 Biological Axis Promotes Angiogenesis In Vitro and In Vivo in Pancreatic Cancer," Gastroenterology 136(5):A-312, XP026111971, 2001.
Barnes, Peter J., "New Therapies for Chronic Obstructive Pulmonary Disease," Med Princ Pract 19:330-338 (2010).
Traves et al., "Specific CXC but not CC Chemokines cause elevated monocyte migration in COPD: a role for CXCR2," Journal of Leukocyte Biology 76(2):441-450 (Aug. 2004).

(Continued)

*Primary Examiner* — Bridget E Bunner
*Assistant Examiner* — Fozia Hamud

(57) ABSTRACT

The present invention relates to polypeptides directed against or specifically binding to chemokine receptor CXCR2 and in particular to polypeptides capable of modulating signal transduction from CXCR2. The invention also relates to nucleic acids, vectors and host cells capable of expressing the polypeptides of the invention, pharmaceutical compositions comprising the polypeptides and uses of said polypeptides and compositions for treatment of diseases involving aberrant functioning of CXCR2.

7 Claims, 1 Drawing Sheet

(56) References Cited

OTHER PUBLICATIONS

Paul, Fundamental Immunology, 3rd Edition, 1993, pp. 292-295.

Casset et al, Biochemical and Biophysical Research Communications, 2003, 307:198-205.

Lederman et al., Mol. Immunol. 1991, 28:1171-1181.

Li et al., Proc Natl Acad Sci USA, 1980, 77:3211-3214.

Ablynx, "Anti-CXCR4 Nanobody (ALX-0651) Potential PoC in 2012", www.ablynx.com/wp-content/uploads/2010/11/7__ALX-06511.pdf (Nov. 7, 2010).

Chapman, et al. "CXCR2 Antagonists for the treatment of pulmonary disease," Pharmacology & Therapeutics 121(1):55-68 (2009).

Jahnichen et al., "CXCR4 nanobodies (VHH-based single variable domains) potently inhibit chemotaxis and HIV-1 replication and mobilize stem cells" PNAS 107(47):20565-20570 (Nov. 23, 2010).

Tijink et al., "Molecular Cancer Therapeutics" Molecular Cancer Therapeutics 7(8):2288-2297 (Aug. 21, 2008).

* cited by examiner

GRO-α concentration response curves in the presence of increasing concentrations of nanobody®
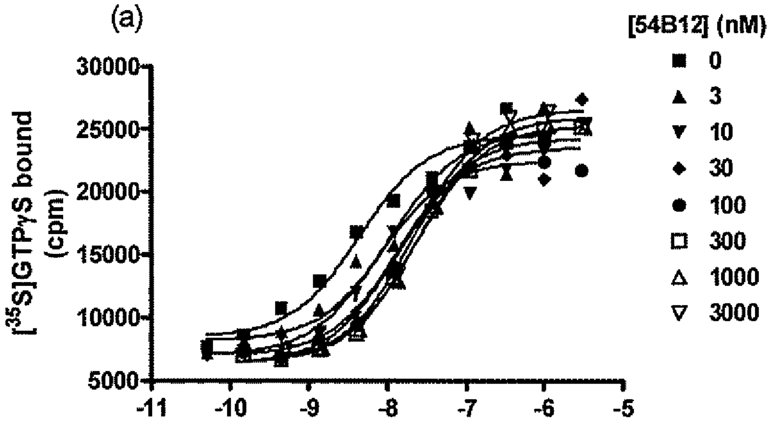
1a
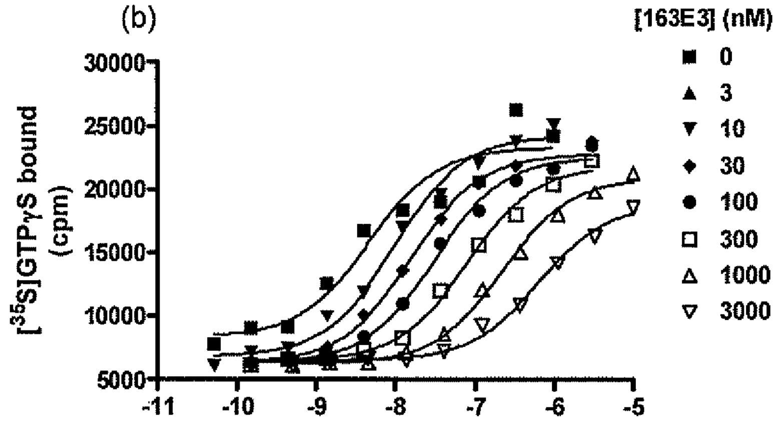
1b
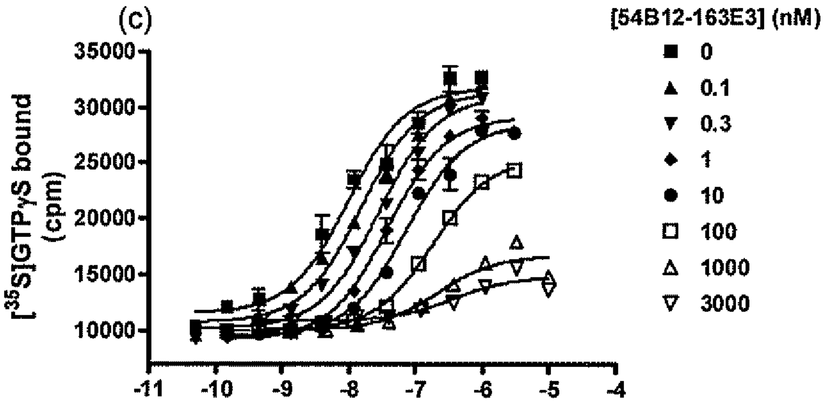
1c

SEQUENCE LISTING

```
<160> NUMBER OF SEQ ID NOS: 248

<210> SEQ ID NO 1
<211> LENGTH: 360
<212> TYPE: PRT
<213> ORGANISM: Homo sapiens

<400> SEQUENCE: 1

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255
```

```
Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360


<210> SEQ ID NO 2
<211> LENGTH: 344
<212> TYPE: PRT
<213> ORGANISM: Homo sapiens

<400> SEQUENCE: 2

Met Glu Asp Leu Ser Asn Tyr Ser Tyr Ser Ser Thr Leu Pro Pro Phe
1               5                   10                  15

Leu Leu Asp Ala Ala Pro Cys Glu Pro Glu Ser Leu Glu Ile Asn Lys
            20                  25                  30

Tyr Phe Val Val Ile Ile Tyr Ala Leu Val Phe Leu Leu Ser Leu Leu
        35                  40                  45

Gly Asn Ser Leu Val Met Leu Val Ile Leu Tyr Ser Arg Val Gly Arg
    50                  55                  60

Ser Val Thr Asp Val Tyr Leu Leu Asn Leu Ala Leu Ala Asp Leu Leu
65                  70                  75                  80

Phe Ala Leu Thr Leu Pro Ile Trp Ala Ala Ser Lys Val Asn Gly Trp
                85                  90                  95

Ile Phe Gly Thr Phe Leu Cys Lys Val Val Ser Leu Leu Lys Glu Val
            100                 105                 110

Asn Phe Tyr Ser Gly Ile Leu Leu Leu Ala Cys Ile Ser Val Asp Arg
        115                 120                 125

Tyr Leu Ala Ile Val His Ala Thr Arg Thr Leu Thr Gln Lys Arg Tyr
    130                 135                 140

Leu Val Lys Phe Ile Cys Leu Ser Ile Trp Gly Leu Ser Leu Leu Leu
145                 150                 155                 160

Ala Leu Pro Val Leu Leu Phe Arg Arg Thr Val Tyr Ser Ser Asn Val
                165                 170                 175

Ser Pro Ala Cys Tyr Glu Asp Met Gly Asn Asn Thr Ala Asn Trp Arg
            180                 185                 190

Met Leu Leu Arg Ile Leu Pro Gln Ser Phe Gly Phe Ile Val Pro Leu
        195                 200                 205

Leu Ile Met Leu Phe Cys Tyr Gly Phe Thr Leu Arg Thr Leu Phe Lys
    210                 215                 220

Ala His Met Gly Gln Lys His Arg Ala Met Arg Val Ile Phe Ala Val
225                 230                 235                 240

Val Leu Ile Phe Leu Leu Cys Trp Leu Pro Tyr Asn Leu Val Leu Leu
                245                 250                 255

Ala Asp Thr Leu Met Arg Thr Gln Val Ile Gln Glu Thr Cys Glu Arg
```

-continued

```
            260                 265                 270

Arg Asn His Ile Asp Arg Ala Leu Asp Ala Thr Glu Ile Leu Gly Ile
        275                 280                 285

Leu His Ser Cys Leu Asn Pro Leu Ile Tyr Ala Phe Ile Gly Gln Lys
    290                 295                 300

Phe Arg His Gly Leu Leu Lys Ile Leu Ala Ile His Gly Leu Ile Ser
305                 310                 315                 320

Lys Asp Ser Leu Pro Lys Asp Ser Arg Pro Ser Phe Val Gly Ser Ser
                325                 330                 335

Ser Gly His Thr Ser Thr Thr Leu
            340


<210> SEQ ID NO 3
<211> LENGTH: 355
<212> TYPE: PRT
<213> ORGANISM: Macaca fascicularis

<400> SEQUENCE: 3

Met Gln Ser Phe Asn Phe Glu Asp Phe Trp Glu Asn Glu Asp Phe Ser
1               5                   10                  15

Asn Tyr Ser Tyr Ser Ser Asp Leu Pro Pro Ser Leu Pro Asp Val Ala
            20                  25                  30

Pro Cys Arg Pro Glu Ser Leu Glu Ile Asn Lys Tyr Phe Val Val Ile
        35                  40                  45

Ile Tyr Ala Leu Val Phe Leu Leu Ser Leu Leu Gly Asn Ser Leu Val
    50                  55                  60

Met Leu Val Ile Leu His Ser Arg Val Gly Arg Ser Ile Thr Asp Val
65                  70                  75                  80

Tyr Leu Leu Asn Leu Ala Met Ala Asp Leu Leu Phe Ala Leu Thr Leu
                85                  90                  95

Pro Ile Trp Ala Ala Ala Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Val
145                 150                 155                 160

Cys Leu Ser Ile Trp Ser Leu Ser Leu Leu Leu Ala Leu Pro Val Leu
                165                 170                 175

Leu Phe Arg Arg Thr Val Tyr Leu Thr Tyr Ile Ser Pro Val Cys Tyr
            180                 185                 190

Glu Asp Met Gly Asn Asn Thr Ala Lys Trp Arg Met Val Leu Arg Ile
        195                 200                 205

Leu Pro Gln Thr Phe Gly Phe Ile Leu Pro Leu Leu Ile Met Leu Phe
    210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr His Leu Val Leu Leu Ala Asp Thr Leu Met
            260                 265                 270

Arg Thr Arg Leu Ile Asn Glu Thr Cys Gln Arg Arg Asn Asn Ile Asp
        275                 280                 285
```

-continued

```
Gln Ala Leu Asp Ala Thr Glu Ile Leu Gly Ile Leu His Ser Cys Leu
    290                 295                 300

Asn Pro Leu Ile Tyr Ala Phe Ile Gly Gln Lys Phe Arg His Gly Leu
305                 310                 315                 320

Leu Lys Ile Leu Ala Thr His Gly Leu Ile Ser Lys Asp Ser Leu Pro
                325                 330                 335

Lys Asp Ser Arg Pro Ser Phe Val Gly Ser Ser Ser Gly His Thr Ser
            340                 345                 350

Thr Thr Leu
        355


<210> SEQ ID NO 4
<211> LENGTH: 14
<212> TYPE: PRT
<213> ORGANISM: Macaca fascicularis

<400> SEQUENCE: 4

Met Gln Ser Phe Asn Phe Glu Asp Phe Trp Glu Asn Glu Asp
1               5                   10


<210> SEQ ID NO 5
<211> LENGTH: 18
<212> TYPE: PRT
<213> ORGANISM: Macaca fascicularis

<400> SEQUENCE: 5

Cys Thr Leu Met Arg Thr Arg Leu Ile Asn Glu Thr Leu Gln Arg Arg
1               5                   10                  15

Asn Cys


<210> SEQ ID NO 6
<211> LENGTH: 26
<212> TYPE: PRT
<213> ORGANISM: Macaca fascicularis

<400> SEQUENCE: 6

Cys Arg Arg Thr Val Tyr Leu Thr Tyr Ile Ser Pro Val Leu Tyr Glu
1               5                   10                  15

Asp Met Gly Asn Asn Thr Ala Leu Trp Cys
            20                  25


<210> SEQ ID NO 7
<211> LENGTH: 19
<212> TYPE: PRT
<213> ORGANISM: Homo sapiens

<400> SEQUENCE: 7

Met Glu Asp Phe Asn Met Glu Ser Asp Ser Phe Glu Asp Phe Trp Lys
1               5                   10                  15

Gly Glu Asp


<210> SEQ ID NO 8
<211> LENGTH: 31
<212> TYPE: PRT
<213> ORGANISM: Homo sapiens

<400> SEQUENCE: 8

Glu Asp Leu Ser Asn Tyr Ser Tyr Ser Ser Thr Leu Pro Pro Phe Leu
1               5                   10                  15

Leu Asp Ala Ala Pro Cys Glu Pro Glu Ser Leu Glu Ile Asn Lys
            20                  25                  30
```

<210> SEQ ID NO 9
<211> LENGTH: 26
<212> TYPE: PRT
<213> ORGANISM: Homo sapiens

<400> SEQUENCE: 9

```
Phe Arg Arg Thr Val Tyr Ser Ser Asn Val Ser Pro Ala Cys Tyr Glu
1               5                   10                  15

Asp Met Gly Asn Asn Thr Ala Asn Trp Arg
            20                  25
```

<210> SEQ ID NO 10
<211> LENGTH: 26
<212> TYPE: PRT
<213> ORGANISM: Homo sapiens

<400> SEQUENCE: 10

```
Cys Arg Arg Thr Val Tyr Ser Ser Asn Val Ser Pro Ala Leu Tyr Glu
1               5                   10                  15

Asp Met Gly Asn Asn Thr Ala Asn Trp Cys
            20                  25
```

<210> SEQ ID NO 11
<211> LENGTH: 18
<212> TYPE: PRT
<213> ORGANISM: Homo sapiens

<400> SEQUENCE: 11

```
Asp Thr Leu Met Arg Thr Gln Val Ile Gln Glu Thr Cys Glu Arg Arg
1               5                   10                  15

Asn His
```

<210> SEQ ID NO 12
<211> LENGTH: 18
<212> TYPE: PRT
<213> ORGANISM: Homo sapiens

<400> SEQUENCE: 12

```
Cys Thr Leu Met Arg Thr Gln Val Ile Gln Glu Thr Leu Glu Arg Arg
1               5                   10                  15

Asn Cys
```

<210> SEQ ID NO 13
<211> LENGTH: 21
<212> TYPE: DNA
<213> ORGANISM: Artificial Sequence
<220> FEATURE:
<223> OTHER INFORMATION: PRIMER

<400> SEQUENCE: 13

```
ggctgagctg ggtggtcctg g                                              21
```

<210> SEQ ID NO 14
<211> LENGTH: 21
<212> TYPE: DNA
<213> ORGANISM: Artificial Sequence
<220> FEATURE:
<223> OTHER INFORMATION: PRIMER

<400> SEQUENCE: 14

```
ggctgagttt ggtggtcctg g                                              21
```

<210> SEQ ID NO 15
<211> LENGTH: 23
<212> TYPE: DNA
<213> ORGANISM: Artificial Sequence
<220> FEATURE:
<223> OTHER INFORMATION: PRIMER

<400> SEQUENCE: 15
ggtacgtgct gttgaactgt tcc 23

<210> SEQ ID NO 16
<211> LENGTH: 55
<212> TYPE: DNA
<213> ORGANISM: Artificial Sequence
<220> FEATURE:
<223> OTHER INFORMATION: PRIMER

<400> SEQUENCE: 16
catttgagtt ggcctagccg gccatggcag aggtgcagct ggtggagtct ggggg 55

<210> SEQ ID NO 17
<211> LENGTH: 18
<212> TYPE: DNA
<213> ORGANISM: Artificial Sequence
<220> FEATURE:
<223> OTHER INFORMATION: PRIMER

<400> SEQUENCE: 17
tgtaaaacga cggccagt 18

<210> SEQ ID NO 18
<211> LENGTH: 18
<212> TYPE: DNA
<213> ORGANISM: Artificial Sequence
<220> FEATURE:
<223> OTHER INFORMATION: PRIMER

<400> SEQUENCE: 18
caggaaacag ctatgacc 18

<210> SEQ ID NO 19
<211> LENGTH: 88
<212> TYPE: DNA
<213> ORGANISM: Artificial Sequence
<220> FEATURE:
<223> OTHER INFORMATION: PRIMER

<400> SEQUENCE: 19
tcagtaacct ggatcccccg ccaccgctgc ctccaccgcc gctacccccg ccaccgctgc 60
ctccaccgcc tgaggagacg gtgacctg 88

<210> SEQ ID NO 20
<211> LENGTH: 84
<212> TYPE: DNA
<213> ORGANISM: Artificial Sequence
<220> FEATURE:
<223> OTHER INFORMATION: PRIMER

<400> SEQUENCE: 20
aggttactga ggatccggcg gtggaggcag cggaggtggg ggctctggtg gcgggggtag 60
cgaggtgcag ctggtggagt ctgg 84

<210> SEQ ID NO 21
<211> LENGTH: 24

<212> TYPE: DNA
<213> ORGANISM: Artificial Sequence
<220> FEATURE:
<223> OTHER INFORMATION: PRIMER

<400> SEQUENCE: 21
gaggtgcaat tggtggagtc tggg 24

<210> SEQ ID NO 22
<211> LENGTH: 24
<212> TYPE: DNA
<213> ORGANISM: Artificial Sequence
<220> FEATURE:
<223> OTHER INFORMATION: PRIMER

<400> SEQUENCE: 22
tgaggagacg gtgacctggg tccc 24

<210> SEQ ID NO 23
<211> LENGTH: 34
<212> TYPE: DNA
<213> ORGANISM: Artificial Sequence
<220> FEATURE:
<223> OTHER INFORMATION: PRIMER

<400> SEQUENCE: 23
tcttggatcc gaggtgcagc tggtggagtc tggg 34

<210> SEQ ID NO 24
<211> LENGTH: 33
<212> TYPE: DNA
<213> ORGANISM: Artificial Sequence
<220> FEATURE:
<223> OTHER INFORMATION: PRIMER

<400> SEQUENCE: 24
accgcctccg gaggagaccg tgacctgggt ccc 33

<210> SEQ ID NO 25
<211> LENGTH: 119
<212> TYPE: PRT
<213> ORGANISM: Artificial Sequence
<220> FEATURE:
<223> OTHER INFORMATION: monovalent anti-CXCR2 Nanobodies

<400> SEQUENCE: 25

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Trp Met Tyr Trp Val Arg Gln Ala Pro Gly Lys Gly Leu Asp Trp Val
35 40 45

Ser Ala Ile Asn Ala Gly Gly Asp Ser Thr Tyr Tyr Ala Asp Pro Val
50 55 60

Lys Gly Arg Phe Thr Ile Ser Arg Asp Asn Asn Lys Asn Thr Leu Tyr
65 70 75 80

Leu Gln Met Asn Ser Leu Lys Pro Glu Asp Thr Ala Leu Tyr Tyr Cys
85 90 95

Ala Thr Val Arg Gly Thr Ala Arg Asp Leu Asp Tyr Trp Gly Gln Gly
100 105 110

Thr Gln Val Thr Val Ser Ser
115

<210> SEQ ID NO 26
<211> LENGTH: 123
<212> TYPE: PRT
<213> ORGANISM: Artificial Sequence
<220> FEATURE:
<223> OTHER INFORMATION: monovalent anti-CXCR2 Nanobodies

<400> SEQUENCE: 26

```
Glu Val Lys Leu Val Glu Ser Gly Gly Gly Leu Val Gln Ala Gly Gly
1               5                   10                  15

Ser Leu Arg Leu Ser Cys Ala Leu Ser Gly Arg Ile Gly Ser Ile Asn
            20                  25                  30

Ala Met Gly Trp Tyr Arg Gln Val Ser Gly Gln Gln Arg Glu Leu Val
        35                  40                  45

Ala Val Ser Arg Ser Gly Gly Ser Thr Asp Ile Ala Asp Ser Val Lys
    50                  55                  60

Gly Arg Phe Thr Ile Ser Arg Asp Asn Gly Lys Asn Thr Val Tyr Leu
65                  70                  75                  80

Gln Met Asp Ser Leu Lys Pro Glu Asp Thr Ala Val Tyr Tyr Cys Tyr
                85                  90                  95

Ala His Thr Ser Ser Tyr Ser Asn Trp Arg Val Tyr Asn Asn Asp Tyr
            100                 105                 110

Trp Gly Gln Gly Thr Gln Val Thr Val Ser Ser
        115                 120
```

<210> SEQ ID NO 27
<211> LENGTH: 116
<212> TYPE: PRT
<213> ORGANISM: Artificial Sequence
<220> FEATURE:
<223> OTHER INFORMATION: monovalent anti-CXCR2 Nanobodies

<400> SEQUENCE: 27

```
Glu Val Gln Leu Val Glu Ser Gly Gly Gly Leu Val Gln Ala Gly Gly
1               5                   10                  15

Ser Leu Arg Leu Thr Cys Ala Ala Ser Gly Arg Ile Gly Thr Ile Asn
            20                  25                  30

Ala Met Gly Trp Tyr Arg Gln Ala Pro Gly Lys Gln Arg Glu Leu Val
        35                  40                  45

Ala Val Ile Thr Ser Gly Gly Arg Ile Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Tyr Asn
                85                  90                  95

Val Glu Thr Val Val Gly Ala Val Tyr Trp Gly Gln Gly Thr Gln Val
            100                 105                 110

Thr Val Ser Ser
        115
```

<210> SEQ ID NO 28
<211> LENGTH: 116
<212> TYPE: PRT
<213> ORGANISM: Artificial Sequence
<220> FEATURE:
<223> OTHER INFORMATION: monovalent anti-CXCR2 Nanobodies

<400> SEQUENCE: 28

```
Glu Val Gln Leu Val Glu Ser Gly Gly Gly Leu Val Gln Ala Gly Gly
```

```
1               5                   10                  15

Ser Leu Arg Leu Ser Cys Ala Ala Ser Gly Arg Met Gly Asn Ile Asn
            20                  25                  30

Ala Met Gly Trp Tyr Arg Gln Ala Pro Gly Lys Glu Arg Glu Leu Val
        35                  40                  45

Ala Lys Ile Thr Arg Gly Gly Ala Ile Thr Tyr Ala Asp Ser Val Lys
    50                  55                  60

Gly Arg Phe Thr Ile Ala Arg Asp Asn Ile Leu Asn Thr Ala Tyr Leu
65                  70                  75                  80

Gln Met Asn Asp Leu Lys Pro Glu Asp Thr Ala Val Tyr Tyr Tyr Asn
                85                  90                  95

Val Asp Gly Gly Pro Ser Gln Asn Tyr Trp Gly Gln Gly Thr Gln Val
            100                 105                 110

Thr Val Ser Ser
        115


<210> SEQ ID NO 29
<211> LENGTH: 126
<212> TYPE: PRT
<213> ORGANISM: Artificial Sequence
<220> FEATURE:
<223> OTHER INFORMATION: monovalent anti-CXCR2 Nanobodies

<400> SEQUENCE: 29

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Arg Val
        35                  40                  45

Ser Cys Ile Ser Gly Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Tyr Trp Gly Leu Thr Leu Arg Leu Trp Met Pro Pro His Arg
            100                 105                 110

Tyr Asp Tyr Trp Gly Gln Gly Thr Gln Val Thr Val Ser Ser
        115                 120                 125


<210> SEQ ID NO 30
<211> LENGTH: 111
<212> TYPE: PRT
<213> ORGANISM: Artificial Sequence
<220> FEATURE:
<223> OTHER INFORMATION: monovalent anti-CXCR2 Nanobodies

<400> SEQUENCE: 30

Glu Val Gln Leu Val Glu Ser Gly Gly Gly Leu Val Gln Ala Gly Gly
1               5                   10                  15

Ser Leu Ser Leu Ser Cys Ala Ala Ser Gly Leu Ile Phe Arg Leu Ser
            20                  25                  30

Gly Met Ala Trp Tyr Arg Gln Ala Pro Gly Arg Gln Arg Glu Trp Val
        35                  40                  45

Ala Val Leu Thr Lys Asp Gly Thr Leu His Tyr Ala Asp Pro Val Lys
    50                  55                  60
```

```
Gly Arg Phe Thr Ile Ser Arg Asn Asn Ala Glu Asn Thr Trp Tyr Leu
65                  70                  75                  80

Gln Met Asn Ser Leu Lys Pro Glu Asp Thr Ala Ile Tyr Tyr Cys Asn
                85                  90                  95

Thr Gly Arg Tyr Trp Gly Gln Gly Thr Gln Val Thr Val Ser Ser
            100                 105                 110


<210> SEQ ID NO 31
<211> LENGTH: 115
<212> TYPE: PRT
<213> ORGANISM: Artificial Sequence
<220> FEATURE:
<223> OTHER INFORMATION: monovalent anti-CXCR2 Nanobodies

<400> SEQUENCE: 31

Glu Val Gln Leu Val Glu Ser Gly Gly Gly Leu Val Gln Ala Gly Gly
1               5                   10                  15

Ser Leu Arg Leu Ser Cys Ala Ala Ser Gly Thr Ile Gly Thr Ile Arg
            20                  25                  30

Ala Met Gly Trp Tyr Arg Gln Ala Pro Gly Lys Gln Arg Glu Leu Val
        35                  40                  45

Ala Leu Ile Thr Ser Thr Gly Arg Ile Asn Tyr Ala Asp Ser Val Lys
    50                  55                  60

Gly Arg Phe Thr Ile Gly Arg Asp Asn Ala Lys Asn Thr Ala Tyr Leu
65                  70                  75                  80

Gln Met Asn Asn Leu Lys Pro Glu Asp Thr Ala Val Tyr Tyr Tyr Asn
                85                  90                  95

Ile Glu Thr Leu Arg Arg Asn Tyr Trp Gly Gln Gly Thr Gln Val Thr
            100                 105                 110

Val Ser Ser
        115


<210> SEQ ID NO 32
<211> LENGTH: 118
<212> TYPE: PRT
<213> ORGANISM: Artificial Sequence
<220> FEATURE:
<223> OTHER INFORMATION: monovalent anti-CXCR2 Nanobodies

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Thr Gly Lys Glu Arg Glu Phe Val
        35                  40                  45

Ala Ala Ile Asn Lys Ser Gly Gly Asn Thr His Tyr Ala Gly Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Arg Asp Thr Ala Val Tyr Tyr Cys
                85                  90                  95

Ala Ala Ser Arg Thr Asn Pro Lys Pro Asp Tyr Trp Gly Gln Gly Thr
            100                 105                 110

Gln Val Thr Val Ser Ser
        115


<210> SEQ ID NO 33
```

<211> LENGTH: 122
<212> TYPE: PRT
<213> ORGANISM: Artificial Sequence
<220> FEATURE:
<223> OTHER INFORMATION: monovalent anti-CXCR2 Nanobodies

<400> SEQUENCE: 33

Glu Val Gln Leu Val Glu Ser Gly Gly Gly Leu Val Gln Ala Gly Gly
1 5 10 15

Ser Leu Arg Leu Ser Cys Ala Ala Ser Gly Arg Ser Phe Ser Arg Ser
20 25 30

Ala Met Gly Trp Leu Arg Gln Ala Pro Gly Lys Glu Arg Glu Phe Val
35 40 45

Ala Gly Ile Ser Trp Gly Gly Asp Asn Ser Tyr Tyr Ala Asp Ser Val
50 55 60

Lys Gly Arg Phe Thr Ile Ser Arg Asp Asn Ala Lys Asn Thr Val Ser
65 70 75 80

Leu Gln Met Asn Ser Leu Lys Pro Gln Asp Thr Ala Val Tyr Tyr Cys
85 90 95

Ala Ala Arg Tyr Arg Gly Gly Ala Ala Val Ala Gly Trp Glu Tyr Trp
100 105 110

Gly Gln Gly Thr Gln Val Thr Val Ser Ser
115 120

<210> SEQ ID NO 34
<211> LENGTH: 124
<212> TYPE: PRT
<213> ORGANISM: Artificial Sequence
<220> FEATURE:
<223> OTHER INFORMATION: monovalent anti-CXCR2 Nanobodies

<400> SEQUENCE: 34

Glu Val Gln Leu Val Glu Ser Gly Gly Gly Leu Val Gln Pro Gly Gly
1 5 10 15

Ser Leu Arg Leu Ser Cys Ala Ala Ser Gly Ser Thr Leu Ala Tyr Tyr
20 25 30

Thr Val Gly Trp Phe Arg Arg Ala Pro Gly Lys Glu Arg Glu Gly Ile
35 40 45

Ser Cys Ile Ser Ser Ser Asp Gly Ser Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Arg Arg Thr Asp Cys Lys Lys Gly Arg Val Gly Ser Gly
100 105 110

Ser Trp Gly Gln Gly Thr Gln Val Thr Val Ser Ser
115 120

<210> SEQ ID NO 35
<211> LENGTH: 125
<212> TYPE: PRT
<213> ORGANISM: Artificial Sequence
<220> FEATURE:
<223> OTHER INFORMATION: monovalent anti-CXCR2 Nanobodies

<400> SEQUENCE: 35

Lys Val Gln Leu Val Glu Ser Gly Gly Gly Leu Val Gln Ala Gly Gly
1 5 10 15

```
Ser Leu Arg Leu Ser Cys Ala Ala Ser Gly Arg Ala Phe Asn Tyr Tyr
            20                  25                  30

Val Met Ala Trp Phe Arg Gln Ala Gln Gly Lys Glu Arg Glu Phe Val
        35                  40                  45

Ala Ala Ile Ser Thr Arg Gly Ser Met Thr Lys Tyr Ser Asp Ser Val
    50                  55                  60

Gln Gly Arg Phe Thr Ile Ser Arg Asp Asn Ala Lys Asn Thr Val Tyr
65                  70                  75                  80

Leu His Met Asn Ser Leu Lys Pro Glu Asp Thr Ala Val Tyr Tyr Cys
                85                  90                  95

Ala Ala Asp Pro Arg Gly Ser Ser Trp Ser Phe Ser Ser Gly Gly Tyr
            100                 105                 110

Asp Tyr Trp Gly Gln Gly Thr Gln Val Thr Val Ser Ser
        115                 120                 125


<210> SEQ ID NO 36
<211> LENGTH: 111
<212> TYPE: PRT
<213> ORGANISM: Artificial Sequence
<220> FEATURE:
<223> OTHER INFORMATION: monovalent anti-CXCR2 Nanobodies

<400> SEQUENCE: 36

Glu Val Gln Leu Val Glu Ser Gly Gly Gly Leu Val Gln Pro Gly Gly
1               5                   10                  15

Ser Val Arg Leu Ser Cys Val Ala Ser Gly Ile Ile Phe Arg Leu Ser
            20                  25                  30

Ala Leu Gly Trp Thr Arg Gln Gly Pro Gly Lys Ala Arg Glu Trp Val
        35                  40                  45

Ala Gly Ile Asn Ser Asp Gly Thr Thr Asn Tyr Ala Asp Pro Val Lys
    50                  55                  60

Gly Arg Phe Thr Ile Ser Arg Asp Asn Ala Lys Asn Thr Ile Tyr Leu
65                  70                  75                  80

His Met Asp Met Leu Lys Pro Glu Asp Thr Ala Val Tyr Tyr Cys Ala
                85                  90                  95

Ser Gly Lys Tyr Arg Gly Gln Gly Thr Gln Val Thr Val Ser Ser
            100                 105                 110


<210> SEQ ID NO 37
<211> LENGTH: 115
<212> TYPE: PRT
<213> ORGANISM: Artificial Sequence
<220> FEATURE:
<223> OTHER INFORMATION: monovalent anti-CXCR2 Nanobodies

<400> SEQUENCE: 37

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Pro Pro Gly Lys Gln Arg Glu Gly Val
        35                  40                  45

Ala Ala Ile Arg Leu Ser Gly Asn Met His Tyr Ala Glu Ser Val Lys
    50                  55                  60

Gly Arg Phe Thr Ile Ser Lys Ala Asn Ala Lys Asn Thr Val Tyr Leu
65                  70                  75                  80

Gln Met Asn Ser Leu Arg Pro Glu Asp Thr Ala Val Tyr Tyr Cys Lys
                85                  90                  95
```

```
Val Asn Ile Arg Gly Gln Asp Tyr Trp Gly Gln Gly Thr Gln Val Thr
            100                 105                 110

Val Ser Ser
        115


<210> SEQ ID NO 38
<211> LENGTH: 120
<212> TYPE: PRT
<213> ORGANISM: Artificial Sequence
<220> FEATURE:
<223> OTHER INFORMATION: monovalent anti-CXCR2 Nanobodies

<400> SEQUENCE: 38

Glu Val Gln Leu Val Glu Ser Gly Gly Gly Leu Val Gln Ala Gly Gly
1               5                   10                  15

Ser Leu Thr Leu Ser Cys Ala Val Ser Gly Ser Ser Phe Arg Ile Asn
            20                  25                  30

Thr Met Gly Trp Tyr Arg Arg Ala Pro Gly Lys Gln Arg Glu Leu Val
        35                  40                  45

Ala Ala Arg Asp Arg Gly Gly Tyr Ile Asn Tyr Val Asp Ser Val Lys
    50                  55                  60

Gly Arg Phe Thr Val Ser Arg Asp Asn Ala Lys Pro Thr Met Tyr Leu
65                  70                  75                  80

Gln Met Asn Ser Leu Lys Pro Glu Asp Thr Ala Val Tyr Tyr Cys His
                85                  90                  95

Ala Gly Thr Gln Asp Arg Thr Gly Arg Asn Phe Asp His Trp Gly Gln
            100                 105                 110

Gly Thr Gln Val Thr Val Ser Ser
        115                 120


<210> SEQ ID NO 39
<211> LENGTH: 126
<212> TYPE: PRT
<213> ORGANISM: Artificial Sequence
<220> FEATURE:
<223> OTHER INFORMATION: monovalent anti-CXCR2 Nanobodies

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Val Ala Ser Gly Ser Ile Val Arg Ile Asn
            20                  25                  30

Thr Met Gly Trp Tyr Arg Gln Thr Pro Gly Lys Gln Arg Glu Leu Val
        35                  40                  45

Ala Asp Ile Thr Ser Gly Gly Asn Ile Asn Tyr Ile Asp Ala Val Lys
    50                  55                  60

Gly Arg Phe Thr Ile Ser Arg Asp Asn Thr Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Ile Val Val Leu Val Gly Val Trp Thr Gln Arg Ala Arg Thr
            100                 105                 110

Gly Asn Tyr Trp Gly Gln Gly Thr Gln Val Thr Val Ser Ser
        115                 120                 125


<210> SEQ ID NO 40
<211> LENGTH: 124
<212> TYPE: PRT
```

```
<213> ORGANISM: Artificial Sequence
<220> FEATURE:
<223> OTHER INFORMATION: monovalent anti-CXCR2 Nanobodies

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Leu
            20                  25                  30

Ser Met Gly Trp Phe Arg Gln Ala Pro Gly Lys Glu Arg Ala Phe Val
        35                  40                  45

Ala Ala Leu Thr Arg Asn Gly Gly Tyr Arg Tyr Tyr Ala Asp Ser Val
    50                  55                  60

Lys Gly Arg Phe Thr Ile Ser Arg Asp Val Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Asp Ser Leu Ser Gly Ser Asp Tyr Leu Gly Thr Asn Leu Asp
            100                 105                 110

Tyr Trp Gly Gln Gly Thr Gln Val Thr Val Ser Ser
        115                 120


<210> SEQ ID NO 41
<211> LENGTH: 124
<212> TYPE: PRT
<213> ORGANISM: Artificial Sequence
<220> FEATURE:
<223> OTHER INFORMATION: monovalent anti-CXCR2 Nanobodies

<400> SEQUENCE: 41

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Arg Glu Phe Val
        35                  40                  45

Ala Ala Ile Thr Trp Asn Gly Gly Arg Val Phe Tyr Thr Ala Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asp Lys Asp Arg Arg Thr Asp Tyr Leu Gly His Pro Val Ala
            100                 105                 110

Tyr Trp Gly Gln Gly Thr Gln Val Thr Val Ser Ser
        115                 120


<210> SEQ ID NO 42
<211> LENGTH: 122
<212> TYPE: PRT
<213> ORGANISM: Artificial Sequence
<220> FEATURE:
<223> OTHER INFORMATION: monovalent anti-CXCR2 Nanobodies

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Ile Phe Ser Ser Asn
            20                  25                  30
```

Ala Met Gly Trp Phe Arg Gln Ala Pro Gly Lys Glu Arg Glu Phe Val
35 40 45

Ala Ala Ile Thr Trp Arg Ser Gly Gly Ser Ala Tyr Tyr Ala Asp Ser
50 55 60

Ala Lys Gly Arg Phe Thr Ile Ser Arg Asp Asn Ala Lys Asn Thr Val
65 70 75 80

Tyr Leu Gln Met Asn Ser Leu Lys Pro Glu Asp Thr Ala Val Tyr Tyr
85 90 95

Cys Ala Ala Gly Gly Ser Ser Trp Leu Ser Phe Pro Pro Asp Tyr Trp
100 105 110

Gly Gln Gly Thr Gln Val Thr Val Ser Ser
115 120

<210> SEQ ID NO 43
<211> LENGTH: 115
<212> TYPE: PRT
<213> ORGANISM: Artificial Sequence
<220> FEATURE:
<223> OTHER INFORMATION: monovalent anti-CXCR2 Nanobodies

<400> SEQUENCE: 43

Glu Val Gln Leu Val Glu Ser Gly Gly Glu Leu Val Gln Pro Gly Gly
1 5 10 15

Ser Leu Arg Leu Ser Cys Ala Ala Ser Gly Ser Ile Leu Thr Ile Asn
20 25 30

Ala Met Gly Trp Tyr Arg Gln Ala Pro Gly Lys Gln Arg Glu Leu Val
35 40 45

Val Arg Arg Thr Arg Gly Gly Ser Thr Thr Tyr Gln Asp Ser Val Lys
50 55 60

Gly Arg Phe Thr Ile Ser Ala Asp Ile Ala Lys Lys Thr Met Tyr Leu
65 70 75 80

Gln Met Asn Ser Leu Lys Pro Glu Asp Thr Ala Val Tyr Tyr Cys Met
85 90 95

Leu Asp Asp Arg Gly Gly Val Tyr Trp Gly Gln Gly Thr Gln Val Thr
100 105 110

Val Ser Ser
115

<210> SEQ ID NO 44
<211> LENGTH: 287
<212> TYPE: PRT
<213> ORGANISM: Artificial Sequence
<220> FEATURE:
<223> OTHER INFORMATION: multivalent anti-CXCR2 Nanobodies

<400> SEQUENCE: 44

Glu Val Gln Leu Val Glu Ser Gly Gly Gly Leu Val Gln Pro Gly Gly
1 5 10 15

Ser Leu Arg Leu Ser Cys Val Ala Ser Gly Ser Ile Val Arg Ile Asn
20 25 30

Thr Met Gly Trp Tyr Arg Gln Thr Pro Gly Lys Gln Arg Glu Leu Val
35 40 45

Ala Asp Ile Thr Ser Gly Gly Asn Ile Asn Tyr Ile Asp Ala Val Lys
50 55 60

Gly Arg Phe Thr Ile Ser Arg Asp Asn Thr Lys Asn Thr Val Tyr Leu
65 70 75 80

Gln Met Asn Ser Leu Lys Pro Glu Asp Thr Ala Val Tyr Tyr Cys Asn

```
                85                  90                  95

Ala Glu Ile Val Val Leu Val Gly Val Trp Thr Gln Arg Ala Arg Thr
            100                 105                 110

Gly Asn Tyr Trp Gly Gln Gly Thr Gln Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Pro Gly
                165                 170                 175

Gly Ser Leu Arg Leu Ser Cys Val Ala Ser Gly Ser Ile Val Arg Ile
            180                 185                 190

Asn Thr Met Gly Trp Tyr Arg Gln Thr Pro Gly Lys Gln Arg Glu Leu
        195                 200                 205

Val Ala Asp Ile Thr Ser Gly Gly Asn Ile Asn Tyr Ile Asp Ala Val
    210                 215                 220

Lys Gly Arg Phe Thr Ile Ser Arg Asp Asn Thr Lys Asn Thr Val Tyr
225                 230                 235                 240

Leu Gln Met Asn Ser Leu Lys Pro Glu Asp Thr Ala Val Tyr Tyr Cys
                245                 250                 255

Asn Ala Glu Ile Val Val Leu Val Gly Val Trp Thr Gln Arg Ala Arg
            260                 265                 270

Thr Gly Asn Tyr Trp Gly Gln Gly Thr Gln Val Thr Val Ser Ser
        275                 280                 285
```

<210> SEQ ID NO 45
<211> LENGTH: 257
<212> TYPE: PRT
<213> ORGANISM: Artificial Sequence
<220> FEATURE:
<223> OTHER INFORMATION: multivalent anti-CXCR2 Nanobodies

<400> SEQUENCE: 45

```
Glu Val Gln Leu Val Glu Ser Gly Gly Gly Leu Val Gln Pro Gly Gly
1               5                   10                  15

Ser Val Arg Leu Ser Cys Val Ala Ser Gly Ile Ile Phe Arg Leu Ser
            20                  25                  30

Ala Leu Gly Trp Thr Arg Gln Gly Pro Gly Lys Ala Arg Glu Trp Val
        35                  40                  45

Ala Gly Ile Asn Ser Asp Gly Thr Thr Asn Tyr Ala Asp Pro Val Lys
    50                  55                  60

Gly Arg Phe Thr Ile Ser Arg Asp Asn Ala Lys Asn Thr Ile Tyr Leu
65                  70                  75                  80

His Met Asp Met Leu Lys Pro Glu Asp Thr Ala Val Tyr Tyr Cys Ala
                85                  90                  95

Ser Gly Lys Tyr Arg Gly Gln Gly Thr Gln Val Thr Val Ser Ser Gly
            100                 105                 110

Gly Gly Gly Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Glu Val Gln Leu Val Glu Ser Gly Gly Gly Leu Val Gln Pro
145                 150                 155                 160

Gly Gly Ser Val Arg Leu Ser Cys Val Ala Ser Gly Ile Ile Phe Arg
```

```
                165                 170                 175

Leu Ser Ala Leu Gly Trp Thr Arg Gln Gly Pro Gly Lys Ala Arg Glu
            180                 185                 190

Trp Val Ala Gly Ile Asn Ser Asp Gly Thr Thr Asn Tyr Ala Asp Pro
        195                 200                 205

Val Lys Gly Arg Phe Thr Ile Ser Arg Asp Asn Ala Lys Asn Thr Ile
    210                 215                 220

Tyr Leu His Met Asp Met Leu Lys Pro Glu Asp Thr Ala Val Tyr Tyr
225                 230                 235                 240

Cys Ala Ser Gly Lys Tyr Arg Gly Gln Gly Thr Gln Val Thr Val Ser
                245                 250                 255

Ser


<210> SEQ ID NO 46
<211> LENGTH: 276
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 46

Glu Val Gln Leu Val Glu Ser Gly Gly Glu Leu Val Gln Pro Gly Gly
1               5                   10                  15

Ser Leu Arg Leu Ser Cys Ala Ala Ser Gly Ser Ile Leu Thr Ile Asn
            20                  25                  30

Ala Met Gly Trp Tyr Arg Gln Ala Pro Gly Lys Gln Arg Glu Leu Val
        35                  40                  45

Val Arg Arg Thr Arg Gly Gly Ser Thr Thr Tyr Gln Asp Ser Val Lys
    50                  55                  60

Gly Arg Phe Thr Ile Ser Ala Asp Ile Ala Lys Lys Thr Met Tyr Leu
65                  70                  75                  80

Gln Met Asn Ser Leu Lys Pro Glu Asp Thr Ala Val Tyr Tyr Cys Met
                85                  90                  95

Leu Asp Asp Arg Gly Gly Val Tyr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Gly Ser Leu Arg Leu Ser Cys Val Ala Ser Gly
                165                 170                 175

Ser Ile Val Arg Ile Asn Thr Met Gly Trp Tyr Arg Gln Thr Pro Gly
            180                 185                 190

Lys Gln Arg Glu Leu Val Ala Asp Ile Thr Ser Gly Gly Asn Ile Asn
        195                 200                 205

Tyr Ile Asp Ala Val Lys Gly Arg Phe Thr Ile Ser Arg Asp Asn Thr
    210                 215                 220

Lys Asn Thr Val Tyr Leu Gln Met Asn Ser Leu Lys Pro Glu Asp Thr
225                 230                 235                 240

Ala Val Tyr Tyr Cys Asn Ala Glu Ile Val Val Leu Val Gly Val Trp
                245                 250                 255

Thr Gln Arg Ala Arg Thr Gly Asn Tyr Trp Gly Gln Gly Thr Gln Val
            260                 265                 270
```

```
Thr Val Ser Ser
        275


<210> SEQ ID NO 47
<211> LENGTH: 276
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Val Ala Ser Gly Ser Ile Val Arg Ile Asn
            20                  25                  30

Thr Met Gly Trp Tyr Arg Gln Thr Pro Gly Lys Gln Arg Glu Leu Val
        35                  40                  45

Ala Asp Ile Thr Ser Gly Gly Asn Ile Asn Tyr Ile Asp Ala Val Lys
    50                  55                  60

Gly Arg Phe Thr Ile Ser Arg Asp Asn Thr Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Ile Val Val Leu Val Gly Val Trp Thr Gln Arg Ala Arg Thr
            100                 105                 110

Gly Asn Tyr Trp Gly Gln Gly Thr Gln Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Glu Leu Val Gln Pro Gly
                165                 170                 175

Gly Ser Leu Arg Leu Ser Cys Ala Ala Ser Gly Ser Ile Leu Thr Ile
            180                 185                 190

Asn Ala Met Gly Trp Tyr Arg Gln Ala Pro Gly Lys Gln Arg Glu Leu
        195                 200                 205

Val Val Arg Arg Thr Arg Gly Gly Ser Thr Thr Tyr Gln Asp Ser Val
    210                 215                 220

Lys Gly Arg Phe Thr Ile Ser Ala Asp Ile Ala Lys Lys Thr Met Tyr
225                 230                 235                 240

Leu Gln Met Asn Ser Leu Lys Pro Glu Asp Thr Ala Val Tyr Tyr Cys
                245                 250                 255

Met Leu Asp Asp Arg Gly Gly Val Tyr Trp Gly Gln Gly Thr Gln Val
            260                 265                 270

Thr Val Ser Ser
        275


<210> SEQ ID NO 48
<211> LENGTH: 261
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 48

Glu Val Gln Leu Val Glu Ser Gly Gly Glu Leu Val Gln Pro Gly Gly
```

```
1               5                   10                  15

Ser Leu Arg Leu Ser Cys Ala Ala Ser Gly Ser Ile Leu Thr Ile Asn
            20                  25                  30

Ala Met Gly Trp Tyr Arg Gln Ala Pro Gly Lys Gln Arg Glu Leu Val
        35                  40                  45

Val Arg Arg Thr Arg Gly Gly Ser Thr Thr Tyr Gln Asp Ser Val Lys
    50                  55                  60

Gly Arg Phe Thr Ile Ser Ala Asp Ile Ala Lys Lys Thr Met Tyr Leu
65                  70                  75                  80

Gln Met Asn Ser Leu Lys Pro Glu Asp Thr Ala Val Tyr Tyr Cys Met
                85                  90                  95

Leu Asp Asp Arg Gly Gly Val Tyr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Gly Ser Val Arg Leu Ser Cys Val Ala Ser Gly
                165                 170                 175

Ile Ile Phe Arg Leu Ser Ala Leu Gly Trp Thr Arg Gln Gly Pro Gly
            180                 185                 190

Lys Ala Arg Glu Trp Val Ala Gly Ile Asn Ser Asp Gly Thr Thr Asn
        195                 200                 205

Tyr Ala Asp Pro Val Lys Gly Arg Phe Thr Ile Ser Arg Asp Asn Ala
    210                 215                 220

Lys Asn Thr Ile Tyr Leu His Met Asp Met Leu Lys Pro Glu Asp Thr
225                 230                 235                 240

Ala Val Tyr Tyr Cys Ala Ser Gly Lys Tyr Arg Gly Gln Gly Thr Gln
                245                 250                 255

Val Thr Val Ser Ser
            260
```

<210> SEQ ID NO 49
<211> LENGTH: 261
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 49

```
Glu Val Gln Leu Val Glu Ser Gly Gly Gly Leu Val Gln Pro Gly Gly
1               5                   10                  15

Ser Val Arg Leu Ser Cys Val Ala Ser Gly Ile Ile Phe Arg Leu Ser
            20                  25                  30

Ala Leu Gly Trp Thr Arg Gln Gly Pro Gly Lys Ala Arg Glu Trp Val
        35                  40                  45

Ala Gly Ile Asn Ser Asp Gly Thr Thr Asn Tyr Ala Asp Pro Val Lys
    50                  55                  60

Gly Arg Phe Thr Ile Ser Arg Asp Asn Ala Lys Asn Thr Ile Tyr Leu
65                  70                  75                  80

His Met Asp Met Leu Lys Pro Glu Asp Thr Ala Val Tyr Tyr Cys Ala
                85                  90                  95

Ser Gly Lys Tyr Arg Gly Gln Gly Thr Gln Val Thr Val Ser Ser Gly
```

-continued

```
            100                 105                 110

Gly Gly Gly Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Glu Val Gln Leu Val Glu Ser Gly Gly Glu Leu Val Gln Pro
145                 150                 155                 160

Gly Gly Ser Leu Arg Leu Ser Cys Ala Ala Ser Gly Ser Ile Leu Thr
                165                 170                 175

Ile Asn Ala Met Gly Trp Tyr Arg Gln Ala Pro Gly Lys Gln Arg Glu
            180                 185                 190

Leu Val Val Arg Arg Thr Arg Gly Gly Ser Thr Thr Tyr Gln Asp Ser
        195                 200                 205

Val Lys Gly Arg Phe Thr Ile Ser Ala Asp Ile Ala Lys Lys Thr Met
    210                 215                 220

Tyr Leu Gln Met Asn Ser Leu Lys Pro Glu Asp Thr Ala Val Tyr Tyr
225                 230                 235                 240

Cys Met Leu Asp Asp Arg Gly Gly Val Tyr Trp Gly Gln Gly Thr Gln
                245                 250                 255

Val Thr Val Ser Ser
            260


<210> SEQ ID NO 50
<211> LENGTH: 272
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Val Ala Ser Gly Ser Ile Val Arg Ile Asn
            20                  25                  30

Thr Met Gly Trp Tyr Arg Gln Thr Pro Gly Lys Gln Arg Glu Leu Val
        35                  40                  45

Ala Asp Ile Thr Ser Gly Gly Asn Ile Asn Tyr Ile Asp Ala Val Lys
    50                  55                  60

Gly Arg Phe Thr Ile Ser Arg Asp Asn Thr Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Ile Val Val Leu Val Gly Val Trp Thr Gln Arg Ala Arg Thr
            100                 105                 110

Gly Asn Tyr Trp Gly Gln Gly Thr Gln Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Pro Gly
                165                 170                 175

Gly Ser Val Arg Leu Ser Cys Val Ala Ser Gly Ile Ile Phe Arg Leu
            180                 185                 190

Ser Ala Leu Gly Trp Thr Arg Gln Gly Pro Gly Lys Ala Arg Glu Trp
```

```
        195                 200                 205

Val Ala Gly Ile Asn Ser Asp Gly Thr Thr Asn Tyr Ala Asp Pro Val
    210                 215                 220

Lys Gly Arg Phe Thr Ile Ser Arg Asp Asn Ala Lys Asn Thr Ile Tyr
225                 230                 235                 240

Leu His Met Asp Met Leu Lys Pro Glu Asp Thr Ala Val Tyr Tyr Cys
                245                 250                 255

Ala Ser Gly Lys Tyr Arg Gly Gln Gly Thr Gln Val Thr Val Ser Ser
            260                 265                 270


<210> SEQ ID NO 51
<211> LENGTH: 272
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 51

Glu Val Gln Leu Val Glu Ser Gly Gly Gly Leu Val Gln Pro Gly Gly
1               5                   10                  15

Ser Val Arg Leu Ser Cys Val Ala Ser Gly Ile Ile Phe Arg Leu Ser
            20                  25                  30

Ala Leu Gly Trp Thr Arg Gln Gly Pro Gly Lys Ala Arg Glu Trp Val
        35                  40                  45

Ala Gly Ile Asn Ser Asp Gly Thr Thr Asn Tyr Ala Asp Pro Val Lys
    50                  55                  60

Gly Arg Phe Thr Ile Ser Arg Asp Asn Ala Lys Asn Thr Ile Tyr Leu
65                  70                  75                  80

His Met Asp Met Leu Lys Pro Glu Asp Thr Ala Val Tyr Tyr Cys Ala
                85                  90                  95

Ser Gly Lys Tyr Arg Gly Gln Gly Thr Gln Val Thr Val Ser Ser Gly
            100                 105                 110

Gly Gly Gly Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Glu Val Gln Leu Val Glu Ser Gly Gly Gly Leu Val Gln Pro
145                 150                 155                 160

Gly Gly Ser Leu Arg Leu Ser Cys Val Ala Ser Gly Ser Ile Val Arg
                165                 170                 175

Ile Asn Thr Met Gly Trp Tyr Arg Gln Thr Pro Gly Lys Gln Arg Glu
            180                 185                 190

Leu Val Ala Asp Ile Thr Ser Gly Gly Asn Ile Asn Tyr Ile Asp Ala
        195                 200                 205

Val Lys Gly Arg Phe Thr Ile Ser Arg Asp Asn Thr Lys Asn Thr Val
    210                 215                 220

Tyr Leu Gln Met Asn Ser Leu Lys Pro Glu Asp Thr Ala Val Tyr Tyr
225                 230                 235                 240

Cys Asn Ala Glu Ile Val Val Leu Val Gly Val Trp Thr Gln Arg Ala
                245                 250                 255

Arg Thr Gly Asn Tyr Trp Gly Gln Gly Thr Gln Val Thr Val Ser Ser
            260                 265                 270


<210> SEQ ID NO 52
<211> LENGTH: 239
<212> TYPE: PRT
```

<213> ORGANISM: Artificial Sequence
<220> FEATURE:
<223> OTHER INFORMATION: Sequences of multivalent anti-CXCR2 Nanobodies

<400> SEQUENCE: 52

Glu Val Gln Leu Val Glu Ser Gly Gly Glu Leu Val Gln Pro Gly Gly
1               5                   10                  15

Ser Leu Arg Leu Ser Cys Ala Ala Ser Gly Ser Ile Leu Thr Ile Asn
            20                  25                  30

Ala Met Gly Trp Tyr Arg Gln Ala Pro Gly Lys Gln Arg Glu Leu Val
        35                  40                  45

Val Arg Arg Thr Arg Gly Gly Ser Thr Thr Tyr Gln Asp Ser Val Lys
    50                  55                  60

Gly Arg Phe Thr Ile Ser Ala Asp Ile Ala Lys Lys Thr Met Tyr Leu
65                  70                  75                  80

Gln Met Asn Ser Leu Lys Pro Glu Asp Thr Ala Val Tyr Tyr Cys Met
                85                  90                  95

Leu Asp Asp Arg Gly Gly Val Tyr Trp Gly Gln Gly Thr Gln Val Thr
            100                 105                 110

Val Ser Ser Gly Gly Gly Gly Ser Gly Gly Gly Ser Glu Val Gln Leu
        115                 120                 125

Val Glu Ser Gly Gly Glu Leu Val Gln Pro Gly Gly Ser Leu Arg Leu
    130                 135                 140

Ser Cys Ala Ala Ser Gly Ser Ile Leu Thr Ile Asn Ala Met Gly Trp
145                 150                 155                 160

Tyr Arg Gln Ala Pro Gly Lys Gln Arg Glu Leu Val Val Arg Arg Thr
                165                 170                 175

Arg Gly Gly Ser Thr Thr Tyr Gln Asp Ser Val Lys Gly Arg Phe Thr
            180                 185                 190

Ile Ser Ala Asp Ile Ala Lys Lys Thr Met Tyr Leu Gln Met Asn Ser
        195                 200                 205

Leu Lys Pro Glu Asp Thr Ala Val Tyr Tyr Cys Met Leu Asp Asp Arg
    210                 215                 220

Gly Gly Val Tyr Trp Gly Gln Gly Thr Gln Val Thr Val Ser Ser
225                 230                 235

<210> SEQ ID NO 53
<211> LENGTH: 274
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 53

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Pro Pro Gly Lys Gln Arg Glu Gly Val
        35                  40                  45

Ala Ala Ile Arg Leu Ser Gly Asn Met His Tyr Ala Glu Ser Val Lys
    50                  55                  60

Gly Arg Phe Thr Ile Ser Lys Ala Asn Ala Lys Asn Thr Val Tyr Leu
65                  70                  75                  80

Gln Met Asn Ser Leu Arg Pro Glu Asp Thr Ala Val Tyr Tyr Cys Lys
                85                  90                  95

```
Val Asn Ile Arg Gly Gln Asp Tyr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Ala Gly Gly Ser Leu Arg Leu Ser Cys Ala Ala Ser Gly
                165                 170                 175

Arg Thr Phe Ser Asp Tyr Ala Met Gly Trp Phe Arg Gln Ala Pro Gly
            180                 185                 190

Lys Glu Arg Glu Phe Val Ala Ala Ile Thr Trp Asn Gly Gly Arg Val
        195                 200                 205

Phe Tyr Thr Ala Ser Val Lys Gly Arg Phe Thr Ile Ser Arg Asp Asn
    210                 215                 220

Ala Lys Asn Thr Met Tyr Leu Gln Met Asn Ser Leu Lys Pro Glu Asp
225                 230                 235                 240

Thr Ala Val Tyr Tyr Cys Ala Ala Asp Lys Asp Arg Arg Thr Asp Tyr
                245                 250                 255

Leu Gly His Pro Val Ala Tyr Trp Gly Gln Gly Thr Gln Val Thr Val
            260                 265                 270

Ser Ser


<210> SEQ ID NO 54
<211> LENGTH: 272
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 54

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Pro Pro Gly Lys Gln Arg Glu Gly Val
        35                  40                  45

Ala Ala Ile Arg Leu Ser Gly Asn Met His Tyr Ala Glu Ser Val Lys
    50                  55                  60

Gly Arg Phe Thr Ile Ser Lys Ala Asn Ala Lys Asn Thr Val Tyr Leu
65                  70                  75                  80

Gln Met Asn Ser Leu Arg Pro Glu Asp Thr Ala Val Tyr Tyr Cys Lys
                85                  90                  95

Val Asn Ile Arg Gly Gln Asp Tyr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Gly Ser Leu Arg Leu Ser Cys Val Ala Ser Gly
                165                 170                 175

Arg Ile Phe Ser Ser Asn Ala Met Gly Trp Phe Arg Gln Ala Pro Gly
```

```
            180                 185                 190

Lys Glu Arg Glu Phe Val Ala Ala Ile Thr Trp Arg Ser Gly Gly Ser
        195                 200                 205

Ala Tyr Tyr Ala Asp Ser Ala Lys Gly Arg Phe Thr Ile Ser Arg Asp
    210                 215                 220

Asn Ala Lys Asn Thr Val Tyr Leu Gln Met Asn Ser Leu Lys Pro Glu
225                 230                 235                 240

Asp Thr Ala Val Tyr Tyr Cys Ala Ala Gly Gly Ser Ser Trp Leu Ser
                245                 250                 255

Phe Pro Pro Asp Tyr Trp Gly Gln Gly Thr Gln Val Thr Val Ser Ser
            260                 265                 270


<210> SEQ ID NO 55
<211> LENGTH: 283
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 55

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Arg Glu Phe Val
        35                  40                  45

Ala Ala Ile Thr Trp Asn Gly Gly Arg Val Phe Tyr Thr Ala Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asp Lys Asp Arg Arg Thr Asp Tyr Leu Gly His Pro Val Ala
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Ala Gly Gly Ser
                165                 170                 175

Leu Arg Leu Ser Cys Ala Ala Ser Gly Arg Thr Phe Ser Asp Tyr Ala
            180                 185                 190

Met Gly Trp Phe Arg Gln Ala Pro Gly Lys Glu Arg Glu Phe Val Ala
        195                 200                 205

Ala Ile Thr Trp Asn Gly Gly Arg Val Phe Tyr Thr Ala Ser Val Lys
    210                 215                 220

Gly Arg Phe Thr Ile Ser Arg Asp Asn Ala Lys Asn Thr Met Tyr Leu
225                 230                 235                 240

Gln Met Asn Ser Leu Lys Pro Glu Asp Thr Ala Val Tyr Tyr Cys Ala
                245                 250                 255

Ala Asp Lys Asp Arg Arg Thr Asp Tyr Leu Gly His Pro Val Ala Tyr
            260                 265                 270

Trp Gly Gln Gly Thr Gln Val Thr Val Ser Ser
```

275 280

<210> SEQ ID NO 56
<211> LENGTH: 281
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 56

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Asp Tyr
20 25 30

Ala Met Gly Trp Phe Arg Gln Ala Pro Gly Lys Glu Arg Glu Phe Val
35 40 45

Ala Ala Ile Thr Trp Asn Gly Gly Arg Val Phe Tyr Thr Ala Ser Val
50 55 60

Lys Gly Arg Phe Thr Ile Ser Arg Asp Asn Ala Lys Asn Thr Met Tyr
65 70 75 80

Leu Gln Met Asn Ser Leu Lys Pro Glu Asp Thr Ala Val Tyr Tyr Cys
85 90 95

Ala Ala Asp Lys Asp Arg Arg Thr Asp Tyr Leu Gly His Pro Val Ala
100 105 110

Tyr Trp Gly Gln Gly Thr Gln Val Thr Val Ser Ser Gly Gly Gly Gly
115 120 125

Ser Gly Gly Gly Gly Ser Gly Gly Gly Gly Ser Gly Gly Gly Gly Ser
130 135 140

Gly Gly Gly Gly Ser Gly Gly Gly Gly Ser Gly Gly Gly Gly Ser Glu
145 150 155 160

Val Gln Leu Val Glu Ser Gly Gly Gly Leu Val Gln Pro Gly Gly Ser
165 170 175

Leu Arg Leu Ser Cys Val Ala Ser Gly Arg Ile Phe Ser Ser Asn Ala
180 185 190

Met Gly Trp Phe Arg Gln Ala Pro Gly Lys Glu Arg Glu Phe Val Ala
195 200 205

Ala Ile Thr Trp Arg Ser Gly Gly Ser Ala Tyr Tyr Ala Asp Ser Ala
210 215 220

Lys Gly Arg Phe Thr Ile Ser Arg Asp Asn Ala Lys Asn Thr Val Tyr
225 230 235 240

Leu Gln Met Asn Ser Leu Lys Pro Glu Asp Thr Ala Val Tyr Tyr Cys
245 250 255

Ala Ala Gly Gly Ser Ser Trp Leu Ser Phe Pro Pro Asp Tyr Trp Gly
260 265 270

Gln Gly Thr Gln Val Thr Val Ser Ser
275 280

<210> SEQ ID NO 57
<211> LENGTH: 279
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 57

Glu Val Gln Leu Val Glu Ser Gly Gly Gly Leu Val Gln Pro Gly Gly
1 5 10 15

```
Ser Leu Arg Leu Ser Cys Val Ala Ser Gly Arg Ile Phe Ser Ser Asn
            20                  25                  30

Ala Met Gly Trp Phe Arg Gln Ala Pro Gly Lys Glu Arg Glu Phe Val
        35                  40                  45

Ala Ala Ile Thr Trp Arg Ser Gly Gly Ser Ala Tyr Tyr Ala Asp Ser
    50                  55                  60

Ala Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Gly Gly Ser Ser Trp Leu Ser Phe Pro Pro Asp Tyr Trp
            100                 105                 110

Gly Gln Gly Thr Gln Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Gln Pro Gly Gly Ser Leu Arg
                165                 170                 175

Leu Ser Cys Val Ala Ser Gly Arg Ile Phe Ser Ser Asn Ala Met Gly
            180                 185                 190

Trp Phe Arg Gln Ala Pro Gly Lys Glu Arg Glu Phe Val Ala Ala Ile
        195                 200                 205

Thr Trp Arg Ser Gly Gly Ser Ala Tyr Tyr Ala Asp Ser Ala Lys Gly
    210                 215                 220

Arg Phe Thr Ile Ser Arg Asp Asn Ala Lys Asn Thr Val Tyr Leu Gln
225                 230                 235                 240

Met Asn Ser Leu Lys Pro Glu Asp Thr Ala Val Tyr Tyr Cys Ala Ala
                245                 250                 255

Gly Gly Ser Ser Trp Leu Ser Phe Pro Pro Asp Tyr Trp Gly Gln Gly
            260                 265                 270

Thr Gln Val Thr Val Ser Ser
        275


<210> SEQ ID NO 58
<211> LENGTH: 274
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 58

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Arg Glu Phe Val
        35                  40                  45

Ala Ala Ile Thr Trp Asn Gly Gly Arg Val Phe Tyr Thr Ala Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95
```

-continued

```
Ala Ala Asp Lys Asp Arg Arg Thr Asp Tyr Leu Gly His Pro Val Ala
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Ala Gly Glu Ser
                165                 170                 175

Leu Arg Leu Ser Cys Ala Ala Ser Gly Ser Thr Phe Asp Phe Lys Val
            180                 185                 190

Met Gly Trp Tyr Arg Gln Pro Pro Gly Lys Gln Arg Glu Gly Val Ala
        195                 200                 205

Ala Ile Arg Leu Ser Gly Asn Met His Tyr Ala Glu Ser Val Lys Gly
    210                 215                 220

Arg Phe Thr Ile Ser Lys Ala Asn Ala Lys Asn Thr Val Tyr Leu Gln
225                 230                 235                 240

Met Asn Ser Leu Arg Pro Glu Asp Thr Ala Val Tyr Tyr Cys Lys Val
                245                 250                 255

Asn Ile Arg Gly Gln Asp Tyr Trp Gly Gln Gly Thr Gln Val Thr Val
            260                 265                 270

Ser Ser


<210> SEQ ID NO 59
<211> LENGTH: 272
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Ile Phe Ser Ser Asn
            20                  25                  30

Ala Met Gly Trp Phe Arg Gln Ala Pro Gly Lys Glu Arg Glu Phe Val
        35                  40                  45

Ala Ala Ile Thr Trp Arg Ser Gly Gly Ser Ala Tyr Tyr Ala Asp Ser
    50                  55                  60

Ala Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Gly Gly Ser Ser Trp Leu Ser Phe Pro Pro Asp Tyr Trp
            100                 105                 110

Gly Gln Gly Thr Gln Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Gln Ala Gly Glu Ser Leu Arg
                165                 170                 175

Leu Ser Cys Ala Ala Ser Gly Ser Thr Phe Asp Phe Lys Val Met Gly
```

```
            180                 185                 190

Trp Tyr Arg Gln Pro Pro Gly Lys Gln Arg Glu Gly Val Ala Ala Ile
        195                 200                 205

Arg Leu Ser Gly Asn Met His Tyr Ala Glu Ser Val Lys Gly Arg Phe
    210                 215                 220

Thr Ile Ser Lys Ala Asn Ala Lys Asn Thr Val Tyr Leu Gln Met Asn
225                 230                 235                 240

Ser Leu Arg Pro Glu Asp Thr Ala Val Tyr Tyr Cys Lys Val Asn Ile
                245                 250                 255

Arg Gly Gln Asp Tyr Trp Gly Gln Gly Thr Gln Val Thr Val Ser Ser
            260                 265                 270


<210> SEQ ID NO 60
<211> LENGTH: 281
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Ile Phe Ser Ser Asn
            20                  25                  30

Ala Met Gly Trp Phe Arg Gln Ala Pro Gly Lys Glu Arg Glu Phe Val
        35                  40                  45

Ala Ala Ile Thr Trp Arg Ser Gly Gly Ser Ala Tyr Tyr Ala Asp Ser
    50                  55                  60

Ala Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Gly Gly Ser Ser Trp Leu Ser Phe Pro Pro Asp Tyr Trp
            100                 105                 110

Gly Gln Gly Thr Gln Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Gln Ala Gly Gly Ser Leu Arg
                165                 170                 175

Leu Ser Cys Ala Ala Ser Gly Arg Thr Phe Ser Asp Tyr Ala Met Gly
            180                 185                 190

Trp Phe Arg Gln Ala Pro Gly Lys Glu Arg Glu Phe Val Ala Ala Ile
        195                 200                 205

Thr Trp Asn Gly Gly Arg Val Phe Tyr Thr Ala Ser Val Lys Gly Arg
    210                 215                 220

Phe Thr Ile Ser Arg Asp Asn Ala Lys Asn Thr Met Tyr Leu Gln Met
225                 230                 235                 240

Asn Ser Leu Lys Pro Glu Asp Thr Ala Val Tyr Tyr Cys Ala Ala Asp
                245                 250                 255

Lys Asp Arg Arg Thr Asp Tyr Leu Gly His Pro Val Ala Tyr Trp Gly
            260                 265                 270

Gln Gly Thr Gln Val Thr Val Ser Ser
```

275 280

<210> SEQ ID NO 61
<211> LENGTH: 281
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 61

Glu Val Gln Leu Val Glu Ser Gly Gly Gly Leu Val Gln Pro Gly Gly
1 5 10 15

Ser Leu Arg Leu Ser Cys Val Ala Ser Gly Ser Ile Val Arg Ile Asn
20 25 30

Thr Met Gly Trp Tyr Arg Gln Thr Pro Gly Lys Gln Arg Glu Leu Val
35 40 45

Ala Asp Ile Thr Ser Gly Gly Asn Ile Asn Tyr Ile Asp Ala Val Lys
50 55 60

Gly Arg Phe Thr Ile Ser Arg Asp Asn Thr Lys Asn Thr Val Tyr Leu
65 70 75 80

Gln Met Asn Ser Leu Lys Pro Glu Asp Thr Ala Val Tyr Tyr Cys Asn
85 90 95

Ala Glu Ile Val Val Leu Val Gly Val Trp Thr Gln Arg Ala Arg Thr
100 105 110

Gly Asn Tyr Trp Gly Gln Gly Thr Gln Val Thr Val Ser Ser Gly Gly
115 120 125

Gly Gly Ser Gly Gly Gly Gly Ser Gly Gly Gly Gly Ser Gly Gly Gly
130 135 140

Gly Ser Gly Gly Gly Gly Ser Gly Gly Gly Gly Ser Gly Gly Gly Gly
145 150 155 160

Ser Glu Val Gln Leu Val Glu Ser Gly Gly Gly Leu Val Gln Ala Gly
165 170 175

Gly Ser Leu Thr Leu Ser Cys Ala Val Ser Gly Ser Thr Phe Arg Ile
180 185 190

Asn Thr Met Gly Trp Tyr Arg Arg Ala Pro Gly Lys Gln Arg Glu Leu
195 200 205

Val Ala Ala Arg Asp Arg Gly Gly Tyr Ile Asn Tyr Val Asp Ser Val
210 215 220

Lys Gly Arg Phe Thr Val Ser Arg Asp Asn Ala Lys Pro Thr Met Tyr
225 230 235 240

Leu Gln Met Asn Ser Leu Lys Pro Glu Asp Thr Ala Val Tyr Tyr Cys
245 250 255

His Ala Gly Thr Gln Asp Arg Thr Gly Arg Asn Phe Asp Arg Trp Gly
260 265 270

Gln Gly Thr Gln Val Thr Val Ser Ser
275 280

<210> SEQ ID NO 62
<211> LENGTH: 277
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 62

Glu Val Gln Leu Val Glu Ser Gly Gly Gly Leu Val Gln Pro Gly Gly
1 5 10 15

```
Ser Leu Arg Leu Ser Cys Val Ala Ser Gly Arg Ile Phe Ser Ser Asn
            20                  25                  30

Ala Met Gly Trp Phe Arg Gln Ala Pro Gly Lys Glu Arg Glu Phe Val
        35                  40                  45

Ala Ala Ile Thr Trp Arg Ser Gly Gly Ser Ala Tyr Tyr Ala Asp Ser
    50                  55                  60

Ala Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Gly Gly Ser Ser Trp Leu Ser Phe Pro Pro Asp Tyr Trp
            100                 105                 110

Gly Gln Gly Thr Gln Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Gln Ala Gly Gly Ser Leu Thr
                165                 170                 175

Leu Ser Cys Ala Val Ser Gly Ser Thr Phe Arg Ile Asn Thr Met Gly
            180                 185                 190

Trp Tyr Arg Arg Ala Pro Gly Lys Gln Arg Glu Leu Val Ala Ala Arg
        195                 200                 205

Asp Arg Gly Gly Tyr Ile Asn Tyr Val Asp Ser Val Lys Gly Arg Phe
    210                 215                 220

Thr Val Ser Arg Asp Asn Ala Lys Pro Thr Met Tyr Leu Gln Met Asn
225                 230                 235                 240

Ser Leu Lys Pro Glu Asp Thr Ala Val Tyr Tyr Cys His Ala Gly Thr
                245                 250                 255

Gln Asp Arg Thr Gly Arg Asn Phe Asp Arg Trp Gly Gln Gly Thr Gln
            260                 265                 270

Val Thr Val Ser Ser
        275
```

<210> SEQ ID NO 63
<211> LENGTH: 279
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 63

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Arg Glu Phe Val
        35                  40                  45

Ala Ala Ile Thr Trp Asn Gly Gly Arg Val Phe Tyr Thr Ala Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95
```

```
Ala Ala Asp Lys Asp Arg Arg Thr Asp Tyr Leu Gly His Pro Val Ala
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Ala Gly Gly Ser
                165                 170                 175

Leu Thr Leu Ser Cys Ala Val Ser Gly Ser Thr Phe Arg Ile Asn Thr
            180                 185                 190

Met Gly Trp Tyr Arg Arg Ala Pro Gly Lys Gln Arg Glu Leu Val Ala
        195                 200                 205

Ala Arg Asp Arg Gly Gly Tyr Ile Asn Tyr Val Asp Ser Val Lys Gly
    210                 215                 220

Arg Phe Thr Val Ser Arg Asp Asn Ala Lys Pro Thr Met Tyr Leu Gln
225                 230                 235                 240

Met Asn Ser Leu Lys Pro Glu Asp Thr Ala Val Tyr Tyr Cys His Ala
                245                 250                 255

Gly Thr Gln Asp Arg Thr Gly Arg Asn Phe Asp Arg Trp Gly Gln Gly
            260                 265                 270

Thr Gln Val Thr Val Ser Ser
        275
```

<210> SEQ ID NO 64
<211> LENGTH: 272
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 64

```
Glu Val Gln Leu Val Glu Ser Gly Gly Glu Leu Val Gln Pro Gly Gly
1               5                   10                  15

Ser Leu Arg Leu Ser Cys Ala Ala Ser Gly Ser Ile Leu Thr Ile Asn
            20                  25                  30

Ala Met Gly Trp Tyr Arg Gln Ala Pro Gly Lys Gln Arg Glu Leu Val
        35                  40                  45

Val Arg Arg Thr Arg Gly Gly Ser Thr Thr Tyr Gln Asp Ser Val Lys
    50                  55                  60

Gly Arg Phe Thr Ile Ser Ala Asp Ile Ala Lys Lys Thr Met Tyr Leu
65                  70                  75                  80

Gln Met Asn Ser Leu Lys Pro Glu Asp Thr Ala Val Tyr Tyr Cys Met
                85                  90                  95

Leu Asp Asp Arg Gly Gly Val Tyr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Gly Ser Leu Arg Leu Ser Cys Val Ala Ser Gly
                165                 170                 175
```

-continued

```
Arg Ile Phe Ser Ser Asn Ala Met Gly Trp Phe Arg Gln Ala Pro Gly
            180                 185                 190

Lys Glu Arg Glu Phe Val Ala Ala Ile Thr Trp Arg Ser Gly Gly Ser
        195                 200                 205

Ala Tyr Tyr Ala Asp Ser Ala Lys Gly Arg Phe Thr Ile Ser Arg Asp
    210                 215                 220

Asn Ala Lys Asn Thr Val Tyr Leu Gln Met Asn Ser Leu Lys Pro Glu
225                 230                 235                 240

Asp Thr Ala Val Tyr Tyr Cys Ala Ala Gly Gly Ser Ser Trp Leu Ser
                245                 250                 255

Phe Pro Pro Asp Tyr Trp Gly Gln Gly Thr Gln Val Thr Val Ser Ser
            260                 265                 270


<210> SEQ ID NO 65
<211> LENGTH: 274
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 65

Glu Val Gln Leu Val Glu Ser Gly Gly Glu Leu Val Gln Pro Gly Gly
1               5                   10                  15

Ser Leu Arg Leu Ser Cys Ala Ala Ser Gly Ser Ile Leu Thr Ile Asn
            20                  25                  30

Ala Met Gly Trp Tyr Arg Gln Ala Pro Gly Lys Gln Arg Glu Leu Val
        35                  40                  45

Val Arg Arg Thr Arg Gly Gly Ser Thr Thr Tyr Gln Asp Ser Val Lys
    50                  55                  60

Gly Arg Phe Thr Ile Ser Ala Asp Ile Ala Lys Lys Thr Met Tyr Leu
65                  70                  75                  80

Gln Met Asn Ser Leu Lys Pro Glu Asp Thr Ala Val Tyr Tyr Cys Met
                85                  90                  95

Leu Asp Asp Arg Gly Gly Val Tyr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Ala Gly Gly Ser Leu Arg Leu Ser Cys Ala Ala Ser Gly
                165                 170                 175

Arg Thr Phe Ser Asp Tyr Ala Met Gly Trp Phe Arg Gln Ala Pro Gly
            180                 185                 190

Lys Glu Arg Glu Phe Val Ala Ala Ile Thr Trp Asn Gly Gly Arg Val
        195                 200                 205

Phe Tyr Thr Ala Ser Val Lys Gly Arg Phe Thr Ile Ser Arg Asp Asn
    210                 215                 220

Ala Lys Asn Thr Met Tyr Leu Gln Met Asn Ser Leu Lys Pro Glu Asp
225                 230                 235                 240

Thr Ala Val Tyr Tyr Cys Ala Ala Asp Lys Asp Arg Arg Thr Asp Tyr
                245                 250                 255

Leu Gly His Pro Val Ala Tyr Trp Gly Gln Gly Thr Gln Val Thr Val
            260                 265                 270
```

Ser Ser

<210> SEQ ID NO 66
<211> LENGTH: 272
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 66

Glu Val Gln Leu Val Glu Ser Gly Gly Gly Leu Val Gln Pro Gly Gly
1 5 10 15

Ser Leu Arg Leu Ser Cys Val Ala Ser Gly Arg Ile Phe Ser Ser Asn
20 25 30

Ala Met Gly Trp Phe Arg Gln Ala Pro Gly Lys Glu Arg Glu Phe Val
35 40 45

Ala Ala Ile Thr Trp Arg Ser Gly Gly Ser Ala Tyr Tyr Ala Asp Ser
50 55 60

Ala Lys Gly Arg Phe Thr Ile Ser Arg Asp Asn Ala Lys Asn Thr Val
65 70 75 80

Tyr Leu Gln Met Asn Ser Leu Lys Pro Glu Asp Thr Ala Val Tyr Tyr
85 90 95

Cys Ala Ala Gly Gly Ser Ser Trp Leu Ser Phe Pro Pro Asp Tyr Trp
100 105 110

Gly Gln Gly Thr Gln Val Thr Val Ser Ser Gly Gly Gly Gly Ser Gly
115 120 125

Gly Gly Gly Ser Gly Gly Gly Gly Ser Gly Gly Gly Gly Ser Gly Gly
130 135 140

Gly Gly Ser Gly Gly Gly Gly Ser Gly Gly Gly Gly Ser Glu Val Gln
145 150 155 160

Leu Val Glu Ser Gly Gly Glu Leu Val Gln Pro Gly Gly Ser Leu Arg
165 170 175

Leu Ser Cys Ala Ala Ser Gly Ser Ile Leu Thr Ile Asn Ala Met Gly
180 185 190

Trp Tyr Arg Gln Ala Pro Gly Lys Gln Arg Glu Leu Val Val Arg Arg
195 200 205

Thr Arg Gly Gly Ser Thr Thr Tyr Gln Asp Ser Val Lys Gly Arg Phe
210 215 220

Thr Ile Ser Ala Asp Ile Ala Lys Lys Thr Met Tyr Leu Gln Met Asn
225 230 235 240

Ser Leu Lys Pro Glu Asp Thr Ala Val Tyr Tyr Cys Met Leu Asp Asp
245 250 255

Arg Gly Gly Val Tyr Trp Gly Gln Gly Thr Gln Val Thr Val Ser Ser
260 265 270

<210> SEQ ID NO 67
<211> LENGTH: 274
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 67

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Asp Tyr
20 25 30

```
Ala Met Gly Trp Phe Arg Gln Ala Pro Gly Lys Glu Arg Glu Phe Val
        35                  40                  45

Ala Ala Ile Thr Trp Asn Gly Gly Arg Val Phe Tyr Thr Ala Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asp Lys Asp Arg Arg Thr Asp Tyr Leu Gly His Pro Val Ala
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Glu Leu Val Gln Pro Gly Gly Ser
                165                 170                 175

Leu Arg Leu Ser Cys Ala Ala Ser Gly Ser Ile Leu Thr Ile Asn Ala
            180                 185                 190

Met Gly Trp Tyr Arg Gln Ala Pro Gly Lys Gln Arg Glu Leu Val Val
        195                 200                 205

Arg Arg Thr Arg Gly Gly Ser Thr Thr Tyr Gln Asp Ser Val Lys Gly
    210                 215                 220

Arg Phe Thr Ile Ser Ala Asp Ile Ala Lys Lys Thr Met Tyr Leu Gln
225                 230                 235                 240

Met Asn Ser Leu Lys Pro Glu Asp Thr Ala Val Tyr Tyr Cys Met Leu
                245                 250                 255

Asp Asp Arg Gly Gly Val Tyr Trp Gly Gln Gly Thr Gln Val Thr Val
            260                 265                 270

Ser Ser


<210> SEQ ID NO 68
<211> LENGTH: 277
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 68

Glu Val Gln Leu Val Glu Ser Gly Gly Gly Leu Val Gln Ala Gly Gly
1               5                   10                  15

Ser Leu Thr Leu Ser Cys Ala Val Ser Gly Ser Thr Phe Arg Ile Asn
            20                  25                  30

Thr Met Gly Trp Tyr Arg Arg Ala Pro Gly Lys Gln Arg Glu Leu Val
        35                  40                  45

Ala Ala Arg Asp Arg Gly Gly Tyr Ile Asn Tyr Val Asp Ser Val Lys
    50                  55                  60

Gly Arg Phe Thr Val Ser Arg Asp Asn Ala Lys Pro Thr Met Tyr Leu
65                  70                  75                  80

Gln Met Asn Ser Leu Lys Pro Glu Asp Thr Ala Val Tyr Tyr Cys His
                85                  90                  95

Ala Gly Thr Gln Asp Arg Thr Gly Arg Asn Phe Asp Arg Trp Gly Gln
            100                 105                 110

Gly Thr Gln Val Thr Val Ser Ser Gly Gly Gly Gly Ser Gly Gly Gly
```

```
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Val Ala Ser Gly Arg Ile Phe Ser Ser Asn Ala Met Gly Trp Phe
            180                 185                 190

Arg Gln Ala Pro Gly Lys Glu Arg Glu Phe Val Ala Ala Ile Thr Trp
        195                 200                 205

Arg Ser Gly Gly Ser Ala Tyr Tyr Ala Asp Ser Ala Lys Gly Arg Phe
    210                 215                 220

Thr Ile Ser Arg Asp Asn Ala Lys Asn Thr Val Tyr Leu Gln Met Asn
225                 230                 235                 240

Ser Leu Lys Pro Glu Asp Thr Ala Val Tyr Tyr Cys Ala Ala Gly Gly
                245                 250                 255

Ser Ser Trp Leu Ser Phe Pro Pro Asp Tyr Trp Gly Gln Gly Thr Gln
            260                 265                 270

Val Thr Val Ser Ser
        275


<210> SEQ ID NO 69
<211> LENGTH: 279
<212> TYPE: PRT
<213> ORGANISM: Artificial Sequence
<220> FEATURE:
<223> OTHER INFORMATION: Sequences of multivalent anti-CXCR2 Nanobodies

<400> SEQUENCE: 69

Glu Val Gln Leu Val Glu Ser Gly Gly Gly Leu Val Gln Ala Gly Gly
1               5                   10                  15

Ser Leu Thr Leu Ser Cys Ala Val Ser Gly Ser Thr Phe Arg Ile Asn
            20                  25                  30

Thr Met Gly Trp Tyr Arg Arg Ala Pro Gly Lys Gln Arg Glu Leu Val
        35                  40                  45

Ala Ala Arg Asp Arg Gly Gly Tyr Ile Asn Tyr Val Asp Ser Val Lys
    50                  55                  60

Gly Arg Phe Thr Val Ser Arg Asp Asn Ala Lys Pro Thr Met Tyr Leu
65                  70                  75                  80

Gln Met Asn Ser Leu Lys Pro Glu Asp Thr Ala Val Tyr Tyr Cys His
                85                  90                  95

Ala Gly Thr Gln Asp Arg Thr Gly Arg Asn Phe Asp Arg Trp Gly Gln
            100                 105                 110

Gly Thr Gln Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

Cys Ala Ala Ser Gly Arg Thr Phe Ser Asp Tyr Ala Met Gly Trp Phe
            180                 185                 190

Arg Gln Ala Pro Gly Lys Glu Arg Glu Phe Val Ala Ala Ile Thr Trp
```

-continued

```
        195                 200                 205

Asn Gly Gly Arg Val Phe Tyr Thr Ala Ser Val Lys Gly Arg Phe Thr
    210                 215                 220

Ile Ser Arg Asp Asn Ala Lys Asn Thr Met Tyr Leu Gln Met Asn Ser
225                 230                 235                 240

Leu Lys Pro Glu Asp Thr Ala Val Tyr Tyr Cys Ala Ala Asp Lys Asp
                245                 250                 255

Arg Arg Thr Asp Tyr Leu Gly His Pro Val Ala Tyr Trp Gly Gln Gly
            260                 265                 270

Thr Gln Val Thr Val Ser Ser
        275


<210> SEQ ID NO 70
<211> LENGTH: 30
<212> TYPE: PRT
<213> ORGANISM: Artificial Sequence
<220> FEATURE:
<223> OTHER INFORMATION: fr1

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30


<210> SEQ ID NO 71
<211> LENGTH: 30
<212> TYPE: PRT
<213> ORGANISM: Artificial Sequence
<220> FEATURE:
<223> OTHER INFORMATION: fr1

<400> SEQUENCE: 71

Glu Val Lys Leu Val Glu Ser Gly Gly Gly Leu Val Gln Ala Gly Gly
1               5                   10                  15

Ser Leu Arg Leu Ser Cys Ala Leu Ser Gly Arg Ile Gly Ser
            20                  25                  30


<210> SEQ ID NO 72
<211> LENGTH: 30
<212> TYPE: PRT
<213> ORGANISM: Artificial Sequence
<220> FEATURE:
<223> OTHER INFORMATION: FR1

<400> SEQUENCE: 72

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp
            20                  25                  30


<210> SEQ ID NO 73
<211> LENGTH: 30
<212> TYPE: PRT
<213> ORGANISM: Artificial Sequence
<220> FEATURE:
<223> OTHER INFORMATION: FR1

<400> SEQUENCE: 73

Glu Val Gln Leu Val Glu Ser Gly Gly Gly Leu Val Gln Ala Gly Gly
1               5                   10                  15

Ser Leu Ser Leu Ser Cys Ala Ala Ser Gly Leu Ile Phe Arg
```

20 25 30

<210> SEQ ID NO 74
<211> LENGTH: 30
<212> TYPE: PRT
<213> ORGANISM: Artificial Sequence
<220> FEATURE:
<223> OTHER INFORMATION: FR1

<400> SEQUENCE: 74

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser
20 25 30

<210> SEQ ID NO 75
<211> LENGTH: 30
<212> TYPE: PRT
<213> ORGANISM: Artificial Sequence
<220> FEATURE:
<223> OTHER INFORMATION: FR1

<400> SEQUENCE: 75

Glu Val Gln Leu Val Glu Ser Gly Gly Gly Leu Val Gln Ala Gly Gly
1 5 10 15

Ser Leu Arg Leu Ser Cys Ala Ala Ser Gly Arg Ser Phe Ser
20 25 30

<210> SEQ ID NO 76
<211> LENGTH: 30
<212> TYPE: PRT
<213> ORGANISM: Artificial Sequence
<220> FEATURE:
<223> OTHER INFORMATION: FR1

<400> SEQUENCE: 76

Glu Val Gln Leu Val Glu Ser Gly Gly Gly Leu Val Gln Pro Gly Gly
1 5 10 15

Ser Leu Arg Leu Ser Cys Ala Ala Ser Gly Ser Thr Leu Ala
20 25 30

<210> SEQ ID NO 77
<211> LENGTH: 30
<212> TYPE: PRT
<213> ORGANISM: Artificial Sequence
<220> FEATURE:
<223> OTHER INFORMATION: FR1

<400> SEQUENCE: 77

Lys Val Gln Leu Val Glu Ser Gly Gly Gly Leu Val Gln Ala Gly Gly
1 5 10 15

Ser Leu Arg Leu Ser Cys Ala Ala Ser Gly Arg Ala Phe Asn
20 25 30

<210> SEQ ID NO 78
<211> LENGTH: 30
<212> TYPE: PRT
<213> ORGANISM: Artificial Sequence
<220> FEATURE:
<223> OTHER INFORMATION: FR1

<400> SEQUENCE: 78

Glu Val Gln Leu Val Glu Ser Gly Gly Gly Leu Val Gln Pro Gly Gly
1 5 10 15

Ser Val Arg Leu Ser Cys Val Ala Ser Gly Ile Ile Phe Arg
20 25 30

<210> SEQ ID NO 79
<211> LENGTH: 30
<212> TYPE: PRT
<213> ORGANISM: Artificial Sequence
<220> FEATURE:
<223> OTHER INFORMATION: FR1

<400> SEQUENCE: 79

Glu Val Gln Leu Val Glu Ser Gly Gly Gly Leu Val Gln Ala Gly Glu
1 5 10 15

Ser Leu Arg Leu Ser Cys Ala Ala Ser Gly Ser Thr Phe Asp
20 25 30

<210> SEQ ID NO 80
<211> LENGTH: 30
<212> TYPE: PRT
<213> ORGANISM: Artificial Sequence
<220> FEATURE:
<223> OTHER INFORMATION: FR1

<400> SEQUENCE: 80

Glu Val Gln Leu Val Glu Ser Gly Gly Gly Leu Val Gln Ala Gly Gly
1 5 10 15

Ser Leu Thr Leu Ser Cys Ala Val Ser Gly Ser Ser Phe Arg
20 25 30

<210> SEQ ID NO 81
<211> LENGTH: 30
<212> TYPE: PRT
<213> ORGANISM: Artificial Sequence
<220> FEATURE:
<223> OTHER INFORMATION: FR1

<400> SEQUENCE: 81

Glu Val Gln Leu Val Glu Ser Gly Gly Gly Leu Val Gln Pro Gly Gly
1 5 10 15

Ser Leu Arg Leu Ser Cys Val Ala Ser Gly Ser Ile Val Arg
20 25 30

<210> SEQ ID NO 82
<211> LENGTH: 30
<212> TYPE: PRT
<213> ORGANISM: Artificial Sequence
<220> FEATURE:
<223> OTHER INFORMATION: FR1

<400> SEQUENCE: 82

Glu Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser
20 25 30

<210> SEQ ID NO 83
<211> LENGTH: 30
<212> TYPE: PRT
<213> ORGANISM: Artificial Sequence
<220> FEATURE:
<223> OTHER INFORMATION: FR1

<400> SEQUENCE: 83

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser
20 25 30

<210> SEQ ID NO 84
<211> LENGTH: 30
<212> TYPE: PRT
<213> ORGANISM: Artificial Sequence
<220> FEATURE:
<223> OTHER INFORMATION: FR1

<400> SEQUENCE: 84

Glu Val Gln Leu Val Glu Ser Gly Gly Gly Leu Val Gln Pro Gly Gly
1 5 10 15

Ser Leu Arg Leu Ser Cys Val Ala Ser Gly Arg Ile Phe Ser
20 25 30

<210> SEQ ID NO 85
<211> LENGTH: 30
<212> TYPE: PRT
<213> ORGANISM: Artificial Sequence
<220> FEATURE:
<223> OTHER INFORMATION: FR1

<400> SEQUENCE: 85

Glu Val Gln Leu Val Glu Ser Gly Gly Glu Leu Val Gln Pro Gly Gly
1 5 10 15

Ser Leu Arg Leu Ser Cys Ala Ala Ser Gly Ser Ile Leu Thr
20 25 30

<210> SEQ ID NO 86
<211> LENGTH: 30
<212> TYPE: PRT
<213> ORGANISM: Artificial Sequence
<220> FEATURE:
<223> OTHER INFORMATION: FR1

<400> SEQUENCE: 86

Glu Val Gln Leu Val Glu Ser Gly Gly Gly Leu Val Gln Ala Gly Gly
1 5 10 15

Ser Leu Arg Leu Thr Cys Ala Ala Ser Gly Arg Ile Gly Thr
20 25 30

<210> SEQ ID NO 87
<211> LENGTH: 30
<212> TYPE: PRT
<213> ORGANISM: Artificial Sequence
<220> FEATURE:
<223> OTHER INFORMATION: FR1

<400> SEQUENCE: 87

Glu Val Gln Leu Val Glu Ser Gly Gly Gly Leu Val Gln Ala Gly Gly
1 5 10 15

Ser Leu Arg Leu Ser Cys Ala Ala Ser Gly Arg Met Gly Asn
20 25 30

<210> SEQ ID NO 88
<211> LENGTH: 30
<212> TYPE: PRT
<213> ORGANISM: Artificial Sequence
<220> FEATURE:
<223> OTHER INFORMATION: FR1

<400> SEQUENCE: 88

Glu Val Gln Leu Val Glu Ser Gly Gly Gly Leu Val Gln Ala Gly Gly

```
1               5                   10                  15

Ser Leu Arg Leu Ser Cys Ala Ala Ser Gly Thr Ile Gly Thr
            20                  25                  30


<210> SEQ ID NO 89
<211> LENGTH: 30
<212> TYPE: PRT
<213> ORGANISM: Artificial Sequence
<220> FEATURE:
<223> OTHER INFORMATION: FR1

<400> SEQUENCE: 89

Glu Val Gln Leu Val Glu Ser Gly Gly Gly Leu Val Gln Ala Gly Gly
1               5                   10                  15

Ser Leu Thr Leu Ser Cys Ala Val Ser Gly Ser Thr Phe Arg
            20                  25                  30


<210> SEQ ID NO 90
<211> LENGTH: 120
<212> TYPE: PRT
<213> ORGANISM: Artificial Sequence
<220> FEATURE:
<223> OTHER INFORMATION: monovalent anti-CXCR2 Nanobodies

<400> SEQUENCE: 90

Glu Val Gln Leu Val Glu Ser Gly Gly Gly Leu Val Gln Ala Gly Gly
1               5                   10                  15

Ser Leu Thr Leu Ser Cys Ala Val Ser Gly Ser Thr Phe Arg Ile Asn
            20                  25                  30

Thr Met Gly Trp Tyr Arg Arg Ala Pro Gly Lys Gln Arg Glu Leu Val
        35                  40                  45

Ala Ala Arg Asp Arg Gly Gly Tyr Ile Asn Tyr Val Asp Ser Val Lys
    50                  55                  60

Gly Arg Phe Thr Val Ser Arg Asp Asn Ala Lys Pro Thr Met Tyr Leu
65                  70                  75                  80

Gln Met Asn Ser Leu Lys Pro Glu Asp Thr Ala Val Tyr Tyr Cys His
                85                  90                  95

Ala Gly Thr Gln Asp Arg Thr Gly Arg Asn Phe Asp Arg Trp Gly Gln
            100                 105                 110

Gly Thr Gln Val Thr Val Ser Ser
        115                 120


<210> SEQ ID NO 91
<211> LENGTH: 14
<212> TYPE: PRT
<213> ORGANISM: Artificial Sequence
<220> FEATURE:
<223> OTHER INFORMATION: FR2

<400> SEQUENCE: 91

Trp Val Arg Gln Ala Pro Gly Lys Gly Leu Asp Trp Val Ser
1               5                   10


<210> SEQ ID NO 92
<211> LENGTH: 14
<212> TYPE: PRT
<213> ORGANISM: Artificial Sequence
<220> FEATURE:
<223> OTHER INFORMATION: FR2

<400> SEQUENCE: 92

Trp Tyr Arg Gln Val Ser Gly Gln Gln Arg Glu Leu Val Ala
```

1 5 10

<210> SEQ ID NO 93
<211> LENGTH: 14
<212> TYPE: PRT
<213> ORGANISM: Artificial Sequence
<220> FEATURE:
<223> OTHER INFORMATION: FR2

<400> SEQUENCE: 93

Trp Phe Arg Gln Ala Pro Gly Lys Glu Arg Glu Arg Val Ser
1 5 10

<210> SEQ ID NO 94
<211> LENGTH: 14
<212> TYPE: PRT
<213> ORGANISM: Artificial Sequence
<220> FEATURE:
<223> OTHER INFORMATION: FR2

<400> SEQUENCE: 94

Trp Tyr Arg Gln Ala Pro Gly Arg Gln Arg Glu Trp Val Ala
1 5 10

<210> SEQ ID NO 95
<211> LENGTH: 14
<212> TYPE: PRT
<213> ORGANISM: Artificial Sequence
<220> FEATURE:
<223> OTHER INFORMATION: FR2

<400> SEQUENCE: 95

Trp Phe Arg Gln Ala Thr Gly Lys Glu Arg Glu Phe Val Ala
1 5 10

<210> SEQ ID NO 96
<211> LENGTH: 14
<212> TYPE: PRT
<213> ORGANISM: Artificial Sequence
<220> FEATURE:
<223> OTHER INFORMATION: FR2

<400> SEQUENCE: 96

Trp Leu Arg Gln Ala Pro Gly Lys Glu Arg Glu Phe Val Ala
1 5 10

<210> SEQ ID NO 97
<211> LENGTH: 14
<212> TYPE: PRT
<213> ORGANISM: Artificial Sequence
<220> FEATURE:
<223> OTHER INFORMATION: FR2

<400> SEQUENCE: 97

Trp Phe Arg Arg Ala Pro Gly Lys Glu Arg Glu Gly Ile Ser
1 5 10

<210> SEQ ID NO 98
<211> LENGTH: 14
<212> TYPE: PRT
<213> ORGANISM: Artificial Sequence
<220> FEATURE:
<223> OTHER INFORMATION: FR2

<400> SEQUENCE: 98

Trp Phe Arg Gln Ala Gln Gly Lys Glu Arg Glu Phe Val Ala
1 5 10

<210> SEQ ID NO 99
<211> LENGTH: 14
<212> TYPE: PRT
<213> ORGANISM: Artificial Sequence
<220> FEATURE:
<223> OTHER INFORMATION: FR2

<400> SEQUENCE: 99

Trp Thr Arg Gln Gly Pro Gly Lys Ala Arg Glu Trp Val Ala
1 5 10

<210> SEQ ID NO 100
<211> LENGTH: 14
<212> TYPE: PRT
<213> ORGANISM: Artificial Sequence
<220> FEATURE:
<223> OTHER INFORMATION: FR2

<400> SEQUENCE: 100

Trp Tyr Arg Gln Pro Pro Gly Lys Gln Arg Glu Gly Val Ala
1 5 10

<210> SEQ ID NO 101
<211> LENGTH: 14
<212> TYPE: PRT
<213> ORGANISM: Artificial Sequence
<220> FEATURE:
<223> OTHER INFORMATION: FR2

<400> SEQUENCE: 101

Trp Tyr Arg Arg Ala Pro Gly Lys Gln Arg Glu Leu Val Ala
1 5 10

<210> SEQ ID NO 102
<211> LENGTH: 14
<212> TYPE: PRT
<213> ORGANISM: Artificial Sequence
<220> FEATURE:
<223> OTHER INFORMATION: FR2

<400> SEQUENCE: 102

Trp Tyr Arg Gln Thr Pro Gly Lys Gln Arg Glu Leu Val Ala
1 5 10

<210> SEQ ID NO 103
<211> LENGTH: 14
<212> TYPE: PRT
<213> ORGANISM: Artificial Sequence
<220> FEATURE:
<223> OTHER INFORMATION: FR2

<400> SEQUENCE: 103

Trp Phe Arg Gln Ala Pro Gly Lys Glu Arg Ala Phe Val Ala
1 5 10

<210> SEQ ID NO 104
<211> LENGTH: 14
<212> TYPE: PRT
<213> ORGANISM: Artificial Sequence
<220> FEATURE:
<223> OTHER INFORMATION: FR2

<400> SEQUENCE: 104

Trp Phe Arg Gln Ala Pro Gly Lys Glu Arg Glu Phe Val Ala
1 5 10

<210> SEQ ID NO 105
<211> LENGTH: 14
<212> TYPE: PRT
<213> ORGANISM: Artificial Sequence
<220> FEATURE:
<223> OTHER INFORMATION: FR2

<400> SEQUENCE: 105

Trp Phe Arg Gln Ala Pro Gly Lys Glu Arg Glu Phe Val Ala
1 5 10

<210> SEQ ID NO 106
<211> LENGTH: 14
<212> TYPE: PRT
<213> ORGANISM: Artificial Sequence
<220> FEATURE:
<223> OTHER INFORMATION: FR2

<400> SEQUENCE: 106

Trp Tyr Arg Gln Ala Pro Gly Lys Gln Arg Glu Leu Val Val
1 5 10

<210> SEQ ID NO 107
<211> LENGTH: 14
<212> TYPE: PRT
<213> ORGANISM: Artificial Sequence
<220> FEATURE:
<223> OTHER INFORMATION: FR2

<400> SEQUENCE: 107

Trp Tyr Arg Gln Ala Pro Gly Lys Gln Arg Glu Leu Val Ala
1 5 10

<210> SEQ ID NO 108
<211> LENGTH: 14
<212> TYPE: PRT
<213> ORGANISM: Artificial Sequence
<220> FEATURE:
<223> OTHER INFORMATION: FR2

<400> SEQUENCE: 108

Trp Tyr Arg Gln Ala Pro Gly Lys Glu Arg Glu Leu Val Ala
1 5 10

<210> SEQ ID NO 109
<211> LENGTH: 14
<212> TYPE: PRT
<213> ORGANISM: Artificial Sequence
<220> FEATURE:
<223> OTHER INFORMATION: FR2

<400> SEQUENCE: 109

Trp Tyr Arg Gln Ala Pro Gly Lys Gln Arg Glu Leu Val Ala
1 5 10

<210> SEQ ID NO 110
<211> LENGTH: 14
<212> TYPE: PRT
<213> ORGANISM: Artificial Sequence
<220> FEATURE:
<223> OTHER INFORMATION: FR2

<400> SEQUENCE: 110

Trp Tyr Arg Arg Ala Pro Gly Lys Gln Arg Glu Leu Val Ala
1 5 10

<210> SEQ ID NO 111
<211> LENGTH: 32
<212> TYPE: PRT
<213> ORGANISM: Artificial Sequence
<220> FEATURE:
<223> OTHER INFORMATION: FR3

<400> SEQUENCE: 111

```
Arg Phe Thr Ile Ser Arg Asp Asn Asn Lys Asn Thr Leu Tyr Leu Gln
1               5                   10                  15

Met Asn Ser Leu Lys Pro Glu Asp Thr Ala Leu Tyr Tyr Cys Ala Thr
            20                  25                  30
```

<210> SEQ ID NO 112
<211> LENGTH: 32
<212> TYPE: PRT
<213> ORGANISM: Artificial Sequence
<220> FEATURE:
<223> OTHER INFORMATION: FR3

<400> SEQUENCE: 112

```
Arg Phe Thr Ile Ser Arg Asp Asn Gly Lys Asn Thr Val Tyr Leu Gln
1               5                   10                  15

Met Asp Ser Leu Lys Pro Glu Asp Thr Ala Val Tyr Tyr Cys Tyr Ala
            20                  25                  30
```

<210> SEQ ID NO 113
<211> LENGTH: 32
<212> TYPE: PRT
<213> ORGANISM: Artificial Sequence
<220> FEATURE:
<223> OTHER INFORMATION: FR3

<400> SEQUENCE: 113

```
Arg Phe Thr Ile Ser Ser Asp Asn Ala Lys Asn Thr Val Tyr Leu Gln
1               5                   10                  15

Met Asn Asn Leu Lys Pro Glu Asp Thr Ala Val Tyr Tyr Cys Ala Ala
            20                  25                  30
```

<210> SEQ ID NO 114
<211> LENGTH: 32
<212> TYPE: PRT
<213> ORGANISM: Artificial Sequence
<220> FEATURE:
<223> OTHER INFORMATION: FR3

<400> SEQUENCE: 114

```
Arg Phe Thr Ile Ser Arg Asn Asn Ala Glu Asn Thr Trp Tyr Leu Gln
1               5                   10                  15

Met Asn Ser Leu Lys Pro Glu Asp Thr Ala Ile Tyr Tyr Cys Asn Thr
            20                  25                  30
```

<210> SEQ ID NO 115
<211> LENGTH: 32
<212> TYPE: PRT
<213> ORGANISM: Artificial Sequence
<220> FEATURE:
<223> OTHER INFORMATION: FR3

<400> SEQUENCE: 115

```
Arg Phe Thr Ile Ser Arg Asp Asn Ala Lys Asn Thr Val Tyr Leu Gln
1               5                   10                  15

Met Asn Ser Leu Lys Pro Arg Asp Thr Ala Val Tyr Tyr Cys Ala Ala
            20                  25                  30
```

<210> SEQ ID NO 116
<211> LENGTH: 32
<212> TYPE: PRT
<213> ORGANISM: Artificial Sequence
<220> FEATURE:
<223> OTHER INFORMATION: FR3

<400> SEQUENCE: 116

Arg Phe Thr Ile Ser Arg Asp Asn Ala Lys Asn Thr Val Ser Leu Gln
1 5 10 15

Met Asn Ser Leu Lys Pro Gln Asp Thr Ala Val Tyr Tyr Cys Ala Ala
20 25 30

<210> SEQ ID NO 117
<211> LENGTH: 32
<212> TYPE: PRT
<213> ORGANISM: Artificial Sequence
<220> FEATURE:
<223> OTHER INFORMATION: FR3

<400> SEQUENCE: 117

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 118
<211> LENGTH: 32
<212> TYPE: PRT
<213> ORGANISM: Artificial Sequence
<220> FEATURE:
<223> OTHER INFORMATION: FR3

<400> SEQUENCE: 118

Arg Phe Thr Ile Ser Arg Asp Asn Ala Lys Asn Thr Val Tyr Leu His
1 5 10 15

Met Asn Ser Leu Lys Pro Glu Asp Thr Ala Val Tyr Tyr Cys Ala Ala
20 25 30

<210> SEQ ID NO 119
<211> LENGTH: 32
<212> TYPE: PRT
<213> ORGANISM: Artificial Sequence
<220> FEATURE:
<223> OTHER INFORMATION: FR3

<400> SEQUENCE: 119

Arg Phe Thr Ile Ser Arg Asp Asn Ala Lys Asn Thr Ile Tyr Leu His
1 5 10 15

Met Asp Met Leu Lys Pro Glu Asp Thr Ala Val Tyr Tyr Cys Ala Ser
20 25 30

<210> SEQ ID NO 120
<211> LENGTH: 32
<212> TYPE: PRT
<213> ORGANISM: Artificial Sequence
<220> FEATURE:
<223> OTHER INFORMATION: FR3

<400> SEQUENCE: 120

Arg Phe Thr Ile Ser Lys Ala Asn Ala Lys Asn Thr Val Tyr Leu Gln
1 5 10 15

Met Asn Ser Leu Arg Pro Glu Asp Thr Ala Val Tyr Tyr Cys Lys Val
20 25 30

<210> SEQ ID NO 121
<211> LENGTH: 32
<212> TYPE: PRT
<213> ORGANISM: Artificial Sequence
<220> FEATURE:
<223> OTHER INFORMATION: FR3

<400> SEQUENCE: 121

Arg Phe Thr Val Ser Arg Asp Asn Ala Lys Pro Thr Met Tyr Leu Gln
1 5 10 15

Met Asn Ser Leu Lys Pro Glu Asp Thr Ala Val Tyr Tyr Cys His Ala
20 25 30

<210> SEQ ID NO 122
<211> LENGTH: 32
<212> TYPE: PRT
<213> ORGANISM: Artificial Sequence
<220> FEATURE:
<223> OTHER INFORMATION: FR3

<400> SEQUENCE: 122

Arg Phe Thr Ile Ser Arg Asp Asn Thr Lys Asn Thr Val Tyr Leu Gln
1 5 10 15

Met Asn Ser Leu Lys Pro Glu Asp Thr Ala Val Tyr Tyr Cys Asn Ala
20 25 30

<210> SEQ ID NO 123
<211> LENGTH: 32
<212> TYPE: PRT
<213> ORGANISM: Artificial Sequence
<220> FEATURE:
<223> OTHER INFORMATION: FR3

<400> SEQUENCE: 123

Arg Phe Thr Ile Ser Arg Asp Val Ala Lys Lys Thr Leu Tyr Leu Gln
1 5 10 15

Met Asn Ser Leu Lys Pro Glu Asp Thr Ala Val Tyr Tyr Cys Ala Ala
20 25 30

<210> SEQ ID NO 124
<211> LENGTH: 32
<212> TYPE: PRT
<213> ORGANISM: Artificial Sequence
<220> FEATURE:
<223> OTHER INFORMATION: FR3

<400> SEQUENCE: 124

Arg Phe Thr Ile Ser Arg Asp Asn Ala Lys Asn Thr Met Tyr Leu Gln
1 5 10 15

Met Asn Ser Leu Lys Pro Glu Asp Thr Ala Val Tyr Tyr Cys Ala Ala
20 25 30

<210> SEQ ID NO 125
<211> LENGTH: 32
<212> TYPE: PRT
<213> ORGANISM: Artificial Sequence
<220> FEATURE:
<223> OTHER INFORMATION: FR3

<400> SEQUENCE: 125

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Cys Ala Ala 20 25 30

<210> SEQ ID NO 126
<211> LENGTH: 32
<212> TYPE: PRT
<213> ORGANISM: Artificial Sequence
<220> FEATURE:
<223> OTHER INFORMATION: FR3

<400> SEQUENCE: 126

Arg Phe Thr Ile Ser Ala Asp Ile Ala Lys Lys Thr Met Tyr Leu Gln
1 5 10 15

Met Asn Ser Leu Lys Pro Glu Asp Thr Ala Val Tyr Tyr Cys Met Leu
20 25 30

<210> SEQ ID NO 127
<211> LENGTH: 32
<212> TYPE: PRT
<213> ORGANISM: Artificial Sequence
<220> FEATURE:
<223> OTHER INFORMATION: FR3

<400> SEQUENCE: 127

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Tyr Asn Val
20 25 30

<210> SEQ ID NO 128
<211> LENGTH: 32
<212> TYPE: PRT
<213> ORGANISM: Artificial Sequence
<220> FEATURE:
<223> OTHER INFORMATION: FR3

<400> SEQUENCE: 128

Arg Phe Thr Ile Ala Arg Asp Asn Ile Leu Asn Thr Ala Tyr Leu Gln
1 5 10 15

Met Asn Asp Leu Lys Pro Glu Asp Thr Ala Val Tyr Tyr Tyr Asn Val
20 25 30

<210> SEQ ID NO 129
<211> LENGTH: 32
<212> TYPE: PRT
<213> ORGANISM: Artificial Sequence
<220> FEATURE:
<223> OTHER INFORMATION: FR3

<400> SEQUENCE: 129

Arg Phe Thr Ile Gly Arg Asp Asn Ala Lys Asn Thr Ala Tyr Leu Gln
1 5 10 15

Met Asn Asn Leu Lys Pro Glu Asp Thr Ala Val Tyr Tyr Tyr Asn Ile
20 25 30

<210> SEQ ID NO 130
<211> LENGTH: 32
<212> TYPE: PRT
<213> ORGANISM: Artificial Sequence
<220> FEATURE:
<223> OTHER INFORMATION: FR3

<400> SEQUENCE: 130

Arg Phe Thr Val Ser Arg Asp Asn Ala Lys Pro Thr Met Tyr Leu Gln
1 5 10 15

Met Asn Ser Leu Lys Pro Glu Asp Thr Ala Val Tyr Tyr Cys His Ala
20 25 30

<210> SEQ ID NO 131
<211> LENGTH: 11
<212> TYPE: PRT
<213> ORGANISM: Artificial Sequence
<220> FEATURE:
<223> OTHER INFORMATION: FR4

<400> SEQUENCE: 131

Trp Gly Gln Gly Thr Gln Val Thr Val Ser Ser
1 5 10

<210> SEQ ID NO 132
<211> LENGTH: 11
<212> TYPE: PRT
<213> ORGANISM: Artificial Sequence
<220> FEATURE:
<223> OTHER INFORMATION: FR4

<400> SEQUENCE: 132

Arg Gly Gln Gly Thr Gln Val Thr Val Ser Ser
1 5 10

<210> SEQ ID NO 133
<211> LENGTH: 11
<212> TYPE: PRT
<213> ORGANISM: Artificial Sequence
<220> FEATURE:
<223> OTHER INFORMATION: FR4

<400> SEQUENCE: 133

Trp Gly Gln Gly Thr Gln Val Thr Val Ser Ser
1 5 10

<210> SEQ ID NO 134
<211> LENGTH: 5
<212> TYPE: PRT
<213> ORGANISM: Artificial Sequence
<220> FEATURE:
<223> OTHER INFORMATION: CDR1

<400> SEQUENCE: 134

Asp Tyr Ala Ile Gly
1 5

<210> SEQ ID NO 135
<211> LENGTH: 5
<212> TYPE: PRT
<213> ORGANISM: Artificial Sequence
<220> FEATURE:
<223> OTHER INFORMATION: CDR1

<400> SEQUENCE: 135

Leu Ser Gly Met Ala
1 5

<210> SEQ ID NO 136
<211> LENGTH: 5
<212> TYPE: PRT
<213> ORGANISM: Artificial Sequence
<220> FEATURE:
<223> OTHER INFORMATION: CDR1

<400> SEQUENCE: 136

Asn Tyr Ala Met Gly 1 5

<210> SEQ ID NO 137
<211> LENGTH: 5
<212> TYPE: PRT
<213> ORGANISM: Artificial Sequence
<220> FEATURE:
<223> OTHER INFORMATION: CDR1

<400> SEQUENCE: 137

Arg Ser Ala Met Gly
1 5

<210> SEQ ID NO 138
<211> LENGTH: 5
<212> TYPE: PRT
<213> ORGANISM: Artificial Sequence
<220> FEATURE:
<223> OTHER INFORMATION: CDR1

<400> SEQUENCE: 138

Tyr Tyr Thr Val Gly
1 5

<210> SEQ ID NO 139
<211> LENGTH: 5
<212> TYPE: PRT
<213> ORGANISM: Artificial Sequence
<220> FEATURE:
<223> OTHER INFORMATION: CDR1

<400> SEQUENCE: 139

Tyr Tyr Val Met Ala
1 5

<210> SEQ ID NO 140
<211> LENGTH: 5
<212> TYPE: PRT
<213> ORGANISM: Artificial Sequence
<220> FEATURE:
<223> OTHER INFORMATION: CDR1

<400> SEQUENCE: 140

Leu Ser Ala Leu Gly
1 5

<210> SEQ ID NO 141
<211> LENGTH: 5
<212> TYPE: PRT
<213> ORGANISM: Artificial Sequence
<220> FEATURE:
<223> OTHER INFORMATION: CDR1

<400> SEQUENCE: 141

Phe Lys Val Met Gly
1 5

<210> SEQ ID NO 142
<211> LENGTH: 5
<212> TYPE: PRT
<213> ORGANISM: Artificial Sequence
<220> FEATURE:
<223> OTHER INFORMATION: CDR1

<400> SEQUENCE: 142

Ile Asn Thr Met Gly
1 5

<210> SEQ ID NO 143
<211> LENGTH: 5
<212> TYPE: PRT
<213> ORGANISM: Artificial Sequence
<220> FEATURE:
<223> OTHER INFORMATION: CDR1

<400> SEQUENCE: 143

Ile Asn Thr Met Gly
1 5

<210> SEQ ID NO 144
<211> LENGTH: 5
<212> TYPE: PRT
<213> ORGANISM: Artificial Sequence
<220> FEATURE:
<223> OTHER INFORMATION: CDR1

<400> SEQUENCE: 144

Ser Leu Ser Met Gly
1 5

<210> SEQ ID NO 145
<211> LENGTH: 5
<212> TYPE: PRT
<213> ORGANISM: Artificial Sequence
<220> FEATURE:
<223> OTHER INFORMATION: CDR1

<400> SEQUENCE: 145

Asp Tyr Ala Met Gly
1 5

<210> SEQ ID NO 146
<211> LENGTH: 5
<212> TYPE: PRT
<213> ORGANISM: Artificial Sequence
<220> FEATURE:
<223> OTHER INFORMATION: CDR1

<400> SEQUENCE: 146

Ser Asn Ala Met Gly
1 5

<210> SEQ ID NO 147
<211> LENGTH: 5
<212> TYPE: PRT
<213> ORGANISM: Artificial Sequence
<220> FEATURE:
<223> OTHER INFORMATION: CDR1

<400> SEQUENCE: 147

Ile Asn Ala Met Gly
1 5

<210> SEQ ID NO 148
<211> LENGTH: 5
<212> TYPE: PRT
<213> ORGANISM: Artificial Sequence
<220> FEATURE:
<223> OTHER INFORMATION: CDR1

<400> SEQUENCE: 148

Ile Asn Ala Met Gly
1 5

<210> SEQ ID NO 149
<211> LENGTH: 5
<212> TYPE: PRT
<213> ORGANISM: Artificial Sequence
<220> FEATURE:
<223> OTHER INFORMATION: CDR1

<400> SEQUENCE: 149

Ile Asn Ala Met Gly
1 5

<210> SEQ ID NO 150
<211> LENGTH: 5
<212> TYPE: PRT
<213> ORGANISM: Artificial Sequence
<220> FEATURE:
<223> OTHER INFORMATION: CDR1

<400> SEQUENCE: 150

Ile Arg Ala Met Gly
1 5

<210> SEQ ID NO 151
<211> LENGTH: 5
<212> TYPE: PRT
<213> ORGANISM: Artificial Sequence
<220> FEATURE:
<223> OTHER INFORMATION: CDR1

<400> SEQUENCE: 151

Ile Asn Thr Met Gly
1 5

<210> SEQ ID NO 152
<211> LENGTH: 17
<212> TYPE: PRT
<213> ORGANISM: Artificial Sequence
<220> FEATURE:
<223> OTHER INFORMATION: CDR2

<400> SEQUENCE: 152

Ala Ile Asn Ala Gly Gly Asp Ser Thr Tyr Tyr Ala Asp Pro Val Lys
1 5 10 15

Gly

<210> SEQ ID NO 153
<211> LENGTH: 16
<212> TYPE: PRT
<213> ORGANISM: Artificial Sequence
<220> FEATURE:
<223> OTHER INFORMATION: CDR2

<400> SEQUENCE: 153

Val Ser Arg Ser Gly Gly Ser Thr Asp Ile Ala Asp Ser Val Lys Gly
1 5 10 15

<210> SEQ ID NO 154
<211> LENGTH: 17
<212> TYPE: PRT
<213> ORGANISM: Artificial Sequence
<220> FEATURE:
<223> OTHER INFORMATION: CDR2

<400> SEQUENCE: 154

Cys Ile Ser Gly Ser Asp Gly Ser Thr Tyr Tyr Ala Asp Ser Val Lys
1 5 10 15

Gly

<210> SEQ ID NO 155
<211> LENGTH: 16
<212> TYPE: PRT
<213> ORGANISM: Artificial Sequence
<220> FEATURE:
<223> OTHER INFORMATION: CDR2

<400> SEQUENCE: 155

Val Leu Thr Lys Asp Gly Thr Leu His Tyr Ala Asp Pro Val Lys Gly
1 5 10 15

<210> SEQ ID NO 156
<211> LENGTH: 17
<212> TYPE: PRT
<213> ORGANISM: Artificial Sequence
<220> FEATURE:
<223> OTHER INFORMATION: CDR2

<400> SEQUENCE: 156

Ala Ile Asn Lys Ser Gly Gly Asn Thr His Tyr Ala Gly Ser Val Lys
1 5 10 15

Gly

<210> SEQ ID NO 157
<211> LENGTH: 17
<212> TYPE: PRT
<213> ORGANISM: Artificial Sequence
<220> FEATURE:
<223> OTHER INFORMATION: CDR2

<400> SEQUENCE: 157

Gly Ile Ser Trp Gly Gly Asp Asn Ser Tyr Tyr Ala Asp Ser Val Lys
1 5 10 15

Gly

<210> SEQ ID NO 158
<211> LENGTH: 17
<212> TYPE: PRT
<213> ORGANISM: Artificial Sequence
<220> FEATURE:
<223> OTHER INFORMATION: CDR2

<400> SEQUENCE: 158

Cys Ile Ser Ser Ser Asp Gly Ser Thr Tyr Tyr Ala Asp Ser Val Lys
1 5 10 15

Gly

<210> SEQ ID NO 159
<211> LENGTH: 17
<212> TYPE: PRT
<213> ORGANISM: Artificial Sequence
<220> FEATURE:
<223> OTHER INFORMATION: CDR2

<400> SEQUENCE: 159

Ala Ile Ser Thr Arg Gly Ser Met Thr Lys Tyr Ser Asp Ser Val Gln
1 5 10 15

Gly

<210> SEQ ID NO 160
<211> LENGTH: 16

<212> TYPE: PRT
<213> ORGANISM: Artificial Sequence
<220> FEATURE:
<223> OTHER INFORMATION: CDR2

<400> SEQUENCE: 160

Gly Ile Asn Ser Asp Gly Thr Thr Asn Tyr Ala Asp Pro Val Lys Gly
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: CDR2

<400> SEQUENCE: 161

Ala Ile Arg Leu Ser Gly Asn Met His Tyr Ala Glu Ser Val Lys Gly
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: CDR2

<400> SEQUENCE: 162

Ala Arg Asp Arg Gly Gly Tyr Ile Asn Tyr Val Asp Ser Val Lys Gly
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: CDR2

<400> SEQUENCE: 163

Asp Ile Thr Ser Gly Gly Asn Ile Asn Tyr Ile Asp Ala Val Lys Gly
1               5                   10                  15

<210> SEQ ID NO 164
<211> LENGTH: 17
<212> TYPE: PRT
<213> ORGANISM: Artificial Sequence
<220> FEATURE:
<223> OTHER INFORMATION: CDR2

<400> SEQUENCE: 164

Ala Leu Thr Arg Asn Gly Gly Tyr Arg Tyr Tyr Ala Asp Ser Val Lys
1               5                   10                  15

Gly

<210> SEQ ID NO 165
<211> LENGTH: 17
<212> TYPE: PRT
<213> ORGANISM: Artificial Sequence
<220> FEATURE:
<223> OTHER INFORMATION: CDR2

<400> SEQUENCE: 165

Ala Ile Thr Trp Asn Gly Gly Arg Val Phe Tyr Thr Ala Ser Val Lys
1               5                   10                  15

Gly

<210> SEQ ID NO 166
<211> LENGTH: 18
<212> TYPE: PRT
<213> ORGANISM: Artificial Sequence
<220> FEATURE:
<223> OTHER INFORMATION: CDR2

<400> SEQUENCE: 166

Ala Ile Thr Trp Arg Ser Gly Gly Ser Ala Tyr Tyr Ala Asp Ser Ala
1 5 10 15

Lys Gly

<210> SEQ ID NO 167
<211> LENGTH: 16
<212> TYPE: PRT
<213> ORGANISM: Artificial Sequence
<220> FEATURE:
<223> OTHER INFORMATION: CDR2

<400> SEQUENCE: 167

Arg Arg Thr Arg Gly Gly Ser Thr Thr Tyr Gln Asp Ser Val Lys Gly
1 5 10 15

<210> SEQ ID NO 168
<211> LENGTH: 16
<212> TYPE: PRT
<213> ORGANISM: Artificial Sequence
<220> FEATURE:
<223> OTHER INFORMATION: CDR2

<400> SEQUENCE: 168

Val Ile Thr Ser Gly Gly Arg Ile Asp Tyr Ala Asp Ser Val Lys Gly
1 5 10 15

<210> SEQ ID NO 169
<211> LENGTH: 16
<212> TYPE: PRT
<213> ORGANISM: Artificial Sequence
<220> FEATURE:
<223> OTHER INFORMATION: CDR2

<400> SEQUENCE: 169

Lys Ile Thr Arg Gly Gly Ala Ile Thr Tyr Ala Asp Ser Val Lys Gly
1 5 10 15

<210> SEQ ID NO 170
<211> LENGTH: 16
<212> TYPE: PRT
<213> ORGANISM: Artificial Sequence
<220> FEATURE:
<223> OTHER INFORMATION: CDR2

<400> SEQUENCE: 170

Leu Ile Thr Ser Thr Gly Arg Ile Asn Tyr Ala Asp Ser Val Lys Gly
1 5 10 15

<210> SEQ ID NO 171
<211> LENGTH: 16
<212> TYPE: PRT
<213> ORGANISM: Artificial Sequence
<220> FEATURE:
<223> OTHER INFORMATION: CDR2

<400> SEQUENCE: 171

Ala Arg Asp Arg Gly Gly Tyr Ile Asn Tyr Val Asp Ser Val Lys Gly
1 5 10 15

<210> SEQ ID NO 172
<211> LENGTH: 10
<212> TYPE: PRT
<213> ORGANISM: Artificial Sequence
<220> FEATURE:
<223> OTHER INFORMATION: CDR3

<400> SEQUENCE: 172

Val Arg Gly Thr Ala Arg Asp Leu Asp Tyr
1 5 10

<210> SEQ ID NO 173
<211> LENGTH: 15
<212> TYPE: PRT
<213> ORGANISM: Artificial Sequence
<220> FEATURE:
<223> OTHER INFORMATION: CDR3

<400> SEQUENCE: 173

His Thr Ser Ser Tyr Ser Asn Trp Arg Val Tyr Asn Asn Asp Tyr
1 5 10 15

<210> SEQ ID NO 174
<211> LENGTH: 17
<212> TYPE: PRT
<213> ORGANISM: Artificial Sequence
<220> FEATURE:
<223> OTHER INFORMATION: CDR3

<400> SEQUENCE: 174

Tyr Trp Gly Leu Thr Leu Arg Leu Trp Met Pro Pro His Arg Tyr Asp
1 5 10 15

Tyr

<210> SEQ ID NO 175
<211> LENGTH: 3
<212> TYPE: PRT
<213> ORGANISM: Artificial Sequence
<220> FEATURE:
<223> OTHER INFORMATION: CDR3

<400> SEQUENCE: 175

Gly Arg Tyr
1

<210> SEQ ID NO 176
<211> LENGTH: 9
<212> TYPE: PRT
<213> ORGANISM: Artificial Sequence
<220> FEATURE:
<223> OTHER INFORMATION: CDR3

<400> SEQUENCE: 176

Ser Arg Thr Asn Pro Lys Pro Asp Tyr
1 5

<210> SEQ ID NO 177
<211> LENGTH: 13
<212> TYPE: PRT
<213> ORGANISM: Artificial Sequence
<220> FEATURE:
<223> OTHER INFORMATION: CDR3

<400> SEQUENCE: 177

Arg Tyr Arg Gly Gly Ala Ala Val Ala Gly Trp Glu Tyr 1 5 10

<210> SEQ ID NO 178
<211> LENGTH: 15
<212> TYPE: PRT
<213> ORGANISM: Artificial Sequence
<220> FEATURE:
<223> OTHER INFORMATION: CDR3

<400> SEQUENCE: 178

Asp Arg Arg Thr Asp Cys Lys Lys Gly Arg Val Gly Ser Gly Ser
1 5 10 15

<210> SEQ ID NO 179
<211> LENGTH: 16
<212> TYPE: PRT
<213> ORGANISM: Artificial Sequence
<220> FEATURE:
<223> OTHER INFORMATION: CDR3

<400> SEQUENCE: 179

Asp Pro Arg Gly Ser Ser Trp Ser Phe Ser Ser Gly Gly Tyr Asp Tyr
1 5 10 15

<210> SEQ ID NO 180
<211> LENGTH: 3
<212> TYPE: PRT
<213> ORGANISM: Artificial Sequence
<220> FEATURE:
<223> OTHER INFORMATION: CDR3

<400> SEQUENCE: 180

Gly Lys Tyr
1

<210> SEQ ID NO 181
<211> LENGTH: 7
<212> TYPE: PRT
<213> ORGANISM: Artificial Sequence
<220> FEATURE:
<223> OTHER INFORMATION: CDR3

<400> SEQUENCE: 181

Asn Ile Arg Gly Gln Asp Tyr
1 5

<210> SEQ ID NO 182
<211> LENGTH: 12
<212> TYPE: PRT
<213> ORGANISM: Artificial Sequence
<220> FEATURE:
<223> OTHER INFORMATION: CDR3

<400> SEQUENCE: 182

Gly Thr Gln Asp Arg Thr Gly Arg Asn Phe Asp His
1 5 10

<210> SEQ ID NO 183
<211> LENGTH: 18
<212> TYPE: PRT
<213> ORGANISM: Artificial Sequence
<220> FEATURE:
<223> OTHER INFORMATION: CDR3

<400> SEQUENCE: 183

Glu Ile Val Val Leu Val Gly Val Trp Thr Gln Arg Ala Arg Thr Gly
1 5 10 15

Asn Tyr

<210> SEQ ID NO 184
<211> LENGTH: 15
<212> TYPE: PRT
<213> ORGANISM: Artificial Sequence
<220> FEATURE:
<223> OTHER INFORMATION: CDR3

<400> SEQUENCE: 184

Asp Ser Leu Ser Gly Ser Asp Tyr Leu Gly Thr Asn Leu Asp Tyr
1 5 10 15

<210> SEQ ID NO 185
<211> LENGTH: 15
<212> TYPE: PRT
<213> ORGANISM: Artificial Sequence
<220> FEATURE:
<223> OTHER INFORMATION: CDR3

<400> SEQUENCE: 185

Asp Lys Asp Arg Arg Thr Asp Tyr Leu Gly His Pro Val Ala Tyr
1 5 10 15

<210> SEQ ID NO 186
<211> LENGTH: 12
<212> TYPE: PRT
<213> ORGANISM: Artificial Sequence
<220> FEATURE:
<223> OTHER INFORMATION: CDR3

<400> SEQUENCE: 186

Gly Gly Ser Ser Trp Leu Ser Phe Pro Pro Asp Tyr
1 5 10

<210> SEQ ID NO 187
<211> LENGTH: 7
<212> TYPE: PRT
<213> ORGANISM: Artificial Sequence
<220> FEATURE:
<223> OTHER INFORMATION: CDR3

<400> SEQUENCE: 187

Asp Asp Arg Gly Gly Val Tyr
1 5

<210> SEQ ID NO 188
<211> LENGTH: 8
<212> TYPE: PRT
<213> ORGANISM: Artificial Sequence
<220> FEATURE:
<223> OTHER INFORMATION: CDR3

<400> SEQUENCE: 188

Glu Thr Val Val Gly Ala Val Tyr
1 5

<210> SEQ ID NO 189
<211> LENGTH: 8
<212> TYPE: PRT
<213> ORGANISM: Artificial Sequence
<220> FEATURE:
<223> OTHER INFORMATION: CDR3

<400> SEQUENCE: 189

Asp Gly Gly Pro Ser Gln Asn Tyr 1 5

<210> SEQ ID NO 190
<211> LENGTH: 7
<212> TYPE: PRT
<213> ORGANISM: Artificial Sequence
<220> FEATURE:
<223> OTHER INFORMATION: CDR3

<400> SEQUENCE: 190

Glu Thr Leu Arg Arg Asn Tyr
1 5

<210> SEQ ID NO 191
<211> LENGTH: 12
<212> TYPE: PRT
<213> ORGANISM: Artificial Sequence
<220> FEATURE:
<223> OTHER INFORMATION: CDR3

<400> SEQUENCE: 191

Gly Thr Gln Asp Arg Thr Gly Arg Asn Phe Asp Arg
1 5 10

<210> SEQ ID NO 192
<211> LENGTH: 357
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 192
gaggtgcagc tggtggagtc tgggggaggc ttggtgcagc ctggggggtc tctgagactc 60
tcctgtgcag cctctggatt caccttcagt acctactgga tgtattgggt ccgtcaggct 120
ccagggaagg ggctcgactg ggtctcagct attaatgctg gtggtgatag cacatactat 180
gcagaccccg tgaagggccg attcaccatc tccagagaca acaacaagaa cacgctgtat 240
ctgcagatga acagcctgaa acctgaggac acggccctgt attactgtgc gaccgtacga 300
ggcacagctc gtgacttgga ctactggggc caggggaccc aggtcaccgt ctcctca 357

<210> SEQ ID NO 193
<211> LENGTH: 369
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 193
gaggtgaagc tggtggagtc tgggggaggc ttggtgcagg ctggggggtc tctgagactc 60
tcctgtgcac tctctggaag gatcggcagt atcaacgcca tgggctggta tcgccaggtt 120
tcaggacaac agcgcgagtt ggtcgcagta agcaggagcg gaggtagcac agacattgct 180
gactccgtga agggccgatt caccatctcc agagacaacg gcaagaacac agtgtatctg 240
cagatggaca gcctgaaacc tgaggacacg gccgtctatt actgttatgc tcatacttca 300
agctatagta attggcgagt ctacaataac gactactggg gccaggggac ccaggtcacc 360
gtctcctca 369

<210> SEQ ID NO 194
<211> LENGTH: 348
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 194

```
gaggtgcagc tggtggagtc tgggggaggc ttggtgcagg ctggggggtc tctgagactt      60
acctgtgcag cctctggacg catcggcact atcaatgcca tgggctggta ccgccaggct     120
ccagggaagc agcgcgagtt ggtcgcagtt attactagtg gtggtaggat agactatgca     180
gactccgtga agggccgatt caccatctcc agagacaatg ccaagaacac ggtgtatctg     240
caaatgaaca gcctgaaacc tgaggacacg gccgtctatt actataatgt agaaacggta     300
gtgggtgccg tctactgggg ccaggggacc caggtcaccg tctcctca                  348
```

<210> SEQ ID NO 195
<211> LENGTH: 348
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 195

```
gaggtgcagc tggtggagtc tgggggaggc ttggtgcagg ctggggggtc tctgagactc      60
tcctgtgcag cctctggaag gatgggcaat atcaatgcca tgggctggta tcgccaggct     120
ccagggaagg agcgcgagtt ggtcgcaaaa attactaggg gtggtgcgat aacctatgca     180
gactccgtga agggccgatt caccatcgcc agagacaata ttctgaacac ggcgtatctg     240
caaatgaacg acctgaaacc tgaggacacg gccgtctatt attataatgt agatggggggg    300
cccagtcaaa actactgggg ccaggggacc caggtcaccg tctcctca                  348
```

<210> SEQ ID NO 196
<211> LENGTH: 378
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 196

```
gaggtgcagc tggtggagtc tgggggaggc ttggtgcagg ctggggggtc tctgagactc      60
tcctgtgcag cctctggatt cactttcgat gattatgcca taggctggtt ccgccaggcc     120
ccagggaagg agcgtgagag ggtctcatgt attagtggta gtgatggtag cacatactat     180
gcagactccg tcaagggccg attcaccatc tccagtgaca cgccaagaa cacggtgtat      240
ctgcaaatga acaacctgaa acccgaggac acggccgttt attattgtgc agcatattgg     300
ggactaacgc tcaggctatg gatgcccccc caccggtatg actactgggg ccaggggacc     360
caggtcaccg tctcctca                                                    378
```

<210> SEQ ID NO 197
<211> LENGTH: 333
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 197

```
gaggtgcagc tggtggagtc tgggggaggc ttggtgcagg ctggggggtc tctgagcctc      60
tcctgtgcag cctctggact tatcttcaga ctcagtggca tggcctggta tcgccaggct     120
ccggggaggc agcgcgagtg ggtcgcagtg cttaccaaag atggtaccct acactatgca     180
```

gaccccgtga agggccgatt caccatctcc agaaacaacg ccgagaacac gtggtatctg 240
caaatgaaca gcctgaaacc tgaggacaca gccatctatt actgtaatac gggccgttac 300
tggggccagg ggacccaggt caccgtctcc tca 333

<210> SEQ ID NO 198
<211> LENGTH: 345
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 198
gaggtgcagc tggtggagtc tgggggaggc ttggtgcagg ctgggggtc actgagactc 60 tcctgtgcag cctctggaac catcggcacg atcagagcca tgggctggta ccgccaggct 120
ccagggaagc agcgcgagtt ggtcgcattg attactagta ctggtaggat aaactatgca 180
gactccgtga agggccgatt caccattgga agagacaatg ccaagaacac ggcgtatctg 240
caaatgaaca acctgaaacc tgaggacacg gccgtctatt actataatat cgaaacacta 300
cgacgtaact actggggcca ggggacccag gtcaccgtct cctca 345

<210> SEQ ID NO 199
<211> LENGTH: 354
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 199
gaggtgcagc tggtggagtc tgggggagga ttggtgcagg ctgggggtc tctgagactc 60 tcctgtgcag cctctggacg cacctttagt aactatgcca tgggctggtt ccgccaggcc 120
acagggaagg agcgtgagtt tgtagcagct attaacaaga gtggtgggaa cacacactat 180
gcaggctccg tgaagggccg attcaccatc tccagagaca acgccaagaa cacggtgtat 240
ctgcaaatga acagcctgaa acctagggac acggccgttt attactgtgc agcgtcgcgg 300
actaacccta agcctgacta ctggggccag gggacccagg tcaccgtctc ctca 354

<210> SEQ ID NO 200
<211> LENGTH: 366
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 200
gaggtgcagc tggtggagtc tgggggagga ttggtgcagg ctggggctc tctgagactc 60 tcctgtgcag cctctggacg ctccttcagt cgcagtgcca tgggctggct ccgccaggct 120
ccagggaagg agcgtgaatt tgtagcaggt attagctggg gtggtgataa ctcatactat 180
gcagactccg tgaagggccg attcaccatc tccagagaca acgccaagaa caccgtgtct 240
ctacaaatga acagcctgaa acctcaggac acggccgttt attactgtgc agcaagatac 300
cggggaggcg cggcagtagc tggttgggag tactggggcc aggggaccca ggtcaccgtc 360
tcctca 366

<210> SEQ ID NO 201
<211> LENGTH: 372
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 201
gaggtgcagc tggtggagtc tgggggaggc ttggtgcagc ctggggggtc tctgagactc 60
tcctgtgcag cctccggatc cactttggcc tattataccg taggctggtt ccgccgggcc 120
ccagggaagg agcgcgaggg gatctcatgt attagtagta gtgatggtag cacatactat 180
gcagactccg tgaagggccg attcaccatc tccagagaca atgccaagaa tacggtgtat 240
ctgcaaatga acagcctgaa acctgaggac acggccgttt attactgtgc ggctgacaga 300
cgtaccgact gtaaaaaggg tagagtcggt tctggttcct ggggccaggg gacccaggtc 360
accgtctcct ca 372

<210> SEQ ID NO 202
<211> LENGTH: 375
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 202
aaggtgcagc tggtggagtc tgggggaggg ctggtgcagg ctgggggctc tctgagactc 60
tcctgtgcag cctccggacg cgccttcaat tactatgtca tggcctggtt ccgccaggct 120
caagggaagg agcgtgagtt tgtagcagct attagcacgc gtggtagtat gacaaagtat 180
tcagactccg tgcagggccg gttcaccatc tccagagaca acgccaagaa cacggtgtat 240
ctgcacatga acagcctgaa acctgaggat acggccgttt attactgtgc agcagaccct 300
cgcggcagta gctggtcatt ttcgtccggg ggttatgact actggggcca ggggacccag 360
gtcaccgtct cctca 375

<210> SEQ ID NO 203
<211> LENGTH: 333
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 203
gaggtgcagc tggtggagtc tgggggaggc ttggtgcagc ctggggggtc tgtgagactc 60
tcctgtgtag cctctggaat catcttcaga ctcagtgcgt tgggttggac acgccagggt 120
ccaggaaagg cgcgcgagtg ggtcgcaggt attaacagtg atggtacgac caactacgcc 180
gaccccgtga agggccgatt caccatctcc agagacaacg ccaagaacac gatatatctg 240
cacatggaca tgctgaaacc tgaggatacg gccgtctatt actgtgcctc cggaaagtac 300
cggggccagg ggacccaggt caccgtctcc tca 333

<210> SEQ ID NO 204
<211> LENGTH: 345
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 204
gaggtgcagc tggtggagtc tgggggaggc ttggtgcagg ctggggagtc tctgagactc 60
tcctgtgcag cctctggaag caccttcgat ttcaaagtca tgggctggta ccgccagcct 120

```
ccagggaagc agcgcgaggg ggtcgcagcg attaggctta gtggtaacat gcactatgca    180

gagtccgtga agggccgatt caccatctcc aaagccaacg ccaagaacac agtgtatctg    240

caaatgaaca gcctgagacc tgaggacacg gccgtctatt actgtaaggt gaacattcgg    300

ggccaggact actggggcca ggggacccag gtcaccgtct cctca                    345
```

<210> SEQ ID NO 205
<211> LENGTH: 360
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 205

```
gaggtgcagc tggtggagtc tggggggaggc ttggtgcagg ctggggggtc tctgacgctc     60

tcctgtgcag tctctggaag ctccttcaga atcaatacca tgggctggta ccgccgggct    120

ccagggaagc agcgcgagtt ggtcgcagct cgtgatagag gtggttacat aaactatgta    180

gattccgtga agggccgatt caccgtctcc agagacaacg ccaagcccac aatgtatctg    240

caaatgaaca gcctgaaacc tgaggacacg gccgtctatt attgtcatgc cgggacccaa    300

gatcggacgg gtcggaattt cgaccactgg ggccagggga cccaggtcac cgtctcctca    360
```

<210> SEQ ID NO 206
<211> LENGTH: 378
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 206

```
gaggtgcagc tggtggagtc tggggggaggc ttggtgcagc ctggggggtc tctgagactc     60

tcctgtgtag cctctggaag catcgtcaga attaatacca tgggctggta ccgccagact    120

ccagggaagc agcgcgagtt ggtcgcagat attaccagtg gtggtaacat aaactatata    180

gacgccgtga agggccgatt caccatctcc agagacaaca ccaagaacac ggtgtatctg    240

caaatgaaca gcctgaaacc tgaggacacg gccgtctatt actgtaatgc agagatcgtt    300

gttctggtgg gagtttggac ccagcgtgcg cggaccggca actactgggg ccaggggacc    360

caggtcaccg tctcctca                                                  378
```

<210> SEQ ID NO 207
<211> LENGTH: 372
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 207

```
gaggtgcagc tggtggagtc tggggggagga ttggtgcagc ctggggggtc tctgagactc     60

tcctgtgcag cctctggacg cacgttcagt agcttgtcca tgggctggtt ccgccaggct    120

ccggggaagg agcgtgcctt tgtagcagcg cttactcgaa atggtggtta cagatactat    180

gcagactccg tgaagggccg attcaccatc tccagagacg tcgccaagaa gaccttatat    240

ctgcaaatga acagcctgaa acctgaggac acggccgtct attactgtgc agcagatagt    300

cttagtggta gtgactactt aggaaccaac ctagactact ggggccaggg gacccaggtc    360

accgtctcct ca                                                        372
```

-continued

<210> SEQ ID NO 208
<211> LENGTH: 372
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 208
gaggtgcagc tggtggagtc tgggggagga ttggtgcagg ctgggggctc tctgagactc 60
tcctgtgcag cctctggacg caccttcagt gactatgcca tgggctggtt ccgccaggct 120
ccagggaagg agcgtgagtt tgtagcagct attacgtgga atggtggtag agtattttat 180
actgcctccg tgaagggccg attcaccatc tccagagaca acgccaagaa cacgatgtat 240
ctgcaaatga acagcctgaa acctgaggac acggccgttt attactgtgc agcagataaa 300
gacagacgta ctgactatct agggcacccc gttgcctact ggggccaggg gacccaggtc 360
accgtctcct ca 372

<210> SEQ ID NO 209
<211> LENGTH: 366
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 209
gaggtgcagc tggtggagtc tgggggagga ttggtgcagc ctgggggctc tctgagactc 60
tcctgtgtag cctctggacg catcttcagt agcaatgcca tgggctggtt ccgccaggct 120
ccagggaagg agcgtgagtt tgtagcggcc attacctgga ggagtggcgg tagcgcgtac 180
tatgcagact ccgcgaaggg ccgattcacc atctccagag acaacgccaa gaacacggtg 240
tatttgcaaa tgaacagcct gaaacctgag gacacggccg tttattattg tgcagctggt 300
ggtagttcct ggttaagttt tccgccggac tactggggcc aggggaccca ggtcaccgtc 360
tcctca 366

<210> SEQ ID NO 210
<211> LENGTH: 345
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 210
gaggtgcagc tggtggagtc tgggggagag ttggtgcagc cgggggggtc tctgagactc 60
tcctgtgcag cctctggaag catcttaact atcaatgcca tgggctggta ccgccaggct 120
ccagggaagc agcgcgagtt ggtagtccgt aggactaggg gtggtagtac aacgtatcaa 180
gactccgtga agggccgatt caccatctcc gcagacattg ccaagaaaac gatgtatctc 240
caaatgaaca gcctgaaacc tgaagacacg gccgtctatt actgtatgct agatgaccgt 300
gggggtgtct actggggtca ggggacccag gtcaccgtct cctca 345

<210> SEQ ID NO 211
<211> LENGTH: 360
<212> TYPE: DNA
<213> ORGANISM: Artificial Sequence
<220> FEATURE:
<223> OTHER INFORMATION: NUCLEIC ACID ENCODING MONOVALENT NANOBODY

<400> SEQUENCE: 211

-continued

```
gaggtgcagc tggtggagtc tgggggaggc ttggtgcagg ctggggggtc tctgacgctc     60

tcctgtgcag tctctggaag caccttcaga atcaatacca tgggctggta ccgccgggct    120

ccagggaagc agcgcgagtt ggtcgcagct cgtgatagag gtggttacat aaactatgta    180

gattccgtga agggccgatt caccgtctcc agagacaacg ccaagcccac aatgtatctg    240

caaatgaaca gcctgaaacc tgaggacacg gccgtctatt attgtcatgc cgggacccaa    300

gatcggacgg gtcggaattt cgaccgctgg ggccagggga cccaggtcac cgtctcctca    360


<210> SEQ ID NO 212
<211> LENGTH: 109
<212> TYPE: PRT
<213> ORGANISM: Homo sapiens

<400> SEQUENCE: 212

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105


<210> SEQ ID NO 213
<211> LENGTH: 115
<212> TYPE: PRT
<213> ORGANISM: Artificial Sequence
<220> FEATURE:
<223> OTHER INFORMATION: Amino acid sequences of sequence-optimised
      variants

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Ile Leu Thr Ile Asn
            20                  25                  30

Ala Met Gly Trp Tyr Arg Gln Ala Pro Gly Lys Gln Arg Glu Leu Val
        35                  40                  45

Val Arg Arg Thr Arg Gly Gly Ser Thr Thr Tyr Gln Asp Ser Val Lys
    50                  55                  60

Gly Arg Phe Thr Ile Ser Ala Asp Ile Ser Lys Lys Thr Met Tyr Leu
65                  70                  75                  80

Gln Met Asn Ser Leu Arg Pro Glu Asp Thr Ala Val Tyr Tyr Cys Leu
                85                  90                  95

Leu Asp Asp Arg Gly Gly Val Tyr Trp Gly Gln Gly Thr Leu Val Thr
            100                 105                 110

Val Ser Ser
        115


<210> SEQ ID NO 214
<211> LENGTH: 115
```

<212> TYPE: PRT
<213> ORGANISM: Artificial Sequence
<220> FEATURE:
<223> OTHER INFORMATION: Amino acid sequences of sequence-optimised variants

<400> SEQUENCE: 214

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Ile Leu Thr Ile Asn
            20                  25                  30

Ala Met Gly Trp Tyr Arg Gln Ala Pro Gly Lys Gln Arg Glu Leu Val
        35                  40                  45

Val Arg Arg Thr Arg Gly Gly Ser Thr Thr Tyr Gln Asp Ser Val Lys
    50                  55                  60

Gly Arg Phe Thr Ile Ser Ala Asp Ile Ser Lys Asn Thr Met Tyr Leu
65                  70                  75                  80

Gln Met Asn Ser Leu Arg Pro Glu Asp Thr Ala Val Tyr Tyr Cys Leu
                85                  90                  95

Leu Asp Asp Arg Gly Gly Val Tyr Trp Gly Gln Gly Thr Leu Val Thr
            100                 105                 110

Val Ser Ser
        115

<210> SEQ ID NO 215
<211> LENGTH: 126
<212> TYPE: PRT
<213> ORGANISM: Artificial Sequence
<220> FEATURE:
<223> OTHER INFORMATION: Amino acid sequences of sequence-optimised variants

<400> SEQUENCE: 215

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Ile Val Arg Ile Asn
            20                  25                  30

Thr Met Gly Trp Tyr Arg Gln Ala Pro Gly Lys Gln Arg Glu Leu Val
        35                  40                  45

Ala Asp Ile Thr Ser Gly Gly Asn Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Glu Ile Val Val Leu Val Gly Val Trp Thr Gln Arg Ala Arg Thr
            100                 105                 110

Gly Asn Tyr Trp Gly Gln Gly Thr Leu Val Thr Val Ser Ser
        115                 120                 125

<210> SEQ ID NO 216
<211> LENGTH: 115
<212> TYPE: PRT
<213> ORGANISM: Artificial Sequence
<220> FEATURE:
<223> OTHER INFORMATION: Amino acid sequences of sequence-optimised variants

<400> SEQUENCE: 216

Glu Val Gln Leu Leu Glu Ser Gly Gly Gly Leu Val Gln Pro Gly Gly

```
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Ala Pro Gly Lys Gln Arg Glu Gly Val
        35                  40                  45

Ala Ala Ile Arg Leu Ser Gly Asn Arg His Tyr Ala Glu Ser Val Lys
    50                  55                  60

Gly Arg Phe Thr Ile Ser Arg Ala Asn Ser Lys Asn Thr Val Tyr Leu
65                  70                  75                  80

Gln Met Asn Ser Leu Arg Pro Glu Asp Thr Ala Val Tyr Tyr Cys Lys
                85                  90                  95

Val Asn Ile Arg Gly Gln Asp Tyr Trp Gly Gln Gly Thr Leu Val Thr
            100                 105                 110

Val Ser Ser
        115


<210> SEQ ID NO 217
<211> LENGTH: 122
<212> TYPE: PRT
<213> ORGANISM: Artificial Sequence
<220> FEATURE:
<223> OTHER INFORMATION: Amino acid sequences of sequence-optimised
      variants

<400> SEQUENCE: 217

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Ser Asn
            20                  25                  30

Ala Met Gly Trp Phe Arg Gln Ala Pro Gly Lys Glu Arg Glu Phe Val
        35                  40                  45

Ala Ala Ile Thr Trp Arg Ser Gly Gly Ser Ala Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Gly Gly Ser Ser Trp Leu Ser Phe Pro Pro Asp Tyr Trp
            100                 105                 110

Gly Gln Gly Thr Leu Val Thr Val Ser Ser
        115                 120


<210> SEQ ID NO 218
<211> LENGTH: 124
<212> TYPE: PRT
<213> ORGANISM: Artificial Sequence
<220> FEATURE:
<223> OTHER INFORMATION: Amino acid sequences of sequence-optimised
      variants

<400> SEQUENCE: 218

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Ser Asp Tyr
            20                  25                  30

Ala Met Gly Trp Phe Arg Gln Ala Pro Gly Lys Glu Arg Glu Phe Val
        35                  40                  45

Ala Ala Ile Thr Trp Asn Gly Gly Arg Val Phe Tyr Thr Ala Ser Val
```

50 55 60

Lys Gly Arg Phe Thr Ile Ser Arg Asp Asn Ser Lys Asn Thr Leu Tyr
65 70 75 80

Leu Gln Met Asn Ser Leu Arg Pro Glu Asp Thr Ala Val Tyr Tyr Cys
85 90 95

Ala Ala Asp Lys Asp Arg Arg Thr Asp Tyr Leu Gly His Pro Val Ala
100 105 110

Tyr Trp Gly Gln Gly Thr Leu Val Thr Val Ser Ser
115 120

<210> SEQ ID NO 219
<211> LENGTH: 120
<212> TYPE: PRT
<213> ORGANISM: Artificial Sequence
<220> FEATURE:
<223> OTHER INFORMATION: Amino acid sequences of sequence-optimised variants

<400> SEQUENCE: 219

Glu Val Gln Leu Leu Glu Ser Gly Gly Gly Leu Val Gln Pro Gly Gly
1 5 10 15

Ser Leu Arg Leu Ser Cys Ala Val Ser Gly Ser Thr Phe Arg Ile Asn
20 25 30

Thr Met Gly Trp Tyr Arg Gln Ala Pro Gly Lys Gln Arg Glu Leu Val
35 40 45

Ala Ala Arg Asp Arg Gly Gly Tyr Ile Asn Tyr Val Asp Ser Val Lys
50 55 60

Gly Arg Phe Thr Ile Ser Arg Asp Asn Ser Lys Pro Thr Met Tyr Leu
65 70 75 80

Gln Met Asn Ser Leu Arg Pro Glu Asp Thr Ala Val Tyr Tyr Cys His
85 90 95

Ala Gly Thr Gln Asp Arg Thr Gly Arg Asn Phe Asp Arg Trp Gly Gln
100 105 110

Gly Thr Leu Val Thr Val Ser Ser
115 120

<210> SEQ ID NO 220
<211> LENGTH: 35
<212> TYPE: PRT
<213> ORGANISM: Artificial Sequence
<220> FEATURE:
<223> OTHER INFORMATION: PEPTIDE LINKER

<400> SEQUENCE: 220

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser
35

<210> SEQ ID NO 221
<211> LENGTH: 272
<212> TYPE: PRT
<213> ORGANISM: Artificial Sequence
<220> FEATURE:
<223> OTHER INFORMATION: amino acid sequences of sequence-optimised biparatopic

<400> SEQUENCE: 221

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Ala Pro Gly Lys Gln Arg Glu Gly Val
        35                  40                  45

Ala Ala Ile Arg Leu Ser Gly Asn Arg His Tyr Ala Glu Ser Val Lys
    50                  55                  60

Gly Arg Phe Thr Ile Ser Arg Ala Asn Ser Lys Asn Thr Val Tyr Leu
65                  70                  75                  80

Gln Met Asn Ser Leu Arg Pro Glu Asp Thr Ala Val Tyr Tyr Cys Lys
                85                  90                  95

Val Asn Ile Arg Gly Gln Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Leu Glu Ser Gly Gly Gly
145                 150                 155                 160

Leu Val Gln Pro Gly Gly Ser Leu Arg Leu Ser Cys Ala Ala Ser Gly
                165                 170                 175

Arg Ile Phe Ser Ser Asn Ala Met Gly Trp Phe Arg Gln Ala Pro Gly
            180                 185                 190

Lys Glu Arg Glu Phe Val Ala Ala Ile Thr Trp Arg Ser Gly Gly Ser
        195                 200                 205

Ala Tyr Tyr Ala Asp Ser Val Lys Gly Arg Phe Thr Ile Ser Arg Asp
    210                 215                 220

Asn Ser Lys Asn Thr Val Tyr Leu Gln Met Asn Ser Leu Arg Pro Glu
225                 230                 235                 240

Asp Thr Ala Val Tyr Tyr Cys Ala Ala Gly Gly Ser Ser Trp Leu Ser
                245                 250                 255

Phe Pro Pro Asp Tyr Trp Gly Gln Gly Thr Leu Val Thr Val Ser Ser
            260                 265                 270


<210> SEQ ID NO 222
<211> LENGTH: 274
<212> TYPE: PRT
<213> ORGANISM: Artificial Sequence
<220> FEATURE:
<223> OTHER INFORMATION: amino acid sequences of sequence-optimised
      biparatopic

<400> SEQUENCE: 222

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Ala Pro Gly Lys Gln Arg Glu Gly Val
        35                  40                  45

Ala Ala Ile Arg Leu Ser Gly Asn Arg His Tyr Ala Glu Ser Val Lys
    50                  55                  60

Gly Arg Phe Thr Ile Ser Arg Ala Asn Ser Lys Asn Thr Val Tyr Leu
65                  70                  75                  80

Gln Met Asn Ser Leu Arg Pro Glu Asp Thr Ala Val Tyr Tyr Cys Lys
                85                  90                  95
```

Val Asn Ile Arg Gly Gln Asp Tyr Trp Gly Gln Gly Thr Leu Val Thr
100 105 110

Val Ser Ser Gly Gly Gly Gly Ser Gly Gly Gly Gly Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Glu Val Gln Leu Leu Glu Ser Gly Gly Gly
145 150 155 160

Leu Val Gln Pro Gly Gly Ser Leu Arg Leu Ser Cys Ala Ala Ser Gly
165 170 175

Arg Thr Phe Ser Asp Tyr Ala Met Gly Trp Phe Arg Gln Ala Pro Gly
180 185 190

Lys Glu Arg Glu Phe Val Ala Ala Ile Thr Trp Asn Gly Gly Arg Val
195 200 205

Phe Tyr Thr Ala Ser Val Lys Gly Arg Phe Thr Ile Ser Arg Asp Asn
210 215 220

Ser Lys Asn Thr Leu Tyr Leu Gln Met Asn Ser Leu Arg Pro Glu Asp
225 230 235 240

Thr Ala Val Tyr Tyr Cys Ala Ala Asp Lys Asp Arg Arg Thr Asp Tyr
245 250 255

Leu Gly His Pro Val Ala Tyr Trp Gly Gln Gly Thr Leu Val Thr Val
260 265 270

Ser Ser

<210> SEQ ID NO 223
<211> LENGTH: 277
<212> TYPE: PRT
<213> ORGANISM: Artificial Sequence
<220> FEATURE:
<223> OTHER INFORMATION: amino acid sequences of sequence-optimised biparatopic

<400> SEQUENCE: 223

Glu Val Gln Leu Leu Glu Ser Gly Gly Gly Leu Val Gln Pro Gly Gly
1 5 10 15

Ser Leu Arg Leu Ser Cys Ala Val Ser Gly Ser Thr Phe Arg Ile Asn
20 25 30

Thr Met Gly Trp Tyr Arg Gln Ala Pro Gly Lys Gln Arg Glu Leu Val
35 40 45

Ala Ala Arg Asp Arg Gly Gly Tyr Ile Asn Tyr Val Asp Ser Val Lys
50 55 60

Gly Arg Phe Thr Ile Ser Arg Asp Asn Ser Lys Pro Thr Met Tyr Leu
65 70 75 80

Gln Met Asn Ser Leu Arg Pro Glu Asp Thr Ala Val Tyr Tyr Cys His
85 90 95

Ala Gly Thr Gln Asp Arg Thr Gly Arg Asn Phe Asp Arg Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Gly Gly Gly Gly Ser Glu Val Gln Leu Leu
145 150 155 160

Glu Ser Gly Gly Gly Leu Val Gln Pro Gly Gly Ser Leu Arg Leu Ser
165 170 175

```
Cys Ala Ala Ser Gly Arg Ile Phe Ser Ser Asn Ala Met Gly Trp Phe
            180                 185                 190

Arg Gln Ala Pro Gly Lys Glu Arg Glu Phe Val Ala Ala Ile Thr Trp
        195                 200                 205

Arg Ser Gly Gly Ser Ala Tyr Tyr Ala Asp Ser Val Lys Gly Arg Phe
    210                 215                 220

Thr Ile Ser Arg Asp Asn Ser Lys Asn Thr Val Tyr Leu Gln Met Asn
225                 230                 235                 240

Ser Leu Arg Pro Glu Asp Thr Ala Val Tyr Tyr Cys Ala Ala Gly Gly
                245                 250                 255

Ser Ser Trp Leu Ser Phe Pro Pro Asp Tyr Trp Gly Gln Gly Thr Leu
            260                 265                 270

Val Thr Val Ser Ser
        275


<210> SEQ ID NO 224
<211> LENGTH: 279
<212> TYPE: PRT
<213> ORGANISM: Artificial Sequence
<220> FEATURE:
<223> OTHER INFORMATION: amino acid sequences of sequence-optimised
      biparatopic

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Val Ser Gly Ser Thr Phe Arg Ile Asn
            20                  25                  30

Thr Met Gly Trp Tyr Arg Gln Ala Pro Gly Lys Gln Arg Glu Leu Val
        35                  40                  45

Ala Ala Arg Asp Arg Gly Gly Tyr Ile Asn Tyr Val Asp Ser Val Lys
    50                  55                  60

Gly Arg Phe Thr Ile Ser Arg Asp Asn Ser Lys Pro Thr Met Tyr Leu
65                  70                  75                  80

Gln Met Asn Ser Leu Arg Pro Glu Asp Thr Ala Val Tyr Tyr Cys His
                85                  90                  95

Ala Gly Thr Gln Asp Arg Thr Gly Arg Asn Phe Asp Arg Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Leu
145                 150                 155                 160

Glu Ser Gly Gly Gly Leu Val Gln Pro Gly Gly Ser Leu Arg Leu Ser
                165                 170                 175

Cys Ala Ala Ser Gly Arg Thr Phe Ser Asp Tyr Ala Met Gly Trp Phe
            180                 185                 190

Arg Gln Ala Pro Gly Lys Glu Arg Glu Phe Val Ala Ala Ile Thr Trp
        195                 200                 205

Asn Gly Gly Arg Val Phe Tyr Thr Ala Ser Val Lys Gly Arg Phe Thr
    210                 215                 220

Ile Ser Arg Asp Asn Ser Lys Asn Thr Leu Tyr Leu Gln Met Asn Ser
225                 230                 235                 240

Leu Arg Pro Glu Asp Thr Ala Val Tyr Tyr Cys Ala Ala Asp Lys Asp
```

```
                245                 250                 255

Arg Arg Thr Asp Tyr Leu Gly His Pro Val Ala Tyr Trp Gly Gln Gly
            260                 265                 270

Thr Leu Val Thr Val Ser Ser
        275


<210> SEQ ID NO 225
<211> LENGTH: 422
<212> TYPE: PRT
<213> ORGANISM: Artificial Sequence
<220> FEATURE:
<223> OTHER INFORMATION: amino acid sequences of sequence-optimised
      biparatopic

<400> SEQUENCE: 225

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Ala Pro Gly Lys Gln Arg Glu Gly Val
        35                  40                  45

Ala Ala Ile Arg Leu Ser Gly Asn Arg His Tyr Ala Glu Ser Val Lys
    50                  55                  60

Gly Arg Phe Thr Ile Ser Arg Ala Asn Ser Lys Asn Thr Val Tyr Leu
65                  70                  75                  80

Gln Met Asn Ser Leu Arg Pro Glu Asp Thr Ala Val Tyr Tyr Cys Lys
                85                  90                  95

Val Asn Ile Arg Gly Gln Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Leu Glu Ser Gly Gly Gly
145                 150                 155                 160

Leu Val Gln Pro Gly Gly Ser Leu Arg Leu Ser Cys Ala Ala Ser Gly
                165                 170                 175

Arg Ile Phe Ser Ser Asn Ala Met Gly Trp Phe Arg Gln Ala Pro Gly
            180                 185                 190

Lys Glu Arg Glu Phe Val Ala Ala Ile Thr Trp Arg Ser Gly Gly Ser
        195                 200                 205

Ala Tyr Tyr Ala Asp Ser Val Lys Gly Arg Phe Thr Ile Ser Arg Asp
    210                 215                 220

Asn Ser Lys Asn Thr Val Tyr Leu Gln Met Asn Ser Leu Arg Pro Glu
225                 230                 235                 240

Asp Thr Ala Val Tyr Tyr Cys Ala Ala Gly Gly Ser Ser Trp Leu Ser
                245                 250                 255

Phe Pro Pro Asp Tyr Trp Gly Gln Gly Thr Leu Val Thr Val Ser Ser
            260                 265                 270

Gly Gly Gly Gly Ser Gly Gly Gly Gly Ser Gly Gly Gly Gly Ser Gly
        275                 280                 285

Gly Gly Gly Ser Gly Gly Gly Gly Ser Gly Gly Gly Gly Ser Gly Gly
    290                 295                 300

Gly Gly Ser Glu Val Gln Leu Val Glu Ser Gly Gly Gly Leu Val Gln
305                 310                 315                 320
```

```
Pro Gly Asn Ser Leu Arg Leu Ser Cys Ala Ala Ser Gly Phe Thr Phe
                325                 330                 335

Ser Ser Phe Gly Met Ser Trp Val Arg Gln Ala Pro Gly Lys Gly Leu
            340                 345                 350

Glu Trp Val Ser Ser Ile Ser Gly Ser Gly Ser Asp Thr Leu Tyr Ala
        355                 360                 365

Asp Ser Val Lys Gly Arg Phe Thr Ile Ser Arg Asp Asn Ala Lys Thr
    370                 375                 380

Thr Leu Tyr Leu Gln Met Asn Ser Leu Arg Pro Glu Asp Thr Ala Val
385                 390                 395                 400

Tyr Tyr Cys Thr Ile Gly Gly Ser Leu Ser Arg Ser Ser Gln Gly Thr
                405                 410                 415

Leu Val Thr Val Ser Ser
            420


<210> SEQ ID NO 226
<211> LENGTH: 426
<212> TYPE: PRT
<213> ORGANISM: Artificial Sequence
<220> FEATURE:
<223> OTHER INFORMATION: amino acid sequences of sequence-optimised
      biparatopic

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Ala Pro Gly Lys Gln Arg Glu Gly Val
        35                  40                  45

Ala Ala Ile Arg Leu Ser Gly Asn Arg His Tyr Ala Glu Ser Val Lys
    50                  55                  60

Gly Arg Phe Thr Ile Ser Arg Ala Asn Ser Lys Asn Thr Val Tyr Leu
65                  70                  75                  80

Gln Met Asn Ser Leu Arg Pro Glu Asp Thr Ala Val Tyr Tyr Cys Lys
                85                  90                  95

Val Asn Ile Arg Gly Gln Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Leu Glu Ser Gly Gly Gly
145                 150                 155                 160

Leu Val Gln Pro Gly Gly Ser Leu Arg Leu Ser Cys Ala Ala Ser Gly
                165                 170                 175

Ser Ile Val Arg Ile Asn Thr Met Gly Trp Tyr Arg Gln Ala Pro Gly
            180                 185                 190

Lys Gln Arg Glu Leu Val Ala Asp Ile Thr Ser Gly Gly Asn Ile Asn
        195                 200                 205

Tyr Ala Asp Ser Val Lys Gly Arg Phe Thr Ile Ser Arg Asp Asn Ser
    210                 215                 220

Lys Asn Thr Val Tyr Leu Gln Met Asn Ser Leu Arg Pro Glu Asp Thr
225                 230                 235                 240

Ala Val Tyr Tyr Cys Asn Ala Glu Ile Val Val Leu Val Gly Val Trp
                245                 250                 255
```

```
Thr Gln Arg Ala Arg Thr Gly Asn Tyr Trp Gly Gln Gly Thr Leu Val
            260                 265                 270

Thr Val Ser Ser Gly Gly Gly Gly Ser Gly Gly Gly Gly Ser Gly Gly
        275                 280                 285

Gly Gly Ser Gly Gly Gly Gly Ser Gly Gly Gly Gly Ser Gly Gly Gly
    290                 295                 300

Gly Ser Gly Gly Gly Gly Ser Glu Val Gln Leu Val Glu Ser Gly Gly
305                 310                 315                 320

Gly Leu Val Gln Pro Gly Asn Ser Leu Arg Leu Ser Cys Ala Ala Ser
                325                 330                 335

Gly Phe Thr Phe Ser Ser Phe Gly Met Ser Trp Val Arg Gln Ala Pro
            340                 345                 350

Gly Lys Gly Leu Glu Trp Val Ser Ser Ile Ser Gly Ser Gly Ser Asp
        355                 360                 365

Thr Leu Tyr Ala Asp Ser Val Lys Gly Arg Phe Thr Ile Ser Arg Asp
    370                 375                 380

Asn Ala Lys Thr Thr Leu Tyr Leu Gln Met Asn Ser Leu Arg Pro Glu
385                 390                 395                 400

Asp Thr Ala Val Tyr Tyr Cys Thr Ile Gly Gly Ser Leu Ser Arg Ser
                405                 410                 415

Ser Gln Gly Thr Leu Val Thr Val Ser Ser
            420                 425


<210> SEQ ID NO 227
<211> LENGTH: 424
<212> TYPE: PRT
<213> ORGANISM: Artificial Sequence
<220> FEATURE:
<223> OTHER INFORMATION: amino acid sequences of sequence-optimised
      biparatopic

<400> SEQUENCE: 227

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Asp Phe Lys
            20                  25                  30

Val Met Gly Trp Tyr Arg Gln Ala Pro Gly Lys Gln Arg Glu Gly Val
        35                  40                  45

Ala Ala Ile Arg Leu Ser Gly Asn Arg His Tyr Ala Glu Ser Val Lys
    50                  55                  60

Gly Arg Phe Thr Ile Ser Arg Ala Asn Ser Lys Asn Thr Val Tyr Leu
65                  70                  75                  80

Gln Met Asn Ser Leu Arg Pro Glu Asp Thr Ala Val Tyr Tyr Cys Lys
                85                  90                  95

Val Asn Ile Arg Gly Gln Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Leu Glu Ser Gly Gly Gly
145                 150                 155                 160

Leu Val Gln Pro Gly Gly Ser Leu Arg Leu Ser Cys Ala Ala Ser Gly
                165                 170                 175

Arg Thr Phe Ser Asp Tyr Ala Met Gly Trp Phe Arg Gln Ala Pro Gly
```

```
            180                 185                 190

Lys Glu Arg Glu Phe Val Ala Ala Ile Thr Trp Asn Gly Gly Arg Val
        195                 200                 205

Phe Tyr Thr Ala Ser Val Lys Gly Arg Phe Thr Ile Ser Arg Asp Asn
    210                 215                 220

Ser Lys Asn Thr Leu Tyr Leu Gln Met Asn Ser Leu Arg Pro Glu Asp
225                 230                 235                 240

Thr Ala Val Tyr Tyr Cys Ala Ala Asp Lys Asp Arg Arg Thr Asp Tyr
                245                 250                 255

Leu Gly His Pro Val Ala Tyr Trp Gly Gln Gly Thr Leu Val Thr Val
            260                 265                 270

Ser Ser Gly Gly Gly Gly Ser Gly Gly Gly Gly Ser Gly Gly Gly Gly
        275                 280                 285

Ser Gly Gly Gly Gly Ser Gly Gly Gly Gly Ser Gly Gly Gly Gly Ser
    290                 295                 300

Gly Gly Gly Gly Ser Glu Val Gln Leu Val Glu Ser Gly Gly Gly Leu
305                 310                 315                 320

Val Gln Pro Gly Asn Ser Leu Arg Leu Ser Cys Ala Ala Ser Gly Phe
                325                 330                 335

Thr Phe Ser Ser Phe Gly Met Ser Trp Val Arg Gln Ala Pro Gly Lys
            340                 345                 350

Gly Leu Glu Trp Val Ser Ser Ile Ser Gly Ser Gly Ser Asp Thr Leu
        355                 360                 365

Tyr Ala Asp Ser Val Lys Gly Arg Phe Thr Ile Ser Arg Asp Asn Ala
    370                 375                 380

Lys Thr Thr Leu Tyr Leu Gln Met Asn Ser Leu Arg Pro Glu Asp Thr
385                 390                 395                 400

Ala Val Tyr Tyr Cys Thr Ile Gly Gly Ser Leu Ser Arg Ser Ser Gln
                405                 410                 415

Gly Thr Leu Val Thr Val Ser Ser
            420


<210> SEQ ID NO 228
<211> LENGTH: 115
<212> TYPE: PRT
<213> ORGANISM: Artificial Sequence
<220> FEATURE:
<223> OTHER INFORMATION: amino acid sequences of sequence-optimised
      biparatopic

<400> SEQUENCE: 228

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110
```

Val Ser Ser
115

<210> SEQ ID NO 229
<211> LENGTH: 30
<212> TYPE: PRT
<213> ORGANISM: Artificial Sequence
<220> FEATURE:
<223> OTHER INFORMATION: FR1

<400> SEQUENCE: 229

Glu Val Gln Leu Leu Glu Ser Gly Gly Gly Leu Val Gln Pro Gly Gly
1 5 10 15

Ser Leu Arg Leu Ser Cys Ala Ala Ser Gly Ser Ile Leu Thr
20 25 30

<210> SEQ ID NO 230
<211> LENGTH: 30
<212> TYPE: PRT
<213> ORGANISM: Artificial Sequence
<220> FEATURE:
<223> OTHER INFORMATION: FR1

<400> SEQUENCE: 230

Glu Val Gln Leu Leu Glu Ser Gly Gly Gly Leu Val Gln Pro Gly Gly
1 5 10 15

Ser Leu Arg Leu Ser Cys Ala Ala Ser Gly Ser Ile Val Arg
20 25 30

<210> SEQ ID NO 231
<211> LENGTH: 30
<212> TYPE: PRT
<213> ORGANISM: Artificial Sequence
<220> FEATURE:
<223> OTHER INFORMATION: FR1

<400> SEQUENCE: 231

Glu Val Gln Leu Leu Glu Ser Gly Gly Gly Leu Val Gln Pro Gly Gly
1 5 10 15

Ser Leu Arg Leu Ser Cys Ala Ala Ser Gly Ser Thr Phe Asp
20 25 30

<210> SEQ ID NO 232
<211> LENGTH: 30
<212> TYPE: PRT
<213> ORGANISM: Artificial Sequence
<220> FEATURE:
<223> OTHER INFORMATION: FR1

<400> SEQUENCE: 232

Glu Val Gln Leu Leu Glu Ser Gly Gly Gly Leu Val Gln Pro Gly Gly
1 5 10 15

Ser Leu Arg Leu Ser Cys Ala Ala Ser Gly Arg Ile Phe Ser
20 25 30

<210> SEQ ID NO 233
<211> LENGTH: 30
<212> TYPE: PRT
<213> ORGANISM: Artificial Sequence
<220> FEATURE:
<223> OTHER INFORMATION: FR1

<400> SEQUENCE: 233

Glu Val Gln Leu Leu Glu Ser Gly Gly Gly Leu Val Gln Pro Gly Gly
1 5 10 15

Ser Leu Arg Leu Ser Cys Ala Ala Ser Gly Arg Thr Phe Ser
20 25 30

<210> SEQ ID NO 234
<211> LENGTH: 30
<212> TYPE: PRT
<213> ORGANISM: Artificial Sequence
<220> FEATURE:
<223> OTHER INFORMATION: FR1

<400> SEQUENCE: 234

Glu Val Gln Leu Leu Glu Ser Gly Gly Gly Leu Val Gln Pro Gly Gly
1 5 10 15

Ser Leu Arg Leu Ser Cys Ala Val Ser Gly Ser Thr Phe Arg
20 25 30

<210> SEQ ID NO 235
<211> LENGTH: 16
<212> TYPE: PRT
<213> ORGANISM: Artificial Sequence
<220> FEATURE:
<223> OTHER INFORMATION: CDR2

<400> SEQUENCE: 235

Asp Ile Thr Ser Gly Gly Asn Ile Asn Tyr Ala Asp Ser Val Lys Gly
1 5 10 15

<210> SEQ ID NO 236
<211> LENGTH: 16
<212> TYPE: PRT
<213> ORGANISM: Artificial Sequence
<220> FEATURE:
<223> OTHER INFORMATION: CDR2

<400> SEQUENCE: 236

Ala Ile Arg Leu Ser Gly Asn Arg His Tyr Ala Glu Ser Val Lys Gly
1 5 10 15

<210> SEQ ID NO 237
<211> LENGTH: 18
<212> TYPE: PRT
<213> ORGANISM: Artificial Sequence
<220> FEATURE:
<223> OTHER INFORMATION: CDR2

<400> SEQUENCE: 237

Ala Ile Thr Trp Arg Ser Gly Gly Ser Ala Tyr Tyr Ala Asp Ser Val
1 5 10 15

Lys Gly

<210> SEQ ID NO 238
<211> LENGTH: 32
<212> TYPE: PRT
<213> ORGANISM: Artificial Sequence
<220> FEATURE:
<223> OTHER INFORMATION: FR3

<400> SEQUENCE: 238

Arg Phe Thr Ile Ser Ala Asp Ile Ser Lys Lys Thr Met Tyr Leu Gln
1 5 10 15

Met Asn Ser Leu Arg Pro Glu Asp Thr Ala Val Tyr Tyr Cys Leu Leu
20 25 30

<210> SEQ ID NO 239

<211> LENGTH: 32
<212> TYPE: PRT
<213> ORGANISM: Artificial Sequence
<220> FEATURE:
<223> OTHER INFORMATION: FR3

<400> SEQUENCE: 239

Arg Phe Thr Ile Ser Ala Asp Ile Ser Lys Asn Thr Met Tyr Leu Gln
1 5 10 15

Met Asn Ser Leu Arg Pro Glu Asp Thr Ala Val Tyr Tyr Cys Leu Leu
20 25 30

<210> SEQ ID NO 240
<211> LENGTH: 32
<212> TYPE: PRT
<213> ORGANISM: Artificial Sequence
<220> FEATURE:
<223> OTHER INFORMATION: FR3

<400> SEQUENCE: 240

Arg Phe Thr Ile Ser Arg Asp Asn Ser Lys Asn Thr Val Tyr Leu Gln
1 5 10 15

Met Asn Ser Leu Arg Pro Glu Asp Thr Ala Val Tyr Tyr Cys Asn Ala
20 25 30

<210> SEQ ID NO 241
<211> LENGTH: 32
<212> TYPE: PRT
<213> ORGANISM: Artificial Sequence
<220> FEATURE:
<223> OTHER INFORMATION: FR3

<400> SEQUENCE: 241

Arg Phe Thr Ile Ser Arg Ala Asn Ser Lys Asn Thr Val Tyr Leu Gln
1 5 10 15

Met Asn Ser Leu Arg Pro Glu Asp Thr Ala Val Tyr Tyr Cys Lys Val
20 25 30

<210> SEQ ID NO 242
<211> LENGTH: 32
<212> TYPE: PRT
<213> ORGANISM: Artificial Sequence
<220> FEATURE:
<223> OTHER INFORMATION: FR3

<400> SEQUENCE: 242

Arg Phe Thr Ile Ser Arg Asp Asn Ser Lys Asn Thr Val Tyr Leu Gln
1 5 10 15

Met Asn Ser Leu Arg Pro Glu Asp Thr Ala Val Tyr Tyr Cys Ala Ala
20 25 30

<210> SEQ ID NO 243
<211> LENGTH: 32
<212> TYPE: PRT
<213> ORGANISM: Artificial Sequence
<220> FEATURE:
<223> OTHER INFORMATION: FR3

<400> SEQUENCE: 243

Arg Phe Thr Ile Ser Arg Asp Asn Ser Lys Asn Thr Leu Tyr Leu Gln
1 5 10 15

Met Asn Ser Leu Arg Pro Glu Asp Thr Ala Val Tyr Tyr Cys Ala Ala
20 25 30

-continued

```
<210> SEQ ID NO 244
<211> LENGTH: 32
<212> TYPE: PRT
<213> ORGANISM: Artificial Sequence
<220> FEATURE:
<223> OTHER INFORMATION: FR3

<400> SEQUENCE: 244

Arg Phe Thr Ile Ser Arg Asp Asn Ser Lys Pro Thr Met Tyr Leu Gln
1               5                   10                  15

Met Asn Ser Leu Arg Pro Glu Asp Thr Ala Val Tyr Tyr Cys His Ala
            20                  25                  30


<210> SEQ ID NO 245
<211> LENGTH: 11
<212> TYPE: PRT
<213> ORGANISM: Artificial Sequence
<220> FEATURE:
<223> OTHER INFORMATION: FR4

<400> SEQUENCE: 245

Trp Gly Gln Gly Thr Leu Val Thr Val Ser Ser
1               5                   10


<210> SEQ ID NO 246
<211> LENGTH: 5
<212> TYPE: PRT
<213> ORGANISM: Artificial Sequence
<220> FEATURE:
<223> OTHER INFORMATION: CDR1

<400> SEQUENCE: 246

Thr Tyr Trp Met Tyr
1               5


<210> SEQ ID NO 247
<211> LENGTH: 14
<212> TYPE: PRT
<213> ORGANISM: Artificial Sequence
<220> FEATURE:
<223> OTHER INFORMATION: FR2

<400> SEQUENCE: 247

Trp Tyr Arg Gln Ala Pro Gly Lys Gln Arg Glu Gly Val Ala
1               5                   10


<210> SEQ ID NO 248
<211> LENGTH: 5
<212> TYPE: PRT
<213> ORGANISM: Artificial Sequence
<220> FEATURE:
<223> OTHER INFORMATION: CDR1

<400> SEQUENCE: 248

Ile Asn Ala Met Gly
1               5
```

METHODS OF TREATMENT USING CHEMOKINE RECEPTOR BINDING POLYPEPTIDES

RELATED APPLICATIONS

This application is a divisional application of U.S. application Ser. No. 13/290,175 filed Nov. 7, 2011, which claims benefit under 35 U.S.C. §119(e) of U.S. Provisional Application No. 61/411,083, filed Nov. 8, 2010, the contents of each are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jan. 4, 2012, is named PAT054087.txt and is 183,210 bytes in size.

BRIEF SUMMARY OF THE INVENTION

The present invention relates to polypeptides directed against or specifically binding to chemokine receptor CXCR2 and in particular to polypeptides capable of modulating signal transduction from CXCR2. The invention also relates to nucleic acids, vectors and host cells capable of expressing the polypeptides of the invention, pharmaceutical compositions comprising the polypeptides and uses of said polypeptides and compositions for treatment of chronic obstructive pulmonary disease (COPD) and other diseases involving aberrant functioning of CXCR2.

BACKGROUND TO THE INVENTION

Chronic obstructive pulmonary disease (COPD) is a term used to describe a range of disorders characterized by airflow limitation that is in most cases both progressive and associated with an abnormal inflammatory response of the lung to noxious particles, with destruction of lung parenchyma resulting in decline in airway function (Barnes P J et al., 2003, Chronic obstructive pulmonary disease: molecular and cellular mechanisms. *Eur. Respir J,* 22, 672-688; Barnes P J et al., 2004, Mediators of chronic obstructive pulmonary disease. *Pharmacol. Rev.* 56, 515-548). Although genetic and environmental factors contribute to the development of COPD, smoking is the most important single cause, with recurrent lung infections leading to a progressive decline in lung function. Stopping smoking reduces progression of the disease only if applied early and has little effect after significant symptoms ensue. Several co-morbid conditions are associated with COPD such as asthma, cardiovascular disease, depression and muscle wasting (Mannino D M and Buist S, 2007 Global burden of COPD: risk factors, prevalence and future trends. *Lancet,* 370, 765-773).

Chemokines predominate among chemotactic factors and therefore, have a key role in orchestrating the chronic inflammation in COPD lungs and its further amplification during acute exacerbations. The biological activity of the chemokines IL-8 (CXCL8), GROα (CXCL1) and ENA-78 (CXCL5) is mediated by two populations of cell-surface receptors CXCR1 and CXCR2, which are present on leukocytes and many other cell types throughout the body. Migration of leukocytes is mediated primarily through CXCR2 which binds several ligands including IL-8, GROα, β, γ, ENA78, and GCP-2. In contrast, CXCR1 is selectively activated by IL-8 and to a lesser extent by GCP-2. It remains unclear whether human neutrophil chemotaxis in vivo is mediated by one or both receptors.

CXCR2 shares 78% homology at the amino acid level with CXCR1 and both receptors are present on neutrophils with different distribution patterns. The expression of CXCR2 on a variety of cells and tissues including CD8+ T cells, NK, monocytes, mast cells, epithelial, endothelial, smooth muscle and a host of cell types in the central nervous system suggests that this receptor may have a broad functional role under both constitutive conditions and in the pathophysiology of a number of acute and chronic diseases. CXCR2 activation stimulates receptor coupling with the Gi family of guanine nucleotide-binding proteins, this in turn stimulates the release of intracellular inositol phosphates, increased intracellular $Ca^{2+}$ and, by ERK1/2-dependent mechanisms, the phosphorylation of intracellular proteins associated with directed cell migration to chemokine gradient. Once activated, CXCR2 is phosphorylated and is rapidly internalized through arrestin/dynamin-dependent mechanisms, resulting in receptor desensitization. This process is similar to that observed with most other GPCRs, but the rate and extent of agonist-induced internalization of CXCR2 is greater than that seen with CXCR1 (Richardson R M, Pridgen B C, Haribabu B, Ali H, Synderman R. 1998 Differential cross-regulation of the human chemokine receptors CXCR1 and CXCR2. Evidence for time-dependent signal generation. *J Biol. Chem.,* 273, 23830-23836).

IL-8 has long been implicated as a mediator of neutrophilic inflammation in COPD (Keatings V M et al., 1996, Differences in IL-8 and tumor necrosis factor-α in induced sputum from patients with COPD and asthma. *Am. J. Respir. Crit. Care Med.* 153, 530-534; Yamamoto C et al. 1997 Airway inflammation in COPD assessed by sputum levels of interleukin-8 *Chest,* 112, 505-510). In biopsies of the bronchial airways, small airways and lung parenchyma from patients with COPD, there is an infiltration of T cells and increased numbers of neutrophils, particularly in the airway lumen (Hogg J C et al. 2004, The nature of small-airway obstruction in chronic obstructive pulmonary disease. *N. Eng. J. Med.* 350, 2645-2653). Neutrophils are increased in the lungs of patients with COPD and this correlates with the degree of disease severity (Keatings V M et al., 1996, Differences in IL-8 and tumor necrosis factor-α in induced sputum from patients with COPD and asthma. *Am. J. Respir. Crit. Care Med.* 153, 530-534). In addition, levels of TNFα are raised in the sputum of patients with COPD and this induces IL-8 from airway epithelial cells (Keatings). GROα concentration is markedly elevated in the induced sputum and bronchial alveolar lavage (BAL) fluid of patients with COPD compared with normal smokers and non-smokers (Traves S L et at 2002, Increased levels of the chemokines GROα and MCP-1 in sputum samples from patients with COPD. *Thorax,* 57, 50-595; Pesci A. et al. 1998, Inflammatory cells and mediators in bronchial lavage of patients with COPD. *Eur Respir J.* 12, 380-386). GROα is secreted by alveolar macrophages and airway epithelial cells in response to TNFα stimulation and selectively activates CXCR2, being chemotactic for neutrophils and monocytes. There is an increase in monocyte chemotactic response to GROα in COPD patients, which might be related to increased turnover or recycling of CXCR2 in these cells (Traves S L et al, 2004, Specific CXC but not CC chemokines cause elevated monocyte migration in COPD: a role for CXCR2, *J Leukoc. Biol.* 76, 441-450). Viral and bacterial lung infection frequently results in severe exacerbations in COPD patients which is characterised by increased numbers of neutrophils in the airways (Wedzicha J A, Seemungal T A., 2007, COPD exacerbations: defining their cause and prevention, *Lancet* 370 (9589): 786-96). Bronchial biopsies of patients with acute severe exacerbations of COPD have significantly increased amounts of ENA-78, IL-8 and CXCR2 mRNA expression (Qiu Y et al, 2003, Biopsy neutrophilia, neutrophil chemokine and receptor gene expression in severe exacerbations of chronic obstructive pulmonary disease. *Am. J. Respir. Crit. Care. Med.* 168, 968-975), and sputum has increased neutrophil counts (Bathoorn E, Liesker J Jw, Postma D S et al, Change in inflammation in out-patient COPD patients from stable phase to a subsequent exacerbation, (2009) Int J COPD, 4(1): 101-9) suggesting a potential role for this receptor in both COPD and severe exacerbations of this disease. Increased expression of CXCR2 mRNA is present in bronchial biopsy specimens, which correlates with the presence of tissue neutrophils (Qiu 2003). ENA-78 is derived predominantly from epithelial cells and there is a marked increase in ENA-78 expression in epithelial cells during exacerbations of COPD (Qiu 2003). Because concentrations of IL-8, GROα and ENA-78 are increased in COPD airways, and all three ligands signal through CXCR2, blocking this common receptor with selective antagonists would be an effective anti-inflammatory strategy in this disease.

COPD evolves slowly and progressively, and disease progression is estimated traditionally with lung-function tests such as spirometric measures of forced expiratory volume (FEV1). Patients with <50% predicted FEV1 are classified as severe. Lung function is closely related to mortality rate, as nearly 35% of severe COPD patients die of the disease within 12 years compared with only 5% of mild to moderate patients. COPD is the fourth leading cause of death in the world (World Health Organization (WHO), *World Health Report*, Geneva, 2000. Available from URL: http://www.who.int/whr/2000/en/whr00_annex_en.pdf) and further increases in its prevalence and mortality can be predicted in the coming decades (Lopez A D, Shibuya K, Rao C et al, 2006, Chronic obstructive pulmonary disease: current burden and future projections, *Eur Respir J*, 27(2), 397-412). Exacerbations are a key factor in the downward spiral of ill health and are largely responsible for the vast majority of COPD hospital admissions (BTS (British Thoracic Society), 2006, Burden of Lung Disease Report, $2^{nd}$ ed, http://www.brit-thoracic.org.uk/Portals/0/Library/BTS %20Publications/burdeon of_lung_disease2007.pdf). Mean yearly rates were 2.3 for symptom- and 2.8 for healthcare-defined exacerbations (O'Reilly J F, Williams A E, Holt K et al, 2006, Prim Care Respir J. 15(6): 346-53). Earlier diagnosis and improved management for patients' exacerbations as well as improved prevention would help reduce the strain these admissions place on already stretched resources. Available treatments for COPD are mainly palliative, and there are no therapies available that halt the decline of lung function or the progressive destruction of the airways associated with the disease. Current treatments such as short- and long-acting β-adrenergic bronchodilators, inhaled anticholinergics (muscarinic antagonists) and inhaled corticosteroids are used to treat the symptoms and exacerbations of the disease. A major limitation with the current corticosteroid therapy is that they are rendered ineffective as patients show resistance to corticosteroids, inactivating the anti-inflammatory action of these drugs. Clearly there is still a huge unmet medical need for novel drugs that prevent the progression of COPD. Chemokine receptor antagonists are an attractive approach to COPD therapy since inflammatory-cell trafficking in COPD is orchestrated by multiple chemokines, so the blockade of chemokine receptors with LMW antagonists might be an effective anti-inflammatory strategy in this disease. A crucial feature in COPD is an amplification of the inflammatory response seen in normal smokers, so the aim of therapy is not to suppress inflammatory cell infiltration completely but to reduce it to the levels seen in normal smokers without COPD. By acting specifically, anti-CXCR2 would avoid the general immune suppression associated with steroids—preservation of CXCR1 activity will allow baseline neutrophil activation, important for host defense in COPD and CF. Most COPD drugs are currently administered by inhalation to reduce systemic side-effects, however, as chemokine antagonists act on the receptors expressed in circulating inflammatory cells, systemic administration would be optimal. This would provide an efficient way to reach the small airways and lung parenchyma which are affected in COPD.

Chemokine receptors, in contrast with cytokines and interleukin receptors, belong to the highly 'druggable' superfamily of 7TM-GPCRs. Despite this, early attempts to find potent antagonists met with more difficulties than it was anticipated based on the experience with GPCRs having small peptide or biogenic amine ligands. Efforts on small-molecule drug-discovery programmes focussing on chemokine-receptor antagonists began to progressively understand the idiosyncrasies of the chemokine receptors and the structural elements required for small molecules to act as antagonists. Interestingly, the structural diversity of CC-chemokine-receptor antagonists, as represented by the number of fundamentally distinct chemical series identified, is considerably higher than for CXC-chemokine-receptor antagonists, which suggests that the relative difficulty of finding antagonists may be different between the two classes of receptors.

Chemokine receptors in general have proved to be difficult targets to antagonise and it has taken a huge effort to identify potent, selective CXCR2 antagonists. The first low molecular weight CXCR2 antagonist was described in 1998, since then a number of non-competitive allosteric CXCR2 antagonists have been developed, several of which have now progressed into clinical trials. Nevertheless there is clearly a need for better and more potent antagonists of CXCR2 function.

Molecules of the immunoglobulin class have seen a huge expansion in their clinical utility over the last ten years or so. Their specificity for a target and the ability to engineer them using recombinant techniques provides huge potential for developing highly directed treatment for disease. Many types of immunogloblin molecule and modified immunoglobulin molecule are potentially available to be suitably engineered including conventional four-chain antibodies, Fab and F(ab)2 fragments, single domain antibodies (D(ab)s), single chain Fvs and Nanobodies. These will be discussed further herein in connection with the invention which concerns polypeptides constructed to be directed against at least two epitopes of CXCR2.

It is therefore an object of the invention to provide a new means of prevention or treatment of chronic obstructive pulmonary disorder or COPD and other diseases associated with aberrant functioning of chemokine receptor CXCR2.

It is a further object of the invention to provide a means of treatment or prevention of COPD and other diseases associated with aberrant functioning of CXCR2 which is an immunotherapy.

It is yet a further object of the invention to provide a polypeptide comprising immunoglobulin CDRs which is an antagonist of CXCR2 signal transduction.

SUMMARY OF THE INVENTION

The present invention relates to a polypeptide comprising at least two immunoglobulin antigen binding domains, which polypeptide is directed against or binds to chemokine receptor CXCR2 wherein said polypeptide includes a first antigen binding domain recognising a first epitope on CXCR2 and a second antigen binding domain recognising a second epitope on CXCR2. A preferred polypeptide of the invention comprises a first antigen binding domain which is capable of binding to a linear peptide consisting of the sequence of amino acids set forth in SEQ ID NO. 7 and a second antigen binding domain which is either not capable of binding or binds with lower affinity to said linear peptide. SEQ ID NO. 7 is the first 19 N-terminal amino acids of human CXCR2. The preferred polypeptide of the invention is biparatopic. As used herein the term "biparatopic" means that a polypeptide comprises two antigen binding domains recognising two different epitopes on the same protein target. However, polypeptides which are multiparatopic i.e containing antigen binding domains recognising three, four or more epitopes on the same target protein, are encompassed within the scope invention, as are polypeptides which are both bi- or multiparatopic and multivalent i.e having also antigen binding domains recognising one or more other target proteins.

In the preferred polypeptides of the invention an amino acid sequence comprising the first antigen binding domain and the amino acid sequence comprising the second antigen binding domain are joined by a linker region. As discussed in more detail herein the linker may or may not be of immunoglobulin origin but is preferably a peptide.

In particularly preferred polypeptides in accordance with the invention, the said first antigen binding domain is comprised within a first immunoglobulin single variable domain and said second antigen binding domain is comprised within a second immunoglobulin single variable domain. At least one of the said first and second immunoglobulin single variable domain may be a $V_L$ domain or be a fragment thereof or may be a $V_H$ domain or be a fragment thereof. Polypeptides wherein each of the first and second antigen binding domains are comprised with $V_L$ domains or fragments thereof or wherein each of the first and second antigen binding domains are comprised within $V_H$ domains or fragments thereof are encompassed within the invention. The polypeptide of the invention may comprise both $V_L$ and $V_H$ amino acid sequences or fragments thereof within a single molecule.

In further preferred embodiments the first and second antigen binding domains are comprised within a first and second immunoglobulin single variable domains which are domain antibodies (dAbs). In a most preferred embodiments at least one and preferably both of said first and second antigen binding domains are comprised with immunoglobulin single variable domains which are a $V_{HH}$ domain or are a fragment thereof from a single heavy chain of a heavy chain antibody obtainable from a camelid or is a humanised version thereof in which at least one humanising substitution has been incorporated into the framework regions.

An immunoglobulin single variable domain which has a $V_{HH}$ sequence of amino acids or a fragment or variant thereof, from of a heavy chain only antibody of the type obtainable from Camelids may be referred to herein in the alternative, as a "$V_{HH}$ domain" or fragment thereof or as a "Nanobody". It must be noted that Nanobody®, Nanobodies® and Nanoclone® are registered trademarks of Ablynx N.V.

In the polypeptides of the invention, each antigen binding domain comprises at least one CDR as defined herein and preferably two or three CDRs. In the preferred polypeptides of the invention, the preferred structure of the immunoglobulin single variable domain is that of a $V_{HH}$ domain or Nanobody and which has the structure:

FR-CDR-FR-CDR-FR-CDR-FR wherein CDR and FR are as further defined herein.

Preferred biparatopic Nanobodies in accordance with the invention have one of the following structures:

i) FR1-CDR1-FR2-CDR2-FR3-CDR3-FR4--LINKER--FR5-CDR4-FR6-CDR5-FR7-CDR6-FR8
ii) FR1-CDR1-FR2-CDR2-FR3-CDR3-FR4--LINKER--FR5-CDR4-FR6-CDR5-FR7-CDR6-FR8--LINKER--HLE
iii) FR1-CDR1-FR2-CDR2-FR3-CDR3-FR4--LINKER--HLE--LINKER--FR5-CDR4-FR6-CDR5-FR7-CDR6-FR8 wherein if FR1-CDR1-FR2-CDR2-FR3-CDR3-FR4 comprises the first antigen binding domain (linear SEQ ID No 7 binder) then FR5-CDR4-FR6-CDR5-FR7-CDR6-FR8 comprises the second antigen domain (linear SEQ ID No 7 non-binder) and if FR1-CDR1-FR2-CDR2-FR3-CDR3-FR4 comprises the second antigen domain (linear SEQ ID No 7 non-binder) then FR5-CDR4-FR6-CDR5-FR7-CDR6-FR8 comprises the first antigen binding domain (linear SEQ ID No. 7 binder) and the HLE is a binding unit providing an increased in vivo half-life.

Fragments or variants of the preferred biparatopic Nanobody above are encompassed by the invention including embodiments where the CDRs and FRs are of Camalid origin or embodiments wherein one of more of the FRs has at least one humanising substitution and are preferably fully humanised.

Particularly preferred biparatopic Nanobodies in accordance with the invention are those designated herein as 163D2/127D1, 163E3/127D1, 163E3/54B12, 163D2/54B12, 2B2/163E3, 2B2/163D2, 97A9/2B2 and 97A9/54B12, the amino acid sequences of which are shown in Table 13 and in particular, variants thereof wherein the FRs include sequence optimising amino acid substitutions as defined herein and such as shown for the component Nanobodies in Table 32.

Additional particularly preferred biparatopic Nanobodies in accordance with the invention are those shown in Table 33.

The polypeptides of the invention are modulators of CXCR2 signal transduction and block, reduce or inhibit CXCR2 activity. They may inhibit the binding of the natural ligand, for example Gro-α, to human CXCR2 with an IC50 of less than 20 nM. Preferably, the polypeptides of the invention and in particular the biparatopic Nanobodies of the invention, are capable of cross-blocking binding to CXCR2 with one or more of 163D2/127D1, 163E3/127D1, 163E3/54B12, 163D2/54B12, 2B2/163E3, 2B2/163D2, 97A9/2B2 and 97A9/54B12 discussed above.

Also encompassed by the invention described herein are the monovalent polypeptide building blocks which are used in the constructions of bi- or multiparatopic or multivalent Nanobodies. Preferred monovalent Nanobodies are each and every polypeptide with the amino acid sequences set forth in Table 9, Table 34 or amino acid sequences in which at least one of the framework regions has at least 80% amino acid identity with an amino acid sequence set forth in Table 9 or table 34. Preferred monovalent Nanobodies are those set forth in Table 9 and but with at least one sequence optimising, substitution in the framework region such as those Nanobodies shown in Table 32 or table 34. Particularly preferred is the monovalent Nanobody designated 137B7 and sequence optimised, versions thereof.

Preferred polypeptides of the invention bind to an epitope of comprising amino acids F11, F14 and W15 of SEQ ID No. 1 (CXCR2). In the preferred biparatopic polypetides of the invention, such as biparatopic nanobodies, the second antigen binding domain binds to an epitope within the external loops of human CXCR2 (amino acid residues 106-120, 184-208 and 274-294 of SEQ ID No. 1). In one embodiment of the invention said epitope is confomational. In an embodiment of the invention said epitope comprises amino acid residues W112, G115, I282 and T285 of SEQ ID No. 1.

The invention also encompasses nucleic acid molecules encoding any polypeptide in accordance with the invention as well as nucleic acids encoding fragments thereof such as nucleic acids encoding the individual Nanobodies which are comprised within the biparatopic Nanobodies. Vectors comprising the nucleic acids of the invention and host cells comprising said vectors and capable of expressing a polypeptide in accordance with the invention are also encompassed within the invention.

In another aspect the invention relates to pharmaceutical compositions comprising a polypeptide in accordance with the invention in combination with a pharmaceutically acceptable carrier, diluent or exipient. As the polypeptides of the invention are able to block, inhibit or reduce the activity of CXCR2 they are useful for treatment of diseases in which abberrent signal transduction from CXCR2 plays a role. Such diseases may include atherosclerosis, glomerulonephritis, Inflammatory Bowel Disease (Crohn's), Angiogenesis, Multiple sclerosis, Psoriasis, Age-related Macular degenerative disease, Ocular Behcet Disease, Uveitis, non-small cell carcinoma, Colon cancer, Pancreatic cancer, Esophageal cancer, Melanoma, Hepatocellular carcinoma or ischaemia perfusion injury. Such diseases may also include conditions of the respiratory tract such as Cystic Fibrosis, severe Asthma, exacerbation of Asthma, allergic Asthma, Acute lung injury, Acute respiratory distress syndrome, Idiopathic pulmonary fibrosis, Airway remodeling, Bronchiolitis obliterans syndrome or Bronchopulmonary dysplasia.

In a particularly preferred embodiment the polypeptides of the invention are for use in treating chronic obstructive pulmonary disorder (COPD) or exacerbations of COPD, which is characterised by migration of leucocytes, in particular neutrophils to lung parenchyma and subsequent distruction thereof, which migration is mediated through CXCR2 signalling. The ability of the polypeptides of the invention to block, inhibit or reduce CXCR2 activity makes them excellent candidates for use in the prevention or treatment of this disease.

For treatment of humans it is preferable that the polypeptide of the invention is directed against or specifically binds to human CXCR2. It is preferred however, if said polypeptide can cross-react with primate CXCR2, in particular Cynomolgus monkey CXCR2 in order that appropriate toxicity testing can be carried out in said monkeys. The polypeptides of the invention may be directed against or specifically bind to CXCR2 homologues from other species if veterinary use is contemplated.

Other aspects of the invention will become apparent from the further discussion herein.

DESCRIPTION OF THE FIGURES

FIG. 1 shows the response curves obtained when the ability of two Nanobodies and a biparatopic Nanobody of the invention to block [$^{35}$S]GTPγS release from CHO-CXCR2 membranes stimulated with agonist Gro-α at is measured at increasing concentrations of Nanobody.

FIG. 1*a* shows the result for Nanobody 54B12 (SEQ ID No 90 in Table 9), FIG. 1*b* shows the result for Nanobdy 163E3 (SEQ ID No 42 in Table 9) and FIG. 1*c* shows the result for biparatopic Nanobody 54B12/163E3 (SEQ ID No 68 in Table 13).

DEFINITIONS

In the present description, examples and claims:

a) Unless indicated or defined otherwise, all terms used have their usual meaning in the art, which will be clear to the skilled person. Reference is for example made to the standard handbooks mentioned below as follows. Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10 Ed. Blackwell Publishing, UK (2001); and Janeway et al., "Immunobiology" (6th Ed.), Garland Science Publishing/Churchill Livingstone, N.Y. (2005).

b) Unless indicated otherwise, the term "immunoglobulin" or "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H$/$V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acid sequences or nucleotide sequences encoding the same, unless the context requires a more limited interpretation.

c) Unless indicated otherwise, the term "immunoglobulin single variable domain" is used as a general term to include but not limited to antigen-binding domains or fragments such as $V_{HH}$ domains or $V_H$ or $V_L$ domains, respectively. The terms antigen-binding molecules or antigen-binding proteins are used interchangeably and include also the term Nanobodies. The immunoglobulin single variable domains further are light chain variable domain sequences (e.g. a $V_L$-sequence), or heavy chain variable domain sequences (e.g. a $V_H$ sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs", or immunoglobulin sequences thar are suitable for use as dAbs, or Nanobodies, including but not limited to $V_{HH}$ sequences. The invention includes immunoglobulin sequences of different origin, comprising mouse, rat, rabbit, donkey, human and camelid immunoglobulin sequences. The immunoglobulin single variable domain includes fully human, humanised, otherwise sequence optimised or chimeric immunoglobulin sequences. The immunoglobulin single variable domain and structure of an immunoglobulin single variable domain can be considered—without however, being limited thereto—to be comprised of four framework regions of "FR's", which are referred to in the art and herein as "Framework region 1" or "FR1"; as "Framework region 2" or "FR2"; as "Framework region 3" or "FR3"; and as Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

d) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, 5106-12, Gonzales et al., Tumour Biol., 2005, 26(1), 31-43, which describe techniques for protein engineering, such as affinity maturation and other techniques for improving the specificity and other desired properties of proteins such as immunoglobulins.

e) Amino acid residues will be indicated according to the standard three-letter or one-letter amino acid code.

f) For the purposes of comparing two or more nucleotide sequences, the percentage of "sequence identity" between a first nucleotide sequence and a second nucleotide sequence may be calculated or determined by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique. The degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

g) For the purposes of comparing two or more amino acid sequences, the percentage of "sequence identity" between a first amino acid sequence and a second amino acid sequence (also referred to herein as "amino acid identity") may be calculated or determined by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein; or using a suitable computer algorithm or technique. For the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, as disclosed in v) below.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Nad. Acad. Sci. USA 81: 140-144, 1984; Kyte & Doolittle; J. Molec. Biol. 157: 105-132, 1981, and Goldman et al., Ann. Rev. Biophys. Chem. 15: 321-353, 1986, all incorporated herein in their entirety by reference. Regarding the primary and secondary structure of Nanobodies, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999).

h) When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences.

i) When a nucleotide sequence or amino acid sequence is said to "comprise" another nucleotide sequence or amino acid sequence, respectively, or to "essentially consist of another nucleotide sequence or amino acid sequence, this may mean that the latter nucleotide sequence or amino acid sequence has been incorporated into the firstmentioned nucleotide sequence or amino acid sequence, respectively, but more usually this generally means that the firstmentioned nucleotide sequence or amino acid sequence comprises within its sequence a stretch of nucleotides or amino acid residues, respectively, that has the same nucleotide sequence or amino acid sequence, respectively, as the latter sequence, irrespective of how the firstmentioned sequence has actually been generated or obtained (which may for example be by any suitable method described herein). By means of a non-limiting example, when a biparatopic immunoglobulin single variable domain, for example a Nanobody, of the invention is said to comprise a CDR sequence, this may mean that said CDR sequence has been incorporated into the biparatopic Nanobody of the invention, but more usually this generally means that the biparatopic Nanobody of the invention contains within its sequence a stretch of amino acid residues with the same amino acid sequence as said CDR sequence, irrespective of how said biparatopic Nanobody has been generated or obtained. It should also be noted that when the latter amino acid sequence has a specific biological or structural function, it preferably has essentially the same, a similar or an equivalent biological or structural function in the firstmentioned amino acid sequence (in other words, the firstmentioned amino acid sequence is preferably such that the latter sequence is capable of performing essentially the same, a similar or an equivalent biological or structural function). For example, when a biparatopic Nanobody of the invention is said to comprise a CDR sequence or framework sequence, respectively, the CDR sequence and framework are preferably capable, in said biparatopic Nanobody, of functioning as a CDR sequence or framework sequence, respectively. Also, when a nucleotide sequence is said to comprise another nucleotide sequence, the firstmentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the firstmentioned, larger nucleotide sequence).

j) A nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis;

k) The term "antigen binding domain" as used herein refers to a sequence of amino acids in an immunoglobulin comprising at least one CDR and being of a conformation to recognise a target antigenic determinant or epitope.

l) The terms "antigenic determinant" and "epitope", which may also be used interchangeably herein, refers to an amino acid sequence within the target CXCR2 which is recognised by the antigen binding domains, whether in linear or non-linear conformation.

m) A polypeptide of the invention such as, for example, a biparatopic Nanobody as described herein or a fragment thereof that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

n) The term "specificity" refers to the number of different types of antigens or antigenic determinants to which a particular antigen-binding domain of a polypeptide of the invention can bind. The specificity of an antigen-binding protein for any particular antigen/epitope can be determined based on affinity and/or avidity, as described on pages 53-56 of WO 08/020,079 (incorporated herein by reference), which also describes some preferred techniques for measuring binding between a polypeptide and the pertinent antigen or epitope. Typically, in each antigen-binding protein (such as the polypeptides of the invention) each antigen binding domain may each independently bind to their antigen/epitope with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, the biparatopic polypeptide of the invention will bind to the desired antigen with an affinity less than 500 nM, preferably less than 200 nM, more preferably less than 10 nM, such as less than 500 pM. Specific binding of the polypeptide of the invention to CXCR2 can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020,079, the dissociation constant may be the actual or apparent dissociation constant. Methods for determining the dissociation constant will be clear to the skilled person, and for example include the techniques mentioned on pages 53-56 of WO 08/020,079.

o) The half-life of a polypeptide of the invention, in particular a biparatopic Nanobody in accordance with the invention can generally be defined as the time taken for the serum concentration of the polypeptide of the invention to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020,079. As also mentioned therein on page 57 of WO 08/020,079, the half-life can be expressed using parameters such as the t1/2-alpha, t1/2-beta and the area under the curve (AUC). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" refers to an increase in the t1/2-beta, either with or without an increase in the t1/2-alpha and/or the AUC or both.

p) In the context of the present invention, "blocking, reducing or inhibiting" the activity of CXCR2 as measured using a suitable in vitro, cellular or in vivo assay may mean either blocking, reducing or inhibiting the activity of a relevant or intended biological activity of CXCR2, by at least 1%, preferably at least 5%, such as at least 10% or at least 25%, for example by at least 50%, at least 60%, at least 70%, at least 80%, or 90% or more, compared to activity CXCR2 in the same assay under the same conditions but without the presence of the polypeptide of the invention.

As will be clear to the skilled person, the inhibiting may also involve effecting a decrease in affinity, avidity, specificity and/or selectivity of CXCR2 for one or more of its ligands or binding partners. and/or effecting a decrease in the sensitivity of CXCR2 for one or more conditions in the medium or surroundings in which CXCR2 is present (such as pH, ion strength, the presence of co-factors, etc.), compared to the same conditions but without the presence of the polypeptide of the invention. As will be clear to the skilled person, this may again be determined in any suitable manner and/or using any suitable assay known per se, depending on the target or antigen involved.

q) As used herein "modulating" may mean allosteric modulation of CXCR2; and/or reducing or inhibiting the binding of CXCR2 to one of its ligands and/or competing with a natural ligand for binding to CXCR2. Modulating may for example also involve effecting a change in respect of the folding or confirmation of CXCR2 or in respect of its ability to change its confirmation (for example, upon binding of a ligand), to associate with other (sub)units, or to disassociate. Modulating may for example also involve effecting a change in the ability of CXCR2 to transport other compounds or to serve as a channel for other compounds (such as ions). Modulating, in particular inhibition or reduction of CXCR2 activity by the polypeptides of the invention, in particular the biparatopic Nanobodies of the invention may be reversible or irreversible, but for pharmaceutical and pharmacological purposes will usually be in a reversible manner.

r) A polypeptide of the invention is said to be "specific for" CXCR2 compared to a second target or antigen when it binds to CXCR2 with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10,000 times or more than the affinity with which it binds a second target or polypeptide. For example, the polypeptide of the invention may bind CXCR2 at a $K_D$ value that is at least 10 times less, such as at least 100 times less, and preferably at least 1000 times less, such as 10.000 times less or even less than that, than the $K_D$ with which it binds to another target or polypeptide or epitope thereof.

s) The terms "cross-block", "cross-blocked" and "cross-blocking" are used interchangeably herein to mean the ability of a immunoglobulin single variable domain or polypeptide to interfere with the binding of other immunoglobulin single variable domains or polypeptides of the invention to a given target. The extent to which an immunoglobulin single variable domain or polypeptide of the invention is able to interfere with the binding of another target, and therefore it can be said to cross-block according to the invention, can be determined using competition binding assays. One particularly suitable quantitative cross-blocking assay uses a FACS- or an ELISA-based approach to measure competition between the labelled (e.g. His-tagged, radioactively or fluorescently labelled) immunoglobulin single variable domain or polypeptide according to the invention and the other binding agent in terms of their binding to the target. The experimental part generally describes a suitable FACS- and ELISA-displacement-based assay for determining whether a binding molecule cross-blocks or is capable of cross-blocking an immunoglobulin single variable domain or polypeptide according to the invention. It will be appreciated that the assay can be used with any of the immunoglobulin single variable domains or other binding agents described herein. Thus, in general, a cross-blocking amino acid sequence or other binding agent according to the invention is one which will bind to the target in the above cross-blocking assay such that, during the assay and in the presence of a second amino acid sequence or other binding agent of the invention, the recorded displacement of the immunoglobulin single variable domain or polypeptide according to the invention is between 50% and 100% of the maximum theoretical displacement by the to be tested potentially cross-blocking agent (e.g. other antibody fragment, $V_{HH}$, dAb or similar $V_H$/$V_L$ variant).

t) A polypeptide in accordance with the invention, is said to be "cross-reactive" for two different antigens or antigenic determinants (such as serum albumin or CXCR2 from two different species of mammal, such as human and cynomolgous monkey) if it is specific for (as defined herein) both these different antigens or antigenic determinants.

u) As defined herein conservative amino acid changes refers to amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, He, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; H is into Asn or into Gln; He into Leu or into Val;

Leu into He or into Val; Lys into Arg, into Gln or into Glu; Met into Leu, into Tyr or into He; Phe into Met, into Leu or into Tyr; Ser into Thr; Thr into Ser; Trp into Tyr; Tyr into Trp; and/or Phe into Val, into He or into Leu.

v) As used herein a CDR is a complementarity determining region of the polypeptides of the invention. A CDR is a stretch of amino acids which alone or in combination with one or more other CDRs establishes the complementarity with the antigen(s) or epitope(s) that the polypeptide of the invention recognises. CDRs are identified in amino acid sequences by certain numbering conventions. In respect of the claims and specific description herein, Kabat numbering is used.

w) As used herein FR is a framework region (sometimes called an FW). Framework regions are stretches of amino acids which flank the one or more CDRs and support them in the correct three-dimensional conformation for antigen or epitope recognition. FRs are not specific to the target antigen or epitope but are specific to the species origin or type of immunoglobulin molecules in which they are present. As discussed in detail herein, in the polypeptides of the invention there is scope for the amino acid sequences of the framework region to be engineered to be different to the framework sequence applied by the source of the immunoglobulin eg Camelid.

x) As used herein CXCR2 refers to a cytokine receptor present at least on the surface of leucocytes and for which the naturally occurring ligand may be Gro-α, β, γ, IL-8, ENA-78 or GCP-2. CXCR2 in general refers herein to any protein exhibiting CXCR2 function regardless of species of origin. However, as used herein human CXCR2 refers to a protein comprising an amino acid sequence as set forth in SEQ ID No 1 or any allelic variant or orthologue thereof and Cynomolgus CXCR2 refers to a protein comprising the amino acid sequence set forth in SEQ ID No 3 or any allelic variant or orthologue thereof.

y) As used herein "sequence-optimisation" refers to facilitating substitutions, insertions or deletions in an amino acid sequence for the purposes of securing particular properties or structural characteristics which may not present in the native sequence. Such substitutions, insertions or deletions may be carried out, for example, for the purpose of chemical stabilisation, for improvements in ability to manufacture, for avoidance of pyroglutamate formation or oxidation or isomerisation. Methods to achieve optimisation in such properties which can be employed for the biparatopic polypeptides, in particular biparatopic Nanobodies of the invention are described in WO 2009/095235 which is incorporated herein by reference. Sequence optimisation techniques may be carried out also for the purpose of humanising a biparatopic polypeptide of the invention in a manner as described herein. Thus, wherever sequence optimisation, sequence optimising or sequenced-optimised is used herein, this encompasses specific reference to humanising substitutions or insertions and to partially or fully humanised biparatopic polypeptides, preferably biparatopic Nanobodies.

DETAILED DESCRIPTION OF THE INVENTION

As aforesaid, in its first aspect the invention provides a polypeptide comprising at least two immunoglobulin antigen binding domains, which polypeptide is directed against or binds to chemokine receptor CXCR2 wherein said polypeptide includes a first antigen binding domain recognising a first epitope on CXCR2 and a second antigen binding domain recognising a second epitope on CXCR2.

A preferred polypeptide of the invention comprises a first antigen binding domain which is capable of binding to a linear peptide consisting of the sequence of amino acids set forth in SEQ ID No 7 and a second antigen binding domain which is either not capable of binding or binds with lower affinity to said linear peptide. SEQ ID No 7 is the first 19 N-terminal amino acids of human CXCR2.

In one embodiment the first antigen binding domain recognises a first epitope comprising or within amino acids 1 to 19 of CXCR2 and said second antigen binding domains recognises a second epitpope on CXCR2 outside amino acids 1 to 19.

The first and second antigen binding domains may be comprised in one or more amino acid sequences characteristic of a molecule of the immunoglobulin class. For example those peptides or polypeptides may each comprise a conventional four chain antibody joined by a linker. In particular the polypeptide of the invention may be one wherein said first and second antigen binding domains are comprised in first and second antibodies respectively each comprising two heavy and two light chains and wherein said first and second antibodies are joined by a linker. Alternatively, said first and second antigen binding domains may be comprised within a single antibody comprising two heavy and two light chains.

In an alternative embodiment of the invention the first and second antigen binding domains are comprised within amino acid sequences which are heavy chain antibodies and in particular the polypeptide of the invention may be one wherein said first antigen binding domain is comprised within a first heavy chain antibody and said second antigen binding domain is comprised within a second heavy chain antibody wherein said first and second heavy chain antibodies are joined by a linker Such heavy chain antibodies may be obtained from the Camelid family and comprise, in nature just two heavy chains each with a constant and variable region. A polypeptide in which said first and second binding domains are comprised within a single heavy chain antibody comprising two heavy chains is also contemplated by the invention.

In another alternative embodiment of the peptides or polypeptides comprising the first and second binding domain may be a single chain Fv (scFv). These comprise a linear fusion of a $V_L$ and $V_H$ domain. Accordingly, the polypeptide of the invention may be one wherein said first and second antigen binding domains are comprised within first and second antibody single chain Fv (scFv) fragments respectively and wherein said first and second scFv fragments are joined by a linker.

In a further alternative the first and second antigen binding domains may be comprised in one or more Fab or F(ab)2 fragments of a conventional four chain antibody. A Fab fragment comprises one constant domain and one variable domain from each of one heavy and one light chain of a conventional antibody. A F(ab)2 fragment comprises two Fab fragments joined by part of the hinge region of a conventional antibody. In particular the polypeptide of the invention may be one wherein said first and second antigen binding domains are comprised within first and second antibody Fab or F(ab)2 fragments respectively and wherein said first and second Fab or F(ab)2 fragments are joined by a linker. In such an embodiment said first antigen binding domain may be comprised within an antibody Fab fragment and said second antigen binding domain is comprised within a F(ab)2 fragment or visa versa.

In a preferred embodiment of the invention, the first antigen binding domain is comprised within a first immunoglobulin single variable domain and said second antigen binding domain is comprised within a second immunoglobulin single variable domain.

A particular example of this embodiment of the invention is where the first and second antigen binding domains are comprised in a domain antibody called a d(ab). d(ab)s comprise single $V_L$ or $V_H$ domains from conventional antibodies. Thus, the polypeptide of the invention may be one wherein said first and second antigen binding domains are comprised within first and second domain antibodies (dAbs) and wherein said first and second dAbs are joined by a linker Said first and second dAbs may be antibody $V_L$ fragments or antibody $V_H$ fragments. In such an embodiment said first antigen binding domain may be comprised in a $V_L$ fragment and said second antigen binding domain may be comprised in a $V_H$ fragment or visa versa.

For a general description of (single) domain antibodies, reference is also made to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

The variable region of a single chain of such a heavy chain antibody is known as the $V_{HH}$ domain and comprises an antibody fragment known as a Nanobody. A Nanobody may comprise the whole $V_{HH}$ domain or a fragment thereof. For a general description of heavy chain antibodies and the variable domains thereof reference is made to the prior art mentioned on page 59 of WO08/020,079 and to the list of references mentioned on pages 41 to 43 of International application WO06/040153. $V_{HH}$ domains have a number of unique structural characteristics and functional properties which make isolated $V_{HH}$ domains (as well as Nanobodies based thereon with the same structural and functional characteristics as naturally occurring $V_{HH}$ domains) and polypeptides containing same highly advantageous as functional antigen binding domains or polypeptides. In particular, $V_{HH}$ domains (which have been "designed" by nature to functionally bind to antigen without the presence, or without any interaction with, a light chain variable domain) and Nanobodies can function as a single, relatively small, functional antigen-binding structural unit, domain or protein. As used herein the term Nanobody encompasses not only naturally occurring $V_{HH}$ domains and fragments thereof but variants and derivatives thereof as discussed in detail herein.

In the most preferred embodiment of the invention the biparatopic polypeptide of the invention is one wherein said first antigen binding domain is comprised within a first Nanobody and said second antigen binding domain is comprised within a second Nanobody and said first and second Nanobodies are joined by a linker.

The structure of the $V_{HH}$ domain may be represented as;

FR-CDR-FR-CDR-FR-CDR-FR and the biparatopic polypeptide of the invention may have one of the following structures:

i) FR1-CDR1-FR2-CDR2-FR3-CDR3-FR4--LINKER--FR5-CDR4-FR6-CDR5-FR7-CDR6-FR8 ii) FR1-CDR1-FR2-CDR2-FR3-CDR3-FR4--LINKER--FR5-CDR4-FR6-CDR5-FR7-CDR6-FR8--LINKER--HLE iii) FR1-CDR1-FR2-CDR2-FR3-CDR3-FR4--LINKER--HLE--LINKER--FR5-CDR4-FR6-CDR5-FR7-CDR6-FR8 wherein if FR1-CDR1-FR2-CDR2-FR3-CDR3-FR4 comprises the first antigen binding domain (linear SEQ ID No 7 binder) then FR5-CDR4-FR6-CDR5-FR7-CDR6-FR8 comprises the second antigen domain (linear SEQ ID No 7 non-binder) and if FR1-CDR1-FR2-CDR2-FR3-CDR3-FR4 comprises the second antigen domain (linear SEQ ID No 7 non-binder) then FR5-CDR4-FR6-CDR5-FR7-CDR6-FR8 comprises the first antigen binding domain (linear SEQ ID No. 7 binder) and the HLE is a binding unit providing an increased in vivo half-life.

Accordingly, as used herein "biparatopic Nanobody in accordance with the invention" refers to a polypeptide comprising two single Nanobodies joined by a linker.

However, biparatopic Nanobodies of the invention may include just one CDR in each Nanobody. If so the preferred CDR is CDR3 and/or CDR6. Biparatopic Nanobodies in accordance with the invention may include however CDR1 or CDR2 or CDR3 or CDR1 and CDR2 or CDR1 and CDR3 or CDR2 and CDR3 or CDR1 and CDR2 and CDR3 in the N-terminal Nanobody and any one of the following combinations in the C-terminal Nanobody: CDR4 or CDR5 or CDR6 or CDR4 and CDR5 or CDR4 and CDR6 or CDR5 and CDR6 or CDR4 and CDR5 and CDR6. As indicated above the biparatopic Nanobody of the invention may comprise all of CDR1, CDR2, CDR3, CDR4, CDR5 and CDR6, each CDR being flanked by an FR.

The FRs may have amino acid sequences consistent with the Camelid source. However, in preferred embodiments one or more of the FRs has at least one sequence optimising, amino acid substitution and preferably one or more and more preferably all, of the FRs are partially or fully humanised. Substitutions for sequence optimisation are discussed in more detail below.

It is mentioned herein also that in embodiments of the invention in which the first and second antigen binding domains are comprised in first and second immunoglobulin single variable domains which are not Nanobodies but in domains or fragments of conventional antibodies as discussed above, for example human antibodies, domains or fragments, it is possible to modify the CDR(s) therein with at least one camelising substitution and optionally generate fully camelised CDRs.

As further described herein, the total number of amino acid residues in a single Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

As further described herein, the amino acid residues of a Nanobody are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication), and accordingly FR1 of a Nanobody may comprise the amino acid residues at positions 1-30, CDR1 of a Nanobody may comprise the amino acid residues at positions 31-35, FR2 of a Nanobody may comprise the amino acids at positions 36-49, CDR2 of a Nanobody may comprise the amino acid residues at positions 50-65, FR3 of a Nanobody may comprise the amino acid residues at positions 66-94, CDR3 of a Nanobody may comprise the amino acid residues at positions 95-102, and FR4 of a Nanobody may comprise the amino acid residues at positions 103-113. In the preferred biparatopic Nanobody of the invention the N-terminal Nanobody may have FRs and CDRs at the positions given above and in the C-terminal Nanobody FR5 of the Nanobody may comprise the amino acid residues at positions 1-30, CDR4 of the Nanobody may comprise the amino acid residues at positions 31-35, FR6 of the Nanobody may comprise the amino acids at positions 36-49, CDR5 of the Nanobody may comprise the amino acid residues at positions 50-65, FR7 of the Nanobody may comprise the amino acid residues at positions 66-94, CDR6 of the Nanobody may comprise the amino acid residues at positions 95-102, and FR8 of the Nanobody may comprise the amino acid residues at positions 103-113.

However, it will be appreciated that CDRs and FRs in an antibody, and in particular a Nanobody, may be identified by numbering systems alternative to Kabat. These include the Chothia, IMGT and AHo systems. Indentification of the positions of the CDRs or FRs of any one of the amino acid sequences identified in Tables 9, 13, 19, 32, 33 and 34 according to these alternative numbering systems can be achieved by analysis of the sequences. For this purpose, reference may be had to the following websites: http://www.biochem.ucl.ac.uk/~martin/(Chothia); http://imgt.cines.fr (IMGT) and http://www.bio.uzh.ch/antibody/index.html (AHo). Specifically, in the preferred biparatopic Nanobodies of the invention described herein, CDRs 1, 2, 3, 4, 5 or 6 may be defined by one of these numbering systems alternative to Kabat but will still be within the scope of the invention.

The Chotia CDRs for some nanobodies according to the invention is shown in Table 35.

Nanobodies may be of the so-called "$V_H3$ class" (i.e. Nanobodies with a high degree of sequence homology to human germline sequences of the $V_H3$ class such as DP-47, DP-51 or DP-29), which Nanobodies are preferred for construction of the biparatopic Nanobodies of this invention. It should however be noted that any type of Nanobody directed against CXCR2, and for example the Nanobodies belonging to the so-called "$V_H4$ class" (i.e. Nanobodies with a high degree of sequence homology to human germline sequences of the $V_H4$ class such as DP-78), as for example described in WO 07/118,670, may be used in the construction of the biparatopic Nanobodies of the invention.

The linker molecule which joins the one or more peptides or polypeptides comprising the first and second antigen binding domains in accordance with the invention may or may not be of immunoglobulin origin. Where the polypeptide of the invention is a biparatopic immunoglobulin single variable domain, for example a Nanobody, the linker joins the C-terminal of one immunoglobulin single variable domain comprising an antigen binding domain to the N-terminal of another immunoglobulin single variable domain comprising an antigen binding domain.

Suitable spacers or linkers for use in the biparatopic polypeptides of the invention for linking the first and second antigen binding domains together, in particular the two Nanobodies together, will be clear to the skilled person, and may generally be any linker or spacer used in the art to link amino acid sequences. Preferably, said linker or spacer is suitable for use in constructing proteins or polypeptides that are intended for pharmaceutical use.

For example, a linker may be a suitable amino acid sequence, and in particular amino acid sequences of between 1 and 50, preferably between 1 and 30, such as between 1 and 10 amino acid residues. Some preferred examples of such amino acid sequences include glyser linkers, for example of the type $(gly_x ser_y)_z$, such as (for example $(gly_4ser)_3$ or $(gly_3ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678).

Some other possible linkers are poly-alanine (such as AAA), as well as the linkers GS30 (SEQ ID NO: 85 in WO 06/122825) and GS9 (SEQ ID NO: 84 in WO 06/122825).

Preferred linkers in accordance with the invention are peptide linkers between 3 and 50 amino acids long, for example linkers of amino acid length 3 to 9, 10 to 15, 16 to 20, 21 to 25, 26 to 35, 36 to 40, 41 to 45 or 46 to 50. In one embodiment of the invention the peptide linker is 35 amino acids long. The linker may consist of just two different amino acids. As aforesaid these may be glycine and serine. Alternatively they may be proline and serine.

In some embodiments of the invention, in particular the biparatopic Nanobodies of the invention, the peptide linker consists of the amino acid sequence:

```
                                      (SEQ ID No 220)
GGGGSGGGGSGGGGSGGGGSGGGGSGGGGSGGGGS.
```

Other suitable linkers generally comprise organic compounds or polymers, in particular those suitable for use in proteins for pharmaceutical use. For instance, poly(ethyleneglycol) moieties have been used to link antibody domains, see for example WO 04/081026.

Thus, in another aspect the invention relates to a molecule comprising at least two polypeptides, which molecule is directed against or binds to chemokine receptor CXCR2, wherein a first polypeptide comprises a first immunoglobulin antigen binding domain and a second polypeptide comprises a second immunoglobulin antigen binding domain wherein said first and second antigen binding domains recognise first and second epitopes on CXCR2 and wherein said at least two polypeptides are joined by a non-peptide linker.

Preferably, in the aspect of the invention the first antigen binding domain is capable of binding to a linear peptide consisting of the sequence of amino acids set forth in SEQ ID No 7 and said second antigen binding domain is either not capable of binding or binds with lower affinity to said linear peptide. Preferably, the first epitope comprises or is within amino acids 1 to 19 of CXCR2 and the second epitope is outside amino acids 1 to 19 of CXCR2.

Preferably, in this aspect of the invention the first and second antigen binding domains are comprised in immunoglobulin single variable domains, wherein said first and second immunoglobulin single variable domains are preferably Nanobodies and in particular any of the Nanobodies specifically described herein.

In all aspects of the invention described herein, an essential property for the linker is that it is of a length and conformation to permit the first and second antigen binding domains to bind to their respective epitopes on CXCR2.

The linker(s) used may also confer one or more other favourable properties or functionality to the polypeptides of the invention, and/or provide one or more sites for the formation of derivatives and/or for the attachment of functional groups (e.g. as described herein for the derivatives of the biparatopic Nanobodies of the invention). For example, linkers containing one or more charged amino acid residues (see Table A-2 on page 48 of the International application WO 08/020,079) can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for ease of expression and production, a polypeptide of the invention will be a linear polypeptide. However, the invention in its broadest sense is not limited thererto.

For example, when a polypeptide of the invention comprises three of more Nanobodies, it is possible to link them by use of a linker with three or more "arms", with each "arm" being linked to a Nanobody, so as to provide a "star-shaped" construct. It is also possible, although usually less preferred to use circular constructs.

In particular, any arrangement of two or more Nanobodies with one or more linkers as identified above may be prepared. For example, a biparatopic, bi-specific Nanobody may be envisaged which comprises two immunoglobulin binding domains directed against or binding to CXCR2 and one or more immunoglobulin binding domains directed against or binding to human serum albumin (HSA) said HSA binding domain can be comprised with a Nanobody which is linked to the CXCR2 binding Nanobodies in any position, for example between two CXCR2 binding Nanobodies, via linkers as defined herein.

The present inventors have prepared biparatopic polypeptides in accordance with the invention. The amino acid sequences of multivalent and biparatopic anti-CXCR2 Nanobodies are shown in Table 13 among the Examples herein. Of these, particularly preferred polypeptides in accordance with the invention are the biparatopic Nanobodies designated in Table 13 as 163D2-127D1, 163E3-127D1, 163E3-54B12, 163D2-54B12, 2B2-163E3, 2B2-163D2, 97A9-2B2, 97A9-54B12, 127D1-163D2, 127D1-163E3, 2B2-97A9, 54B12-163D2, 54B12-163E3, 163D2-2B2 and 163E3,-2B2 as well as 127D1-97A9, 54B12-97A9 and 97A9-127D1 and sequence-optimised, variants thereof. All of these biparatopic Nanobodies comprise a first Nanobody comprising a first antigen binding domain which is capable of binding to a linear peptide consisting of the sequence of amino acids set forth in SEQ ID No 7 (amino acids 1-19 of CXCR2) and a second Nanobody comprising a second antigen binding domain which is either not capable of binding or binds with lower affinity to said linear peptide (see Table 8). Particularly preferred in accordance with the invention are 163D2-127D1, 163E3-127D1, 163E3-54B12, 163D2-54B12, 2B2-163E3, 2B2-163D2, 97A9-2B2 and 97A9-54B12.

1) 163D2-127D1 (SEQ ID No 58)

This embodiment of the invention relates to a biparatopic Nanobody wherein said second Nanobody as defined above includes at least one CDR comprising an amino acid sequence selected from the group consisting of SEQ ID Nos 145, 165 and 185 or an amino acid sequence having at least 80% amino acid sequence identity with the amino acid sequences of SEQ ID Nos 145, 165 or 185 and wherein said first Nanobody includes at least one CDR comprising an amino acid sequence selected from the group consisting of SEQ ID Nos 141, 161 and 181 or an amino acid sequence having at least 80% amino acid identity with the amino acid sequences of SEQ ID Nos 141, 161 or 181.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said second Nanobody CDR1 comprises an amino acid sequence as set forth in SEQ ID No 145, CDR2 comprises the amino acid sequence set forth in SEQ ID No 165 and CDR3 comprises the amino acid sequence set forth in SEQ ID No 185 and wherein in said first Nanobody CDR4 comprises an amino acid sequence as set forth in SEQ ID No 141, CDR5 comprises the amino acid sequence set forth in SEQ ID No 161 and CDR6 comprises the amino acid sequence set forth in SEQ ID No 181 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 145, 165, 185, 141, 161 or 181.

The amino acid sequences may differ from those set forth in any of SEQ ID Nos 145, 165, 185, 141, 161 or 181 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 83, FR2 comprises an amino acid sequence as set forth in SEQ ID No 104, FR3 comprises an amino acid sequence as set forth in SEQ ID No 124, FR4 comprises an amino acid sequence set forth in SEQ ID No 131, FR5 comprises an amino acid sequence as set forth in SEQ ID No 79, FR6 comprises an amino acid sequence as set forth in SEQ ID No 100, FR7 comprises an amino acid sequence as set forth in SEQ ID No 120 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 83, 104, 124, 131, 79, 100, or 120.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID No 58 or a polypeptide having at least 80% amino acid identity, at least 85%, at least 90% or at least 95% amino acid sequence identity with the amino acid sequence of SEQ ID No 58.

In another embodiment of this aspect of the invention the biparatopic Nanobody comprises the amino acid sequence set forth in SEQ ID No 58 or a sequence of amino acids having at least 80% amino acid sequence identity with the SEQ ID No 58 or at least 80% amino acid sequence identity with the framework regions thereof according to Kabut numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 58 but modified in the framework regions to include one or more sequence-optimising substitutions, preferably one or more of those identified as suitable in Table 28 for the 163D2 Nanobody and in Table 26 for the 127D1 Nanobody. Preferably the 163D2 Nanobody comprises the amino acid sequence set forth in SEQ ID No 218 or a sequence of amino acids having at least 80%, at least 85%, at least 90% or at least 95% amino acid sequence identity with SEQ ID No 218 and the 127D1 Nanobody comprises the amino acid sequence set forth in SEQ ID No 216 or a sequence of amino acids having at least 80%, at least 85%, at least 90% or at least 95% amino acid sequence identity with SEQ ID No 216. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

2) 163E3-127D1 (SEQ ID No 59)

This embodiment of the invention relates to a biparatopic Nanobody wherein said second Nanobody includes at least one CDR comprising an amino acid sequence selected from the group consisting of SEQ ID Nos 146, 166 and 186 or an amino acid sequence having at least 80% amino acid sequence identity with the amino acid sequences of SEQ ID Nos 146, 166 or 186 and wherein said first Nanobody includes at least one CDR selected from the group consisting of SEQ ID Nos 141, 161 and 181 or an amino acid sequence having at least 80% amino acid identity with the amino acid sequences of SEQ ID Nos 141, 161 or 181.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said second Nanobody CDR1 comprises an amino acid sequence as set forth in SEQ ID No 146, CDR2 comprises the amino acid sequence set forth in SEQ ID No 166 and CDR3 comprises the amino acid sequence set forth in SEQ ID No 186 and wherein in said first Nanobody CDR4 comprises an amino acid sequence as set forth in SEQ ID No 141, CDR5 comprises the amino acid sequence set forth in SEQ ID No 161 and CDR6 comprises the amino acid sequence set forth in SEQ ID No 181 or the amino acid sequences of CDR1, CDR2, CDR3, CDR4, CDR5 or CDR6 have at least 80% amino acid identity, at least 85%, at least 90% or at least 95% amino acid sequence identity with the any one of the amino acid sequences set forth in SEQ ID Nos 146, 166, 186, 141, 161 or 181.

The amino acid sequences may differ from those set forth in SEQ ID Nos 146, 166, 186, 141, 161 or 181 only in conservative amino acid changes. The amino acid sequences may differ from any of the sequence IDs above only in one, two or three amino acids.

In a preferred embodiment this aspect of the invention FR1 comprises an amino acid sequence as set forth in SEQ ID No 84, FR2 comprises an amino acid sequence as set forth in SEQ ID No 105, FR3 comprises an amino acid sequence as set forth in SEQ ID No 125, FR4 comprises an amino acid sequence set forth in SEQ ID No 131, FR5 comprises an amino acid sequence as set forth in SEQ ID No 79, FR6 comprises an amino acid sequence as set forth in SEQ ID No 100, FR7 comprises an amino acid sequence as set forth in SEQ ID No 120 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, or at least 85%, at least 90% or at least 95% amino acid sequence identity with amino acid sequences set forth in any of SEQ ID Nos 84, 105, 125, 131, 79, 100, or 120.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a preferred embodiment of this aspect of the invention the biparatopic Nanobody comprises the amino acid sequence set forth in SEQ ID No 59 or an amino acid sequence having at least 80% amino acid identity, or at least 85%, or at least 90%, or at least 95% identity with the amino acid sequence of SEQ ID No 59.

In one embodiment of this aspect of the invention the biparatopic Nanobody comprises the amino acid sequence set forth in SEQ ID NO 59 or an amino acid sequence having at least 80% identity with SEQ ID 59, or at least 80% amino acid sequence identity with the framework regions thereof according to kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 59 but modified in the framework regions to include one or more sequence-optimising substitutions, preferably one or more of those identified as suitable in Table 24 for the 163E3 Nanobody and in Table 26 for the 127D1 Nanobody. Preferably the 163E3 Nanobody comprises the amino acid sequence set forth in SEQ ID No 217 or a sequence of amino acids having at least 80%, at least 85%, at least 90% or at least 95% amino acid sequence identity with SEQ ID No 217 and the 127D1 Nanobody comprises the amino acid sequence set forth in SEQ ID No 216 or a sequence of amino acids having at least 80%, at least 85%, at least 90% or at least 95% amino acid sequence identity with SEQ ID No 216. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

3) 163E3/54B12 (SEQ ID No 62)

This embodiment of the invention relates to a biparatopic Nanobody wherein said second Nanobody includes at least one CDR comprising an amino acid sequence selected from the group consisting of SEQ ID Nos 146, 166 and 186 or an amino acid sequence having at least 80% amino acid sequence identity with the amino acid sequences of SEQ ID Nos 146, 166 or 186 and wherein said first Nanobody includes at least one CDR selected from the group consisting of SEQ ID Nos 151, 171 and 191 or an amino acid sequence having at least 80% amino acid identity with the amino acid sequences of SEQ ID Nos 151, 171 or 191.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said second Nanobody CDR1 comprises an amino acid sequence as set forth in SEQ ID No 146, CDR2 comprises the amino acid sequence set forth in SEQ ID No 166 and CDR3 comprises the amino acid sequence set forth in SEQ ID No 186 and wherein in said first Nanobody CDR4 comprises an amino acid sequence as set forth in SEQ ID No 151, CDR5 comprises the amino acid sequence set forth in SEQ ID No 171 and CDR6 comprises the amino acid sequence set forth in SEQ ID No 191 or wherein CDR1, CDR2, CDR3, CDR4, CDR5 or CDR6 have at least 80% amino acid identity, preferably at least 85% or at least 90% or at least 95% amino acid sequence identity with the any one of the amino acid sequences set forth in SEQ ID Nos 146, 166, 186, 151, 171 or 191.

The amino acid sequences may differ from those set forth in SEQ ID Nos 146, 166, 186, 151, 171, 191 only in conservative amino acid changes. The amino acid sequences may differ from any of the sequence IDs above only in one, two or three amino acids.

In accordance with this aspect of the invention FR1 comprises an amino acid sequence as set forth in SEQ ID No 84, FR2 comprises an amino acid sequence as set forth in SEQ ID No 105, FR3 comprises an amino acid sequence as set forth in SEQ ID No 125, FR4 comprises an amino acid sequence set forth in SEQ ID No 131, FR5 comprises an amino acid sequence as set forth in SEQ ID No 89, FR6 comprises an amino acid sequence as set forth in SEQ ID No 110, FR7 comprises an amino acid sequence as set forth in SEQ ID No 130 and/or FR8 comprises an amino acid sequence as set forth in SEQ ID No 131.

In the alternative, FRI, FR2, FR3, FR4, FR5, FR6, FR7 and FR8 have amino acid sequences with at least 80% amino acid identity, or at least 85% or at least 90% or at least 95% amino acid identity with amino acid sequences set forth in any of SEQ ID Nos 84, 105, 125, 131, 89, 110 or 130.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a preferred embodiment the biparatopic Nanobody comprises the amino acid sequence set forth in SEQ ID No 62 or an amino acid sequence having at least 80% amino acid identity, at least 85%, at least 90% or at least 95% amino acid identity with the amino acid sequence of SEQ ID No 62.

In one preferred embodiment the biparatopic Nanobody of the invention comprises the amino acid sequence set forth in SEQ ID No 62 or an amino acid sequence having at least 80% amino acid identity to SEQ ID No 62 or at least 80% amino acid sequence identity with the framework regions thereof according to Kabat numbering which biparatopic Nanobody can inhibit binding of GRO-α to human CXCR2 at an IC50 of less than 20 nM.

In another preferred embodiment of this aspect of the invention, the biparatopic Nanobody of the invention comprises substantially the CDR sequences set forth in SEQ ID No 62 but modified in the framework regions to include one or more sequence-optimising substitutions, preferably one or more of those identified as suitable in Table 24 for the 163E3 Nanobody and in Table 30 for the 51B12 Nanobody. Preferably the 163E3 Nanobody comprises the amino acid sequence set forth in SEQ ID No 217 or a sequence of amino acids having at least 80%, at least 85%, at least 90% or at least 95% amino acid sequence identity with SEQ ID No 217 and the 54B12 Nanobody comprises the amino acid sequence set forth in SEQ ID No 219 or a sequence of amino acids having at least 80%, at least 85%, at least 90% or at least 95% amino acid sequence identity with SEQ ID No 219. For example, the framework regions of these Nanobodies may have the sequence of the framework regions FR1, FR2, FR3 or FR4 according to Kabat numbering which are shown in any one of SEQ ID Nos 212 to 219 in Table 32. Preferably such a sequence-optimised biparatopic Nanobody can inhibit the binding of Gro-α to human CXCR2 with an IC 50 of less than 20 nM.

4) 163D2/54B12 (SEQ ID No 63)

This embodiment of the invention relates to a biparatopic Nanobody wherein said second Nanobody includes at least one CDR comprising an amino acid sequence selected from the group consisting of SEQ ID Nos 145, 165 and 185 or an amino acid sequence having at least 80% amino acid sequence identity with the amino acid sequences of SEQ ID Nos 145, 165 or 185 and wherein said first Nanobody includes at least one CDR selected from the group consisting of SEQ ID Nos 151, 171 and 191 or an amino acid sequence having at least 80% amino acid identity with the amino acid sequences of SEQ ID Nos 151, 171 or 191.

Preferably the biparatopic Nanabody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 145, CDR2 comprises the amino acid sequence set forth in SEQ ID No 165 and CDR3 comprises the amino acid sequence set forth in SEQ ID No 185 and wherein in said second Nanobody CDR4 comprises an amino acid sequence as set forth in SEQ ID No 151, CDR5 comprises the amino acid sequence set forth in SEQ ID No 171 and CDR6 comprises the amino acid sequence set forth in SEQ ID No 191 or wherein CDR1, CDR2, CDR3, CDR4, CDR5 or CDR6 have at least 80%, preferably at least 85%, or at least 90% or at least 95% amino acid identity with the any one of the amino acid sequences set forth in SEQ ID Nos 145, 165, 185, 151, 171, or 191.

The amino acid sequences may differ from those set forth in SEQ ID Nos 145, 165, 185, 151, 171 or 191 by only in conservative amino acid changes. The amino acid sequences may differ from those of any of the above sequence Ids only in one, two or three amino acids.

In accordance with this aspect of the invention FR1 comprises an amino acid sequence as set forth in SEQ ID No 83, FR2 comprises an amino acid sequence as set forth in SEQ ID No 104, FR3 comprises an amino acid sequence as set forth in SEQ ID No 124, FR4 comprises an amino acid sequence set forth in SEQ ID No 131, FR5 comprises an amino acid sequence as set forth in SEQ ID No 89, FR6 comprises an amino acid sequence as set forth in SEQ ID No 110, FR7 comprises an amino acid sequence as set forth in SEQ ID No 130 and/or FR8 comprises an amino acid sequence as set forth in SEQ ID No 131.

In the alternative FRI, FR2, FR3, FR4, FR5, FR6, FR7 and FR8 may have amino acid sequences with at least 80%, at least 85% at least 90% or at least 95% amino acid identity with amino acid sequences set forth in any of SEQ ID Nos 83, 104, 124, 131, 89, 110, or 130.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a preferred embodiment, the biparatopic Nanobody of the invention comprises the amino acid sequence set forth in SEQ ID No 63 or a polypeptide having at least 80%, at least 85% at least 90% or at least 95% amino acid identity with the amino acid sequence of SEQ ID No 63.

In one preferred embodiment, the biparatopic Nanobody of the invention comprises the amino acid sequence set forth in SEQ ID No 63 or amino acid sequence having at least 80% amino acid identity to SEQ ID No 63, or at least 80% amino acid sequence identity to the framework regions according to Kabat numbering which biparatopic Nanobody can inhibit binding of Gro-α to human CXCR2 at an IC50 of less than 2.0E-09M.

In another preferred embodiment of this aspect of the invention, the biparatopic Nanobody of the invention comprises substantially the CDR sequences set forth in SEQ ID No 63 but modified in the framework regions to include one or more sequence-optimising substitutions, preferably one or more of those identified as suitable in Table 28 for the 163D2 Nanobody and in Table 30 for the 54B12 Nanobody. Preferably the 163D2 Nanobody comprises the amino acid sequence set forth in SEQ ID No 218 or a sequence of amino acids having at least 80%, at least 85%, at least 90% or at least 95% amino acid sequence identity with SEQ ID No 218 and the 54B12 Nanobody comprises the amino acid sequence set forth in SEQ ID No 219 or a sequence of amino acids having at least 80%, at least 85%, at least 90% or at least 95% amino acid sequence identity with SEQ ID No 219. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

5) 2B2/163E3 (SEQ ID No 64)

This embodiment of the invention relates to a biparatopic Nanobody wherein said first Nanobody includes at least one CDR comprising an amino acid sequence selected from the group consisting of SEQ ID Nos 147, 167 and 187 or an amino acid sequence having at least 80% amino acid sequence identity with the amino acid sequences of SEQ ID Nos 147, 167 or 187 and wherein said second Nanobody includes at least one CDR selected from the group consisting of SEQ ID Nos 146, 166 and 186 or an amino acid sequence having at least 80% amino acid identity with the amino acid sequences of SEQ ID Nos 146, 166 or 186.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 147, CDR2 comprises the amino acid sequence set forth in SEQ ID No 167 and CDR3 comprises the amino acid sequence set forth in SEQ ID No 187 and wherein in said second Nanobody CDR4 comprises an amino acid sequence as set forth in SEQ ID No 146, CDR5 comprises the amino acid sequence set forth in SEQ ID No 166 and CDR6 comprises the amino acid sequence set forth in SEQ ID No 186. or wherein CDR1, CDR2, CDR3, CDR4, CDR5 or CDR6 have at least 80%, preferably at least 85%, at least 90% or at least 95% amino acid identity with the any one of the amino acid sequences set forth in SEQ ID Nos 147, 167, 187, 164, 146 or 186.

The amino acid sequences may differ from those set forth in SEQ ID Nos 147, 167, 187, 146, 166 or 186 only in conservative amino acid changes. The amino acid sequences may differ from those of any of the above sequence Ids only in one, two or three amino acids.

In accordance with the aspect of the invention, FR1 comprises an amino acid sequence as set forth in SEQ ID No 85, FR2 comprises an amino acid sequence as set forth in SEQ ID No 106, FR3 comprises an amino acid sequence as set forth in SEQ ID No 126, FR4 comprises an amino acid sequence set forth in SEQ ID No 131, FR5 comprises an amino acid sequence as set forth in SEQ ID No 84, FR6 comprises an amino acid sequence as set forth in SEQ ID No 105, FR7 comprises an amino acid sequence as set forth in SEQ ID No 125 and/or FR8 comprises an amino acid sequence as set forth in SEQ ID No 131.

In the alternative, FR1, FR2, FR3, FR4, FR5, FR6, FR7 and FR8 have amino acid sequences with at least 80%, at least 85%, at least 90% or at least 95% amino acid identity with amino acid sequences set forth in any of SEQ ID Nos 85, 106, 126, 131, 84, 105, or 125.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a preferred embodiment the biparatopic Nanobody in accordance with the invention comprises the amino acid sequence set forth in SEQ ID No 64 or a polypeptide having at least 80%, at least 85%, at least 90% or at least 95% amino acid identity with the amino acid sequence of SEQ ID No 64.

A preferred embodiment of the biparatopic Nanobody of the invention comprises the amino acid sequence set forth in SEQ ID No 64 or an amino acid sequence having at least 80% amino acid identity with SEQ ID No 64, or at least 80% amino acid sequence identity with the framework regions thereof according to Kabat numbering which biparatopic Nanobody can inhibit binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 64 but modified in the framework regions to include one or more sequence-optimising substitutions, preferably one or more of those identified as suitable in Table 20 for the 2B2 Nanobody and in Table 24 for the 163E2 Nanobody. Preferably the 2B2 Nanobody comprises the amino acid sequence set forth in SEQ ID No 2130R 214 or a sequence of amino acids having at least 80%, at least 85%, at least 90% or at least 95% amino acid sequence identity with either SEQ ID No 213 or 214 and the 163E3 Nanobody comprises the amino acid sequence set forth in SEQ ID No 217 or a sequence of amino acids having at least 80%, at least 85%, at least 90% or at least 95% amino acid sequence identity with SEQ ID No 217. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

6) 2B2/163D2 (SEQ ID No 65)

This embodiment of the invention relates to a biparatopic Nanobody wherein said first Nanobody includes at least one CDR comprising an amino acid sequence selected from the group consisting of SEQ ID Nos 147, 167 and 187 or an amino acid sequence having at least 80% amino acid sequence identity with the amino acid sequences of SEQ ID Nos 147, 167 or 187 and wherein said second Nanobody includes at least one CDR selected from the group consisting of SEQ ID Nos 145, 165 and 185 or an amino acid sequence having at least 80% amino acid identity with the amino acid sequences of SEQ ID Nos 145, 165 or 185.

Preferably, the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 147, CDR2 comprises the amino acid sequence set forth in SEQ ID No 167 and CDR3 comprises the amino acid sequence set forth in SEQ ID No 187 and wherein in said second Nanobody CDR4 comprises an amino acid sequence as set forth in SEQ ID No 145, CDR5 comprises the amino acid sequence set forth in SEQ ID No 165 and CDR6 comprises the amino acid sequence set forth in SEQ ID No 185, or wherein CDR1, CDR2, CDR3, CDR4, CDR5 or CDR6 have at least 80%, at least 85%, at least 90% or at least 95% amino acid identity with the any one of the amino acid sequences set forth in SEQ ID Nos 147, 167, 187, 145, 165 or 185.

The amino acid sequences may differ from those set forth in SEQ ID Nos 147, 167, 187, 145, 165 or 185 only in conservative amino acid changes. The amino acid sequences may differ from those of any of the above sequence Ids only in one, two or three amino acids.

In accordance with this aspect of the invention, FR1 comprises an amino acid sequence as set forth in SEQ ID No 85, FR2 comprises an amino acid sequence as set forth in SEQ ID No 106, FR3 comprises an amino acid sequence as set forth in SEQ ID No 126, FR4 comprises an amino acid sequence set forth in SEQ ID No 131, FR5 comprises an amino acid sequence as set forth in SEQ ID No 83, FR6 comprises an amino acid sequence as set forth in SEQ ID No 104, FR7 comprises an amino acid sequence as set forth in SEQ ID No 124 and/or FR8 comprises an amino acid sequence as set forth in SEQ ID No 131.

In the alternative, FR1, FR2, FR3, FR4, FR5, FR6, FR7 and FR8 have amino acid sequences with at least 80%, at least 85%, at least 90% or at least 95% amino acid identity with amino acid sequences set forth in any of SEQ ID Nos 85, 106, 126, 131, 83, 104, or 124.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

A preferred biparatopic Nanobody in accordance with the invention comprises the amino acid sequence set forth in SEQ ID No 65 or a polypeptide having at least 80%, at least 85%, at least 90% or at least 95% amino acid identity with the amino acid sequence of SEQ ID No 65.

A preferred embodiment of the biparatopic Nanobody of the invention comprises the amino acid sequence set forth in SEQ ID No 65 or an amino acid sequence having at least 80% amino acid identity with SEQ ID No 65, or at least 80% amino acid identity with the framework regions thereof according to Kabat numbering which biparatopic Nanobody can inhibit binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 65 but modified in the framework regions to include one or more sequence-optimising substitutions, preferably one or more of those identified as suitable in Table 20 for the 2B2 Nanobody and in Table 28 for the 163D2 Nanobody. Preferably the 2B2 Nanobody comprises the amino acid sequence set forth in SEQ ID No 213 or 214 a sequence of amino acids having at least 80%, at least 85%, at least 90% or at least 95% amino acid sequence identity with SEQ ID No 213 or 214 and the 163D2 Nanobody comprises the amino acid sequence set forth in SEQ ID No 218 or a sequence of amino acids having at least 80%, at least 85%, at least 90% or at least 95% amino acid sequence identity with SEQ ID No 218. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

7) 97A9/2B2 (SEQ ID No 47)

This embodiment of the invention relates to a biparatopic Nanobody wherein said second Nanobody includes at least one CDR comprising an amino acid sequence selected from the group consisting of SEQ ID Nos 143, 163 and 183 or an amino acid sequence having at least 80% amino acid sequence identity with the amino acid sequences of SEQ ID Nos 143, 163 or 183 and wherein said first Nanobody includes at least one CDR selected from the group consisting of SEQ ID Nos 147, 167 and 187 or an amino acid sequence having at least 80% amino acid identity with the amino acid sequences of SEQ ID Nos 147, 167 or 187.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said second Nanobody CDR1 comprises an amino acid sequence as set forth in SEQ ID No 143, CDR2 comprises the amino acid sequence set forth in SEQ ID No 163 and CDR3 comprises the amino acid sequence set forth in SEQ ID No 183 and wherein in said first Nanobody CDR4 comprises an amino acid sequence as set forth in SEQ ID No 147, CDR5 comprises the amino acid sequence set forth in SEQ ID No 167 and CDR6 comprises the amino acid sequence set forth in SEQ ID No 187 or wherein CDR1, CDR2, CDR3, CDR4, CDR5 or CDR6 have at least 80%, at least 85%, at least 90% or at least 95% amino acid identity with the any one of the amino acid sequences set forth in SEQ ID Nos 143, 163, 183, 147, 167, or 187.

The amino acid sequences may differ from those set forth in SEQ ID Nos 143, 163, 183, 147, 167 or 187 only in conservative amino acid changes. The amino acid sequences may differe from those of any of the above sequence Ids only in one, two or three amino acids.

In accordance with the aspect of the invention, FR1 comprises an amino acid sequence as set forth in SEQ ID No 81, FR2 comprises an amino acid sequence as set forth in SEQ ID No 102, FR3 comprises an amino acid sequence as set forth in SEQ ID No 122, FR4 comprises an amino acid sequence set forth in SEQ ID No 133, FR5 comprises an amino acid sequence as set forth in SEQ ID No 85, FR6 comprises an amino acid sequence as set forth in SEQ ID No 106, FR7 comprises an amino acid sequence as set forth in SEQ ID No 126 and/or FR8 comprises an amino acid sequence as set forth in SEQ ID No 131.

In the alternative, FR1, FR2, FR3, FR4, FR5, FR6, FR7 and FR8 have amino acid sequences with at least 80%, at least 85%, at least 90% or at least 95% amino acid identity with amino acid sequences set forth in any of SEQ ID Nos 81, 102, 122, 133, 85, 106, 126 or 131.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

A preferred biparatopic Nanobody comprises the amino acid sequence set forth in SEQ ID No 47 or a polypeptide having at least 80%, at least 85%, at least 90% or at least 95% amino acid identity with the amino acid sequence of SEQ ID No 47.

In a particularly preferred embodiment, the biparatopic Nanobody of the invention comprises the amino acid sequence set forth in SEQ ID No 47 or an amino acid sequence having at least 80% amino acid identity with SEQ ID No 47, or at least 80% amino acid sequence identity with the framework regions thereof according to Kabat numbering which biparatopic Nanobody can inhibit binding of Gro-α to human CXCR2 with a IC50 of less than 20 nM.

In another preferred embodiment of this aspect of the invention, the biparatopic Nanobody of the invention comprises substantially the CDR sequences set forth in SEQ ID No 47 but modified in the framework regions to include one or more sequence optimising substitutions, preferably one or more of those identified as suitable in Table 22 for the 97A9

Nanobody and in Table 20 for the 2B2 Nanobody. Preferably the 97A9 Nanobody comprises the amino acid sequence set forth in SEQ ID No 215 or a sequence of amino acids having at least 80%, at least 85%, at least 90% or at least 95% amino acid sequence identity with SEQ ID No 215 and the 2B2 Nanobody comprises the amino acid sequence set forth in SEQ ID No 213 or 214 or a sequence of amino acids having at least 80%, at least 85%, at least 90% or at least 95% amino acid sequence identity with either SEQ ID No 213 or SEQ ID No 214. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

8) 97A9/54B12 (SEQ ID No 61)

This embodiment of the invention relates to a biparatopic Nanobody wherein said second Nanobody includes at least one CDR comprising an amino acid sequence selected from the group consisting of SEQ ID Nos 143, 163 and 183 or an amino acid sequence having at least 80% amino acid sequence identity with the amino acid sequences of SEQ ID Nos 143, 163 or 183 and wherein said first Nanobody includes at least one CDR selected from the group consisting of SEQ ID Nos 151, 171 and 191 or an amino acid sequence having at least 80% amino acid identity with the amino acid sequences of SEQ ID Nos 151, 171 or 191.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said second Nanobody CDR1 comprises an amino acid sequence as set forth in SEQ ID No 143, CDR2 comprises the amino acid sequence set forth in SEQ ID No 163 and CDR3 comprises the amino acid sequence set forth in SEQ ID No 183 and wherein in said first Nanobody CDR4 comprises an amino acid sequence as set forth in SEQ ID No 151, CDR5 comprises the amino acid sequence set forth in SEQ ID No 171 and CDR6 comprises the amino acid sequence set forth in SEQ ID No 191, or wherein CDR1, CDR2, CDR3, CDR4, CDR5 or CDR6 have at least 80%, at least 85%, at least 90% or at least 95% amino acid identity with the any one of the amino acid sequences set forth in SEQ ID Nos 143, 163, 183, 151, 171 or 191.

The amino acid sequences may differ from those set forth in SEQ ID Nos 143, 163, 183, 151, 271 or 191 only in conservative amino acid changes. The amino acid sequences may differ from any of the sequence Idx above in only one, two or three amino acids.

In accordance with this aspect of the invention, FR1 comprises an amino acid sequence as set forth in SEQ ID No 81, FR2 comprises an amino acid sequence as set forth in SEQ ID No 102, FR3 comprises an amino acid sequence as set forth in SEQ ID No 122, FR4 comprises an amino acid sequence 133, FR5 comprises an amino acid sequence as set forth in SEQ ID No 89, FR6 comprises an amino acid sequence as set forth in SEQ ID No 110, FR7 comprises an amino acid sequence as set forth in SEQ ID No 130 and/or FR8 comprises an amino acid sequence as set forth in SEQ ID No 131.

In the alternative, FR1, FR2, FR3, FR4, FR5, FR6, FR7 and FR8 have amino acid sequences with at least 80%, at least 85%, at least 90% or at least 95% amino acid identity with amino acid sequences set forth in any of SEQ ID Nos 81, 102, 122, 133, 89, 110, 130 or 131.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a preferred embodiment, the biparatopic Nanobody comprises the amino acid sequence set forth in SEQ ID No 61 or a polypeptide having at least 80%, at least 85%, at least 90% or at least 95% amino acid identity with the amino acid sequence of SEQ ID No 61.

In a particularly preferred embodiment, the biparatopic Nanobody of the invention comprises the amino acid sequence set forth in SEQ ID No 61 or an amino acid having at least 80% identity with the amino acid sequence of SEQ ID No 61, or at least 80% identity with the framework regions thereof according to Kabat numbering which biparatopic Nanobody can inhibit binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 61 but modified in the framework regions to include one or more sequence-optimising substitutions, preferably one or more of those identified as suitable in Table 22 for the 97A9 Nanobody and in Table 30 for the 54B12 Nanobody. Preferably the 97A9 Nanobody comprises the amino acid sequence set forth in SEQ ID No 215 or a sequence of amino acids having at least 80%, at least 85%, at least 90% or at least 95% amino acid sequence identity with SEQ ID No 215 and the 54B12 Nanobody comprises the amino acid sequence set forth in SEQ ID No 219 or a sequence of amino acids having at least 80%, at least 85%, at least 90% or at least 95% amino acid sequence identity with SEQ ID No 219. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

9) 127D1/163D2 (SEQ ID No 53)

This embodiment of the invention relates to a biparatopic Nanobody wherein said first Nanobody as defined above includes at least one CDR comprising an amino acid sequence selected from the group consisting of SEQ ID Nos 141, 161 and 181 or an amino acid sequence having at least 80% amino acid sequence identity with the amino acid sequences of SEQ ID Nos 141, 161 or 181 and wherein said second Nanobody includes at least one CDR comprising an amino acid sequence selected from the group consisting of SEQ ID Nos 145, 165 and 185 or an amino acid sequence having at least 80% amino acid identity with the amino acid sequences of SEQ ID Nos 145, 165 or 185.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 141, CDR2 comprises the amino acid sequence set forth in SEQ ID No 161 and CDR3 comprises the amino acid sequence set forth in SEQ ID No 181 and wherein in said second Nanobody CDR4 comprises an amino acid sequence as set forth in SEQ ID No 145, CDR5 comprises the amino acid sequence set forth in SEQ ID No 165 and CDR6 comprises the amino acid sequence set forth in SEQ ID No 185 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 141, 161, 181, 145, 165 or 185.

The amino acid sequences may differ from those set forth in any of SEQ ID Nos 145, 165, 185, 141, 161 or 181 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 79, FR2 comprises an amino acid sequence as set forth in SEQ ID No 100, FR3 comprises an amino acid sequence as set forth in SEQ ID No 120, FR4 comprises an amino acid sequence set forth in SEQ ID No 131, FR5 comprises an amino acid sequence as set forth in SEQ ID No 83, FR6 comprises an amino acid sequence as set forth in SEQ ID No 104, FR7 comprises an amino acid sequence as set forth in SEQ ID No 124 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 79, 100, 120, 131, 83, 104, or 124.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID No 53 or a polypeptide having at least 80% amino acid identity, at least 85%, at least 90% or at least 95% amino acid sequence identity with the amino acid sequence of SEQ ID No 53.

In another embodiment of this aspect of the invention the biparatopic Nanobody comprises the amino acid sequence set forth in SEQ ID No 53 or a sequence of amino acids having at least 80% amino acid sequence identity with the SEQ ID No 53 or with the framework regions thereof which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 54 but modified in the framework regions to include one or more sequence-optimising substitutions, preferably one or more of those identified as suitable in Table 26 for the 127D1 Nanobody and in Table 28 for the 163D2 Nanobody. Preferably the 127D1 Nanobody comprises the amino acid sequence set forth in SEQ ID No 216 a sequence of amino acids having at least 80%, at least 85%, at least 90% or at least 95% amino acid sequence identity with SEQ ID No 216 and the 163D2 Nanobody comprises the amino acid sequence set forth in SEQ ID No 218 or a sequence of amino acids having at least 80%, at least 85%, at least 90% or at least 95% amino acid sequence identity with SEQ ID No 218. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

10) 127D1/163E3 (SEQ ID No 54)

This embodiment of the invention relates to a biparatopic Nanobody wherein said first Nanobody as defined above includes at least one CDR comprising an amino acid sequence selected from the group consisting of SEQ ID Nos 141, 161 and 181 or an amino acid sequence having at least 80% amino acid sequence identity with the amino acid sequences of SEQ ID Nos 141, 161 or 181 and wherein said second Nanobody includes at least one CDR comprising an amino acid sequence selected from the group consisting of SEQ ID Nos 146, 166 and 186 or an amino acid sequence having at least 80% amino acid identity with the amino acid sequences of SEQ ID Nos 146, 166 or 186.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 141, CDR2 comprises the amino acid sequence set forth in SEQ ID No 161 and CDR3 comprises the amino acid sequence set forth in SEQ ID No 181 and wherein in said second Nanobody CDR4 comprises an amino acid sequence as set forth in SEQ ID No 146, CDR5 comprises the amino acid sequence set forth in SEQ ID No 166 and CDR6 comprises the amino acid sequence set forth in SEQ ID No 186 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 146, 166, 186, 141, 161 or 181.

The amino acid sequences may differ from those set forth in any of SEQ ID Nos 146, 166, 186, 141, 161 or 181 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 79, FR2 comprises an amino acid sequence as set forth in SEQ ID No 100, FR3 comprises an amino acid sequence as set forth in SEQ ID No 120, FR4 comprises an amino acid sequence set forth in SEQ ID No 131, FR5 comprises an amino acid sequence as set forth in SEQ ID No 84, FR6 comprises an amino acid sequence as set forth in SEQ ID No 105, FR7 comprises an amino acid sequence as set forth in SEQ ID No 125 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 79, 100, 120, 131, 84, 105, or 125.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID No 54 or a polypeptide having at least 80% amino acid identity, at least 85%, at least 90% or at least 95% amino acid sequence identity with the amino acid sequence of SEQ ID No 54.

In another embodiment of this aspect of the invention the biparatopic Nanobody comprises the amino acid sequence set forth in SEQ ID No 54 or a sequence of amino acids having at least 80% amino acid sequence identity with the SEQ ID No 54 or at least 80% amino acid sequence identity with the framework regions thereof according to Kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 54 but modified in the framework regions to include one or more sequence-optimising substitutions, preferably one or more of those identified as suitable in Table 26 for the 127D1 Nanobody and in Table 24 for the 163E3 Nanobody. Preferably the 127D1 Nanobody comprises the amino acid sequence set forth in SEQ ID No 216 a sequence of amino acids having at least 80%, at least 85%, at least 90% or at least 95% amino acid sequence identity with SEQ ID No 216 and the 163E3 Nanobody comprises the amino acid sequence set forth in SEQ ID No 217 or a sequence of amino acids having at least 80%, at least 85%, at least 90% or at least 95% amino acid sequence identity with SEQ ID No 217. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

11) 127D1/97A9 (SEQ ID Nos 37 and 39)

This embodiment of the invention relates to a biparatopic Nanobody wherein said first Nanobody as defined above includes at least one CDR comprising an amino acid sequence selected from the group consisting of SEQ ID Nos 141, 161 and 181 or an amino acid sequence having at least 80% amino acid sequence identity with the amino acid sequences of SEQ ID Nos 141, 161 or 181 and wherein said second Nanobody includes at least one CDR comprising an amino acid sequence selected from the group consisting of SEQ ID Nos 143, 163 and 183 or an amino acid sequence having at least 80% amino acid identity with the amino acid sequences of SEQ ID Nos 143, 163 or 183.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 141, CDR2 comprises the amino acid sequence set forth in SEQ ID No 161 and CDR3 comprises the amino acid sequence set forth in SEQ ID No 181 and wherein in said second Nanobody CDR4 comprises an amino acid sequence as set forth in SEQ ID No 143, CDR5 comprises the amino acid sequence set forth in SEQ ID No 163 and CDR6 comprises the amino acid sequence set forth in SEQ ID No 183 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 141, 161, 181, 143, 163 or 183.

The amino acid sequences may differ from those set forth in any of SEQ ID Nos 141, 161, 181, 143, 163 or 183 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 79, FR2 comprises an amino acid sequence as set forth in SEQ ID No 100, FR3 comprises an amino acid sequence as set forth in SEQ ID No 120, FR4 comprises an amino acid sequence set forth in SEQ ID No 131, FR5 comprises an amino acid sequence as set forth in SEQ ID No 81, FR6 comprises an amino acid sequence as set forth in SEQ ID No 102, FR7 comprises an amino acid sequence as set forth in SEQ ID No 122 and/or FR8 comprises an amino acid sequence as set forth in SEQ ID No 133.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 79, 100, 120, 131, 81, 102, 122, or 133.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises a first antigen binding domain comprising the amino acid sequences set forth in SEQ ID No 37 and a second antigen binding domain comprising the amino acid sequence set forth in SEQ ID No 39 or a polypeptide having at least 80% amino acid identity, at least 85%, at least 90% or at least 95% amino acid sequence identity with the amino acid sequence set forth in SEQ ID Nos 37 and 39.

In another embodiment of this aspect of the invention the biparatopic Nanobody comprises the amino acid sequence set forth in SEQ ID Nos 37 and 39 or a sequence of amino acids having at least 80% amino acid sequence identity with the SEQ ID Nos 37 and 39 or with the framework regions thereof according to Kabat numbering which biparatopic polypeptide can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID Nos 37 and 39 but modified in the framework regions to include one or more sequence optimising substitutions, preferably one or more of those identified as suitable in Table 26 for the 127D1 Nanobody and in Table 22 for the 97A9 Nanobody. Preferably the 127D1 Nanobody comprises the amino acid sequence set forth in SEQ ID No 216 or a sequence of amino acids having at least 80%, at least 85%, at least 90% or at least 95% amino acid sequence identity with SEQ ID No 216 and the 97A9 Nanobody comprises the amino acid sequence set forth in SEQ ID No 215 or a sequence of amino acids having at least 80%, at least 85%, at least 90% or at least 95% amino acid sequence identity with SEQ ID No 215. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

12) 2B2/97A9 (SEQ ID No 46)

This embodiment of the invention relates to a biparatopic Nanobody wherein said first Nanobody as defined above includes at least one CDR comprising an amino acid sequence selected from the group consisting of SEQ ID Nos 147, 167 and 187 or an amino acid sequence having at least 80% amino acid sequence identity with the amino acid sequences of SEQ ID Nos 147, 167 or 187 and wherein said second Nanobody includes at least one CDR comprising an amino acid sequence selected from the group consisting of SEQ ID Nos 143, 163 and 183 or an amino acid sequence having at least 80% amino acid identity with the amino acid sequences of SEQ ID Nos 143, 163 or 183.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 147, CDR2 comprises the amino acid sequence set forth in SEQ ID No 167 and CDR3 comprises the amino acid sequence set forth in SEQ ID No 187 and wherein in said second Nanobody CDR4 comprises an amino acid sequence as set forth in SEQ ID No 143, CDR5 comprises the amino acid sequence set forth in SEQ ID No 163 and CDR6 comprises the amino acid sequence set forth in SEQ ID No 183 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 147, 167, 187, 143, 163 or 183.

The amino acid sequences may differ from those set forth in any of SEQ ID Nos 147, 167, 187, 143, 163 or 183 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 85, FR2 comprises an amino acid sequence as set forth in SEQ ID No 106, FR3 comprises an amino acid sequence as set forth in SEQ ID No 126, FR4 comprises an amino acid sequence set forth in SEQ ID No 131, FR5 comprises an amino acid sequence as set forth in SEQ ID No 81, FR6 comprises an amino acid sequence as set forth in SEQ ID No 102, FR7 comprises an amino acid sequence as set forth in SEQ ID No 122 and/or FR8 comprises an amino acid sequence as set forth in SEQ ID No 133.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 85, 106, 126, 131, 81, 102, 122 or 133.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID No 46 or a polypeptide having at least 80% amino acid identity, at least 85%, at least 90% or at least 95% amino acid sequence identity with the amino acid sequence of SEQ ID No 46.

In another embodiment of this aspect of the invention the biparatopic Nanobody comprises the amino acid sequence set forth in SEQ ID No 46 or a sequence of amino acids having at least 80% amino acid sequence identity with the SEQ ID No 46 or at least 80% amino acid sequence identity to the framework regions thereof according to Kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 46 but modified in the framework regions to include one or more sequence-optimising substitutions, preferably one or more of those identified as suitable in Table 20 for the 2B2 Nanobody and in Table 22 for the 97A9 Nanobody. Preferably the 2B2 Nanobody comprises the amino acid sequence set forth in SEQ ID No 213 or 214 or a sequence of amino acids having at least 80%, at least 85%, at least 90% or at least 95% amino acid sequence identity with either SEQ ID No 213 or 214 and the 97A9 Nanobody comprises the amino acid sequence set forth in SEQ ID No 215 or a sequence of amino acids having at least 80%, at least 85%, at least 90% or at least 95% amino acid sequence identity with SEQ ID No 215. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

13) 54B12/163D2 (SEQ ID No 69)

This embodiment of the invention relates to a biparatopic Nanobody wherein said first Nanobody as defined above includes at least one CDR comprising an amino acid sequence selected from the group consisting of SEQ ID Nos 151, 171 and 191 or an amino acid sequence having at least 80% amino acid sequence identity with the amino acid sequences of SEQ ID Nos 151, 171 or 191 and wherein said second Nanobody includes at least one CDR comprising an amino acid sequence selected from the group consisting of SEQ ID Nos 145, 165 and 185 or an amino acid sequence having at least 80% amino acid identity with the amino acid sequences of SEQ ID Nos 145, 165 or 185.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 151, CDR2 comprises the amino acid sequence set forth in SEQ ID No 171 and CDR3 comprises the amino acid sequence set forth in SEQ ID No 191 and wherein in said second Nanobody CDR4 comprises an amino acid sequence as set forth in SEQ ID No 145, CDR5 comprises the amino acid sequence set forth in SEQ ID No 165 and CDR6 comprises the amino acid sequence set forth in SEQ ID No 185 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 151, 171, 191, 145, 165 or 185.

The amino acid sequences may differ from those set forth in any of SEQ ID Nos 151, 171, 191, 145, 165 or 185 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 89, FR2 comprises an amino acid sequence as set forth in SEQ ID No 110, FR3 comprises an amino acid sequence as set forth in SEQ ID No 130, FR4 comprises an amino acid sequence set forth in SEQ ID No 131, FR5 comprises an amino acid sequence as set forth in SEQ ID No 83, FR6 comprises an amino acid sequence as set forth in SEQ ID No 104, FR7 comprises an amino acid sequence as set forth in SEQ ID No 124 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 89, 110, 130, 131, 83, 104, or 124.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID No 69 or a polypeptide having at least 80% amino acid identity, at least 85%, at least 90% or at least 95% amino acid sequence identity with the amino acid sequence of SEQ ID No 69.

In another embodiment of this aspect of the invention the biparatopic Nanobody comprises the amino acid sequence set forth in SEQ ID No 69 or a sequence of amino acids having at least 80% amino acid sequence identity with the SEQ ID No 69 or at least 80% amino acid sequence identity with the framework regions thereof according to Kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 69 but modified in the framework regions to include one or more sequence-optimising substitutions, preferably one or more of those identified as suitable in Table 30 for the 54B12 Nanobody and in Table 28 for the 163D2 Nanobody. Preferably the 54B12 Nanobody comprises the amino acid sequence set forth in SEQ ID No 219 or a sequence of amino acids having at least 80%, at least 85%, at least 90% or at least 95% amino acid sequence identity with SEQ ID No 219 and the 163D2 Nanobody comprises the amino acid sequence set forth in SEQ ID No 218 or a sequence of amino acids having at least 80%, at least 85%, at least 90% or at least 95% amino acid sequence identity with SEQ ID No 218. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

14) 54B12/163E3 (SEQ ID No 68)

This embodiment of the invention relates to a biparatopic Nanobody wherein said first Nanobody as defined above includes at least one CDR comprising an amino acid sequence selected from the group consisting of SEQ ID Nos 151, 171 and 191 or an amino acid sequence having at least 80% amino acid sequence identity with the amino acid sequences of SEQ ID Nos 151, 171 or 191 and wherein said second Nanobody includes at least one CDR comprising an amino acid sequence selected from the group consisting of SEQ ID Nos 146, 166 and 186 or an amino acid sequence having at least 80% amino acid identity with the amino acid sequences of SEQ ID Nos 146, 166 or 186.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 151, CDR2 comprises the amino acid sequence set forth in SEQ ID No 171 and CDR3 comprises the amino acid sequence set forth in SEQ ID No 191 and wherein in said second Nanobody CDR4 comprises an amino acid sequence as set forth in SEQ ID No 146, CDR5 comprises the amino acid sequence set forth in SEQ ID No 166 and CDR6 comprises the amino acid sequence set forth in SEQ ID No 186 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 151, 171, 191, 146, 166 or 186.

The amino acid sequences may differ from those set forth in any of SEQ ID Nos 151, 171, 191, 146, 166 or 186 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 89, FR2 comprises an amino acid sequence as set forth in SEQ ID No 110, FR3 comprises an amino acid sequence as set forth in SEQ ID No 130, FR4 comprises an amino acid sequence set forth in SEQ ID No 131, FR5 comprises an amino acid sequence as set forth in SEQ ID No 84, FR6 comprises an amino acid sequence as set forth in SEQ ID No 105, FR7 comprises an amino acid sequence as set forth in SEQ ID No 125 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 89, 110, 130, 131, 84, 105, or 125.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID No 68 or a polypeptide having at least 80% amino acid identity, at least 85%, at least 90% or at least 95% amino acid sequence identity with the amino acid sequence of SEQ ID No 68.

In another embodiment of this aspect of the invention the biparatopic Nanobody comprises the amino acid sequence set forth in SEQ ID No 68 or a sequence of amino acids having at least 80% amino acid sequence identity with the SEQ ID No 68 or at least 80% amino acid sequence identity with the framework regions thereof according to Kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 68 but modified in the framework regions to include one or more sequence optimising substitutions, preferably one or more of those identified as suitable in Table 30 for the 54B12 Nanobody and in Table 24 for the 163E3 Nanobody. Preferably the 54B12 Nanobody comprises the amino acid sequence set forth in SEQ ID No 219 or a sequence of amino acids having at least 80%, at least 85%, at least 90% or at least 95% amino acid sequence identity with SEQ ID No 219 and the 163E3 Nanobody comprises the amino acid sequence set forth in SEQ ID No 217 or a sequence of amino acids having at least 80%, at least 85%, at least 90% or at least 95% amino acid sequence identity with SEQ ID No 217. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

15) 54B12/97A9 (SEQ ID Nos 90 and 39)

This embodiment of the invention relates to a biparatopic Nanobody wherein said first Nanobody as defined above includes at least one CDR comprising an amino acid sequence selected from the group consisting of SEQ ID Nos 141, 161 and 181 or an amino acid sequence having at least 80% amino acid sequence identity with the amino acid sequences of SEQ ID Nos 141, 161 or 181 and wherein said second Nanobody includes at least one CDR comprising an amino acid sequence selected from the group consisting of SEQ ID Nos 143, 163 and 183 or an amino acid sequence having at least 80% amino acid identity with the amino acid sequences of SEQ ID Nos 143, 163 or 183.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said first Nanobody CDR1 comprises an amino acid sequence as set forth in SEQ ID No 141, CDR2 comprises the amino acid sequence set forth in SEQ ID No 161 and CDR3 comprises the amino acid sequence set forth in SEQ ID No 181 and wherein in said second Nanobody CDR4 comprises an amino acid sequence as set forth in SEQ ID No 143, CDR5 comprises the amino acid sequence set forth in SEQ ID No 163 and CDR6 comprises the amino acid sequence set forth in SEQ ID No 183 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 141, 161, 181, 143, 163 or 183.

The amino acid sequences may differ from those set forth in any of SEQ ID Nos 141, 161, 181, 143, 163 or 183 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 89, FR2 comprises an amino acid sequence as set forth in SEQ ID No 110, FR3 comprises an amino acid sequence as set forth in SEQ ID No 130, FR4 comprises an amino acid sequence set forth in SEQ ID No 131, FR5 comprises an amino acid sequence as set forth in SEQ ID No 81, FR6 comprises an amino acid sequence as set forth in SEQ ID No 102, FR7 comprises an amino acid sequence as set forth in SEQ ID No 122 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 89, 110, 130, 131, 81, 102, or 122.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequences set forth in SEQ ID Nos 90 and 39 or a polypeptide having at least 80% amino acid identity, at least 85%, at least 90% or at least 95% amino acid sequence identity with the amino acid sequence of SEQ ID Nos 90 and 39.

In another embodiment of this aspect of the invention the biparatopic Nanobody comprises the amino acid sequence set forth in SEQ ID Nos 90 and 39 or a sequence of amino acids having at least 80% amino acid sequence identity with the SEQ ID Nos 90 and 39 or at least 80% amino acid sequence identity with the framework regions thereof according to Kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID Nos 90 and 39 but modified in the framework regions to include one or more sequence-optimising substitutions, preferably one or more of those identified as suitable in Table 30 for the 54B12 Nanobody and in Table 22 for the 97A9 Nanobody. Preferably the 54B12 Nanobody comprises the amino acid sequences set forth in SEQ ID Nos 90 and 39 or a sequence of amino acids having at least 80%, at least 85%, at least 90% or at least 95% amino acid sequence identity with SEQ ID Nos 90 and/or 39 and the 97A9 Nanobody comprises the amino acid sequence set forth in SEQ ID No 215 or a sequence of amino acids having at least 80%, at least 85%, at least 90% or at least 95% amino acid sequence identity with SEQ ID No 215. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

16) 97A9/127D1 (SEQ ID Nos 39 and 37)

This embodiment of the invention relates to a biparatopic Nanobody wherein said second Nanobody as defined above includes at least one CDR comprising an amino acid sequence selected from the group consisting of SEQ ID Nos 143, 163 and 183 or an amino acid sequence having at least 80% amino acid sequence identity with the amino acid sequences of SEQ ID Nos 143, 163 or 183 and wherein said first Nanobody includes at least one CDR comprising an amino acid sequence selected from the group consisting of SEQ ID Nos 141, 161 and 181 or an amino acid sequence having at least 80% amino acid identity with the amino acid sequences of SEQ ID Nos 141, 161 or 181.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said second Nanobody CDR1 comprises an amino acid sequence as set forth in SEQ ID No 143, CDR2 comprises the amino acid sequence set forth in SEQ ID No 163 and CDR3 comprises the amino acid sequence set forth in SEQ ID No 183 and wherein in said first Nanobody CDR4 comprises an amino acid sequence as set forth in SEQ ID No 141, CDR5 comprises the amino acid sequence set forth in SEQ ID No 161 and CDR6 comprises the amino acid sequence set forth in SEQ ID No 181 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 143, 163, 183, 141, 161 or 181.

The amino acid sequences may differ from those set forth in any of SEQ ID Nos 143, 163, 183, 141, 161 or 181 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 81, FR2 comprises an amino acid sequence as set forth in SEQ ID No 102, FR3 comprises an amino acid sequence as set forth in SEQ ID No 122, FR4 comprises an amino acid sequence set forth in SEQ ID No 133, FR5 comprises an amino acid sequence as set forth in SEQ ID No 79, FR6 comprises an amino acid sequence as set forth in SEQ ID No 100, FR7 comprises an amino acid sequence as set forth in SEQ ID No 120 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 81, 102, 122, 133, 79, 100, 120 or 131.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID Nos 39 and 37 or a polypeptide having at least 80% amino acid identity, at least 85%, at least 90% or at least 95% amino acid sequence identity with the amino acid sequence of SEQ ID Nos 39 and/or 37.

In another embodiment of this aspect of the invention the biparatopic Nanobody comprises the amino acid sequence set forth in SEQ ID Nos 39 and 37 or a sequence of amino acids having at least 80% amino acid sequence identity with the SEQ ID Nos 39 and/or 37 or at least 80% amino acid sequence identity with the framework regions thereof according to Kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID Nos 39 and 37 but modified in the framework regions to include one or more sequence-optimising substitutions, preferably one or more of those identified as suitable in Table 22 for the 97A9 Nanobody and in Table 26 for the 97A9 Nanobody. Preferably the 97A9 Nanobody comprises the amino acid sequence set forth in SEQ ID Nos 39 and 37 or a sequence of amino acids having at least 80%, at least 85%, at least 90% or at least 95% amino acid sequence identity with SEQ ID Nos 39 and 37 and the 127D1 Nanobody comprises the amino acid sequence set forth in SEQ ID No 216 or a sequence of amino acids having at least 80%, at least 85%, at least 90% or at least 95% amino acid sequence identity with SEQ ID No 216. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

17) 163D2/2B2 (SEQ ID No 67)

This embodiment of the invention relates to a biparatopic Nanobody wherein said second Nanobody as defined above includes at least one CDR comprising an amino acid sequence selected from the group consisting of SEQ ID Nos 145, 165 and 185 or an amino acid sequence having at least 80% amino acid sequence identity with the amino acid sequences of SEQ ID Nos 145, 165 or 185 and wherein said first Nanobody includes at least one CDR comprising an amino acid sequence selected from the group consisting of SEQ ID Nos 147, 167 and 187 or an amino acid sequence having at least 80% amino acid identity with the amino acid sequences of SEQ ID Nos 147, 167 or 187.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said second Nanobody CDR1 comprises an amino acid sequence as set forth in SEQ ID No 145, CDR2 comprises the amino acid sequence set forth in SEQ ID No 165 and CDR3 comprises the amino acid sequence set forth in SEQ ID No 185 and wherein in said first Nanobody CDR4 comprises an amino acid sequence as set forth in SEQ ID No 147, CDR5 comprises the amino acid sequence set forth in SEQ ID No 167 and CDR6 comprises the amino acid sequence set forth in SEQ ID No 187 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 145, 165, 185, 147, 167 or 187.

The amino acid sequences may differ from those set forth in any of SEQ ID Nos 145, 165, 185, 147, 167 or 187 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 83, FR2 comprises an amino acid sequence as set forth in SEQ ID No 104, FR3 comprises an amino acid sequence as set forth in SEQ ID No 124, FR4 comprises an amino acid sequence set forth in SEQ ID No 131, FR5 comprises an amino acid sequence as set forth in SEQ ID No 85, FR6 comprises an amino acid sequence as set forth in SEQ ID No 106, FR7 comprises an amino acid sequence as set forth in SEQ ID No 126 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 83, 104, 124, 131, 85, 106, or 126.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID No 67 or a polypeptide having at least 80% amino acid identity, at least 85%, at least 90% or at least 95% amino acid sequence identity with the amino acid sequence of SEQ ID No 67.

In another embodiment of this aspect of the invention the biparatopic Nanobody comprises the amino acid sequence set forth in SEQ ID No 67 or a sequence of amino acids having at least 80% amino acid sequence identity with the SEQ ID No 67 at least 80% amino acid sequence identity with the framework regions thereof according to Kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 67 but modified in the framework regions to include one or more sequence-optimising substitutions, preferably one or more of those identified as suitable in Table 28 for the 163D2 Nanobody and in Table 20 for the 2B2 Nanobody. Preferably the 163D2 Nanobody comprises the amino acid sequence set forth in SEQ ID No 218 or a sequence of amino acids having at least 80%, at least 85%, at least 90% or at least 95% amino acid sequence identity with SEQ ID No 218 and the 2B2 Nanobody comprises the amino acid sequence set forth in SEQ ID Nos 213 or 214 or a sequence of amino acids having at least 80%, at least 85%, at least 90% or at least 95% amino acid sequence identity with either of SEQ ID Nos 213 or 214. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

18) 163E3/2B2 (SEQ ID No 66)

This embodiment of the invention relates to a biparatopic Nanobody wherein said second Nanobody as defined above includes at least one CDR comprising an amino acid sequence selected from the group consisting of SEQ ID Nos 146, 166 and 186 or an amino acid sequence having at least 80% amino acid sequence identity with the amino acid sequences of SEQ ID Nos 146, 166 or 186 and wherein said first Nanobody includes at least one CDR comprising an amino acid sequence selected from the group consisting of SEQ ID Nos 147, 167 and 187 or an amino acid sequence having at least 80% amino acid identity with the amino acid sequences of SEQ ID Nos 147, 167 or 187.

Preferably the biparatopic Nanobody comprises the structure:

FR1-CDR1-FR2-CDR2-FR3-CDR3-FR4--LINKER--FR5-CDR4-FR6-CDR5-FR7-CDR6-FR8 wherein in said second Nanobody CDR1 comprises an amino acid sequence as set forth in SEQ ID No 146, CDR2 comprises the amino acid sequence set forth in SEQ ID No 166 and CDR3 comprises the amino acid sequence set forth in SEQ ID No 186 and wherein in said first Nanobody CDR4 comprises an amino acid sequence as set forth in SEQ ID No 147, CDR5 comprises the amino acid sequence set forth in SEQ ID No 167 and CDR6 comprises the amino acid sequence set forth in SEQ ID No 187 or in which the amino acid sequences of CDR1, CDR2, CDR3, CDR4, CDR5 or CDR6 have at least 80% amino acid sequence identity, or at least 85% or at least 90% or at least 95% amino acid sequence identity with the any one of the amino acid sequences set forth in SEQ ID Nos 146, 166, 186, 147, 167 or 187.

The amino acid sequences may differ from those set forth in any of SEQ ID Nos 146, 166, 186, 147, 167 or 187 only in conservative amino acid changes. The amino acid sequences may differ from any of the sequence IDs above only in one, two or three amino acids.

In a preferred embodiment of this aspect of the invention FR1 comprises an amino acid sequence as set forth in SEQ ID No 84, FR2 comprises an amino acid sequence as set forth in SEQ ID No 105, FR3 comprises an amino acid sequence as set forth in SEQ ID No 125, FR4 comprises an amino acid sequence set forth in SEQ ID No 131, FR5 comprises an amino acid sequence as set forth in SEQ ID No 85, FR6 comprises an amino acid sequence as set forth in SEQ ID No 106, FR7 comprises an amino acid sequence as set forth in SEQ ID No 126 and/or FR8 comprises an amino acid sequence as set forth in SEQ ID No 131.

In the alternative FRI, FR2, FR3, FR4, FR5, FR6, FR7 and FR8 may have amino acid sequences with at least 80% amino acid identity, at least 85%, at least 90% or at least 95% amino acid sequence identity with amino acid sequences set forth in any of SEQ ID Nos 84, 105, 125, 131, 85, 106, or 126.

For example, in this aspect of the invention FR1 and/or FR4 may comprise the sequence of amino acids set forth in any one of SEQ ID Nos 70 to 89, FR2 and/or FR5 may comprise the sequence of amino acids set forth in any one of SEQ ID Nos 91 to 110, FR3 and/or FR6 may comprise the sequence of amino acids as set forth in any one of SEQ ID Nos 111 to 130 and FR4 and/or FR8 may comprise the sequence of amino acids set forth in any one of SEQ ID Nos 131 to 133.

In a particularly preferred embodiment of this aspect of the invention the biparatopic Nanobody comprises the amino acid sequence set forth in SEQ ID No 66 or a polypeptide having at least 80% amino acid identity, at least 85%, at least 90% or at least 95% amino acid sequence identity with the amino acid sequence of SEQ ID No 66.

In another embodiment of this aspect of the invention the biparatopic Nanobody comprises the amino acid sequence set forth in SEQ ID No 66 or a sequence of amino acids having at least 80% amino acid sequence identity with the SEQ ID No 66 or at least 80% amino acid sequence identity with the framework regions thereof according to Kabat numbering which biparatopic Nanobody can inhibit the binding of Gro-α to human CXCR2 with an IC50 of less than 20 nM.

In another preferred embodiment of this aspect of the invention, the biparatopic Nanobody of the invention comprises substantially the CDR sequences set forth in SEQ ID No 66 but modified in the framework regions to include one or more sequence-optimising substitutions, preferably one or more of those identified as suitable in Table 24 for the 163E3 Nanobody and in Table 20 for the 2B2 Nanobody. Preferably the 163E3 Nanobody comprises the amino acid sequence set forth in SEQ ID No 217 or a sequence of amino acids having at least 80%, at least 85%, at least 90% or at least 95% amino acid sequence identity with SEQ ID No 217 and the 2B2 Nanobody comprises the amino acid sequence set forth in SEQ ID Nos 213 or 214 or a sequence of amino acids having at least 80%, at least 85%, at least 90% or at least 95% amino acid sequence identity with either of SEQ ID Nos 213 or 214. For example, the framework regions of these Nanobodies may have the sequence of the framework regions FR1, FR2, FR3 or FR4 according to Kabat numbering which are shown in any one of SEQ ID Nos 213 to 219 in Table 32. Preferably such a sequence-optimised biparatopic Nanobody can inhibit the binding of Gro-α to human CXCR2 with an IC 50 of less than 20 nM.

As already discussed herein, it is desirable if the preferred biparatopic Nanobodies of the invention including the specific embodiments and variants thereof designated 163D2/127D1, 163E3/127D1, 163E3/54B12, 163D2/54B12, 2B2/163E3, 2B2/163D2, 97A9/2B2, 97A9/54B12, 127D1/163D2, 127D1/163E3, 127D1/97A9, 2B2/97A9, 54B12/163D2, 54B12/163E3, 54B12/97A9, 97A9/127D1, 163D2/2B2 or 163E3/2B2 have within their framework regions at least one sequence-optimising, amino acid substitution and said framework regions may be partially or fully humanised for example. It is desirable if the extent of sequence optimisation results in biparatopic Nanobody having 80 to 90% sequence identity at least in respect of the framework regions, with SEQ ID Nos 58, 59, 62, 63, 64, 65, 47, 61, 53, 54, 46, 69, 68, 67 or 66.

Embodiments of the invention further comprise polypeptides wherein the first antigen binding domain is selected from SEQ ID No. 213, 214, 216 and 219 or a polypeptide having at least 80%, such as at least 90%, for example at least 95% identity to one of these, and the second antigen binding domain is selected from SEQ ID No. 215, 217 and 218, or a polypeptide having at least 80%, such as at least 90%, for example at least 95% identity to one of these.

(0079-0076)

In one embodiment of the invention the polypeptide comprises in said second immunoglobulin of a single variable domain CDR1 comprises an amino acid sequence as set forth in SEQ ID No 141, CDR2 comprises the amino acid sequence set forth in SEQ ID No 236 and CDR3 comprises the amino acid sequence set forth in SEQ ID No 181 and further comprises in said first immunoglobulin of a single variable domain CDR4 comprises an amino acid sequence as set forth in SEQ ID No 146, CDR5 comprises the amino acid sequence set forth in SEQ ID No 237 and CDR6 comprises the amino acid sequence set forth in SEQ ID No 186. In further embodiments the amino acid sequences of CDR1, CDR2, CDR3, CDR4, CDR5 or CDR6 have at least 80%, such as at least 90%, for example at least 95% amino acid identity with the any one of the amino acid sequences set forth in SEQ ID Nos 141, 236, 181, 146, 237 or 186.

In a further embodiment the polypeptide comprises amino acid sequences differing from those set forth in SEQ ID Nos 141, 236, 181, 146, 237 or 186 only in conservative amino acid changes.

In a further embodiment the polypeptide comprises a first antigen binding domain is selected from SEQ ID No. 216 or a polypeptide having at least 80% such as at least 90%, for example at least 95% identity to SEQ ID No.216, and the second antigen binding domain is selected from SEQ ID No. 217 or a polypeptide having at least 80%, such as at least 90%, for example at least 95% identity to SEQ ID No.217.

In yet a further embodiment the polypeptide comprises SEQ ID No.221.

(0079-0086)

In one embodiment of the invention the polypeptide comprises in said second immunoglobulin of a single variable domain CDR1 comprises an amino acid sequence as set forth in SEQ ID No 141, CDR2 comprises the amino acid sequence set forth in SEQ ID No 236 and CDR3 comprises the amino acid sequence set forth in SEQ ID No 181 and further comprises in said first immunoglobulin of a single variable domain CDR4 comprises an amino acid sequence as set forth in SEQ ID No 145, CDR5 comprises the amino acid sequence set forth in SEQ ID No 165 and CDR6 comprises the amino acid sequence set forth in SEQ ID No 185. In further embodiments the amino acid sequences of CDR1, CDR2, CDR3, CDR4, CDR5 or CDR6 have at least 80%, such as at least 90%, for example at least 95% amino acid identity with the any one of the amino acid sequences set forth in SEQ ID Nos 141, 236, 181, 145, 165 or 185.

In a further embodiment the polypeptide comprises amino acid sequences differing from those set forth in SEQ ID Nos 141, 236, 181, 145, 165 or 185 only in conservative amino acid changes.

In a further embodiment the polypeptide comprises a first antigen binding domain is selected from SEQ ID No. 216 or a polypeptide having at least 80% such as at least 90%, for example at least 95% identity to SEQ ID No.216, and the second antigen binding domain is selected from SEQ ID No. 218 or a polypeptide having at least 80%, such as at least 90%, for example at least 95% identity to SEQ ID No.218.

In yet a further embodiment the polypeptide comprises SEQ ID No.222.

(0079-0061)

In one embodiment of the invention the polypeptide comprises in said second immunoglobulin of a single variable domain CDR1 comprises an amino acid sequence as set forth in SEQ ID No 141, CDR2 comprises the amino acid sequence set forth in SEQ ID No 236 and CDR3 comprises the amino acid sequence set forth in SEQ ID No 181 and further comprises in said first immunoglobulin of a single variable domain CDR4 comprises an amino acid sequence as set forth in SEQ ID No 143, CDR5 comprises the amino acid sequence set forth in SEQ ID No 235 and CDR6 comprises the amino acid sequence set forth in SEQ ID No 183. In further embodiments the amino acid sequences of CDR1, CDR2, CDR3, CDR4, CDR5 or CDR6 have at least 80%, such as at least 90%, for example at least 95% amino acid identity with the any one of the amino acid sequences set forth in SEQ ID Nos 141, 236, 181, 143, 235 or 183.

In a further embodiment the polypeptide comprises amino acid sequences differing from those set forth in SEQ ID Nos 141, 236, 181, 143, 235 or 183 only in conservative amino acid changes.

In a further embodiment the polypeptide comprises a first antigen binding domain is selected from SEQ ID No. 216 or a polypeptide having at least 80% such as at least 90%, for example at least 95% identity to SEQ ID No.216, and the second antigen binding domain is selected from SEQ ID No. 215 or a polypeptide having at least 80%, such as at least 90%, for example at least 95% identity to SEQ ID No.215, separated by a linker with the SEQ ID No.220.

(0104-0076)

In one embodiment of the invention the polypeptide comprises in said second immunoglobulin of a single variable domain CDR1 comprises an amino acid sequence as set forth in SEQ ID No 151, CDR2 comprises the amino acid sequence set forth in SEQ ID No 171 and CDR3 comprises the amino acid sequence set forth in SEQ ID No 191 and further comprises in said first immunoglobulin of a single variable domain CDR4 comprises an amino acid sequence as set forth in SEQ ID No 146, CDR5 comprises the amino acid sequence set forth in SEQ ID No 237 and CDR6 comprises the amino acid sequence set forth in SEQ ID No 186. In further embodiments the amino acid sequences of CDR1, CDR2, CDR3, CDR4, CDR5 or CDR6 have at least 80%, such as at least 90%, for example at least 95% amino acid identity with the any one of the amino acid sequences set forth in SEQ ID Nos 151, 171, 191, 146, 237 or 186.

In a further embodiment the polypeptide comprises amino acid sequences differing from those set forth in SEQ ID Nos 151, 171, 191, 146, 237 or 186 only in conservative amino acid changes.

In a further embodiment the polypeptide comprises a first antigen binding domain is selected from SEQ ID No. 219 or a polypeptide having at least 80% such as at least 90%, for example at least 95% identity to SEQ ID No.219, and the second antigen binding domain is selected from SEQ ID No. 217 or a polypeptide having at least 80%, such as at least 90%, for example at least 95% identity to SEQ ID No.217.

In yet a further embodiment the polypeptide comprises SEQ ID No.223.

(0104-0086)

In one embodiment of the invention the polypeptide comprises in said second immunoglobulin of a single variable domain CDR1 comprises an amino acid sequence as set forth in SEQ ID No 151, CDR2 comprises the amino acid sequence set forth in SEQ ID No 171 and CDR3 comprises the amino acid sequence set forth in SEQ ID No 191 and further comprises in said first immunoglobulin of a single variable domain CDR4 comprises an amino acid sequence as set forth in SEQ ID No 145, CDR5 comprises the amino acid sequence set forth in SEQ ID No 165 and CDR6 comprises the amino acid sequence set forth in SEQ ID No 185. In further embodiments the amino acid sequences of CDR1, CDR2, CDR3, CDR4, CDR5 or CDR6 have at least 80%, such as at least 90%, for example at least 95% amino acid identity with the any one of the amino acid sequences set forth in SEQ ID Nos 151, 171, 191, 145, 165 or 185.

In a further embodiment the polypeptide comprises amino acid sequences differing from those set forth in SEQ ID Nos 151, 171, 191, 145, 165 or 185 only in conservative amino acid changes.

In a further embodiment the polypeptide comprises a first antigen binding domain is selected from SEQ ID No. 219 or a polypeptide having at least 80% such as at least 90%, for example at least 95% identity to SEQ ID No.219, and the second antigen binding domain is selected from SEQ ID No. 218 or a polypeptide having at least 80%, such as at least 90%, for example at least 95% identity to SEQ ID No.218.

In yet a further embodiment the polypeptide comprises SEQ ID No.224.

(0104-0061)

In one embodiment of the invention the polypeptide comprises in said second immunoglobulin of a single variable domain CDR1 comprises an amino acid sequence as set forth in SEQ ID No 151, CDR2 comprises the amino acid sequence set forth in SEQ ID No 171 and CDR3 comprises the amino acid sequence set forth in SEQ ID No 191 and further comprises in said first immunoglobulin of a single variable domain CDR4 comprises an amino acid sequence as set forth in SEQ ID No 143, CDR5 comprises the amino acid sequence set forth in SEQ ID No 235 and CDR6 comprises the amino acid sequence set forth in SEQ ID No 183. In further embodiments the amino acid sequences of CDR1, CDR2, CDR3, CDR4, CDR5 or CDR6 have at least 80%, such as at least 90%, for example at least 95% amino acid identity with the any one of the amino acid sequences set forth in SEQ ID Nos 151, 171, 191, 143, 235 or 183.

In a further embodiment the polypeptide comprises amino acid sequences differing from those set forth in SEQ ID Nos 151, 171, 191, 143, 235 or 183 only in conservative amino acid changes.

In a further embodiment the polypeptide comprises a first antigen binding domain is selected from SEQ ID No. 219 or a polypeptide having at least 80% such as at least 90%, for example at least 95% identity to SEQ ID No.219, and the second antigen binding domain is selected from SEQ ID No. 215 or a polypeptide having at least 80%, such as at least 90%, for example at least 95% identity to SEQ ID No.215, separated by a linker with the SEQ ID No.220.

In relation to the foregoing discussion of preferred embodiments in accordance with the invention, it will be understood that although it specifically relates to biparatopic Nanobodies the disclosure also relates to biparatopic polypeptides directed against or binding CXCR2 wherein the first and second binding domains are comprised in conventional four chain antibodies, heavy chain antibodies, single chain Fvs, Fabs or Fab(2)s, but which have one or more of the functional or structural characteristics of the foregoing preferred embodiments.

Also expressly disclosed are embodiments in which the first and second antigen binding domains are comprised within immunoglobulin single variable domains such as $V_L$ domains, $V_H$ domains, (dAb)s and $V_{HH}$ domains and fragments thereof which have one or more functional or structural characteristics of each of the foregoing embodiments.

In another aspect the invention provides polypeptides, and in particular immunoglobulin single variable domains such as a $V_{HH}$ domain or Nanobody which are monovalent with respect to CXCR2 binding and which are building blocks for the biparatopic polypeptides of the invention and may be regarded as intermediates in the process of production thereof. Preferred monovalent immunoglobulin single variable domains are those polypeptides with SEQ ID Nos 25 to 43 and 90 shown in Table 9 or polypeptides with at least 80%, at least 85%, at least 90% or at least 95% amino acid sequence identity to any one of SEQ ID Nos 25 to 43 and 90.

A preferred monovalent polypeptide is that designated 137B7 and comprising the amino acid sequence set forth in SEQ ID No 36 or an amino acid sequence having at least 80%, at least 85%, at least 90% or at least 95% amino acid sequence identity with SEQ ID No 36. In a preferred embodiment the framework regions of SEQ ID No 36 have one or more sequence-optimising, amino acid substitutions. Other preferred monovalent polypeptides are those designated 127D1, 2B2, 54B12, 97A9, 163D2 and 163E3, including those which have been sequence-optimised in the framework regions.

For example, 127D1 may comprise the amino acid sequence of SEQ ID No 37 in which one or more sequence-optimising amino acid substitutions as contemplated in Table 26 have been made and preferably the polypeptide comprises the amino acid sequence set for in SEQ ID No 216.

2B2 may comprise the amino acid sequence of SEQ ID No 43 in which one or more sequence-optimising substitutions as contemplated in Table 20 have been made and preferably the polypeptide comprises the amino acid sequence set forth in SEQ ID No 213 or 214.

54B12 may comprise the SEQ ID No 90 in which one or more sequence-optimising substitutions as contemplated in Table 30 have been made and preferably the polypeptide comprises the amino acid sequence set forth in SEQ ID No 219.

97A9 may comprise the SEQ ID No 39 in which one or more sequence-optimising substitutions as contemplated in Table 22 have been made and preferably the polypeptide comprises the amino acid sequence set forth in SEQ ID No. 215.

163D2 may comprise the amino acid sequence of SEQ ID No 41 in which one or more of the sequence-optimising substitutions as contemplated in Table 28 have been made and preferably the polypeptide comprises the amino acid sequence set forth in SEQ ID No 218.

163E3 may comprise the amino acid sequence set forth in SEQ ID No. 42 in which one or more sequence-optimising substitutions as contemplated in Table 24 have been made and preferably the polypeptide comprises the amino acid sequence set forth in SEQ ID No 217.

Also encompassed within this aspect of the invention are monovalent polypeptides, in particular immunoglobulin single variable domains such as Nanobodies which are capable of cross-blocking binding to CXCR2 with a polypeptide having the amino acid sequence set forth in any one of SEQ ID Nos 58, 59, 62, 63, 64, 65, 47 or 61.

Any of the preferred monovalent Nanobodies discussed above and in particular 137B7 may be used for the applications recited herein, for example, in the treatment of COPD.

Biparatopic polypeptides in accordance with the invention, in particular the preferred biparatopic immunoglobulin single variable domains discussed above, including all camelised and humanised versions thereof are modulators of CXCR2 and in particular inhibit CXC2 signal transduction.

Preferably, the CDR sequences and FR sequences in the biparatopic polypeptides, in particular biparatopic immunoglobulin single variable domains of the invention are such that they:

- binds to CXCR2 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

- bind to CXCR2 with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

- bind to CXCR2 with a $k_{off}$-rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}s^{-1}$.

Preferably, CDR sequences and FR sequences present in the polypeptides and biparatopic immunoglobulin single variable domains of the invention are such that they bind to CXCR2 with an affinity less than 500 nM, preferably less than 200 nM, more preferably less than 10 nM, such as less than 500 pM.

In particular, as shown in the Examples herein, the preferred biparatopic Nanobodies of the invention are able to inhibit binding of Gro-α to human CXCR2 with an IC50 less than 20 nM. Preferred biparatopic Nanobodies in accordance with the invention may also inhibit agonist induced (Gro-α) Ca release from CXCR2 bearing RBL cells with an IC50 of less than 100 nM. Preferred biparatopic Nanobodies in accordance with the invention may also inhibit agonist induced (Gro-α) [$^{35}$S]GTPγS accumulation in CXCR2-CHO membranes with an IC50 of less than 50 nM. Preferred biparatopic Nanobodies of the invention may also inhibit human white blood cell shape change on exposure to Gro-α with an IC50 of less than <1 nm or Cynomologous white blood cell shape change with an IC50 of less than <2 nm.

In accordance with a most preferred aspect of the invention, a bioparatopic polypeptide of the invention such as a biparatopic immunoglobulin single variable domain, e.g. a Nanobody as described herein will cross-block binding to CXCR2 polypeptide having the amino acid sequence of SEQ ID No 1 with any or all of the polypeptides set forth in SEQ ID Nos 58, 59, 62, 63, 64, 65, 47 or 61. Cross-blocking may be measured by any of the methods well-known to those skilled in the art.

For pharmaceutical use, the polypeptides of the invention are preferably directed against human CXCR2, for example, a polypeptide comprising an amino acid sequence as set for in SEQ ID No 1; whereas for veterinary purposes, the polypeptides of the invention are preferably directed against CXCR2 from the species to be treated, or at least cross-reactive with CXCR2 from the species to be treated.

Furthermore, a biparatopic polypeptide of the invention may optionally, and in addition to the at least two antigen binding domains for binding against CXCR2, contain one or more further binding sites or domains for binding against other epitopes, antigens, proteins or targets.

The efficacy of the polypeptides of the invention, and of compositions comprising the same, can be tested using any suitable in vitro assay, cell-based assay, in vivo assay and/or animal model known per se, or any combination thereof, suitable for indicating that the polypeptide may be useful for treating COPD or any other disease involving aberrant CXCR2 signal transduction. Suitable assays and animal models will be clear to the skilled person.

Also, according to the invention, polypeptides that are directed against human CXCR2 may or may not show cross-reactivity with CXCR2 from one or more other species of warm-blooded animal. However, preferably the polypeptides of the invention directed against human CXCR2 will show cross reactivity with CXCR2 from one or more other species of primates (such as, without limitation, monkeys from the genus *Macaca* (such as, and in particular, cynomologus monkeys (*Macaca fascicularis*) and/or rhesus monkeys (*Macaca mulatta*)) and baboon (*Papio ursinus*)) for the purposes of toxicity testing. Preferred cross-reactivity is with CXCR2 from Cynomologus monkeys. Cross-reactivity with one or more species of animals that are often used in animal models for diseases (for example mouse, rat, rabbit, pig or dog), and in particular in animal models for diseases and disorders associated with CXCR2 may be desirable. In this respect, it will be clear to the skilled person that such cross-reactivity, when present, may have advantages from a drug development point of view, since it allows the amino acid sequences and polypeptides against human CXCR2 to be tested in such disease models.

More generally, polypeptides of the invention that are cross-reactive with CXCR2 from multiple species of mammal will usually be advantageous for use in veterinary applications, since it will allow the same polypeptide to be used across multiple species.

Preferably, the biparatopic polypeptides of the invention are not cross-reactive with CXCR1 or CXCR4.

In the biparatopic polypeptides of the invention, at least one antigen binding site may be directed against an interaction site, i.e. a site at which CXCR2 would interact with another molecule, for example, its natural ligand or ligands.

The biparatopic polypeptide e.g. immunoglobulin single variable domain of the invention may be such that the second antigen binding domain does not bind the linear peptide of SEQ ID No 7 recognises an epitope comprising or within the peptides set forth herein as SEQ ID Nos 8, 9, 10, 11 or 12. In addition, the first antigen binding domain may recognise an epitope comprising or within the peptide of SEQ ID No 7.

In embodiments of the invention which cross-react with Cynomologus monkey CXCR2 the first antigen binding domain also recognises an epitope comprising or within the peptide of SEQ ID No 4. The second antigen binding domain in such an embodiment may recognise an epitope comprising or within the peptides of SEQ ID No 5 or 6.

Also provided within the scope of the invention are types of biparatopic polypeptides, in particular biparatopic Nanobodies that will generally bind to all naturally occurring or synthetic analogs, variants, mutants, alleles, parts and fragments of CXCR2; or at least to those analogs, variants, mutants, alleles, parts and fragments of CXCR2 that contain one or more antigenic determinants or epitopes that are essentially the same as the antigenic determinant(s) or epitope(s) to which the polypeptides of the invention bind in CXCR2 (e.g. in wild-type CXCR2 of SEQ ID No 1). In such a case, the polypeptides of the invention may bind to such analogs, variants, mutants, alleles, parts and fragments with an affinity and/or specificity that are the same as, or that are different from (i.e. higher than or lower than), the affinities and specifications discussed above with which the polypeptides of the invention binds to (wild-type) CXCR2.

Also, as will be clear to the skilled person, polypeptides that are biparatopic bind with higher avidity to CXCR2 than a corresponding single antigen binding domain polypeptide.

It is also within the scope of the invention to use parts, fragments, analogs, mutants, variants, alleles and/or derivatives of the biparatopic polypeptides, in particular the biparatopic immunoglobulin single variable domains of the invention in the various therapeutic contexts discussed herein, provided always they include the relevant functional domains equivalent to the full polypeptide. Such parts, fragments, analogs, mutants, variants, alleles or derivatives may have all the functional features discussed above for the biparatopic polypeptides of the invention.

In another aspect, the invention relates to a biparatopic polypeptide, optionally biparatopic immunoglobulin single variable domains which optionally further comprises one or more other groups, residues, moieties or binding units. Such further groups, residues, moieties, binding units or amino acid sequences may or may not provide further functionality to the polypeptide of the invention and may or may not modify the properties thereof.

For example, such further groups, residues, moieties or binding units may be one or more additional amino acid sequences, such that the invention is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, such groups may be linked to the one or more polypeptides of the invention so as to provide a "derivative" of a polypeptide of the invention, as further described herein.

In such constructs, the one or more polypeptides of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting construct is a fusion (protein) or fusion (polypeptide).

As will be clear from the further description above and herein, this means that the biparatopic polypeptides of the invention can be used as a "building block" to form further polypeptides of the invention, i.e. by suitably combining them with other groups, residues, moieties or binding units, in order to form constructs as described herein which are multiparatopic and optionally multivalent or multispecific, bi/multivalent and bi/multispecific.

The polypeptides of this aspect of the invention can generally be prepared by a method which comprises at least one step of suitably linking the one or more polypeptides of the invention to the one or more further groups, residues, moieties or binding units, optionally via the one or more suitable linkers.

In one specific aspect of the invention, the biparatopic polypeptide of the invention is modified to have an increased half-life, compared to the corresponding unmodified polypeptide of the invention. Some preferred polypeptides will become clear to the skilled person based on the further disclosure herein, and for example comprise amino acid sequences or polypeptides of the invention that have been chemically modified to increase the half-life thereof (for example, by means of pegylation, pasylation or hesylation); polypeptides of the invention may comprise at least one additional binding site for binding to a serum protein (such as serum albumin); or polypeptides of the invention may comprise at least one amino acid sequence that is linked to at least one moiety (and in particular at least one amino acid sequence) that increases the half-life of the polypeptide of the invention. Examples of polypeptides of the invention that comprise such half-life extending moieties or amino acid sequences include polypeptides which suitably link to one or more serum proteins or fragments thereof (such as (human) serum albumin or suitable fragments thereof) or to one or more binding units that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum proteins such as serum albumin (such as human serum albumin), serum immunoglobulins such as IgG, or transferrine; polypeptides which are linked to an Fc portion (such as a human Fc) or a suitable part or fragment thereof. Polypeptides of the invention which are linked to one or more small proteins or peptides that can bind to serum proteins (such as, without limitation, the proteins and peptides described in WO 91/01743, WO 01/45746, WO 02/076489 and to the US provisional application of Ablynx N.V. entitled "*Peptides capable of binding to serum proteins*" of Ablynx N.V. filed on Dec. 5, 2006 (see also PCT/EP2007/063348) are also incorporated within the invention.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a biparatopic Nanobody of the invention. A biparatopic polypeptide of the invention may be modified so as to suitably introduce one or more cysteine residues for attachment of PEG, or an amino acid sequence comprising one or more cysteine residues for attachment of PEG may be fused to the N- and/or C-terminus of a biparatopic polypeptide, all using techniques of protein engineering known per se to the skilled person.

Preferably, for the biparatopic immunoglobulin single variable domains and polypeptides of the invention, a PEG is used with a molecular weight of more than 5000, such as more than 10,000 and less than 200,000, such as less than 100,000; for example in the range of 20,000-80,000.

Pegylation may be applied to one or both of the immunoglobulin variable domains and/or to any peptide linker region. Suitable pegylation techniques are described in EP 1639011.

As an alternative to PEG, half-life may be extended by a technique know as HESylation which involves attachment of hydroxyethyl starch (HES) derivatives to the polypeptides of the invention. The hydroxyethyl starch used is an amylopectin derived from waxy maize starch which has been modified by means of acid hydrolysis to adjust molecular weight and in which the glucose residues have been hydroxyethylated. Further details may be obtained from Pavisic R, et al., Int J Pharm (2010) Mar. 15, 387 (1-2):110-9.

Generally, polypeptides of the invention with increased half-life preferably have a half-life that is at least 1.5 times, preferably at least 2 times, such as at least 5 times, for example at least 10 times or more than 20 times, greater than the half-life of the corresponding polypeptide of the invention per se. For example, the polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding polypeptide of the invention per se.

In a preferred aspect of the invention, such polypeptides of the invention have a serum half-life that is increased with more than 1 hours, preferably more than 2 hours, more preferably more than 6 hours, such as more than 12 hours, or even more than 24, 48 or 72 hours, compared to the corresponding polypeptides of the invention per se.

In another preferred aspect of the invention, polypeptides of the invention exhibit a serum half-life in human of at least about 12 hours, preferably at least 24 hours, more preferably at least 48 hours, even more preferably at least 72 hours or more. For example, polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

The invention further relates to methods for preparing or generating polypeptides, nucleic acids, host cells and compositions of the invention as described herein.

Generally, these methods may comprise the steps of:

a) providing a set, collection or library of polypeptides; and b) screening said set, collection or library of polypeptides for amino acid sequences that can bind to and/or have affinity for CXCR2; and c) isolating the amino acid sequence(s) that can bind to and/or have affinity for CXCR2].

The set, collection or library of polypeptides may be a set, collection or library of immunoglobulin sequences (as described herein), such as a naïve set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of polypeptides may be a set, collection or library of heavy chain variable domains (such as $V_H$ domains or $V_{HH}$ domains) or of light chain variable domains. For example, the set, collection or library of polypeptides may be a set, collection or library of domain antibodies or single domain antibodies, or may be a set, collection or library of amino acid sequences that are capable of functioning as a domain antibody or single domain antibody.

In a preferred aspect of this method, the set, collection or library of polypeptides may be an immune set, collection or library of immunoglobulin sequences, for example derived from a mammal, for example, a Llama that has been suitably immunised with CXCR2 or with a suitable antigenic determinant based thereon or derived therefrom, such as an antigenic part, fragment, region, domain, loop or other epitope thereof.

In the above methods, the set, collection or library of peptides or polypeptides may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In another aspect, the method for generating polypeptides for use in the construction of biparatopic polypeptide in accordance with the invention comprises at least the steps of:

a) providing a collection or sample of cells expressing polypeptides;

b) screening said collection or sample of cells for cells that express a polypeptide that can bind to and/or have affinity for CXCR2; and c) either (i) isolating said polypeptide; or (ii) isolating from said cell a nucleic acid sequence that encodes said polypeptide, followed by expressing said polypeptide.

For example, when the desired polypeptide is an immunoglobulin sequence, the collection or sample of cells may for example be a collection or sample of B-cells. Also, in this method, the sample of cells may be derived from a mammal, for example, a Llama that has been suitably immunised with CXCR2 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the preparation of the preferred biparatopic Nanobodies of the invention identified herein, Llamas were immunised with mammalian cells expressing human CXCR2, mammalian cells expressing Cynomolgus CXCR2, DNA encoding full-length human CXCR2, DNA encoding Δ1-17 human CXCR2, DNA encoding Cynomolgus CXCR2 and the peptides set forth in Table 5

The screening method as described above may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820 (2001).

In another aspect, the method for generating a polypeptide directed against CXCR2 for use in construction of a polypeptide in accordance with the invention may comprise at least the steps of:

a) providing a set, collection or library of nucleic acid sequences encoding the polypeptide;
b) screening said set, collection or library of nucleic acid sequences for nucleic acid sequences that encode an amino acid sequence that can bind to and/or has affinity for CXCR2; and
c) isolating said nucleic acid sequence, followed by expressing said polypeptide.

In such a method, the set, collection or library of nucleic acid sequences encoding the polypeptide may for example be a set, collection or library of nucleic acid sequences encoding a naïve set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

Also, in such a method, the set, collection or library of nucleic acid sequences may encode a set, collection or library of heavy chain variable domains (such as $V_H$ domains or $V_{HH}$ domains) or of light chain variable domains. For example, the set, collection or library of nucleic acid sequences may encode a set, collection or library of domain antibodies or single domain antibodies, or a set, collection or library of amino acid sequences that are capable of functioning as a domain antibody or single domain antibody.

In a preferred aspect of this method, the set, collection or library of nucleic acid sequences may be an immune set, collection or library of nucleic acid sequences, for example derived from a mammal that has been suitably immunised with CXCR2 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the generation of polypeptides of the present invention, Llamas were immunised with the antigens as explained above.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

In another aspect, the method for generating a polypeptide directed against CXCR2 which may be used in the biparatopic polypeptides in accordance with the invention may at least comprise the steps of:

a) providing a set, collection or library of nucleic acid sequences encoding polypeptides;
b) screening said set, collection or library of nucleic acid sequences for nucleic acid sequences that encode an amino acid sequence that can bind to and/or has affinity for CXCR2 and that is cross-blocked or is cross blocking a biparatopic Nanobody of the invention, e.g. one encoded by SEQ ID NOs 58, 59, 62, 63, 64, 65, 47 or 61; and
c) isolating said nucleic acid sequence, followed by expressing said polypeptide.

The invention also relates to biparatopic polypeptides that are obtained by the above methods, or alternatively by a method that comprises one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis and constructing a biparatopic polypeptide therefrom.

The above method may be performed in any suitable manner, as will be clear to the skilled person and discussed in more detail below. Reference is for example made to EP 0 542 810, WO 05/19824, WO 04/051268 and WO 04/106377. For example, the screening of step b) is preferably performed using a flow cytometry technique such as FACS. For this, reference is for example made to Lieby et al., Blood, Vol. 97, No. 12, 3820. Particular reference is made to the so-called "Nanoclone™" technique described in International application WO 06/079372 by Ablynx N.V.

Another technique for obtaining $V_{HH}$ sequences or Nanobody sequences directed against CXCR2 involves suitably immunizing a transgenic mammal that is capable of expressing heavy chain antibodies (i.e. so as to raise an immune response and/or heavy chain antibodies directed against CXCR2, obtaining a suitable biological sample from said transgenic mammal that contains (nucleic acid sequences encoding) said $V_{HH}$ sequences or Nanobody sequences (such as a blood sample, serum sample or sample of B-cells), and then generating $V_{HH}$ sequences directed against CXCR2, starting from said sample, using any suitable technique known per se (such as any of the methods described herein or a hybridoma technique). For example, for this purpose, heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

Other suitable methods and techniques for obtaining the Nanobodies for use in the invention and/or nucleic acids encoding the same, starting from naturally occurring $V_H$ sequences or preferably $V_{HH}$ sequences, will be clear from the skilled person, and may for example include the techniques that are mentioned on page 64 of WO 08/00279As mentioned herein.

$V_{HH}$ domains or Nanobodies may be characterised by one or more "Hallmark Residues" within their FRs. The hallmark residues are those residues which characterise the FR as from a Camelid, for example, Llama source. Accordingly, hallmark residues are a desirable target for substitution, preferable a humanising substitution.

According to Kabat numbering the hallmark residues may be at positions 11, 37, 44, 45, 47, 83, 84, 103, 104 or 108 in a Nanobody. Non-limiting examples of (suitable combinations of) such framework sequences and alternative hallmark residues are given on pages 65 to 98 of WO 2008/020079 which pages are incorporated herein in their entirety. Other humanised or partially humanised sequences known in the art are also contemplated and encompassed within the invention.

As already discussed herein, a Nanobody for use in the invention may have at least "one amino acid difference" (as defined herein) in at least one of the framework regions compared to the corresponding framework region of a naturally occurring human $V_H$ domain, and in particular compared to the corresponding framework region of DP-47. More specifically, according to one non-limiting aspect of the invention, a Nanobody may have at least "one amino acid difference" (as defined herein) at least one of the Hallmark residues (including those at positions 108, 103 and/or 45) compared to the corresponding framework region of a naturally occurring human $V_H$ domain, and in particular compared to the corresponding framework region of DP-47. Usually, a Nanobody will have at least one such amino acid difference with a naturally occurring $V_H$ domain in at least one of FR2 and/or FR4, and in particular at least one of the Hallmark residues in FR2 and/or FR4 (again, including those at positions 108, 103 and/or 45).

Also, a humanised Nanobody of the invention may be as defined herein, but with the proviso that it has at least "one amino acid difference" (as defined herein) in at least one of the framework regions compared to the corresponding framework region of a naturally occurring $V_{HH}$ domain. More specifically, according to one non-limiting aspect of the invention, a humanised or otherwise sequence optimised Nanobody may be as defined herein, but with the proviso that it has at least "one amino acid difference" (as defined herein) at least one of the Hallmark residues (including those at positions 108, 103 and/or 45) compared to the corresponding framework region of a naturally occurring $V_{HH}$ domain. Usually, a humanised or otherwise sequence optimised Nanobody will have at least one such amino acid difference with a naturally occurring $V_{HH}$ domain in at least one of FR2 and/or FR4, and in particular at least one of the Hallmark residues in FR2 and/or FR4 (again, including those at positions 108, 103 and/or 45).

As will be clear from the disclosure herein, it is also within the scope of the invention to use natural or synthetic analogs, mutants, variants, alleles, homologs and orthologs (herein collectively referred to as "analogs") of the immunoglobulin single variable domain of the invention as defined herein, and in particular analogs of the biparatopic Nanobodies of SEQ ID NOs 58, 59, 62, 63, 64, 65, 47, 61, 53, 54, 46, 69, 68, 67 or 66.

Generally, in such analogs, one or more amino acid residues may have been replaced, deleted and/or added, compared to the immunoglobulin single variable domains of the invention as defined herein. Such substitutions, insertions or deletions may be made in one or more of the framework regions and/or in one or more of the CDR's. When such substitutions, insertions or deletions are made in one or more of the framework regions, they may be made at one or more of the Hallmark residues and/or at one or more of the other positions in the framework residues, although substitutions, insertions or deletions at the Hallmark residues are generally less preferred (unless these are suitable humanising substitutions as described herein).

By means of non-limiting examples, a substitution may for example be a conservative substitution (as described herein) and/or an amino acid residue may be replaced by another amino acid residue that naturally occurs at the same position in another $V_{HH}$ domain (see WO 2008/020079 for some non-limiting examples of such substitutions), although the invention is generally not limited thereto. Thus, any one or more substitutions, deletions or insertions, or any combination thereof, that either improve the properties of, for example, a Nanobody for use in a biparatopic Nanobody of the invention or that at least do not detract too much from the desired properties or from the balance or combination of desired properties of the invention (i.e. to the extent that the Nanobody or biparatopic Nanobody is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the Nanobodies thus obtained.

For example, and depending on the host organism used to express the biparatopic Nanobody or polypeptide of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

Generally herein, facilitating substitutions, insertions or deletions in amino acid sequence for the purposes of securing particular properties or structural characteristics not present in the native sequence, including "humanising" substitutions is referred to as "sequence optimisation". In this respect, reference may be had to the definition section herein at item (y).

The analogs are preferably such that they can bind to CXCR2 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the biparatopic Nanobodies of the invention. The analogs are preferably also such that they retain the favourable properties the biparatopic Nanobodies, as described herein.

Also, according to one preferred aspect, the analogs have a degree of sequence identity of at least 70%, preferably at least 80%, more preferably at least 90%, such as at least 95% or 99% or more; and/or preferably have at most 20, preferably at most 10, even more preferably at most 5, such as 4, 3, 2 or only 1 amino acid difference (as defined herein), with one of the biparatopic Nanobodies of SEQ ID Nos 58, 59, 62, 63, 64, 65, 47, 61, 53, 54, 46, 69, 68, 67 or 66.

Also, the framework sequences and CDR's of the analogs are preferably such that they are in accordance with the preferred aspects defined herein. More generally, as described herein, the analogs will have (a) a Q at position 108; and/or (b) a charged amino acid or a cysteine residue at position 45 and preferably an E at position 44, and more preferably E at position 44 and R at position 45; and/or (c) P, R or S at position 103.

One preferred class of analogs of the biparatopic $V_{HH}$ domains or Nanobodies of the invention have been humanised (i.e. compared to the sequence of a naturally occurring Nanobody). As mentioned, such humanisation generally involves replacing one or more amino acid residues in the sequence of a naturally occurring $V_{HH}$ with the amino acid residues that occur at the same position in a human $V_H$ domain, such as a human $V_H3$ domain. Examples of possible humanising substitutions other than those specifically disclosed in Tables 20, 22, 24, 26, 28 and 30 herein although other combinations of humanising substitutions will be clear to the skilled person from a comparison between the sequence of a Nanobody and the sequence of a naturally occurring human $V_H$ domain and from the disclosure of WO 2008/020079 as already disclosed herein.

Generally, as a result of humanisation, the immunoglobulin single variable domains, in particular Nanobodies of the invention may become more "human-like", while still retaining the favorable properties of the Nanobodies of the invention as described herein. As a result, such humanised Nanobodies may have several advantages, such as a reduced immunogenicity, compared to the corresponding naturally occurring $V_{HH}$ domains. Again, based on the disclosure herein and optionally after a limited degree of routine experimentation, the skilled person will be able to make humanising substitutions or suitable combinations of humanising substitutions which optimize or achieve a desired or suitable balance between the favourable properties provided by the humanising substitutions on the one hand and the favourable properties of naturally occurring $V_{HH}$ domains on the other hand.

The Nanobodies for incorporation in the biparatopic Nanobodies of the invention may be suitably humanised at any framework residue(s), such as at one or more Hallmark residues (as defined herein) or at one or more other framework residues (i.e. non-Hallmark residues) or any suitable combination thereof. One preferred humanising substitution for Nanobodies of the "P,R,S-103 group" or the "KERE group" is Q108 into L108. Nanobodies of the "GLEW class" may also be humanised by a Q108 into L108 substitution, provided at least one of the other Hallmark residues contains a camelid (camelising) substitution (as defined herein). For example, as mentioned above, one particularly preferred class of humanised Nanobodies has GLEW or a GLEW-like sequence at positions 44-47; P, R or S (and in particular R) at position 103, and an L at position 108.

The humanised and other analogs, and nucleic acid sequences encoding the same, can be provided in any manner known per se, for example using one or more of the techniques mentioned on pages 103 and 104 of WO 08/020,079.

As mentioned therein, it will be also be clear to the skilled person that the immunoglobulin single variable domains of the invention (including their analogs) can be designed and/or prepared starting from human $V_H$ sequences (i.e. amino acid sequences or the corresponding nucleotide sequences), such as for example from human $V_H3$ sequences such as DP-47, DP-51 or DP-29, i.e. by introducing one or more camelising substitutions (i.e. changing one or more amino acid residues in the amino acid sequence of said human $V_H$ domain into the amino acid residues that occur at the corresponding position in a $V_{HH}$ domain), so as to provide the sequence of a Nanobody of the invention and/or so as to confer the favourable properties of a Nanobody to the sequence thus obtained. Again, this can generally be performed using the various methods and techniques referred to in the previous paragraph, using an amino acid sequence and/or nucleotide sequence for a human $V_H$ domain as a starting point.

Some preferred, but non-limiting camelising substitutions can be derived from WO 2008/020079. It will also be clear that camelising substitutions at one or more of the Hallmark residues will generally have a greater influence on the desired properties than substitutions at one or more of the other amino acid positions, although both and any suitable combination thereof are included within the scope of the invention. For example, it is possible to introduce one or more camelising substitutions that already confer at least some the desired properties, and then to introduce further camelising substitutions that either further improve said properties and/or confer additional favourable properties. Again, the skilled person will generally be able to determine and select suitable camelising substitutions or suitable combinations of camelising substitutions, based on the disclosure herein and optionally after a limited degree of routine experimentation, which may for example involve introducing a limited number of possible camelising substitutions and determining whether the favourable properties of immunoglobulin single variable domains are obtained or improved (i.e. compared to the original $V_H$ domain). Generally, however, such camelising substitutions are preferably such that the resulting an amino acid sequence at least contains (a) a Q at position 108; and/or (b) a charged amino acid or a cysteine residue at position 45 and preferably also an E at position 44, and more preferably E at position 44 and R at position 45; and/or (c) P, R or S at position 103; and optionally one or more further camelising substitutions. More preferably, the camelising substitutions are such that they result in an immunoglobulin single variable domain for use in the invention and/or in an analog thereof (as defined herein), such as in a humanised analog and/or preferably in an analog that is as defined in the preceding paragraphs.

Immumoglobulin single variable domains such as Nanobodies can also be derived from $V_H$ domains by the incorporation of substitutions that are rare in nature, but nonetheless, structurally compatible with the VH domain fold. For example, but without being limiting, these substitutions may include on or more of the following: Gly at position 35, Ser, Val or Thr at position 37, Ser, Thr, Arg, Lys, His, Asp or Glu at position 39, Glu or His at position 45, Trp, Leu, Val, Ala, Thr, or Glu at position 47, S or R at position 50. (Barthelemy et al. J Biol. Chem. 2008 Feb. 8; 283(6):3639-54. Epub 2007 Nov. 28)

The invention also comprises derivatives of the biparatopic polypeptides of the invention. Such derivatives can generally be obtained by modification, and in particular by chemical and/or biological (e.g enzymatical) modification, of the biparatopic polypeptides of the invention and/or of one or more of the amino acid residues that form the biparatopic polypeptides of the invention.

Examples of such modifications, as well as examples of amino acid residues within the polypeptide sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the biparatopic polypeptide of the invention, and in particular of one or more functional groups, residues or moieties that confer one or more desired properties or functionalities to the biparatopic polypeptide of the invention. Example of such functional groups will be clear to the skilled person.

For example, such modification may comprise the introduction (e.g. by covalent binding or in any other suitable manner) of one or more functional groups that increase the half-life, the solubility and/or the absorption of the polypeptide of the invention, that reduce the immunogenicity and/or the toxicity of the polypeptide of the invention, that eliminate or attenuate any undesirable side effects of the polypeptide of the invention, and/or that confer other advantageous properties and/or reduce the undesired properties of the biparatopic Nanobodies and/or polypeptides of the invention; or any combination of two or more of the foregoing. Examples of such functional groups and techniques for introducing them will be clear to the skilled person, and can generally comprise all functional groups known in the art as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a biparatopic polypeptide of the invention, or optionally via a suitable linker or spacer, as will again be clear to the skilled person.

Another, usually less preferred modification comprises N-linked or O-linked glycosylation, usually as part of co-translational and/or post-translational modification, depending on the host cell used for expressing the biparatopic Nanobody or polypeptide of the invention.

Yet another modification may comprise the introduction of one or more detectable labels or other signal-generating groups or moieties, depending on the intended use of the labelled polypeptide or Nanobody. Suitable labels and techniques for attaching, using and detecting them will be clear to the skilled person, and for example include, but are not limited to, the fluorescent labels, phosphorescent labels, chemiluminescent labels, bioluminescent labels, radio-isotopes, metals, metal chelates, metallic cations, chromophores and enzymes, such as those mentioned on page 109 of WO 08/020,079.

Other suitable labels will be clear to the skilled person, and for example include moieties that can be detected using NMR or ESR spectroscopy.

Such labelled biparatopic Nanobodies and polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethylenetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the biparatopic polypeptide or Nanobody of the invention to another protein, polypeptide or chemical compound that is bound to the other half of the binding pair, i.e. through formation of the binding pair. For example, a biparatopic Nanobody of the invention may be conjugated to biotin, and linked to another protein, polypeptide, compound or carrier conjugated to avidin or streptavidin. For example, such a conjugated biparatopic Nanobody may be used as a reporter, for example in a diagnostic system where a detectable signal-producing agent is conjugated to avidin or streptavidin. Such binding pairs may for example also be used to bind the biparatopic Nanobody of the invention to a carrier, including carriers suitable for pharmaceutical purposes. One non-limiting example are the liposomal formulations described by Cao and Suresh, Journal of Drug Targetting, 8, 4, 257 (2000). Such binding pairs may also be used to link a therapeutically active agent to the Nanobody of the invention.

For some applications, in particular for those applications in which it is intended to kill a cell that expresses the CXCR2 target against which the biparatopic polypeptides or immunoglobulin single variable domains of the invention are directed (e.g. in the treatment of cancer), or to reduce or slow the growth and/or proliferation such a cell, the biparatopic polypeptides of the invention may also be linked to a toxin or to a toxic residue or moiety. Examples of toxic moieties, compounds or residues which can be linked to a biparatopic polypeptide of the invention to provide—for example—a cytotoxic compound will be clear to the skilled person and can for example be found in the prior art cited above and/or in the further description herein. One example is the so-called ADEPT™ technology described in WO 03/055527.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

Preferably, the derivatives are such that they bind to CXCR2 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the biparatopic Nanobodies of the invention.

As mentioned above, the invention also relates to proteins or polypeptides that essentially consist of or comprise at least one biparatopic polypeptide of the invention. By "essentially consist of" is meant that the amino acid sequence of the polypeptide of the invention either is exactly the same as the amino acid sequence of a biparatopic polypeptide of the invention or corresponds to the amino acid sequence of such a polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence of the biparatopic polypeptide.

Said amino acid residues may or may not change, alter or otherwise influence the (biological) properties of the polypeptide and may or may not add further functionality thereto. For example, such amino acid residues:

can comprise an N-terminal Met residue, for example as result of expression in a heterologous host cell or host organism.

may form a signal sequence or leader sequence that directs secretion of the biparatopic polypeptide from a host cell upon synthesis. Suitable secretory leader peptides will be clear to the skilled person, and may be as further described herein. Usually, such a leader sequence will be linked to the N-terminus of the biparatopic polypeptide;

may form a sequence or signal that allows the biparatopic polypeptide to be directed towards and/or to penetrate or enter into specific organs, tissues, cells, or parts or compartments of cells, and/or that allows the biparatopic polypeptide to penetrate or cross a biological barrier such as a cell membrane, a cell layer such as a layer of epithelial cells, a tumor including solid tumors, or the blood-brain-barrier. Examples of such amino acid sequences will be clear to the skilled person and include those mentioned in paragraph c) on page 112 of WO 08/020,079.

may form a "tag", for example an amino acid sequence or residue that allows or facilitates the purification of the biparatopic Nanobody, for example using affinity techniques directed against said sequence or residue. Thereafter, said sequence or residue may be removed (e.g. by chemical or enzymatical cleavage) to provide the biparatopic polypeptide sequence (for this purpose, the tag may optionally be linked to the biparatopic polypeptide sequence via a cleavable linker sequence or contain a cleavable motif). Some preferred, but non-limiting examples of such residues are multiple histidine residues, glutatione residues and a myc-tag (see for example SEQ ID NO:31 of WO 06/12282).

may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the biparatopic polypeptides or Nanobodies of the invention.

According to another aspect, a biparatopic polypeptide of the invention comprises a biparatopic Nanobody of the invention, which is fused at its amino terminal end, at its carboxy terminal end, or both at its amino terminal end and at its carboxy terminal end to at least one further peptide or polypeptide, i.e. so as to provide a fusion protein comprising said biparatopic Nanobody of the invention and the one or more further peptides or polypeptides. Such a fusion will also be referred to herein as a "Nanobody fusion".

Preferably, the further peptide or polypeptide is such that it confers one or more desired properties or functionalities to the biparatopic Nanobody or the polypeptide of the invention.

For example, the further peptide or polypeptide may also provide a further binding site, which binding site may be directed against any desired protein, polypeptide, antigen, antigenic determinant or epitope (including but not limited to the same protein, polypeptide, antigen, antigenic determinant or epitope against which the biparatopic polypeptide of the invention is directed, or a different protein, polypeptide, antigen, antigenic determinant or epitope).

Example of such peptides or polypeptides will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005).

For example, such a peptide or polypeptide may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the polypeptide of the invention per se. Some non-limiting examples of such peptides and polypeptides are serum proteins, such as human serum albumin (see for example WO 00/27435) or haptenic molecules (for example haptens that are recognized by circulating antibodies, see for example WO 98/22141).

In particular, it has been described in the art that linking fragments of immunoglobulins (such as $V_H$ domains) to serum albumin or to fragments thereof can be used to increase the half-life. Reference is for made to WO 00/27435 and WO 01/077137). According to the invention, the biparatopic polypeptides, preferabaly the biparaptopic Nanobody of the invention is preferably either directly linked to serum albumin (or to a suitable fragment thereof) or via a suitable linker, and in particular via a suitable peptide linked so that the polypeptide of the invention can be expressed as a genetic fusion (protein). According to one specific aspect, the biparatopic Nanobody of the invention may be linked to a fragment of serum albumin that at least comprises the domain III of serum albumin or part thereof. Reference is for example made to WO 07/112,940 of Ablynx N.V.

Alternatively, as already discussed herein, the further peptide or polypeptide may provide a further binding site or binding unit that is directed against a serum protein (such as, for example, human serum albumin or another serum protein such as IgG), so as to provide increased half-life in serum. Such amino acid sequences for example include the Nanobodies described below, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, as well as to WO 08/028,977, WO 08/043,821, WO 08/043,822 by Ablynx N.V. and US provisional application of Ablynx N.V. entitled "*Peptides capable of binding to serum proteins*" filed on Dec. 5, 2006 ((see also PCT/EP2007/063348).

Such peptides or polypeptides may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see for example WO 06/0122787) and/or amino acid sequences that are capable of binding to amino acid residues on serum albumin that do not form part of domain III of serum albumin (see again for example WO 06/0122787); amino acid sequences that have or can provide an increased half-life (see for example WO 08/028,977 by Ablynx N.V.); amino acid sequences against human serum albumin that are cross-reactive with serum albumin from at least one species of mammal, and in particular with at least one species of primate (such as, without limitation, monkeys from the genus Macaca (such as, and in particular, cynomologus monkeys (*Macaca fascicularis*) and/or rhesus monkeys (*Macaca mulatta*)) and baboon (*Papio ursinus*), reference is again made to WO 08/028,977; amino acid sequences that can bind to serum albumin in a pH independent manner (see for example WO 08/043,821 by Ablynx N.V. entitled "*Amino acid sequences that bind to serum proteins in a manner that is essentially independent of the pH, compounds comprising the same, and uses thereof*") and/or amino acid sequences that are conditional binders (see for example WO 08/043,822 by Ablynx N.V. entitled "*Amino acid sequences that bind to a desired molecule in a conditional manner*").

According to another aspect, the one or more further peptide, polypeptide or protein sequences may comprise one or more parts, fragments or domains of conventional 4-chain antibodies (and in particular human antibodies) and/or of heavy chain antibodies. For example, although usually less preferred, a biparatopic Nanobody of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

The biparatopic polypeptide or Nanobody may also be linked to one or more (preferably human) $C_H1$, $C_H2$ and/or $C_H3$ domains, optionally via a linker sequence. For instance, a biparatopic Nanobody linked to a suitable $C_H1$ domain could for example be used—together with suitable light chains—to generate antibody fragments/structures analogous to conventional Fab fragments or $F(ab')_2$ fragments, but in which one or (in case of an $F(ab')_2$ fragment) one or both of the conventional $V_H$ domains have been replaced by a biparatopic Nanobody of the invention. Also, two biparatopic polypeptides could be linked to a $C_H3$ domain (optionally via a linker) to provide a construct with increased half-life in vivo.

According to one specific aspect of a polypeptide of the invention, one or more biparatopic polypeptides or Nanobodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further peptides or polypeptides may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanised derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the Nanobodies of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra. Coupling of a polypeptide, for example a Nanobody of the invention to an Fc portion may also lead to an increased half-life, compared to the corresponding polypeptide of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more biparatopic polypeptides, such as Nanobodies and one or more constant domains with increased half-life in vivo will be clear to the skilled person, and may for example comprise two Nanobodies linked to a $C_H3$ domain, optionally via a linker sequence. Generally, any fusion protein or derivatives with increased half-life will preferably have a molecular weight of more than 50 kD, the cut-off value for renal absorption.

In another one specific, but non-limiting, aspect, in order to form a polypeptide of the invention, one or more amino acid sequences of the invention may be linked (optionally via a suitable linker or hinge region) to naturally occurring, synthetic or semisynthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al., J Biol Chem 1996 271 7494, describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

The further peptides or polypeptides may also form a signal sequence or leader sequence that directs secretion of the biparatopic Nanobody or the polypeptide of the invention from a host cell upon synthesis (for example to provide a pre-, pro- or prepro-form of the polypeptide of the invention, depending on the host cell used to express the polypeptide of the invention).

The further peptide or polypeptide may also form a sequence or signal that allows the biparatopic Nanobody or polypeptide of the invention to be directed towards and/or to penetrate or enter into specific organs, tissues, cells, or parts or compartments of cells, and/or that allows the biparatopic Nanobody or polypeptide of the invention to penetrate or cross a biological barrier such as a cell membrane, a cell layer such as a layer of epithelial cells, a tumor including solid tumors, or the blood-brain-barrier. Suitable examples of such amino acid sequences will be clear to the skilled person, and for example include, but are not limited to, those mentioned on page 118 of WO 08/020,079.

For some applications, in particular for those applications in which it is intended to kill a cell that expresses the target against which the biparatopic polypeptides of the invention are directed (e.g. in the treatment of cancer), or to reduce or slow the growth and/or proliferation of such a cell, the biparatopic polypeptides of the invention may also be linked to a (cyto)toxic protein or polypeptide. Examples of such toxic proteins and polypeptides which can be linked to a Nanobody of the invention to provide—for example—a cytotoxic polypeptide of the invention will be clear to the skilled person and can for example be found in the prior art cited above and/or in the further description herein. One example is the so-called ADEPT™ technology described in WO 03/055527.

According to one optional, but non-limiting aspect, said one or more further peptide or polypeptide comprises at least one further Nanobody, so as to provide a polypeptide of the invention that comprises at least three, such as four, five or more Nanobodies, in which said Nanobodies may optionally be linked via one or more linker sequences (as defined herein).

Finally, it is also within the scope of the invention that the biparatopic polypeptides of the invention may contain two or more Nanobodies and one or more further peptides or polypeptides (as mentioned herein).

For multivalent and multispecific polypeptides containing two or more $V_{HH}$ domains and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103 and WO 99/23221. Some other examples of some specific multispecific and/or multivalent polypeptide of the invention can be found in the applications by Ablynx N.V. referred to herein.

One preferred example of a multispecific polypeptide of the invention comprises at least one biparatopic Nanobody of the invention and at least one Nanobody that provides for an increased half-life. Such Nanobodies may for example be Nanobodies that are directed against a serum protein, and in particular a human serum protein, such as human serum albumin, thyroxine-binding protein, (human) transferrin, fibrinogen, an immunoglobulin such as IgG, IgE or IgM, or against one of the serum proteins listed in WO 04/003019. Of these, Nanobodies that can bind to serum albumin (and in particular human serum albumin) or to IgG (and in particular human IgG, see for example Nanobody VH-1 described in the review by Muyldermans, supra) are particularly preferred (although for example, for experiments in mice or primates, Nanobodies against or cross-reactive with mouse serum albumin (MSA) or serum albumin from said primate, respectively, can be used. However, for pharmaceutical use, Nanobodies against human serum albumin or human IgG will usually be preferred). Nanobodies that provide for increased half-life and that can be used in the polypeptides of the invention include the Nanobodies directed against serum albumin that are described in WO 04/041865, in WO 06/122787 and in the further patent applications by Ablynx N.V., such as those mentioned above.

For example, some preferred Nanobodies that provide for increased half-life for use in the present invention include Nanobodies that can bind to amino acid residues on (human) serum albumin that are not involved in binding of serum albumin to FcRn (see for example WO 06/0122787); Nanobodies that are capable of binding to amino acid residues on serum albumin that do not form part of domain III of serum albumin (see for example WO 06/0122787); Nanobodies that have or can provide an increased half-life (see for example WO 08/028,977 by Ablynx N.V mentioned herein); Nanobodies against human serum albumin that are cross-reactive with serum albumin from at least one species of mammal, and in particular with at least one species of primate (such as, without limitation, monkeys from the genus *Macaca* (such as, and in particular, cynomologus monkeys (*Macaca fascicularis*) and/or rhesus monkeys (*Macaca mulatta*)) and baboon (*Papio ursinus*)) (see for example WO 08/028,977 by Ablynx N.V)); Nanobodies that can bind to serum albumin in a pH independent manner (see for example WO2008/043821 by Ablynx N.V. mentioned herein) and/or Nanobodies that are conditional binders (see for example WO 08/043,822 by Ablynx N.V.).

Some particularly preferred Nanobodies that provide for increased half-life and that can be used in the polypeptides of the invention include the Nanobodies ALB-1 to ALB-10 disclosed in WO 06/122787 (see Tables II and III) of which ALB-8 (SEQ ID NO: 62 in WO 06/122787) is particularly preferred.

According to a specific aspect of the invention, the polypeptides of the invention contain, besides the two or more Nanobodies, at least one Nanobody against human serum albumin.

Further additional peptides or polypeptides which may be added or attached or fused to the biparatopic polypeptides of the invention include a polymer composed of Proline, Alanine and Serine (a PAS sequence). PAS sequences may be comprised of 200-600 residues and lead to dramatically increased hydrodynamic volume resulting in prolongation of plasma half-life. Serum half-life of the biparatopic polypeptides of the invention may also be extended by fusion to a 864 amino acid polypeptide called XTEN as described in Schellenbrger et al., (2009), Nature Biotechnology 27, No 12, p 1186-1190.

Generally, any polypeptides of the invention with increased half-life that contain one or more biparatopic Nanobodies of the invention, and any derivatives of the biparatopic Nanobodies of the invention or of such polypeptides that have an increased half-life, preferably have a half-life that is at least 1.5 times, preferably at least 2 times, such as at least 5 times, for example at least 10 times or more than 20 times, greater than the half-life of the corresponding Nanobody of the invention per se. For example, such a derivative or polypeptides with increased half-life may have a half-life that is increased with more than 1 hours, preferably more than 2 hours, more preferably more than 6 hours, such as more than 12 hours, or even more than 24, 48 or 72 hours, compared to the corresponding Nanobody of the invention per se.

In a preferred, but non-limiting aspect of the invention, such derivatives or polypeptides may exhibit a serum half-life in human of at least about 12 hours, preferably at least 24 hours, more preferably at least 48 hours, even more preferably at least 72 hours or more. For example, such derivatives or polypeptides may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Another preferred, but non-limiting example of a multispecific polypeptide of the invention comprises at least one biparatopic Nanobody of the invention and at least one Nanobody that directs the polypeptide of the invention towards, and/or that allows the polypeptide of the invention to penetrate or to enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such Nanobodies include Nanobodies that are directed towards specific cell-surface proteins, markers or epitopes of the desired organ, tissue or cell (for example cell-surface markers associated with tumor cells), and the single-domain brain targeting antibody fragments described in WO 02/057445 and WO 06/040153, of which FC44 (SEQ ID NO: 189 of WO 06/040153) and FC5 (SEQ ID NO: 190 of WO 06/040154) are preferred examples.

In the polypeptides of the invention, the two or more Nanobodies and the one or more polypeptides may be directly linked to each other (as for example described in WO 99/23221) and/or may be linked to each other via one or more suitable spacers or linkers, or any combination thereof.

According to one aspect of the invention, the polypeptide of the invention is in essentially isolated from, as defined herein.

The amino acid sequences, biparatopic Nanobodies, polypeptides and nucleic acids of the invention can be prepared in a manner known per se, as will be clear to the skilled person from the further description herein. For example, the biparatopic Nanobodies and polypetides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies, polypeptides and nucleic acids include the methods and techniques described herein.

As will be clear to the skilled person, one particularly useful method for preparing a biparatopic Nanobody and/or a polypeptide of the invention generally comprises the steps of:

i) the expression, in a suitable host cell or host organism (also referred to herein as a "host of the invention") or in another suitable expression system of a nucleic acid that encodes said biparatopic Nanobody or polypeptide of the invention (also referred to herein as a "nucleic acid of the invention"), optionally followed by:

ii) isolating and/or purifying said biparatopic Nanobody or polypeptide of the invention thus obtained.

In particular, such a method may comprise the steps of:

i) cultivating and/or maintaining a host of the invention under conditions that are such that said host of the invention expresses and/or produces at least one biparatopic Nanobody and/or polypeptide of the invention, optionally followed by:

ii) isolating and/or purifying the biparatopic Nanobody or polypeptide of the invention thus obtained.

In another aspect, the invention relates to a nucleic acid molecule that encodes an a polypeptide of the invention (or a suitable fragment thereof). Such a nucleic acid will also be referred to herein as a "nucleic acid of the invention" and may for example be in the form of a genetic construct, as further described herein.

In preferred embodiments the invention provides a nucleic acid molecule encoding an amino acid sequence selected from the group of amino acid sequences set forth in SEQ ID Nos 25 to 43, 90 and SEQ ID Nos 213 to 219 relating to the specific individual Nanobodies of Tables 9 and 32. Alternatively, nucleic acid molecules in accordance with the invention comprise nucleic acid molecules encoding the multivalent and biparatopic Nanobody constructs of SEQ ID Nos 44 to 69. Further, nucleic acid molecules in accordance with the invention comprise molecules with the nucleic acid sequences of SEQ ID Nos 192 to 211 relating to the Nanobodies identified in Table 18.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences for the polypeptides of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a polypeptide of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring form of CXCR2 as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises:

i) at least one nucleic acid of the invention; operably connected to ii) one or more regulatory elements, such as a promoter and optionally a suitable terminator;

and optionally also iii) one or more further elements of genetic constructs known per se;

in which the terms "operably connected" and "operably linked" have the meaning given on pages 131-134 of WO 08/020,079; and in which the "regulatory elements", "promoter", "terminator" and "further elements" are as described on pages 131-134 of WO 08/020,079; and in which the genetic constructs may further be as described on pages 131-134 of WO 08/020,079.

The nucleic acids of the invention and/or the genetic constructs of the invention may be used to transform a host cell or host organism, i.e. for expression and/or production of the biparatopic Nanobody or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example those described on pages 134 and 135 of WO 08/020,079; as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The biparatopic Nanobodies and polypeptides of the invention can also be introduced and expressed in one or more cells, tissues or organs of a multicellular organism, for example for prophylactic and/or therapeutic purposes (e.g. as a gene therapy), as further described on pages 135 and 136 of in WO 08/020,079 and in the further references cited in WO 08/020, 079.

For expression of the Nanobodies in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The biparatopic Nanobodies and polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or turbers (for example in tobacco, maize, soybean or alfalfa) or in for example pupae of the silkworm *Bombix mori*.

Furthermore, the biparatopic Nanobodies and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of biparatopic polypeptides and Nanobodies is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of biparatopic Nanobodies or Nanobody-containing protein therapeutics include strains of *E. coli, Pichia pastoris, S. cerevisiae* that are suitable for large scale expression/production/fermentation, and in particular for large scale pharmaceutical (i.e. GMP grade) expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired biparatopic Nanobody or polypeptide to be obtained.

Thus, according to one aspect of the invention, the biparatopic Nanobody or polypeptide of the invention is glycosylated. According to another non-limiting aspect of the invention, the amino acid sequence, Nanobody or polypeptide of the invention is non-glycosylated.

According to one preferred, but non-limiting aspect of the invention, the biparatopic Nanobody or polypeptide of the invention is produced in a bacterial cell, in particular a bacterial cell suitable for large scale pharmaceutical production, such as cells of the strains mentioned above.

According to another preferred, but non-limiting aspect of the invention, biparatopic Nanobody or polypeptide of the invention is produced in a yeast cell, in particular a yeast cell suitable for large scale pharmaceutical production, such as cells of the species mentioned above.

According to yet another preferred, but non-limiting aspect of the invention, the biparatopic Nanobody or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

As further described on pages 138 and 139 of WO 08/020, 079, when expression in a host cell is used to produce the biparatopic Nanobodies and the polypeptides of the invention, these produced either intracellullarly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. Thus, according to one non-limiting aspect of the invention, the biparatopic Nanobody or polypeptide of the invention is an amino acid sequence, Nanobody or polypeptide that has been produced intracellularly and that has been isolated from the host cell, and in particular from a bacterial cell or from an inclusion body in a bacterial cell. According to another non-limiting aspect of the invention, the biparatopic Nanobody or polypeptide of the invention is a Nanobody or polypeptide that has been produced extracellularly, and that has been isolated from the medium in which the host cell is cultivated.

Some preferred, but non-limiting promoters for use with these host cells include those mentioned on pages 139 and 140 of WO 08/020,079.

Some preferred, but non-limiting secretory sequences for use with these host cells include those mentioned on page 140 of WO 08/020,079.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the polypeptide of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), a biparatopic Nanobody or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences of the invention, the transformed host cell or transformed host organism may generally be kept, maintained and/or cultured under conditions such that the (desired) biparatopic Nanobody or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the polypeptide of the invention may be expressed in a constitutive manner, in a transient manner, or only when suitably induced.

It will also be clear to the skilled person that the biparatopic Nanobody or polypeptide of the invention may (first) be generated in an immature form (as mentioned above), which may then be subjected to post-translational modification, depending on the host cell/host organism used. Also, the biparatopic Nanobody or polypeptide of the invention may be glycosylated, again depending on the host cell/host organism used.

The biparatopic Nanobody or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, Nanobody or polypeptide of the invention) and/or preparative immunological techniques (i.e. using antibodies against the amino acid sequence to be isolated).

Generally, for pharmaceutical use, the polypeptides of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, (for example, via a nebulizer, metered dose inhaler (MDI) or dry powder inhaler (DPI) or via the nasal route), by a skin patch, by an implant, by a suppository, by subs-lingual route, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one biparatopic polypeptide of the invention preferably at least one biparatopic immunoglobulin single variable domain and more preferably at least one biparatopic Nanobody in accordance with the invention, and at least one suitable carrier, diluent or excipient (i.e. suitable for pharmaceutical use), and optionally one or more further active substances.

Generally, the biparatopic polypeptides of the invention can be formulated and administered in any suitable manner known per se, for which reference is for example made to the general background art cited above (and in particular to WO 04/041862, WO 04/041863, WO 04/041865, WO 04/041867 and WO 08/020,079) as well as to the standard handbooks, such as Remington's Pharmaceutical Sciences, $18^{th}$ Ed., Mack Publishing Company, USA (1990), Remington, the Science and Practice of Pharmacy, 21th Edition, Lippincott Williams and Wilkins (2005); or the Handbook of Therapeutic Antibodies (S. Dubel, Ed.), Wiley, Weinheim, 2007 (see for example pages 252-255).

For example, the biparatopic polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020,079. Usually, aqueous solutions or suspensions will be preferred.

The biparatopic polypeptides of the invention including biparatopic immunoglobulin single variable domains and Nanobodies can also be administered using gene therapy methods of delivery. See, e.g., U.S. Pat. No. 5,399,346, which is incorporated by reference in its entirety. Using a gene therapy method of delivery, primary cells transfected with the gene encoding a biparatopic or polypeptide of the invention can additionally be transfected with tissue specific promoters to target specific organs, tissue, grafts, tumors, or cells and can additionally be transfected with signal and stabilization sequences for subcellularly localized expression.

Thus, the biparatopic and polypeptides, immunoglobulin single variable domains and Nanobodies of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the biparatopic polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the biparatopic polypeptide, immunoglobulin single variable domain or Nanobody of the invention. Their percentage in the compositions and preparations may, of course, be varied and may conveniently be between about 2 to about 60% of the weight of a given unit dosage form. The biparatopic polypeptide of the invention in such therapeutically useful compositions is such that an effective dosage level will be obtained.

The tablets, troches, pills, capsules, and the like may also contain binders, excipients, disintegrating agents, lubricants and sweetening or flavouring agents, for example those mentioned on pages 143-144 of WO 08/020,079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the biparatopic Nanobodies and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the biparatopic Nanobodies, immunoglobulin single variable domains and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The biparatopic Nanobodies, immunoglobulin single variable domains and polypeptides of the invention may also be administered intravenously or intraperitoneally by infusion or injection, as further described on pages 144 and 145 of WO 08/020,079.

For topical administration, the biparatopic Nanobodies, immunoglobulin single variable domains and polypeptides of the invention may be applied in pure form, i.e., when they are liquids. However, it will generally be desirable to administer them to the skin as compositions or formulations, in combination with a dermatologically acceptable carrier, which may be a solid or a liquid, as further described on page 145 of WO 08/020,079.

Generally, the concentration of the biparatopic Nanobodies, immunoglobulin single variable domains and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of biparatopic Nanobodies, immunoglobulin single variable domains and polypeptides of the invention required for use in treatment will vary not only with the particular biparatopic Nanobody or polypeptide selected but also with the route of administration, the nature of the condition being treated and the age and condition of the patient and will be ultimately at the discretion of the attendant physician or clinician. Also the dosage of the biparatopic Nanobodies and polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another of its aspects, the invention relates to a method of treating diseases or conditions which involve aberrant functioning of CXCR2 signal transduction by administering an effective amount of a polypeptide or pharmaceutical composition in accordance with the invention and preferably biparatopic immunoglobulin single variable domains or Nanobodies or composition containing same in accordance with the invention. As discussed herein, CXCR2 signal transduction mediates an inflammatory response in the lungs in patients suffering from chronic obstructive pulmonary disease (COPD) causing destruction of lung parenchyma. Migration of leukocytes, which are seen in elevated numbers in the lungs of patients suffering with COPD is mediated by CXCR2 on the surface of such cells and which binds several ligands including IL-8, Gro-α, β, γ, EMA 78 and GCP-2. Increased numbers of neutrophils in the lungs correlates with severity of the disease. Further, Gro-α concentration is markedly elevated in the induced sputum and bronchial lavage (BAL) fluid of patients with COPD. Accordingly, CXCR2 antagonism is expected to prevent, treat or alleviate the distressing symptoms of this disease.

Accordingly, the invention relates to methods of preventing or treating COPD or exacerbations of COPD comprising administering a biparatopic polypeptide such as a biparatopic immunoglobulin single variable domains or Nanobodies of the invention and in particular, pharmaceutical compositions thereof. The invention also relates to use of said biparatopic polypeptide, including biparatopic Nanobodies and compositions containing them for treating COPD and exacerbations of COPD.

It will be readily apparent to the skilled reader that the biparatopic polypeptides of the invention, in particular the biparatopic immunoglobulin single variable domains or Nanobodies and compositions thereof, are also useful in the treatment of other diseases in which aberrant function of CXCR2 signal transduction is involved, for example, other conditions of the respiratory tract such as Cystic Fibrosis, severe Asthma, exacerbations of Asthma, allergic Asthma, Acute lung injury, Acute Respiratory Distress Syndrome, Idiopathic Pulmonary Fibrosis, Airway remodelling, Bronchiolitis Obliterans Syndrome or Bronchopulmonary dysplasia.

Further diseases and conditions which may be prevented or treated by the biparatopic polypeptides of the invention, for example, the biparatopic immunoglobulin single variable domains or Nanobodies and pharmaceutical compositions thereof are Atherosclerosis, Glomerulonephritis, Inflammatory Bowel disease (Crohn's), Angiogenesis, and diseases characterised by new blood vessel development including Macular degeneration, Diabetic retinopathy and Diabetic neuropathy, Multiple Sclerosis, Psoriasis, Age-related Macular degenerative disease, Ocular Behcet Disease, Uveitis, Pulmonary Arterial Hypertension (PAH) including idiopathic PAH, familial PAH and associated PAH, Chronic inflammatory diseases, Rheumatoid arthritis, Osteoarthritis, non-small cell carcinoma, Colon cancer, Pancreatic cancer, Esophageal cancer, Ovarian cancer, Breast cancer, Solid tumours and Metasases, Melanoma, Hepatocellular carcinoma or Ischaemia reperfusion injury.

Further diseases and conditions which may be prevented or treated by the biparatopic polypeptides of the invention, for example, the biparatopic immunoglobulin single variable domains or Nanobodies and pharmaceutical compositions thereof are Hemolytic transfusion induced-vaso-occlusion crisis in Sickle cell disease, Ischemia/reperfusion injury, Acute stroke/myocardial infarct, Closed head injury, Post-traumatic inflammation and Insulin resistant diabetes.

For the above methods, the biparatopic Nanobodies, immunoglobulin single variable domains and/or polypeptides of the invention and/or the compositions comprising the same can be administered in any suitable manner, depending on the specific pharmaceutical formulation or composition to be used. Thus, the biparatopic Nanobodies and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. In general for COPD, inhalation is not a preferred route. The clinician will be able to select a suitable route of administration and a suitable pharmaceutical formulation or composition to be used in such administration, depending on an individual patient's needs.

The biparatopic Nanobodies, immunoglobulin single variable domains and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific biparatopic Nanobodies, immunoglobulin single variable domains or polypeptide of the invention to be used, the specific route of administration and pharmaceutical formulation or composition to be used, the age, gender, weight, diet, general condition of the patient, and similar factors well known to the clinician.

Generally, for the prevention and/or treatment of the diseases and disorders mentioned herein, in particular COPD, the amount to be administered will depend on the potency of the specific biparatopic Nanobody, immunoglobulin single variable domains or polypeptide of the invention to be used, the specific route of administration and the specific pharmaceutical formulation or composition used. Generally it will be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

The biparatopic Nanobodies, immunoglobulin single variable domains and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

For example, it would be possible to combine the biparatopic polypeptides, such as biparatopic Nanobodies of the invention with conventional treatments for COPD such as short- and long-acting β-adrenergic bronchodilators, inhaled anticholinergics (muscarinic antagonists) and inhaled corticosteroids.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention will now be further described by means of the following non-limiting preferred aspects, examples and figures.

All publications referred to herein and incorporated herein by reference.

Deposit Information

Six deposits of plasmid DNA with inserts encloding polypeptides of the sequence optimized nanobodies shown in Table 32 were made on 15 Jun. 2010 at DSMZ-Deutsche SammlUng von Mikroorganismen and Zallkulturem GmbH, Inhoffenstrasse, 7B, D-38124, Braunschweig, Germany by Novartis Pharma AG, Switzerland. The deposits were made in accordance with the Budapest Treaty on the International Recognition of the Deposit of Microorganisms for the purposes of Patent Procedure of 28 Apr. 1997 and have Accession Numbers as follows:

| Wild Type Construct | Optimized Construct | DSM Number |
|---|---|---|
| 2B2 | C100CXCR20059 | DSM 23723 |
| 97A9 | C100CXCR20061 | DSM 23724 |
| 163E3 | C100CXCR20076 | DSM 23725 |
| 127D1 | C100CXCR20079 | DSM 23726 |
| 163D2 | C100CXCR20086 | DSM 23727 |
| 54B12 | C100CXCR20104 | DSM 23728 |

1. Human and Cyno CXCR2 Cloning

TABLE 1

| | |
|---|---|
| Human CXCR2 SEQ ID NO. 1 | MEDFNMESDSFEDFWKGEDLSNYSYSSTLPPFLLDAAPCEPESL<br>EINKYFVVIIYALVFLLSLLGNSLVMLVILYSRVGRSVTDVYLLN<br>LALADLLFALTLPIWAASKVNGWIFGTFLCKVVSLLKEVNFYS<br>GILLLACISVDRYLAIVHATRTLTQKRYLVKFICLSIWGLSLLLA<br>LPVLLFRRTVYSSNVSPACYEDMGNNTANWRMLLRILPQSFGFI<br>VPLLIMLFCYGFTLRTLFKAHMGQKHRAMRVIFAVVLIFLLCW<br>LPYNLVLLADTLMRTQVIQETCERRNHIDRALDATEILGILHSCL<br>NPLIYAFIGQKFRHGLLKILAIHGLISKDSLPKDSRPSFVGSSSGH<br>TSTTL |
| Human Δ1-17 CXCR2 SEQ ID NO. 2 | MEDLSNYSYSSTLPPFLLDAAPCEPESLEINKYFVVIIYALVFLLS<br>LLGNSLVMLVILYSRVGRSVTDVYLLNLALADLLFALTLPIWA<br>ASKVNGWIFGTFLCKVVSLLKEVNFYSGILLLACISVDRYLAIV<br>HATRTLTQKRYLVKFICLSIWGLSLLLALPVLLFRRTVYSSNVSP<br>ACYEDMGNNTANWRMLLRILPQSFGFIVPLLIMLFCYGFTLRTL<br>FKAHMGQKHRAMRVIFAVVLIFLLCWLPYNLVLLADTLMRTQ<br>VIQETCERRNHIDRALDATEILGILHSCLNPLIYAFIGQKFRHGLL<br>KILAIHGLISKDSLPKDSRPSFVGSSSGHTSTTL |
| Cynomolgus CXCR2 SEQ ID NO. 3 | MQSFNFEDFWENEDFSNYSYSSDLPPSLPDVAPCRPESLEINKYF<br>VVIIYALVFLLSLLGNSLVMLVILHSRVGRSITDVYLLNLAMAD<br>LLFALTLPIWAAAKVNGWIFGTFLCKVVSLLKEVNFYSGILLLA<br>CISVDRYLAIVHATRTLTQKRYLVKFVCLSIWSLSLLLALPVLLF<br>RRTVYLTYISPVCYEDMGNNTAKWRMVLRILPQTFGFILPLLIM<br>LFCYGFTLRTLFKAHMGQKHRAMRVIFAVVLIFLLCWLPYHLV<br>LLADTLMRTRLINETCQRRNNIDQALDATEILGILHSCLNPLIYA<br>FIGQKFRHGLLKILATHGLISKDSLPKDSRPSFVGSSSGHTSTTL |

pcDNA3.1(+) (Invitrogen, V790-20) is designed for high-level, constitutive expression in a variety of mammalian cell lines. It contains the human cytomegalovirus immediate-early promoter, the bovine growth hormone (BGH) polyadenylation signal, a neomycin selection marker for mammalian cells, and an ampicillin resistance gene for selection in *E. coli.* pVAX1 (Invitrogen, V260-20) is a plasmid vector designed for DNA vaccines. It contains the human cytomegalovirus immediate-early promoter, the bovine growth hormone (BGH) polyadenylation signal and a kanamycin resistance gene for selection in *E. coli*.

TABLE 2

Constructs:

| Receptor | Vector | Construction |
|---|---|---|
| Human CXCR2 (N-terminal 3xHA-tag) | pcDNA4/TO | Subcloned a DNA sequence encoding three HA tags followed by the hu CXCR2 sequence, bracketed by a HindIII and XhoI restriction enzyme site at the 5' and 3' end, respectively, in pcDNA4/TO |
| Human N-terminal CCR9 chimera CXCR2 (N-terminal 3xHA-tag) | pcDNA4/TO | Subcloned a DNA sequence encoding three HA tags followed by the first 39 amino acids for hu CCR9, a TEV protease site, and the hu CXCR2 sequence minus the N-terminal 43 amino acids, bracketed by a HindIII and XhoI restriction enzyme site at the 5' and 3' end, respectively, in pcDNA4/TO |
| Human Δ 1-17 CXCR2 (N-terminal 3xHA-tag) | pcDNA4/TO | Subcloned a DNA sequence encoding three HA tags followed by the hu CXCR2 sequence lacking the N-terminal 17 amino acids, bracketed by a HindIII and XhoI restriction enzyme site at the 5' and 3' end, respectively, in pcDNA4/TO |
| Human CXCR2 | pXoon | Human CXCR2 („CXCR2) cDNA (GENBANK: L19593) was amplified by PCR using a 5' primer containing an EcoR I cleavage site and a 3' primer containing a Not I site. The PCR product was ligated into a pXOON plasmid vector |
| Cynomolgus CXCR2 | pcDNA3.1 | The cynomolgus CXCR2 cDNA was amplified from a spleen/thymus cynomolgus cDNA library. NotI and Xhoi restriction enzyme sites were added via PCR and teh resulting fragment was cloned into pcDNA3.1 |
| Human CXCR2 | pVAX1 | PCR (NheI-NotI) on pXoon__hCXCR2 |
| Cynomolgus CXCR2 | pVAX1 | NheI-XhoI from pcDNA3.1__cCXCR2 |
| Human Δ1-17 CXCR2 | pVAX1 | PCR (HindIII-XhoI) on pcDNA3.1__3xHA-Δ1-17-hCXCR2 |
| Human Δ1-17 | pcDNA3.1 | HindIII-XhoI from pCR4Blunt- |

TABLE 2-continued

| Constructs: | | |
|---|---|---|
| Receptor | Vector | Construction |
| CXCR2 (N-terminal 3xHA-tag) | | TOPO_3xHA-Δ1-17-hCXCR2 |
| Human CXCR2 | pcDNA3.1 | NheI-XhoI from pVAX1_hCXCR2 |

2. Establishment of CHO, CaKi, RBL and HEK293T Cell Lines Expressing Human and Cynomolgus CXCR2

TABLE 3

| Cell lines: | | | |
|---|---|---|---|
| Host | Transformation | Receptor | Vector |
| CHO | Stable | Human Δ1-17 CXCR2 (N-terminal 3xHA-tag) | pcDNA3.1 |
| HEK293T Caki info' to add | Transient | Cynomolgus CXCR2 | pcDNA3.1 |
| / | DNA immunization | Human CXCR2 | pVAX1 |
| / | DNA immunization | Cynomolgus CXCR2 | pVAX1 |
| / | DNA immunization | Human Δ1-17 CXCR2 | pVAX1 |
| RBL | Stable | Human CXCR2 cDNA | pSFFV-Neo |
| RBL-2H3 | Stable | Cynomolgus CXCR2 cDNA | pcDNA3.1 |
| CHO-Trex | Stable | (HA)3-huCXCR2 | pcDNA4/TO |
| CHO-Trex | Stable | (HA)3-huCCR9-huCXCR2 | pcDNA4/TO |
| CHO-Trex | Stable | (HA)3-huCXCR2 ΔN1-17 | pcDNA4/TO |
| L2071 | Stable | Human CXCR1 | pSFFV neo |
| CEM | Endogenous | CXCR4 | — |

CHO-K1 Δ1-17 Human CXCR2 (N-Terminal 3×HA Tag)

CHO-K1 cells were transfected with plasmid pcDNA3.1_3×HA-Δ1-17-hCXCR2 using the Amaxa electroporation system (Program U 23 in solution T). The transfected cell pool was kept under selection pressure (1000 αg/mL G418) from day two after transfection. Eight days later, a human CXCR2 positive population was identified with the use of FMAT Blue-labeled human GRO-α. FMAT Blue labeling of human Gro-α (Biosource, PHC 1063) was done using the FMAT Blue Monofunctional Reactive Dye Kit according to the manufacturer's instructions (Applied Biosystems, 4328408). Single cells were sorted into 96-well cell culture plates using a FACSaria (BD Biosciences). Growing clones were tested for Δ1-17 human CXCR2 expression on a FACSarray (BD Biosciences) device with the use of FMAT Blue-labeled human GRO-α. CHO-K1 clones with the highest expression were selected (MCF value of 9000).

HEK293T Cynomolgus CXCR2

HEK293T cells were transfected with plasmid pcDNA3.1_cCXCR2 using the FuGene HD Transfection Reagent (Roche). Two days after transfection, cells were tested for cCXCR2 expression on a FACSarray (BD Biosciences) device with the use of 50 nM FMAT Blue labeled GRO-α. Cells with good expression (MCF value of around 12000) were used further.

RBL-2H3 Cynomolgus CXCR2

Rat Basophil Leukemia cells (RBL-2H3), grown at 37° C./5% $CO_2$ and routinely subcultured in MEM Eagle media (Invitrogen) supplemented with 1× Non-Essential Amino Acids, 0.15% sodium bicarbonate, 1 mM sodium pyruvate and 15% Fetal Bovine Serum (Invitrogen), were subjected to nucleofection by electroporation (Amaxa Biosystems) according to the manufacturer's protocol. Transfected cells were incubated at 37° C./5% $CO_2$, and 24 hours post-transfection antibiotic selection was initiated by adding Geneticin to a final concentration of 1 mg/mL. Transfected cells were grown and sub-cultured for 3-5 days in selection media before being subjected to single-cell sorting by serial dilution into 96-well plates. After approximately two weeks, actively growing colonies were expanded and subsequently analysed for cynoCXCR2 transcript expression. Positive clones were then further expanded for analysis.

CHO-Trex (HA)3-huCXCR2 and (HA)3huCCR9-CXCR2 Hybrid

Chinese Hamster Ovary T-Rex (T-Rex™-CHO, Invitrogen, #R718-07) were maintained at 37° C. as monolayer cultures in Ham's F12 medium containing 2 mM L-Glutamine, supplemented with 10% tetracycline-free fetal bovine serum (FBS) (Biosera), 1% Penicillin/Streptomycin & 10 μg/mL of Blasticidin. This Tetracycline-Regulated Expression (T-Rex™) cell line stably expresses the tetracycline repressor (TetR). Stable cell lines expressing both CXCR2 constructs were then produced using a nucleofection procedure (Cell line Nucleofector Kit T, Amaxa Biosystem, program U-23). Transfected cells were incubated at 37° C./5% $CO_2$, and treated with 300 μg/mL of Zeocin 48 hours post-transfection. The cells were cultured for a couple of weeks in the presence of Zeocin to allow selection of positive transformants, after which a single-cell sorting was carried out using the Mo-Flo FACS sorter. Two weeks later, actively growing colonies were expanded while being maintained in their regular media at a Zeocin concentration of 300 μg/mL.

3. Human Gro-α, Cynomolgus Gro-α, Human IL-8, Human ENA-78

TABLE 4

| NVTS - IL-8, ENA-78, cynomolgus Gro-a | | |
|---|---|---|
| Ligand | Comment | Source |
| human GROα | recombinant | Biosource (PHC1063) |
| Human IL-8 | recombinant | Novartis Vienna |
| Human ENA-78 | recombinant | Peprotech ltd (300-22) |
| Cyno GROα | recombinant | ALMAC Sciences |

4. Peptides

Peptides representing different N-terminal and extracellular loop (EL) stretches of human and cynomolgus CXCR2 were ordered from Bachem (Table 5). In the peptides denoted as "cyclic", the first and last amino acid were replaced by a cysteine residue and naturally occurring internal cysteines of the wild type sequence were replaced by a leucine residue. These peptides were cyclized through the flanking cysteine residues.

TABLE 5

| Name | Sequence | Modification |
|---|---|---|
| Cynomolgus 1 to 14 | MQSFNFEDFWENED SEQ ID NO. 4 | C-terminally conjugated to biotin |

TABLE 5-continued

| Name | Sequence | Modification |
|---|---|---|
| Cynomolgus EL3 cyclic | CTLMRTRLINETLQRRNC SEQ ID NO. 5 | N-terminally conjugated to biotin or KLH |
| Cynomolgus EL2 cyclic | CRRTVYLTYISPVLYEDMGNNTAL WC SEQ ID NO. 6 | N-terminally conjugated to biotin or KLH |
| Human 1 to 19 | MEDFNMESDSFEDFWKGED SEQ ID NO. 7 | C-terminally conjugated to biotin |
| Human 18 to 48 | EDLSNYSYSSTLPPFLLDAAPCEPE SLEINK SEQ ID NO. 8 | C-terminally conjugated to biotin |
| Human EL2 | FRRTVYSSNVSPACYEDMGNNTA NWR SEQ ID NO. 9 | N-terminally conjugated to biotin or KLH |
| Human EL2 cyclic | CRRTVYSSNVSPALYEDMGNNTA NWC SEQ ID NO. 10 | N-terminally conjugated to biotin or KLH |
| Human EL3 | DTLMRTQVIQETCERRNH SEQ ID NO. 11 | N-terminally conjugated to biotin or KLH |
| Human EL3 cyclic | CTLMRTQVIQETLERRNC SEQ ID NO. 12 | N-terminally conjugated to biotin or KLH |

5. Immunisations

Three llamas were immunised seven to nine times with mammalian cells expressing human CXCR2 and one llama was immunised six times with mammalian cells expressing cynomolgus CXCR2. This regimen was followed by four administrations of peptide-Keyhole Limpet Hemocyanin (KLH) conjugate cocktails mixed in (in)complete Freund's Adjuvant, the peptides representing the extracellular loops numbers 2 and 3 of both human and cynomolgus CXCR2 (See Table 5). Eight other llamas were immunised four to five times with DNA encoding human full length CXCR2 or Δ1-17 CXCR2 expressed from pVAX1 followed by one administration of mammalian cells expressing human full length CXCR2. Three additional llamas were immunised four times with DNA encoding cynomolgus CXCR2 expressed from pVAX1 followed by one administration of mammalian cells expressing cynomolgus CXCR2. Immune blood and lymph node samples were taken four and eight days after administration of each of the antigens.

6. Library Constructions cDNA samples were made from total RNA preparations of the immune blood and lymph node samples. Nucleotide sequences encoding Nanobodies were amplified from the cDNA samples of all llamas immunised with human or cynomolgus CXCR2 in a one-step RT-PCR reaction using primers ABL051, ABL052 and ABL003. Primer sequences are shown in Table 6. The 700 bp amplicons amplified from the IgG2 and IgG3 cDNA's in the sample were isolated from gel and subsequently used as template in a nested PCR reaction using the ABL050 primer containing SfiI restriction enzyme site and the ABL003 primer. The PCR products were subsequently digested with SfiI and BstEII (naturally occurring in FR4 of VHH genes) and ligated into the corresponding restriction sites of phagemid vector pAX50 to obtain a library after electroporation in *Escherichia coli* TG-1. pAX50 is an expression vector derived from pUC119 which contained the LacZ promoter, a coliphage pIII protein coding sequence, a resistance gene for ampicillin or carbenicillin, a multicloning site and the gen3 leader sequence. In frame with the Nanobody® coding sequence, the vector coded for a C-terminal c-myc tag and a (His)6 tag. The phagemid vector allows for production of phage particles, expressing the individual Nanobodies as a fusion protein with the geneIII product.

TABLE 6

| Primer sequences | | |
|---|---|---|
| ABL051 | GGCTGAGCTGGGTGGTCCTGG | SEQ ID NO. 13 |
| ABL052 | GGCTGAGTTTGGTGGTCCTGG | SEQ ID NO. 14 |
| ABL003 | GGTACGTGCTGTTGAACTGTTCC | SEQ ID NO. 15 |
| ABL050 | CATTTGAGTTGGCCTAGCCGGCCATGGCAGAGGTGCAGCTGGT GGAGTCTGGGGG | SEQ ID NO. 16 |
| M13Fwd | TGTAAAACGACGGCCAGT | SEQ ID NO. 17 |
| M13Rev | CAGGAAACAGCTATGACC | SEQ ID NO. 18 |
| Rev_30GlySer | TCAGTAACCTGGATCCCCCGCCACCGCTGCCTCCACCGCCGCTA CCCCCGCCACCGCTGCCTCCACCGCCTGAGGAGACGGTGACCTG | SEQ ID NO. 19 |

TABLE 6-continued

| Primer sequences | | |
|---|---|---|
| For_GlySer35 | AGGTTACTGAGGATCCGGCGGTGGAGGCAGCGGAGGTGGGGG CTCTGGTGGCGGGGGTAGCGAGGTGCAGCTGGTGGAGTCTGG | SEQ ID NO. 20 |
| Fwd-EVQL-MfeI | GAGGTGCAATTGGTGGAGTCTGGG | SEQ ID NO. 21 |
| Rev-TVSS-BstEII | TGAGGAGACGGTGACCTGGGTCCC | SEQ ID NO. 22 |
| Fwd-EVQL-BamHI | TCTTGGATCCGAGGTGCAGCTGGTGGAGTCTGGG | SEQ ID NO. 23 |
| Rev-TVSS-BspEI | ACCGCCTCCGGAGGAGACCGTGACCTGGGTCCC | SEQ ID NO. 24 |

7. Selections

The abovementioned pAX50 Nanobody libraries, expressed on the surface of bacteriophages were selected using peptides, membrane extracts and whole cells presenting CXCR2 epitopes.

Selections using peptides consisted in incubating the phage libraries on 0-1000 nM of biotinylated peptides (See Table 5) captured on neutravidine-coated (Pierce, 31000) Maxisorp microtiter plates (Nunc, 430341). Alternatively, the phage libraries were incubated in solution with 10 nM biotinylated peptide, followed by capture of the peptide-phage complexes on streptavidin coated Dynabeads (Invitrogen, 112-06D). Blocking was performed using PBS supplemented with 1% casein. Phages prepared from the libraries were added and incubated for 1 hour (in PBS supplemented with 0.1% casein and 0.1% tween20). Unbound phages were washed away (with PBS supplemented with 0.05% tween20); bound phage were eluted by addition of trypsin (1 mg/ml in PBS) for 15 min. Second selection rounds were performed essentially as described above.

Selections using membrane extracts were performed by coating immunotubes (Nunc, 444474) with 50 ug/mL (total protein) membrane extracts prepared from cells expressing human CXCR2 (Perkin Elmer, ES-145-M400UA and 6110524400UA). As negative control, membrane extracts prepared from CHO cells expressing human FPR1 (Perkin Elmer, 6110527400UA) were coated in parallel. Blocking was performed using PBS supplemented with 4% Marvel skimmed milk powder. Phages were incubated for 2 hours (in PBS supplemented with 1% Marvel). Unbound phages were washed away with PBS; bound phages were eluted by addition of trypsin (1 mg/ml in PBS) for 15 min. Second round selections were performed essentially as described above. In some cases, phages binding to irrelevant cell background epitopes were specifically depleted by pre-absorbing the phage on successive tubes or wells coated with control membrane extracts. Next, the incubation on the coated human CXCR2 membrane extracts was performed in the presence of control membrane extract in solution. In other experiments, one or two rounds of selection on peptides were followed by one round of selection on membrane extracts, or vice versa.

In another set of experiments, 1 to 5 million mammalian cells expressing human or cynomolgus CXCR2 were incubated with the phage libraries in PBS supplemented with 10% FBS and 1% Marvel skimmed milk powder. Untransformed cell lines were used as negative controls. Unbound phages were washed away with PBS; bound phage were eluted by addition of trypsin (1 mg/ml in PBS) for 15 min. Second rounds were performed essentially as described above but on a different cell line background than the first round.

In other experiments, phages were incubated with membrane extracts or mammalian cells expressing CXCR2 in the presence of 1 μM of peptides (See Table 5) in solution, to deplete for phages expressing Nanobodies binding to regions represented by these peptides.

8. Preparation of Periplasmic Extracts

Eluted phages were allowed to infect exponentially growing TG-1 cells which were then plated on carbenicillin containing LB agar plates. Carbenicillin-resistant clones were analyzed for the presence of insert and sequences of positive clones were verified. Clones of interest were grown in TB medium supplemented with carbenicillin and induced by addition of IPTG for expression. The expression was allowed to continue for 4 hours at 37° C., followed by spinning down the cells. Overnight frozen cell pellets from *E. coli* expression cultures were dissolved in PBS (1/10th of the original culture volume) and incubated at 4° C. for 1 hour under gentle shaking conditions. Then, the cells were spun down once more and the supernatant, containing the proteins secreted into the periplasmic space, was stored.

9. Screening

Periplasmic extracts (as described above) were analyzed on FACS for competition with Gro-α in binding to human CXCR2. $2\times10^5$ cells were incubated with a ½ dilution of periplasmic extracts in FACS buffer (PBS+10% fetal bovine serum (Sigma, F7524)) for 30 minutes at 4° C. Then, an equal volume of 6 nM of FMAT Blue-labeled human Gro-α in FACS buffer was added and incubation was continued for another 30 minutes at 4° C. in the dark. Cells were then washed three times in FACS buffer and finally resuspended in FACS buffer. Dead cells were stained with propidium iodide (Sigma, P4170). Samples were then analyzed on a FACSarray (BD Biosciences). Table 7 lists Nanobodies of which the periplasmic extracts displayed competition with Gro-α on human CXCR2.

TABLE 7

Gro-α competition on human CXCR2 (periplasmic extracts)

| Name | FACS Gro-α competition (% inhibition) |
|---|---|
| 126B11 | 36.9 |
| 97A9 | 85.9 |
| 127D1 | 46.7 |
| 137B7 | 90.3 |
| 137A8 | 55.8 |

TABLE 7-continued

| Gro-α competition on human CXCR2 (periplasmic extracts) | |
|---|---|
| Name | FACS Gro-α competition (% inhibition) |
| 139A8 | 78.5 |
| 139D5 | 56.8 |
| 139H2 | 50.5 |
| 143A5 | 72.6 |
| 143B3 | 70.8 |
| 159B10 | 75.8 |
| 144D1 | 32.7 |
| 145D3 | 77.9 |
| 147A1 | 58.3 |
| 146A6 | 42.7 |
| 145C9 | 53.5 |
| 163D2 | 86.8 |
| 163E3 | 80.1 |
| 2B2 | 38.1 |
| Blanc control | 0.4 |

In another setup, periplasmic extracts were analyzed for binding to human 1 to 19 peptide by ELISA. MaxiSorb plates (Nunc, 430341) were coated for two hours with neutravidin followed by one hour blocking (PBS, 1% casein). Then 100 nM biotinylated human 1 to 19 peptide was added to these plates for one hour (PBS, 0.1% casein, 0.05% tween20) followed by one hour incubation with 10-fold dilutions of periplasmic extracts. Unbound periplasmic extracts were washed away (PBS supplemented with 0.05% tween20) and bound Nanobodies were detected using mouse anti-myc (Roche, 11667149001) followed by rabbit anti-mouse-HRP conjugate (Dakocytomation, P0260). Table 8 summarizes the ratios of the binding signals of anti-CXCR2 Nanobodies over an irrelevant control Nanobody.

TABLE 8

| Binding to human CXCR2 1 to 19 peptide of periplasmic extracts | |
|---|---|
| Name | 1-19 Nter peptide ELISA (ratio of binding signal relative to blank control) |
| 54B12 | 75.5 |
| 53E7 | 13.3 |
| 97A9 | 0.8 |
| 127D1 | 39.5 |
| 137B7 | 1.0 |
| 137A8 | 1.2 |
| 139A8 | 1.0 |
| 139D5 | 0.8 |
| 139H2 | 1.7 |
| 159B10 | 0.8 |
| 163D2 | 0.5 |
| 163E3 | 0.6 |
| 2B2 | 58.6 |

10. Sequences

TABLE 9

| Sequences of monovalent anti-CXCR2 Nanobodies | | |
|---|---|---|
| 143B03 | SEQ ID NO. 25 | EVQLVESGGGLVQPGGSLRLSCAASGFTFSTYWMYWVR QAPGKGLDWVSAINAGGDSTYYADPVKGRFTISRDNNKN TLYLQMNSLKPEDTALYYCATVRGTARDLDYWGQGTQV TVSS |
| 139D05 | SEQ ID NO. 26 | EVKLVESGGGLVQAGGSLRLSCALSGRIGSINAMGWYRQ VSGQQRELVAVSRSGGSTDIADSVKGRFTISRDNGKNTVY LQMDSLKPEDTAVYYCYAHTSSYSNWRVYNNDYWGQG TQVTVSS |
| 146A06 | SEQ ID NO. 27 | EVQLVESGGGLVQAGGSLRLTCAASGRIGTINAMGWYRQ APGKQRELVAVITSGGRIDYADSVKGRFTISRDNAKNTVY LQMNSLKPEDTAVYYYNVETVVGAVYWGQGTQVTVSS |
| 147A01 | SEQ ID NO. 28 | EVQLVESGGGLVQAGGSLRLSCAASGRMGNINAMGWYR QAPGKERELVAKITRGGAITYADSVKGRFTIARDNILNTA YLQMNDLKPEDTAVYYYNVDGGPSQNYWGQGTQVTVSS |
| 145C09 | SEQ ID NO. 29 | EVQLVESGGGLVQAGGSLRLSCAASGFTFDDYAIGWFRQ APGKERERVSCISGSDGSTYYADSVKGRFTISSDNAKNTV YLQMNNLKPEDTAVYYCAAYWGLTLRLWMPPHRYDYW GQGTQVTVSS |
| 145D03 | SEQ ID NO. 30 | EVQLVESGGGLVQAGGSLSLSCAASGLIFRLSGMAWYRQ APGRQREWVAVLTKDGTLHYADPVKGRFTISRNNAENT WYLQMNSLKPEDTAIYYCNTGRYWGQGTQVTVSS |
| 144D01 | SEQ ID NO. 31 | EVQLVESGGGLVQAGGSLRLSCAASGTIGTIRAMGWYRQ APGKQRELVALITSTGRINYADSVKGRFTIGRDNAKNTAY LQMNNLKPEDTAVYYYNIETLRRNYWGQGTQVTVSS |
| 139H02 | SEQ ID NO. 32 | EVQLVESGGGLVQAGGSLRLSCAASGRTFSNYAMGWFR QATGKEREFVAAINKSGGNTHYAGSVKGRFTISRDNAKN TVYLQMNSLKPRDTAVYYCAASRTNPKPDYWGQGTQVT VSS |
| 139A08 | SEQ ID NO. 33 | EVQLVESGGGLVQAGGSLRLSCAASGRSFSRSAMGWLRQ APGKEREFVAGISWGGDNSYYADSVKGRFTISRDNAKNT VSLQMNSLKPQDTAVYYCAARYRGGAAVAGWEYWGQG TQVTVSS |
| 137A08 | SEQ ID NO. 34 | EVQLVESGGGLVQPGGSLRLSCAASGSTLAYYTVGWFRR APGKEREGISCISSSDGSTYYADSVKGRFTISRDNAKNTVY LQMNSLKPEDTAVYYCAADRRTDCKKGRVGSGSWGQGT |

TABLE 9-continued

| Sequences of monovalent anti-CXCR2 Nanobodies | | |
|---|---|---|
| | | QVTVSS |
| 143A05 | SEQ ID NO. 35 | KVQLVESGGGLVQAGGSLRLSCAASGRAFNYYVMAWFRQAQGKEREFVAAISTRGSMTKYSDSVQGRFTISRDNAKNTVYLHMNSLKPEDTAVYYCAADPRGSSWSFSSGGYDYWGQGTQVTVSS |
| 137B07 | SEQ ID NO. 36 | EVQLVESGGGLVQPGGSVRLSCVASGIIFRLSALGWTRQGPGKAREWVAGINSDGTTNYADPVKGRFTISRDNAKNTIYLHMDMLKPEDTAVYYCASGKYRGQGTQVTVSS |
| 127D01 | SEQ ID NO. 37 | EVQLVESGGGLVQAGESLRLSCAASGSTFDFKVMGWYRQPPGKQREGVAAIRLSGNMHYAESVKGRFTISKANAKNTVYLQMNSLRPEDTAVYYCKVNIRGQDYWGQGTQVTVSS |
| 126B11 | SEQ ID NO. 38 | EVQLVESGGGLVQAGGSLTLSCAVSGSSFRINTMGWYRRAPGKQRELVAARDRGGYINYVDSVKGRFTVSRDNAKPTMYLQMNSLKPEDTAVYYCHAGTQDRTGRNFDHWGQGTQVTVSS |
| 097A09 | SEQ ID NO. 39 | EVQLVESGGGLVQPGGSLRLSCVASGSIVRINTMGWYRQTPGKQRELVADITSGGNINYIDAVKGRFTISRDNTKNTVYLQMNSLKPEDTAVYYCNAEIVVLVGVWTQRARTGNYWGQGTQVTVSS |
| 159B10 | SEQ ID NO. 40 | EVQLVESGGGLVQPGGSLRLSCAASGRTFSSLSMGWFRQAPGKERAFVAALTRNGGYRYYADSVKGRFTISRDVAKKTLYLQMNSLKPEDTAVYYCAADSLSGSDYLGTNLDYWGQGTQVTVSS |
| 163D02 | SEQ ID NO. 41 | EVQLVESGGGLVQAGGSLRLSCAASGRTFSDYAMGWFRQAPGKEREFVAAITWNGGRVFYTASVKGRFTISRDNAKNTMYLQMNSLKPEDTAVYYCAADKDRRTDYLGHPVAYWGQGTQVTVSS |
| 163E03 | SEQ ID NO. 42 | EVQLVESGGGLVQPGGSLRLSCVASGRIFSSNAMGWFRQAPGKEREFVAAITWRSGGSAYYADSAKGRFTISRDNAKNTVYLQMNSLKPEDTAVYYCAAGGSSWLSFPPDYWGQGTQVTVSS |
| 2B2 | SEQ ID NO. 43 | EVQLVESGGELVQPGGSLRLSCAASGSILTINAMGWYRQAPGKQRELVVRRTRGGSTTYQDSVKGRFTISADIAKKTMYLQMNSLKPEDTAVYYCMLDDRGGVYWGQGTQVTVSS |
| 54B12 | SEQ ID NO. 90 | EVQLVESGGGLVQAGGSLTLSCAVSGSTFRINTMGWYRRAPGKQRELVAARDRGGYINYVDSVKGRFTVSRDNAKPTMYLQMNSLKPEDTAVYYCHAGTQDRTGRNFDRWGQGTQVTVSS |

Lead Characterisation Monovalent Nanobodies

11. Construction of Monovalent Nanobodies

Nanobody containing DNA fragments, obtained by PCR on functional phagemid clones with Fwd-EVQL-MfeI and Rev-TVSS-BstEII primers (Table 1), were digested with MfeI and BstEII, ligated into the pAX100 vector and transformed into *E. coli* TG-1 competent cells. pAX100 is an expression vector derived from pUC119 which contained the LacZ promoter, a resistance gene for kanamycin, a multicloning site and the OmpA leader sequence. In frame with the Nanobody coding sequence, the vector coded for a C-terminal c-myc tag and a His6 tag. Kanamycin resistant clones were analyzed for the presence of insert and sequences of positive clones were verified.

12. Small Scale Expression

TG-1 cells containing expression vectors encoding the Nanobodies of interest were grown in baffled shaker flasks containing TB medium plus 100 μg/ml kanamycin and induced by addition of 1 mM IPTG for expression. The expression was allowed to continue for 4 hours at 37° C. After collecting the cells, periplasmic extracts were prepared and the His6-tagged Nanobodies were purified by immobilized metal affinity chromatography (HisTrap FF Crude, GE Healthcare) followed by desalting (HiPrep 26/10, GE Healthcare) or gel filtration chromatography (Superdex 75 HR16/10, GE Healthcare) in PBS.

13. Ligand Competition Assay

Purified monovalent anti-CXCR2 Nanobodies were titrated against 3 nM FMAT-Blue-labeled Gro-α in the FACS ligand competition assay on human and cynomolgus CXCR2 (Table 10). On human CXCR2, blocking potencies range between double digit nM and sub-nM whereas on cynomolgus CXCR2, they range between single and double digit nM.

TABLE 10

Ligand competition potencies of monovalent anti-CXCR2 Nanobodies

| | Human CXCR2 | | Cynomolgus CXCR2 | |
|---|---|---|---|---|
| | IC50 (M) | % inhibition of max | IC50 (M) | % inhibition of max |
| 137B7 | 1.11E−09 | 93.5 | NA | NA |
| 163D2 | 6.95E−09 | 96.4 | 1.48E−08 | 91.0 |
| 127D1 | 3.09E−10 | 61.1 | 4.41E−09 | 82.6 |

TABLE 10-continued

| Ligand competition potencies of monovalent anti-CXCR2 Nanobodies | | | | |
|---|---|---|---|---|
| | Human CXCR2 | | Cynomolgus CXCR2 | |
| | IC50 (M) | % inhibition of max | IC50 (M) | % inhibition of max |
| 97A9 | 1.72E−08 | 93.9 | 6.41E−08 | 53.0 |
| 163E3 | 8.96E−09 | 92.4 | 1.48E−08 | 83.5 |
| 54B12 | 8.57E−10 | 35.0 | 3.95E−08 | 63.0 |
| 2B2 | 2.07E−09 | 42.7 | 3.16E−08 | 64.0 |

NA: no activity could be measured

14. Functional Assays Using Recombinant Cell Lines (1) Measuring Agonist Induced Release of Intracellular Calcium (FLIPR)

RBL cells expressing either human or cynomolgus CXCR2 receptor were seeded in 96-well plates and incubated overnight at 37° C. On the day of the experiment, the cells were loaded with Fluo-4 dye for 30 mins at 37° C., followed by a 30 minute incubation with purified monovalent anti-CXCR2 Nanobodies. Finally, the addition of GRO-α was performed using a Fluorometric Imaging Plate Reader (FLIPR) followed by the detection of a fluorescent signal, corresponding to the release of intracellular calcium. A selectivity assay was performed using L2071 cells expressing human CXCR1. The assay protocol remained the same as described for CXCR2 however IL-8 was used as the agonist. A summary of the mean $IC_{50}$ values is shown in Table 11, in addition, none of the Nanobodies tested showed any inhibition of agonist induced release of intracellular calcium at the CXCR1 receptor at the concentrations tested (1 μM maximum concentration).

(2) Measuring Agonist Stimulated Accumulation of [$^{35}$S] GTPγS

Purified monovalent anti-CXCR2 Nanobodies were incubated for 60 minutes with GRO-α, GDP, SPA beads and CHO-CXC2 membranes, prepared from CHO cells expressing human CXCR2 receptor, in a 96-well plate. This was followed by the addition of [$^{35}$S]GTPγS and a further 60 minute incubation. Finally, the plate was centrifuged prior to being read on the Topcount. A summary of the mean $IC_{50}$ values is shown in Table 11.

TABLE 11

$IC_{50}$ values for purified monovalent anti-CXCR2 Nanobodies ® in functional assays using recombinant cell lines

| | FLIPR | | | | [$^{35}$S]GTPγS | |
|---|---|---|---|---|---|---|
| | Human CXCR2 | | Cynomolgus CXCR2 | | Human CXCR2 | |
| | $IC_{50}$ (M) | % inhibition max | $IC_{50}$ (M) | % inhibition max | $IC_{50}$ (M) | % inhibition max |
| 137B7 | 6.71E−9 | 100 | NA | — | ND | — |
| 163D2 | 1.91E−9 | 100 | 3.72E−8 | 100 | 5.32E−8 | 100 |
| 127D1 | 2.19E−8 | 100 | 7.53E−7 | 100* | 1.25E−8 | 66.0 |
| 97A9 | 3.99E−8 | 100 | 6.40E−7 | 100 | 5.03E−8 | 100 |
| 163E3 | 4.43E−8 | 100 | 1.58E−7 | 100 | 6.47E−8 | 100 |
| 54B12 | 1.53E−7 | 100 | 4.08E−6 | 100* | 1.54E−8 | 71.8 |
| 2B2 | 4.41e−7 | 100 | 3.85E−6 | 100* | 1.03E−7 | 71.3 |

*Curves fixed to 100% inhibition as no plateau was obtained at the concentrations tested.

NA—no activity could be measured.

ND—not determined.

15. Functional Assays Using Primary Neutrophils (1) Human Neutrophil Whole Blood Shape Change Assay (hWBSC)

Donors were healthy normal volunteers on no systemic medication (Novartis Horsham donor panel). Whole blood, anticoagulated with 52 mM EDTA (sterile) was collected in a ratio of 1 mL EDTA to 9 mL blood. Blood was collected at room temperature and pre-warmed to 37° C. prior to use. 80 μL of whole blood was preincubated with CXCR2 Nanobodies for 10 mins at room temperature (10 points per dose response (0.03−1.144×$10^{-7}$ μM), prior to stimulation with chemokine; 10 μL rhGROα (2 nM approximate $EC_{70}$ concentration) was added to all wells except the zero compound, to which 10 μL shape change assay buffer was added. Samples were shaken gently and incubated for a further 5 minutes at 37° C. The tubes were then placed on ice and 250 μL of ice cold optimised CellFix™ solution was added tubes shaken gently and incubated for further 5 minutes after which time 1.4 mL of 1× ammonium chloride lysis solution was added to all tubes and left on ice for a further 20 minutes. Following red cell lysis, samples were analyzed on a FACS-Calibur flow cytometer (Becton Dickinson). Cell populations were identified by forward scatter/side scatter (FSC/SSC) gating, followed by FSC/FL-2 plots using the gated granulocytes from the first plot. Neutrophils were distinguished from eosinophils on the FL-2 plot, as the latter have a higher autofluorescence. 5000 events were counted per sample.

(2) Human Neutrophil Chemotaxis Assay

Donors were healthy normal volunteers on no systemic medication (Novartis Horsham donor panel). Whole blood anticoagulanted with 52 mM EDTA (sterile) was collected in a ratio of 1 mL EDTA to 9 mL blood. Leukocytes were isolated using standard protocols: 4% dextran was added to 20 mL anticoagulated blood, mixed gently then incubated on ice for 30 mins, to allow the red blood cells to sediment. The supernatant containing peripheral blood mononuclear cells (PMN), was then layered onto Ficoll-Paque® density gradient and centrifuged at 300×g for 25 mins at 18° C. The PMN rich fraction was resuspended in 500 μL 1×PBS and red cell lysis was carried out using hypotonic shock. 20 mL ice cold, sterile, endotoxin-free distilled water was added to the pellet and lysis was allowed to occur for 30-40 seconds before 20 mL 2×PBS was added. The sample was mixed gently and centrifuged at 300×g for 10 mins at 18° C., to obtain the granulocytes. The granulocyte pellet was resuspended in 500 μL 1×PBS and washed twice with 50 mL of ×1 PBS. The granulocyte pellet was resuspended in RPMI 1640, pH 7.4, plus 2.5% FBS, counted and diluted to a final concentration of 2e$^{6}$/mL. Migration was measured using transwell plates with 3 μm PET membranes from Becton Dickinson. Briefly, 6 nM of GROα ($EC_{80}$-$EC_{100}$) was added to the bottom wells (1000 μL/well) of the plate before the multiwell insert was lowered into position, PMN which had been preincubated with varying concentrations of Nanobody (0.13-1000 nM for monovalents or 0.6 pM-30 nM for biparatopics) for 30 minutes at RT were then added to the insert (500 μL/well). Plates were then incubated at 37° C. for 90 minutes cells which had migrated in to the bottom chamber were counted using a FACSCalibur flow cytometer. The flow cytometer was set to count for number of events within the R2 gate on the FSC/FL-2 plot for a set time of 20 seconds per sample.

(3) Cynomologus Neutrophil Whole Blood Shape Change Assay (CynoWBSC)

Venous blood taken from the either the forearm or leg was anticoagulanted with 3.8% sodium citrate (sterile) in a ratio of 1 mL sodium citrate to 9 mL blood. Blood was collected at room temperature and pre-warmed to 37° C. prior to use. 80 μL of whole blood was preincubated with CXCR2 Nanobodies for 10 mins at room temperature (10 points per dose response (0.03–1.144×10$^{-7}$ μM), prior to stimulation with chemokine; 10 μL rhGROα (30 nM approximate $EC_{70\text{-}90}$ concentration) was added to all wells except the zero compound, to which 10 μL shape change assay buffer was added. Samples were shaken gently and incubated for a further 5 minutes at 37° C. The tubes were then placed on ice and 250 μL of ice cold optimised CellFix™ solution was added tubes shaken gently and incubated for further 5 minutes after which time 2 mL of lysis buffer (Sigma Aldrich #R7757) was added to all tubes and left on ice for a further 40-60 minutes. Following red cell lysis, samples were analyzed on a FACSCalibur flow cytometer (Becton Dickinson). Cell populations were identified by forward scatter/side scatter (FSC/SSC) gating, followed by FSC/FL-2 plots using the gated granulocytes from the first plot. Neutrophils were distinguished from eosinophils on the FL-2 plot, as the latter have a higher autofluorescence. 5000 events were counted per sample.

TABLE 12

$IC_{50}$ values for purified monovalent anti-CXCR2 Nanobodies in functional assays using primary neutrophils and rhGROα

| | HumanWBSC $IC_{50}$ (nM) | Cynomologus WBSC $IC_{50}$ (nM) | Human Chemotaxis $IC_{50}$ (nM) |
|---|---|---|---|
| 163D2 | 6.6 ± 3.1 | >100 | |
| 127D1 | 4.9 ± 2.9 | >100 | 3.9 |
| 97A9 | 11.6 ± 5.47 | >100 | 4.8 |
| 163E3 | 9.4 ± 6.2 | >100 | 1.3 |
| 54B12 | 19.7 | >100 | |
| 2B2 | 29.5 ± 23.4 | >100 | 50 |

Multivalent Nanobodies

16. Construction of Bivalent Nanobodies

Two approaches were used to construct bivalent Nanobodies.

PCR amplifications were run on plasmid DNA encoding the monovalent building blocks. The N-terminal building blocking was amplified using Fwd-EVQL-MfeI and a reverse primer encoding part of the GlySer linker whereas the C-terminal building block was amplified using a forward primer encoding the remaining part of the GlySer linker and Rev-TVSS-BstEII (Table 6). The N-terminal fragment was digested with MfeI and BamHI, the C-terminal fragment was digested with BamHI and BstII; these were then simultaneously ligated into the pAX100 vector and transformed into *E. coli* TG-1 competent cells.

Alternatively, different PCR amplifications were run on plasmid DNA encoding the monovalent building blocks. The N-terminal building blocking was amplified using Fwd-EVQL-MfeI and Rev-TVSS-BspEI whereas the C-terminal building block was amplified using Fwd-EVQL-BamHI and Rev-TVSS-BstEII (Table 6). The N-terminal fragment was digested with MfeI and BamHI, the C-terminal fragment was digested with BspEI and BstII. The N-terminal fragment was ligated (MfeI-BspEI) into a pAX100-derivative containing the coding information for the GlySer linker, and transformed into *E. coli* TG-1 competent cells. Plasmid DNA from this transformation mixture was prepared and digested with BspEI and BstEII and the C-terminal fragment was then ligated into the pAX100 vector and transformed into *E. coli* TG-1 competent cells.

Kanamycin resistant clones were analyzed for the presence of insert and sequences of positive clones were verified.

17. Sequences of Multivalent Anti-CXCR2 Nanobodies

TABLE 13

| | | |
|---|---|---|
| CXCR20011 | 97A9-35GS-<br>97A9<br>SEQ ID NO.<br>44 | EVQLVESGGGLVQPGGSLRLSCVASGSIVRINTMGWY<br>RQTPGKQRELVADITSGGNINYIDAVKGRFTISRDNTK<br>NTVYLQMNSLKPEDTAVYYCNAEIVVLVGVWTQRA<br>RTGNYWGQGTQVTVSSGGGGSGGGGSGGGGSGGGG<br>SGGGGSGGGGSGGGGSEVQLVESGGGLVQPGGSLRL<br>SCVASGSIVRINTMGWYRQTPGKQRELVADITSGGNI<br>NYIDAVKGRFTISRDNTKNTVYLQMNSLKPEDTAVY<br>YCNAEIVVLVGVWTQRARTGNYWGQGTQVTVSS |
| CXCR20012 | 137B7-<br>35GS-<br>137B7<br>SEQ ID NO.<br>45 | EVQLVESGGGLVQPGGSVRLSCVASGIIFRLSALGWT<br>RQGPGKAREWVAGINSDGTTNYADPVKGRFTISRDN<br>AKNTIYLHMDMLKPEDTAVYYCASGKYRGQGTQVT<br>VSSGGGGSGGGGSGGGGSGGGGSGGGGSGGGGSGG<br>GGSEVQLVESGGGLVQPGGSVRLSCVASGIIFRLSALG<br>WTRQGPGKAREWVAGINSDGTTNYADPVKGRFTISR<br>DNAKNTIYLHMDMLKPEDTAVYYCASGKYRGQGTQ<br>VTVSS |
| CXCR20013 | 2B2-35GS-<br>97A9<br>SEQ ID NO.<br>46 | EVQLVESGGELVQPGGSLRLSCAASGSILTINAMGWY<br>RQAPGKQRELVVRRTRGGSTTYQDSVKGRFTISADIA<br>KKTMYLQMNSLKPEDTAVYYCMLDDRGGVYWGQG<br>TQVTVSSGGGGSGGGGSGGGGSGGGGSGGGGSGGG<br>GSGGGGSEVQLVESGGGLVQPGGSLRLSCVASGSIVR |

TABLE 13-continued

| | | |
|---|---|---|
| | | INTMGWYRQTPGKQRELVADITSGGNINYIDAVKGRF TISRDNTKNTVYLQMNSLKPEDTAVYYCNAEIVVLV GVWTQRARTGNYWGQGTQVTVSS |
| CXCR20014 | 97A9-35GS-2B2 SEQ ID NO. 47 | EVQLVESGGGLVQPGGSLRLSCVASGSIVRINTMGWY RQTPGKQRELVADITSGGNINYIDAVKGRFTISRDNTK NTVYLQMNSLKPEDTAVYYCNAEIVVLVGVWTQRA RTGNYWGQGTQVTVSSGGGGSGGGGSGGGGSGGGG SGGGGSGGGGSGGGGSEVQLVESGGELVQPGGSLRL SCAASGSILTINAMGWYRQAPGKQRELVVRRTRGGS TTYQDSVKGRFTISADIAKKTMYLQMNSLKPEDTAV YYCMLDDRGGVYWGQGTQVTVSS |
| CXCR20015 | 2B2-35GS-137B7 SEQ ID NO. 48 | EVQLVESGGELVQPGGSLRLSCAASGSILTINAMGWY RQAPGKQRELVVRRTRGGSTTYQDSVKGRFTISADIA KKTMYLQMNSLKPEDTAVYYCMLDDRGGVYWGQG TQVTVSSGGGGSGGGGSGGGGSGGGGSGGGGSGGG GSGGGGSEVQLVESGGGLVQPGGSVRLSCVASGIIFR LSALGWTRQGPGKAREWVAGINSDGTTNYADPVKG RFTISRDNAKNTIYLHMDMLKPEDTAVYYCASGKYR GQGTQVTVSS |
| CXCR20016 | 137B7-35GS-2B2 SEQ ID NO. 49 | EVQLVESGGGLVQPGGSVRLSCVASGIIFRLSALGWT RQGPGKAREWVAGINSDGTTNYADPVKGRFTISRDN AKNTIYLHMDMLKPEDTAVYYCASGKYRGQGTQVT VSSGGGGSGGGGSGGGGSGGGGSGGGGSGGGGSGG GGSEVQLVESGGELVQPGGSLRLSCAASGSILTINAM GWYRQAPGKQRELVVRRTRGGSTTYQDSVKGRFTIS ADIAKKTMYLQMNSLKPEDTAVYYCMLDDRGGVY WGQGTQVTVSS |
| CXCR20017 | 97A9-35GS-137B7 SEQ ID NO. 50 | EVQLVESGGGLVQPGGSLRLSCVASGSIVRINTMGWY RQTPGKQRELVADITSGGNINYIDAVKGRFTISRDNTK NTVYLQMNSLKPEDTAVYYCNAEIVVLVGVWTQRA RTGNYWGQGTQVTVSSGGGGSGGGGSGGGGSGGGG SGGGGSGGGGSGGGGSEVQLVESGGGLVQPGGSVRL SCVASGIIFRLSALGWTRQGPGKAREWVAGINSDGTT NYADPVKGRFTISRDNAKNTIYLHMDMLKPEDTAVY YCASGKYRGQGTQVTVSS |
| CXCR20018 | 137B7-35GS-97A9 SEQ ID NO. 51 | EVQLVESGGGLVQPGGSVRLSCVASGIIFRLSALGWT RQGPGKAREWVAGINSDGTTNYADPVKGRFTISRDN AKNTIYLHMDMLKPEDTAVYYCASGKYRGQGTQVT VSSGGGGSGGGGSGGGGSGGGGSGGGGSGGGGSGG GGSEVQLVESGGGLVQPGGSLRLSCVASGSIVRINTM GWYRQTPGKQRELVADITSGGNINYIDAVKGRFTISR DNTKNTVYLQMNSLKPEDTAVYYCNAEIVVLVGVW TQRARTGNYWGQGTQVTVSS |
| CXCR20019 | 2B2-9GS-2B2 SEQ ID NO. 52 | EVQLVESGGELVQPGGSLRLSCAASGSILTINAMGWY RQAPGKQRELVVRRTRGGSTTYQDSVKGRFTISADIA KKTMYLQMNSLKPEDTAVYYCMLDDRGGVYWGQG TQVTVSSGGGGSGGGSEVQLVESGGELVQPGGSLRLS CAASGSILTINAMGWYRQAPGKQRELVVRRTRGGST TYQDSVKGRFTISADIAKKTMYLQMNSLKPEDTAVY YCMLDDRGGVYWGQGTQVTVSS |
| CXCR20020 | 127D1-35GS-163D2 SEQ ID NO. 53 | EVQLVESGGGLVQAGESLRLSCAASGSTFDFKVMGW YRQPPGKQREGVAAIRLSGNMHYAESVKGRFTISKAN AKNTVYLQMNSLRPEDTAVYYCKVNIRGQDYWGQG TQVTVSSGGGGSGGGGSGGGGSGGGGSGGGGSGGG GSGGGGSEVQLVESGGGLVQAGGSLRLSCAASGRTFS DYAMGWFRQAPGKEREFVAAITWNGGRVFYTASVK GRFTISRDNAKNTMYLQMNSLKPEDTAVYYCAADKD RRTDYLGHPVAYWGQGTQVTVSS |
| CXCR20021 | 127D1-35GS-163E3 SEQ ID NO. 54 | EVQLVESGGGLVQAGESLRLSCAASGSTFDFKVMGW YRQPPGKQREGVAAIRLSGNMHYAESVKGRFTISKAN AKNTVYLQMNSLRPEDTAVYYCKVNIRGQDYWGQG TQVTVSSGGGGSGGGGSGGGGSGGGGSGGGGSGGG GSGGGGSEVQLVESGGGLVQPGGSLRLSCVASGRIFS SNAMGWFRQAPGKEREFVAAITWRSGGSAYYADSA KGRFTISRDNAKNTVYLQMNSLKPEDTAVYYCAAGG SSWLSFPPDYWGQGTQVTVSS |
| CXCR20022 | 163D2-35GS-163D2 SEQ ID NO. 55 | EVQLVESGGGLVQAGGSLRLSCAASGRTFSDYAMGW FRQAPGKEREFVAAITWNGGRVFYTASVKGRFTISRD NAKNTMYLQMNSLKPEDTAVYYCAADKDRRTDYLG HPVAYWGQGTQVTVSSGGGGSGGGGSGGGGSGGGG SGGGGSGGGGSGGGGSEVQLVESGGGLVQAGGSLRL |

TABLE 13-continued

| | | |
|---|---|---|
| | | SCAASGRTFSDYAMGWFRQAPGKEREFVAAITWNGG<br>RVFYTASVKGRFTISRDNAKNTMYLQMNSLKPEDTA<br>VYYCAADKDRRTDYLGHPVAYWGQGTQVTVSS |
| CXCR20023 | 163D2-<br>35GS-<br>163E3<br>SEQ ID NO.<br>56 | EVQLVESGGGLVQAGGSLRLSCAASGRTFSDYAMGW<br>FRQAPGKEREFVAAITWNGGRVFYTASVKGRFTISRD<br>NAKNTMYLQMNSLKPEDTAVYYCAADKDRRTDYLG<br>HPVAYWGQGTQVTVSSGGGGSGGGGSGGGGSGGGG<br>SGGGGSGGGGSGGGGSEVQLVESGGGLVQPGGSLRL<br>SCVASGRIFSSNAMGWFRQAPGKEREFVAAITWRSGG<br>SAYYADSAKGRFTISRDNAKNTVYLQMNSLKPEDTA<br>VYYCAAGGSSWLSFPPDYWGQGTQVTVSS |
| CXCR20024 | 163E3-<br>35GS-<br>163E3<br>SEQ ID NO.<br>57 | EVQLVESGGGLVQPGGSLRLSCVASGRIFSSNAMGWF<br>RQAPGKEREFVAAITWRSGGSAYYADSAKGRFTISRD<br>NAKNTVYLQMNSLKPEDTAVYYCAAGGSSWLSFPPD<br>YWGQGTQVTVSSGGGGSGGGGSGGGGSGGGGSGGG<br>GSGGGGSGGGGSEVQLVESGGGLVQPGGSLRLSCVA<br>SGRIFSSNAMGWFRQAPGKEREFVAAITWRSGGSAY<br>YADSAKGRFTISRDNAKNTVYLQMNSLKPEDTAVYY<br>CAAGGSSWLSFPPDYWGQGTQVTVSS |
| CXCR20025 | 163D2-<br>35GS-<br>127D1<br>SEQ ID NO.<br>58 | EVQLVESGGGLVQAGGSLRLSCAASGRTFSDYAMGW<br>FRQAPGKEREFVAAITWNGGRVFYTASVKGRFTISRD<br>NAKNTMYLQMNSLKPEDTAVYYCAADKDRRTDYLG<br>HPVAYWGQGTQVTVSSGGGGSGGGGSGGGGSGGGG<br>SGGGGSGGGGSGGGGSEVQLVESGGGLVQAGESLRL<br>SCAASGSTFDFKVMGWYRQPPGKQREGVAAIRLSGN<br>MHYAESVKGRFTISKANAKNTVYLQMNSLRPEDTAV<br>YYCKVNIRGQDYWGQGTQVTVSS |
| CXCR20026 | 163E3-<br>35GS-<br>127D1<br>SEQ ID NO.<br>59 | EVQLVESGGGLVQPGGSLRLSCVASGRIFSSNAMGWF<br>RQAPGKEREFVAAITWRSGGSAYYADSAKGRFTISRD<br>NAKNTVYLQMNSLKPEDTAVYYCAAGGSSWLSFPPD<br>YWGQGTQVTVSSGGGGSGGGGSGGGGSGGGGSGGG<br>GSGGGGSGGGGSEVQLVESGGGLVQAGESLRLSCAA<br>SGSTFDFKVMGWYRQPPGKQREGVAAIRLSGNMHY<br>AESVKGRFTISKANAKNTVYLQMNSLRPEDTAVYYC<br>KVNIRGQDYWGQGTQVTVSS |
| CXCR20027 | 163E3-<br>35GS-<br>163D2<br>SEQ ID NO.<br>60 | EVQLVESGGGLVQPGGSLRLSCVASGRIFSSNAMGWF<br>RQAPGKEREFVAAITWRSGGSAYYADSAKGRFTISRD<br>NAKNTVYLQMNSLKPEDTAVYYCAAGGSSWLSFPPD<br>YWGQGTQVTVSSGGGGSGGGGSGGGGSGGGGSGGG<br>GSGGGGSGGGGSEVQLVESGGGLVQAGGSLRLSCAA<br>SGRTFSDYAMGWFRQAPGKEREFVAAITWNGGRVFY<br>TASVKGRFTISRDNAKNTMYLQMNSLKPEDTAVYYC<br>AADKDRRTDYLGHPVAYWGQGTQVTVSS |
| CXCR20028 | 97A9-35GS-<br>54B12<br>SEQ ID NO.<br>61 | EVQLVESGGGLVQPGGSLRLSCVASGSIVRINTMGWY<br>RQTPGKQRELVADITSGGNINYIDAVKGRFTISRDNTK<br>NTVYLQMNSLKPEDTAVYYCNAEIVVLVGVWTQRA<br>RTGNYWGQGTQVTVSSGGGGSGGGGSGGGGSGGGG<br>SGGGGSGGGGSGGGGSEVQLVESGGGLVQAGGSLTL<br>SCAVSGSTFRINTMGWYRRAPGKQRELVAARDRGGY<br>INYVDSVKGRFTVSRDNAKPTMYLQMNSLKPEDTAV<br>YYCHAGTQDRTGRNFDRWGQGTQVTVSS |
| CXCR20029 | 163E3-<br>35GS-<br>54B12<br>SEQ ID NO.<br>62 | EVQLVESGGGLVQPGGSLRLSCVASGRIFSSNAMGWF<br>RQAPGKEREFVAAITWRSGGSAYYADSAKGRFTISRD<br>NAKNTVYLQMNSLKPEDTAVYYCAAGGSSWLSFPPD<br>YWGQGTQVTVSSGGGGSGGGGSGGGGSGGGGSGGG<br>GSGGGGSGGGGSEVQLVESGGGLVQAGGSLTLSCAV<br>SGSTFRINTMGWYRRAPGKQRELVAARDRGGYINYV<br>DSVKGRFTVSRDNAKPTMYLQMNSLKPEDTAVYYC<br>HAGTQDRTGRNFDRWGQGTQVTVSS |
| CXCR20030 | 163D2-<br>35GS-<br>54B12<br>SEQ ID NO.<br>63 | EVQLVESGGGLVQAGGSLRLSCAASGRTFSDYAMGW<br>FRQAPGKEREFVAAITWNGGRVFYTASVKGRFTISRD<br>NAKNTMYLQMNSLKPEDTAVYYCAADKDRRTDYLG<br>HPVAYWGQGTQVTVSSGGGGSGGGGSGGGGSGGGG<br>SGGGGSGGGGSGGGGSEVQLVESGGGLVQAGGSLTL<br>SCAVSGSTFRINTMGWYRRAPGKQRELVAARDRGGY<br>INYVDSVKGRFTVSRDNAKPTMYLQMNSLKPEDTAV<br>YYCHAGTQDRTGRNFDRWGQGTQVTVSS |
| CXCR20031 | 2B2-35GS-<br>163E3<br>SEQ ID NO.<br>64 | EVQLVESGGELVQPGGSLRLSCAASGSILTINAMGWY<br>RQAPGKQRELVVRRTRGGSTTYQDSVKGRFTISADIA<br>KKTMYLQMNSLKPEDTAVYYCMLDDRGGVYWGQG<br>TQVTVSSGGGGSGGGGSGGGGSGGGGSGGGGSGGG |

TABLE 13-continued

| | | |
|---|---|---|
| | | GSGGGGSEVQLVESGGGLVQPGGSLRLSCVASGRIFS<br>SNAMGWFRQAPGKEREFVAAITWRSGGSAYYADSA<br>KGRFTISRDNAKNTVYLQMNSLKPEDTAVYYCAAGG<br>SSWLSFPPDYWGQGTQVTVSS |
| CXCR20032 | 2B2-35GS-<br>163D2<br>SEQ ID NO.<br>65 | EVQLVESGGELVQPGGSLRLSCAASGSILTINAMGWY<br>RQAPGKQRELVVRRTRGGSTTYQDSVKGRFTISADIA<br>KKTMYLQMNSLKPEDTAVYYCMLDDRGGVYWGQG<br>TQVTVSSGGGGSGGGGSGGGGSGGGGSGGGGSGGG<br>GSGGGGSEVQLVESGGGLVQAGGSLRLSCAASGRTFS<br>DYAMGWFRQAPGKEREFVAAITWNGGRVFYTASVK<br>GRFTISRDNAKNTMYLQMNSLKPEDTAVYYCAADKD<br>RRTDYLGHPVAYWGQGTQVTVSS |
| CXCR20033 | 163E3-<br>35GS-2B2<br>SEQ ID NO.<br>66 | EVQLVESGGGLVQPGGSLRLSCVASGRIFSSNAMGWF<br>RQAPGKEREFVAAITWRSGGSAYYADSAKGRFTISRD<br>NAKNTVYLQMNSLKPEDTAVYYCAAGGSSWLSFPPD<br>YWGQGTQVTVSSGGGGSGGGGSGGGGSGGGGSGGG<br>GSGGGGSGGGGSEVQLVESGGELVQPGGSLRLSCAA<br>SGSILTINAMGWYRQAPGKQRELVVRRTRGGSTTYQ<br>DSVKGRFTISADIAKKTMYLQMNSLKPEDTAVYYCM<br>LDDRGGVYWGQGTQVTVSS |
| CXCR20034 | 163D2-<br>35GS-2B2<br>SEQ ID NO.<br>67 | EVQLVESGGGLVQAGGSLRLSCAASGRTFSDYAMGW<br>FRQAPGKEREFVAAITWNGGRVFYTASVKGRFTISRD<br>NAKNTMYLQMNSLKPEDTAVYYCAADKDRRTDYLG<br>HPVAYWGQGTQVTVSSGGGGSGGGGSGGGGSGGGG<br>SGGGGSGGGGSGGGGSEVQLVESGGELVQPGGSLRL<br>SCAASGSILTINAMGWYRQAPGKQRELVVRRTRGGS<br>TTYQDSVKGRFTISADIAKKTMYLQMNSLKPEDTAV<br>YYCMLDDRGGVYWGQGTQVTVSS |
| CXCR20035 | 54B12-<br>35GS-<br>163E3<br>SEQ ID NO.<br>68 | EVQLVESGGGLVQAGGSLTLSCAVSGSTFRINTMGW<br>YRRAPGKQRELVAARDRGGYINYVDSVKGRFTVSRD<br>NAKPTMYLQMNSLKPEDTAVYYCHAGTQDRTGRNF<br>DRWGQGTQVTVSSGGGGSGGGGSGGGGSGGGGSGG<br>GGSGGGGSGGGGSEVQLVESGGGLVQPGGSLRLSCV<br>ASGRIFSSNAMGWFRQAPGKEREFVAAITWRSGGSA<br>YYADSAKGRFTISRDNAKNTVYLQMNSLKPEDTAVY<br>YCAAGGSSWLSFPPDYWGQGTQVTVSS |
| CXCR20036 | 54B12-<br>35GS-<br>163D2<br>SEQ ID NO.<br>69 | EVQLVESGGGLVQAGGSLTLSCAVSGSTFRINTMGW<br>YRRAPGKQRELVAARDRGGYINYVDSVKGRFTVSRD<br>NAKPTMYLQMNSLKPEDTAVYYCHAGTQDRTGRNF<br>DRWGQGTQVTVSSGGGGSGGGGSGGGGSGGGGSGG<br>GGSGGGGSGGGGSEVQLVESGGGLVQAGGSLRLSCA<br>ASGRTFSDYAMGWFRQAPGKEREFVAAITWNGGRVF<br>YTASVKGRFTISRDNAKNTMYLQMNSLKPEDTAVYY<br>CAADKDRRTDYLGHPVAYWGQGTQVTVSS |

18. Ligand Competition Assay

Multivalent anti-CXCR2 Nanobodies were titrated against 3 nM FMAT-Blue-labeled Gro-α in the FACS ligand competition assay on human and cynomolgus CXCR2 (Table 14). On human CXCR2, blocking potencies range between double digit nM and sub-nM whereas on cynomolgus CXCR2, they range between single and double digit nM.

TABLE 14

Ligand competition analysis of multivalent anti-CXCR2 Nanobodies

| | | Human CXCR2 | | Cynomolgus CXCR2 | |
|---|---|---|---|---|---|
| | | IC50 (M) | % inhibition of max | IC50 (M) | % inhibition of max |
| CXCR20011 | 97A9-35GS-97A9 | 3.52E−08 | 99.0 | 9.74E−08 | 60.0 |
| CXCR20012 | 137B7-35GS-137B7 | 6.06E−10 | 99.1 | ND | ND |
| CXCR20013 | 2B2-35GS-97A9 | 9.00E−10 | 90.0 | 4.20E−09 | 98.5 |
| CXCR20014 | 97A9-35GS-2B2 | 1.59E−09 | 99.7 | 3.90E−09 | 98.5 |

TABLE 14-continued

Ligand competition analysis of multivalent anti-CXCR2 Nanobodies

| | | Human CXCR2 | | Cynomolgus CXCR2 | |
|---|---|---|---|---|---|
| | | IC50 (M) | % inhibition of max | IC50 (M) | % inhibition of max |
| CXCR20015 | 2B2-35GS-137B7 | 7.00E−10 | 99.0 | 9.90E−08 | 81.5 |
| CXCR20016 | 137B7-35GS-2B2 | 8.00E−10 | 100.0 | 5.70E−09 | 88.0 |
| CXCR20017 | 97A9-35GS-137B7 | 3.40E−09 | 99.0 | 2.95E−08 | 73.0 |
| CXCR20018 | 137B7-35GS-97A9 | 1.90E−09 | 98.0 | 5.08E−08 | 47.0 |
| CXCR20019 | 2B2-9GS-2B2 | 4.40E−11 | 50.6 | 1.8E−09 | 81.0 |
| CXCR20020 | 127D1-35GS-163D2 | 9.90E−10 | 100.0 | 1.78E−09 | 98.5 |
| CXCR20021 | 127D1-35GS-163E3 | 1.09E−09 | 99.5 | 1.85E−09 | 98.5 |
| CXCR20022 | 163D2-35GS-163D2 | 4.14E−09 | 100.0 | 8.01E−09 | 98.0 |

TABLE 14-continued

Ligand competition analysis of multivalent anti-CXCR2 Nanobodies

| | | Human CXCR2 | | Cynomolgus CXCR2 | |
|---|---|---|---|---|---|
| | | IC50 (M) | % in-hibition of max | IC50 (M) | % in-hibition of max |
| CXCR20023 | 163D2-35GS-163E3 | 4.28E−09 | 99.0 | 6.61E−09 | 96.0 |
| CXCR20024 | 163E3-35GS-163E3 | 5.27E−09 | 99.0 | 5.32E−09 | 95.0 |
| CXCR20025 | 163D2-35GS-127D1 | 9.00E−10 | 99.0 | 2.08E−09 | 98.5 |
| CXCR20026 | 163E3-35GS-127D1 | 9.00E−10 | 99.5 | 1.82E−09 | 99.0 |
| CXCR20027 | 163E3-35GS-163D2 | 4.90E−09 | 100.0 | 6.42E−09 | 97.0 |
| CXCR20028 | 97A9-35GS-54B12 | 1.63E−09 | 98.5 | 3.80E−09 | 96.0 |
| CXCR20029 | 163E3-35GS-54B12 | 1.13E−09 | 98.5 | 2.09E−09 | 98.5 |
| CXCR20030 | 163D2-35GS-54B12 | 7.86E−10 | 99.5 | 1.74E−09 | 98.5 |
| CXCR20031 | 2B2-35GS-163E3 | 4.90E−10 | 100.0 | 1.98E−09 | 99.0 |
| CXCR20032 | 2B2-35GS-163D2 | 5.00E−10 | 100.0 | 1.91E−09 | 99.0 |
| CXCR20033 | 163E3-35GS-2B2 | 6.50E−10 | 100.0% | 2.20E−09 | 99.0% |
| CXCR20034 | 163D2-35GS-2B2 | 8.00E−10 | 100.0% | 2.55E−09 | 99.0% |
| CXCR20035 | 54B12-35GS-163E3 | 1.00E−09 | 99.0% | 3.23E−09 | 99.0% |
| CXCR20036 | 54B12-35GS-163D2 | 7.00E−10 | 98.0% | 2.27E−09 | 98.0% |

ND: not determined

19. Functional Assays Using Recombinant Cell Lines (1) Measuring Agonist Induced Release of Intracellular Calcium (FLIPR)

RBL cells expressing either human or cynomolgus CXCR2 receptor were seeded in 96-well plates and incubated overnight at 37° C. On the day of the experiment, the cells were loaded with Fluo-4 dye for 30 mins at 37° C., followed by a 30 minute incubation with purified multivalent anti-CXCR2 Nanobodies. Finally, the addition of GRO-α was performed using a Fluorometric Imaging Plate Reader (FLIPR) followed by the detection of a fluorescent signal, corresponding to the release of intracellular calcium. Selectivity assays were performed using L2071 cells expressing human CXCR1, with IL-8 as the agonist and CEM cells endogenously expressing human CXCR4 with SDF-1 as the agonist, however the assay protocol remained the same as described for CXCR2. A summary of the mean $IC_{50}$ values is shown in Table 15 in addition, none of the Nanobodies tested showed any inhibition of agonist induced release of intracellular calcium at either CXCR1 or CXCR4 at the concentrations tested (1 μM maximum concentration).

(2) Measuring Agonist Stimulated Accumulation of $[^{35}S]$ GTPγS

Purified multivalent anti-CXCR2 Nanobodies were incubated for 60 minutes with agonist (GRO-α, IL-8 or ENA-78) GDP, SPA beads and CHO-CXC2 membranes, prepared from CHO cells expressing human CXCR2 receptor, in a 96-well plate. This was followed by the addition of $[^{35}S]$GTPγS and a further 60 minute incubation. Finally, the plate was centrifuged prior to being read on the Topcount. A summary of the mean IC50 values is shown in Table 15.

TABLE 15

$IC_{50}$ values for purified multivalent anti-CXCR2 Nanobodies in a functional assay measuring release of intracellular calcium using recombinant cell lines

| | | Human CXCR2 | | Cynomolgus CXCR2 | |
|---|---|---|---|---|---|
| | | $IC_{50}$ (M) | % in-hibition of max | $IC_{50}$ (M) | % in-hibition of max |
| CXCR20011 | 97A9-35GS-97A9 | 1.37E−7 | 100 | ND | ND |
| CXCR20012 | 137B7-35GS-137B7 | ND | ND | ND | ND |
| CXCR20013 | 2B2-35GS-97A9 | 2.93E−9 | 100 | 2.92E−8 | 100 |
| CXCR20014 | 97A9-35GS-2B2 | 6.84E−9 | 100 | 1.37E−8 | 100 |
| CXCR20015 | 2B2-35GS-137B7 | 2.78E−9 | 100 | 2.87E−6 | 100* |
| CXCR20016 | 137B7-35GS-2B2 | 2.36E−9 | 100 | 1.10E−6 | 100* |
| CXCR20017 | 97A9-35GS-137B7 | 2.29e−8 | 100 | 1.08E−6 | 100* |
| CXCR20018 | 137B7-35GS-97A9 | ND | ND | ND | ND |
| CXCR20019 | 2B2-9GS-2B2 | ND | ND | ND | ND |
| CXCR20020 | 127D1-35GS-163D2 | 6.98E−9 | 100 | 1.64E−9 | 100 |
| CXCR20021 | 127D1-35GS-163E3 | 7.32E−9 | 100 | 2.31E−9 | 100 |
| CXCR20022 | 163D2-35GS-163D2 | 9.34E−9 | 100 | 8.64E−9 | 100 |
| CXCR20023 | 163D2-35GS-163E3 | 1.48E−8 | 100 | 1.20E−8 | 100 |
| CXCR20024 | 163E3-35GS-163E3 | 2.64E−8 | 100 | 1.18E−8 | 100 |
| CXCR20025 | 163D2-35GS-127D1 | 1.22E−8 | 100 | 7.88E−9 | 100 |
| CXCR20026 | 163E3-35GS-127D1 | 1.23E−8 | 100 | 9.10E−9 | 100 |
| CXCR20027 | 163E3-35GS-163D2 | 1.78E−8 | 100 | 1.27E−8 | 100 |
| CXCR20028 | 97A9-35GS-54B12 | 2.19E−8 | 100 | 1.70E−8 | 100 |
| CXCR20029 | 163E3-35GS-54B12 | 1.71E−8 | 100 | 1.01E−8 | 100 |
| CXCR20030 | 163D2-35GS-54B12 | 1.18E−8 | 100 | 6.36E−9 | 100 |
| CXCR20031 | 2B2-35GS-163E3 | 1.52E−8 | 100 | 4.26E−9 | 100 |
| CXCR20032 | 2B2-35GS-163D2 | 1.47E−8 | 100 | 3.65E−9 | 100 |
| CXCR20033 | 163E3-35GS-2B2 | 1.79E−8 | 100 | 4.46E−9 | 100 |
| CXCR20034 | 163D2-35GS-2B2 | 1.18E−8 | 100 | 9.47E−9 | 100 |
| CXCR20035 | 54B12-35GS-163E3 | 1.02E−8 | 100 | 8.72E−9 | 100 |
| CXCR20036 | 54B12-35GS-163D2 | 7.86E−9 | 100 | 4.27E−9 | 100 |

*Curves fixed to 100% inhibition as no plateau was obtained at the concentrations tested.

ND—not determined.

TABLE 16

IC$_{50}$ values for purified multivalent anti-CXCR2 Nanobodies in a functional assay measuring accumulation of [$^{35}$S]GTPγS in human CHO-CXCR2 cell membranes

| | | Human CXCR2 (using different agonists) | | | | | |
|---|---|---|---|---|---|---|---|
| | | GRO-α | | IL-8 | | ENA-78 | |
| | | IC$_{50}$ (M) | % inhibition of max | IC$_{50}$ (M) | % inhibition of max | IC$_{50}$ (M) | % inhibition of max |
| CXCR20014 | 97A9-35GS-2B2 | 1.38E−9 | 100 | 1.13E−9 | 100 | 1.66E−9 | 100 |
| CXCR20020 | 127D1-35GS-163D2 | 6.34E−10 | 100 | 6.19E−10 | 100 | 7.07E−10 | 100 |
| CXCR20021 | 127D1-35GS-163E3 | 5.51E−10 | 100 | 8.27E−10 | 100 | 7.87E−10 | 100 |
| CXCR20022 | 163D2-35GS-163D2 | 2.85E−8 | 100 | ND | ND | ND | ND |
| CXCR20023 | 163D2-35GS-163E3 | 2.66E−8 | 100 | ND | ND | ND | ND |
| CXCR20024 | 163E3-35GS-163E3 | 3.03E−8 | 100 | ND | ND | ND | ND |
| CXCR20025 | 163D2-35GS-127D1 | 8.91E−10 | 100 | ND | ND | ND | ND |
| CXCR20026 | 163E3-35GS-127D1 | 8.09E−10 | 100 | ND | ND | ND | ND |
| CXCR20028 | 97A9-35GS-54B12 | 1.38E−9 | 100 | ND | ND | ND | ND |
| CXCR20030 | 163D2-35GS-54B12 | 1.02E−9 | 100 | 1.09E−9 | 100 | 1.30E−9 | 100 |
| CXCR20031 | 2B2-35GS-163E3 | ND | ND | 8.40E−10 | 100 | 1.38E−9 | 100 |
| CXCR20032 | 2B2-35GS-163D2 | ND | ND | 9.97E−10 | 100 | 1.16E−10 | 100 |
| CXCR20033 | 163E3-35GS-2B29 | 1.01E−9 | 100 | ND | ND | ND | ND |
| CXCR20034 | 163D2-35GS-2B2 | 9.95E−10 | 100 | ND | ND | ND | ND |
| CXCR20035 | 54B12-35GS-163E3 | 8.44E−10 | 100 | 7.17E−10 | 100 | 1.17E−9 | 100 |

ND—not determined (3) Schild Analysis to Determine the Mechanism of Action of Anti-CXCR2 Nanobodies Schild analysis was carried out using IL-8 and GRO-α stimulated [$^{35}$S]GTPγS accumulation assays. This assay format allows for the equilibration of agonist and Nanobody prior to the addition of [$^{35}$S]GTPγS and as a consequence, any artefacts of hemi-equilbrium which could lead to mis-interpretation of the mechanism should be avoided. To do this agonist concentration response curves were determined in the presence of increasing concentrations of Nanobody. The data for two monovalent Nanobodies 54B12 and 163E3 and the resulting multivalent Nanobody are given as examples and are shown in FIG. 1. The data shows concentration response curves for GRO-α but similar data was observed when IL-8 was used.

Monovalent Nanobodies 54B12 and 163E3 both show an allosteric mechanism of action but with differential effects on the inhibition of the agonist. The allosteric mechanism of 54B12 and other 1-19 binders is exemplified by parallel rightward shifts of the agonist concentration response curve at low Nanobody concentrations, which are not further shifted to the right in the presence of increasing concentrations of Nanobody (FIG. 1(*a*)). The saturable nature of this effect, without a diminution of the maximum agonist response is indicative of allosteric effects on the affinity of the agonist. In contrast, the allosteric mechanism of 163E3 and other non 1-19 binders is exemplified by parallel rightward shifts of the agonist concentration response curve in combination with reductions in the maximum agonist response at higher Nanobody concentrations (FIG. 1(*b*)). This effect may be saturable but this was not observed at the concentrations used, however, the key observation is the reduction in maximum agonist response which is indicative of allosteric effects on the efficacy of the agonist. Finally, the multivalent Nanobody 54B12-163E3 combines both allosteric mechanisms to produce effects on the agonist concentration response curve which are exemplified by parallel rightward shifts at much lower Nanobody concentrations and significant diminution of the maximum agonist response. (FIG. 1(*c*)).

The current definition of an allosteric modulator is that it binds at a site distinct from the agonist (orthosteric ligand) binding site and that both the orthosteric ligand and allosteric modulator are bound to the receptor at the same time. Although the inventors currently do not have the data to confirm this and not wishing to be bound by theory, it is not believed that the Nanobody binding site is distinct from the agonist binding site but that the binding sites overlap. Data is also not available to show that both agonist and Nanobody are bound to the receptor at the same time although the Schild analysis data would suggest that these Nanobodies are allosteric modulators of CXCR2.

20. Functional Assays—NSC

Methods same as described in section 15

TABLE 17

$IC_{50}$ values for purified biparatopic ant-CXCR2 Nanobodies in functional assays using primary human or cynomologus neutrophils (vs rhGROα, mean ± SD)

| | Human WBSC IC50 (nM) | Cynomologus WBSC $IC_{50}$ (nM) | Human Chemotaxis $IC_{50}$ (nM) |
|---|---|---|---|
| 97A9-2B2 | 0.445 ± 0.08 | 0.16 ± 0.16 | 0.16 |
| 163D2-2B2 | 0.29 ± 0.17 | 0.44 ± 0.14 | 0.145 |
| 163E3-2B2 | 0.345 ± 0.15 | 0.42 ± 0.12 | 0.145 |
| 127D1-163D2 | 0.17 | 0.12 ± 0.09 | 0.145 |
| 163E3-127D1 | 0.165 ± 0.06 | 0.26 ± 0.25 | 0.14 |
| 97A9-54B12 | 0.43 ± 0.18 | 1.72 ± 0.43 | |
| 163D2-54B12 | 0.215 ± 0.02 | 0.56 ± 0.46 | |
| 54B12-163E3 | 0.24 ± 0.155 | 0.43 ± 0.38 | |

TABLE 18

| | | |
|---|---|---|
| 143B03 | SEQ ID NO. 192 | GAGGTGCAGCTGGTGGAGTCTGGGGGAGGCTTGGTGCAGCCTGGGGGGTCTCTGAGACTCTCCTGTGCAGCCTCTGGATTCACCTTCAGTACCTACTGGATGTATTGGGTCCGTCAGGCTCCAGGGAAGGGGCTCGACTGGGTCTCAGCTATTAATGCTGGTGGTGATAGCACATACTATGCAGACCCCGTGAAGGGCCGATTCACCATCTCCAGAGACAACAACAAGAACACGCTGTATCTGCAGATGAACAGCCTGAAACCTGAGGACACGGCCCTGTATTACTGTGCGACCGTACGAGGCACAGCTCGTGACTTGGACTACTGGGGCCAGGGGACCCAGGTCACCGTCTCCTCA |
| 139D05 | SEQ ID NO. 193 | GAGGTGAAGCTGGTGGAGTCTGGGGGAGGCTTGGTGCAGGCTGGGGGGTCTCTGAGACTCTCCTGTGCACTCTCTGGAAGGATCGGCAGTATCAACGCCATGGGCTGGTATCGCCAGGTTTCAGGACAACAGCGCGAGTTGGTCGCAGTAAGCAGGAGCGGAGGTAGCACAGACATTGCTGACTCCGTGAAGGGCCGATTCACCATCTCCAGAGACAACGGCAAGAACACAGTGTATCTGCAGATGGACAGCCTGAAACCTGAGGACACGGCCGTCTATTACTGTTATGCTCATACTTCAAGCTATAGTAATTGGCGAGTCTACAATAACGACTACTGGGGCCAGGGGACCCAGGTCACCGTCTCCTCA |
| 146A06 | SEQ ID NO. 194 | GAGGTGCAGCTGGTGGAGTCTGGGGGAGGCTTGGTGCAGGCTGGGGGGTCTCTGAGACTTACCTGTGCAGCCTCTGGACGCATCGGCACTATCAATGCCATGGGCTGGTACCGCCAGGCTCCAGGGAAGCAGCGCGAGTTGGTCGCAGTTATTACTAGTGGTGGTAGGATAGACTATGCAGACTCCGTGAAGGGCCGATTCACCATCTCCAGAGACAATGCCAAGAACACGGTGTATCTGCAAATGAACAGCCTGAAACCTGAGGACACGGCCGTCTATTACTATAATGTAGAAACGGTAGTGGGTGCCGTCTACTGGGGCCAGGGGACCCAGGTCACCGTCTCCTCA |

TABLE 18-continued

| | | |
|---|---|---|
| 147A01 | SEQ ID NO. 195 | GAGGTGCAGCTGGTGGAGTCTGGGGGAGGCTTGGTGCAGGCTGGGGGGTCTCTGAGACTCTCCTGTGCAGCCTCTGGAAGGATGGGCAATATCAATGCCATGGGCTGGTATCGCCAGGCTCCAGGGAAGGAGCGCGAGTTGGTCGCAAAAATTACTAGGGGTGGTGCGATAACCTATGCAGACTCCGTGAAGGGCCGATTCACCATCGCCAGAGACAATATTCTGAACACGGCGTATCTGCAAATGAACGACCTGAAACCTGAGGACACGGCCGTCTATTATTATAATGTAGATGGGGGGCCCAGTCAAAACTACTGGGGCCAGGGGACCCAGGTCACCGTCTCCTCA |
| 145C09 | SEQ ID NO. 196 | GAGGTGCAGCTGGTGGAGTCTGGGGGAGGCTTGGTGCAGGCTGGGGGGTCTCTGAGACTCTCCTGTGCAGCCTCTGGATTCACTTTCGATGATTATGCCATAGGCTGGTTCCGCCAGGCCCCAGGGAAGGAGCGTGAGAGGGTCTCATGTATTAGTGGTAGTGATGGTAGCACATACTATGCAGACTCCGTCAAGGGCCGATTCACCATCTCCAGTGACAACGCCAAGAACACGGTGTATCTGCAAATGAACAACCTGAAACCCGAGGACACGGCCGTTTATTATTGTGCAGCATATTGGGGACTAACGCTCAGGCTATGGATGCCCCCCCACCGGTATGACTACTGGGGCCAGGGGACCCAGGTCACCGTCTCCTCA |
| 145D03 | SEQ ID NO. 197 | GAGGTGCAGCTGGTGGAGTCTGGGGGAGGCTTGGTGCAGGCTGGGGGGTCTCTGAGCCTCTCCTGTGCAGCCTCTGGACTTATCTTCAGACTCAGTGGCATGGCCTGGTATCGCCAGGCTCCGGGGAGGCAGCGCGAGTGGGTCGCAGTGCTTACCAAAGATGGTACCCTACACTATGCAGACCCCGTGAAGGGCCGATTCACCATCTCCAGAAACAACGCCGAGAACACGTGGTATCTGCAAATGAACAGCCTGAAACCTGAGGACACAGCCATCTATTACTGTAATACGGGCCGTTACTGGGGCCAGGGGACCCAGGTCACCGTCTCCTCA |
| 144D01 | SEQ ID NO. 198 | GAGGTGCAGCTGGTGGAGTCTGGGGGAGGCTTGGTGCAGGCTGGGGGGTCACTGAGACTCTCCTGTGCAGCCTCTGGAACCATCGGCACGATCAGAGCCATGGGCTGGTACCGCCAGGCTCCAGGGAAGCAGCGCGAGTTGGTCGCATTGATTACTAGTACTGGTAGGATAAACTATGCAGACTCCGTGAAGGGCCGATTCACCATTGGAAGAGACAATGCCAAGAACACGGCGTATCTGCAAATGAACAACCTGAAACCTGAGGACACGGCCGTCTATTACTATAATATCGAAACACTACGACGTAACTACTGGGGCCAGGGGACCCAGGTCACCGTCTCCTCA |
| 139H02 | SEQ ID NO. 199 | GAGGTGCAGCTGGTGGAGTCTGGGGGAGGATTGGTGCAGGCTGGGGGGTCTCTGAGACTCTCCTGTGCAGCCTCTGGACGCACCTTTAGTAACTATGCCATGGGCTGGTTCCGCCAGGCCACAGGGAAGGAGCGTGAGTTTGTAGCAGCTATTAACAAGAGTGGTGGGAACACACACTATGCAGGCTCCGTGAAGGGCCGATTCACCATCTCCAGAGACAACGCCAAGAACACGGTGTATCTGCAAATGAACAGCCTGAAACCTAGGGACACGGCCGTTTATTACTGTGCAGCGTCGCGGACTAACCCTAAGCCTGACTACTGGGGCCAGGGGACCCAGGTCACCGTCTCCTCA |
| 139A08 | SEQ ID NO. 200 | GAGGTGCAGCTGGTGGAGTCTGGGGGAGGATTGGTGCAGGCTGGGGGCTCTCTGAGACTCTCCTGTGCAGCCTCTGGACGCTCCTTCAGTCGCAGTGCCATGGGCTGGCTCCGCCAGGCTCCAGGGAAGGAGCGTGAATTTGTAGCAGGTATTAGCTGGGGTGGTGATAACTCATACTATGCAGACTCCGTGAAGGGCCGATTCACCATCTCCAGAGACAACGCCAAGAACACCGTGTCTCTACAAATGAACAGCCTGAAACCTCAGGACACGGCCGTTTATTACTGTGCAGCAAGATACCGGGGAGGCGCGGCAGTAGCTGGTTGGGAGTACTGGGGCCAGGGGACCCAGGTCACCGTCTCCTCA |
| 137A08 | SEQ ID NO. 201 | GAGGTGCAGCTGGTGGAGTCTGGGGGAGGCTTGGTGCAGCCTGGGGGGTCTCTGAGACTCTCCTGTGCAGCCTCCGGATCCACTTTGGCCTATTATACCGTAGGCTGGTTCCGCCGGGCCCCAGGGAAGGAGCGCGAGGGGATCTCATGTATTAGTAGTAGTGATGGTAGCACATACTATGCAGACTCCGTGAAGGGCCGATTCACCATCTCCAGAGACAATGCCAAGAATACGGTGTATCTGCAAATGAACAGCCTGAAACCTGAG |

TABLE 18-continued

| | | |
|---|---|---|
| | | GACACGGCCGTTTATTACTGTGCGGCTGACAGACGTACCGACTGTAAAAAGGGTAGAGTCGGTTCTGGTTCCTGGGGCCAGGGGACCCAGGTCACCGTCTCCTCA |
| 143A05 | SEQ ID NO. 202 | AAGGTGCAGCTGGTGGAGTCTGGGGGAGGGCTGGTGCAGGCTGGGGGCTCTCTGAGACTCTCCTGTGCAGCCTCCGGACGCGCCTTCAATTACTATGTCATGGCCTGGTTCCGCCAGGCTCAAGGGAAGGAGCGTGAGTTTGTAGCAGCTATTAGCACGCGTGGTAGTATGACAAAGTATTCAGACTCCGTGCAGGGCCGGTTCACCATCTCCAGAGACAACGCCAAGAACACGGTGTATCTGCACATGAACAGCCTGAAACCTGAGGATACGGCCGTTTATTACTGTGCAGCAGACCCTCGCGGCAGTAGCTGGTCATTTTCGTCCGGGGGTTATGACTACTGGGGCCAGGGGACCCAGGTCACCGTCTCCTCA |
| 137B07 | SEQ ID NO. 203 | GAGGTGCAGCTGGTGGAGTCTGGGGGAGGCTTGGTGCAGCCTGGGGGGTCTGTGAGACTCTCCTGTGTAGCCTCTGGAATCATCTTCAGACTCAGTGCGTTGGGTTGGACACGCCAGGGTCCAGGAAAGGCGCGCGAGTGGGTCGCAGGTATTAACAGTGATGGTACGACCAACTACGCCGACCCCGTGAAGGGCCGATTCACCATCTCCAGAGACAACGCCAAGAACACGATATATCTGCACATGGACATGCTGAAACCTGAGGATACGGCCGTCTATTACTGTGCCTCCGGAAAGTACCGGGGCCAGGGGACCCAGGTCACCGTCTCCTCA |
| 127D01 | SEQ ID NO. 204 | GAGGTGCAGCTGGTGGAGTCTGGGGGAGGCTTGGTGCAGGCTGGGGAGTCTCTGAGACTCTCCTGTGCAGCCTCTGGAAGCACCTTCGATTTCAAAGTCATGGGCTGGTACCGCCAGCCTCCAGGGAAGCAGCGCGAGGGGGTCGCAGCGATTAGGCTTAGTGGTAACATGCACTATGCAGAGTCCGTGAAGGGCCGATTCACCATCTCCAAAGCCAACGCCAAGAACACAGTGTATCTGCAAATGAACAGCCTGAGACCTGAGGACACGGCCGTCTATTACTGTAAGGTGAACATTCGGGGCCAGGACTACTGGGGCCAGGGGACCCAGGTCACCGTCTCCTCA |
| 126B11 | SEQ ID NO. 205 | GAGGTGCAGCTGGTGGAGTCTGGGGGAGGCTTGGTGCAGGCTGGGGGGTCTCTGACGCTCTCCTGTGCAGTCTCTGGAAGCTCCTTCAGAATCAATACCATGGGCTGGTACCGCCGGGCTCCAGGGAAGCAGCGCGAGTTGGTCGCAGCTCGTGATAGAGGTGGTTACATAAACTATGTAGATTCCGTGAAGGGCCGATTCACCGTCTCCAGAGACAACGCCAAGCCCACAATGTATCTGCAAATGAACAGCCTGAAACCTGAGGACACGGCCGTCTATTATTGTCATGCCGGGACCCAAGATCGGACGGGTCGGAATTTCGACCACTGGGGCCAGGGGACCCAGGTCACCGTCTCCTCA |
| 097A09 | SEQ ID NO. 206 | GAGGTGCAGCTGGTGGAGTCTGGGGGAGGCTTGGTGCAGCCTGGGGGGTCTCTGAGACTCTCCTGTGTAGCCTCTGGAAGCATCGTCAGAATTAATACCATGGGCTGGTACCGCCAGACTCCAGGGAAGCAGCGCGAGTTGGTCGCAGATATTACCAGTGGTGGTAACATAAACTATATAGACGCCGTGAAGGGCCGATTCACCATCTCCAGAGACAACACCAAGAACACGGTGTATCTGCAAATGAACAGCCTGAAACCTGAGGACACGGCCGTCTATTACTGTAATGCAGAGATCGTTGTTCTGGTGGGAGTTTGGACCCAGCGTGCGCGGACCGGCAACTACTGGGGCCAGGGGACCCAGGTCACCGTCTCCTCA |

TABLE 18-continued

| | | |
|---|---|---|
| 159B10 | SEQ ID NO. 207 | GAGGTGCAGCTGGTGGAGTCTGGGGGAGGATTGGTGCAGCCTGGGGGGTCTCTGAGACTCTCCTGTGCAGCCTCTGGACGCACGTTCAGTAGCTTGTCCATGGGCTGGTTCCGCCAGGCTCCGGGGAAGGAGCGTGCCTTTGTAGCAGCGCTTACTCGAAATGGTGGTTACAGATACTATGCAGACTCCGTGAAGGGCCGATTCACCATCTCCAGAGACGTCGCCAAGAAGACCTTATATCTGCAAATGAACAGCCTGAAACCTGAGGACACGGCCGTCTATTACTGTGCAGCAGATAGTCTTAGTGGTAGTGACTACTTAGGAACCAACCTAGACTACTGGGGCCAGGGGACCCAGGTCACCGTCTCCTCA |
| 163D02 | SEQ ID NO. 208 | GAGGTGCAGCTGGTGGAGTCTGGGGGAGGATTGGTGCAGGCTGGGGGCTCTCTGAGACTCTCCTGTGCAGCCTCTGGACGCACCTTCAGTGACTATGCCATGGGCTGGTTCCGCCAGGCTCCAGGGAAGGAGCGTGAGTTTGTAGCAGCTATTACGTGGAATGGTGGTAGAGTATTTTATACTGCCTCCGTGAAGGGCCGATTCACCATCTCCAGAGACAACGCCAAGAACACGATGTATCTGCAAATGAACAGCCTGAAACCTGAGGACACGGCCGTTTATTACTGTGCAGCAGATAAAGACAGACGTACTGACTATCTAGGGCACCCCGTTGCCTACTGGGGCCAGGGGACCCAGGTCACCGTCTCCTCA |
| 163E03 | SEQ ID NO. 209 | GAGGTGCAGCTGGTGGAGTCTGGGGGAGGATTGGTGCAGCCTGGGGGCTCTCTGAGACTCTCCTGTGTAGCCTCTGGACGCATCTTCAGTAGCAATGCCATGGGCTGGTTCCGCCAGGCTCCAGGGAAGGAGCGTGAGTTTGTAGCGGCCATTACCTGGAGGAGTGGCGGTAGCGCGTACTATGCAGACTCCGCGAAGGGCCGATTCACCATCTCCAGAGACAACGCCAAGAACACGGTGTATTTGCAAATGAACAGCCTGAAACCTGAGGACACGGCCGTTTATTATTGTGCAGCTGGTGGTAGTTCCTGGTTAAGTTTTCCGCCGGACTACTGGGGCCAGGGGACCCAGGTCACCGTCTCCTCA |
| 2B2 | SEQ ID NO. 210 | GAGGTGCAGCTGGTGGAGTCTGGGGGAGAGTTGGTGCAGCCGGGGGGGTCTCTGAGACTCTCCTGTGCAGCCTCTGGAAGCATCTTAACTATCAATGCCATGGGCTGGTACCGCCAGGCTCCAGGGAAGCAGCGCGAGTTGGTAGTCCGTAGGACTAGGGGTGGTAGTACAACGTATCAAGACTCCGTGAAGGGCCGATTCACCATCTCCGCAGACATTGCCAAGAAAACGATGTATCTCCAAATGAACAGCCTGAAACCTGAAGACACGGCCGTCTATTACTGTATGCTAGATGACCGTGGGGGTGTCTACTGGGGTCAGGGGACCCAGGTCACCGTCTCCTCA |
| 54B12 | SEQ ID NO. 211 | GAGGTGCAGCTGGTGGAGTCTGGGGGAGGCTTGGTGCAGGCTGGGGGGTCTCTGACGCTCTCCTGTGCAGTCTCTGGAAGCACCTTCAGAATCAATACCATGGGCTGGTACCGCCGGGCTCCAGGGAAGCAGCGCGAGTTGGTCGCAGCTCGTGATAGAGGTGGTTACATAAACTATGTAGATTCCGTGAAGGGCCGATTCACCGTCTCCAGAGACAACGCCAAGCCCACAATGTATCTGCAAATGAACAGCCTGAAACCTGAGGACACGGCCGTCTATTATTGTCATGCCGGGACCCAAGATCGGACGGGTCGGAATTTCGACCGCTGGGGCCAGGGGACCCAGGTCACCGTCTCCTCA |

Leadpanel-CDR+FR CXCR2 Kabat

TABLE 19

| | Framework 1 | CDR1 | Framework 2 | CDR2 | Framework 3 | CDR3 | Framework 4 |
|---|---|---|---|---|---|---|---|
| 143B03 | EVQLVESGGGLVQPGGSLRLSCAASGFTFS SEQ ID NO. 70 | TYWMY SEQ ID NO. 132 | WVRQAPGKGLDWVS SEQ ID NO. 91 | AINAGGDSTYYADPVKG SEQ ID NO. 152 | RFTISRDNNKNTLYLQMNSLKPEDTALYYCAT SEQ ID NO. 111 | VRGTARDLDY SEQ ID NO. 172 | WGQGTQVTVSS SEQ ID NO. 131 |

TABLE 19-continued

| | Framework 1 | CDR1 | Framework 2 | CDR2 | Framework 3 | CDR3 | Framework 4 |
|---|---|---|---|---|---|---|---|
| 139D05 | EVKLVESGGGLVQA GGSLRLSCALSGRIGS SEQ ID NO. 71 | INAMG SEQ ID NO. 133 | WYRQVSGQ QRELVA SEQ ID NO. 92 | VSRSGGSTDI ADSVKG SEQ ID NO. 153 | RFTISRDNGKNTVYL QMDSLKPEDTAVYY CYA SEQ ID NO. 112 | HTSSYSNWRVYN NDY SEQ ID NO. 173 | WGQGTQ VTVSS SEQ ID NO. 131 |
| 145C09 | EVQLVESGGGLVQA GGSLRLSCAASGFTFD SEQ ID NO. 72 | DYAIG SEQ ID NO. 134 | WFRQAPGK ERERVS SEQ ID NO. 93 | CISGSDGSTY YADSVKG SEQ ID NO. 154 | RFTISSDNAKNTVYL QMNNLKPEDTAVY YCAA SEQ ID NO. 113 | YWGLTLRLWMPP HRYDY SEQ ID NO. 174 | WGQGTQ VTVSS SEQ ID NO. 131 |
| 145D03 | EVQLVESGGGLVQA GGSLSLSCAASGLIFR SEQ ID NO. 73 | LSGMA SEQ ID NO. 135 | WYRQAPGR QREWVA SEQ ID NO. 94 | VLTKDGTLHY ADPVKG SEQ ID NO. 155 | RFTISRNNAENTWY LQMNSLKPEDTAIY YCNT SEQ ID NO. 114 | GRY SEQ ID NO. 175 | WGQGTQ VTVSS SEQ ID NO. 131 |
| 139H02 | EVQLVESGGGLVQA GGSLRLSCAASGRTFS SEQ ID NO. 74 | NYAMG SEQ ID NO. 136 | WFRQATGK EREFVA SEQ ID NO. 95 | AINKSGGNTH YAGSVKG SEQ ID NO. 156 | RFTISRDNAKNTVYL QMNSLKPRDTAVYY CAA SEQ ID NO. 115 | SRTNPKPDY SEQ ID NO. 176 | WGQGTQ VTVSS SEQ ID NO. 131 |
| 139A08 | EVQLVESGGGLVQA GGSLRLSCAASGRSFS SEQ ID NO. 75 | RSAMG SEQ ID NO. 137 | WLRQAPGK EREFVA SEQ ID NO. 96 | GISWGGDNSY YADSVKG SEQ ID NO. 157 | RFTISRDNAKNTVSL QMNSLKPQDTAVYY CAA SEQ ID NO. 116 | RYRGGAAVAGW EY SEQ ID NO. 177 | WGQGTQ VTVSS SEQ ID NO. 131 |
| 137A08 | EVQLVESGGGLVQP GGSLRLSCAASGSTLA SEQ ID NO. 76 | YYTVG SEQ ID NO. 138 | WFRRAPGKE REGIS SEQ ID NO. 97 | CISSSDGSTYY ADSVKG SEQ ID NO. 158 | RFTISRDNAKNTVYL QMNSLKPEDTAVYY CAA SEQ ID NO. 117 | DRRTDCKKGRVG SGS SEQ ID NO. 178 | WGQGTQ VTVSS SEQ ID NO. 131 |
| 143A05 | KVQLVESGGGLVQA GGSLRLSCAASGRA FN SEQ ID NO. 77 | YYVMA SEQ ID NO. 139 | WFRQAQGK EREFVA SEQ ID NO. 98 | AISTRGSMTK YSDSVQG SEQ ID NO. 159 | RFTISRDNAKNTVYL HMNSLKPEDTAVYY CAA SEQ ID NO. 118 | DPRGSSWSFSSGG YDY SEQ ID NO. 179 | WGQGTQ VTVSS SEQ ID NO. 131 |
| 137B07 | EVQLVESGGGLVQP GGSVRLSCVASGIIFR SEQ ID NO. 78 | LSALG SEQ ID NO. 140 | WTRQGPGK AREWVA SEQ ID NO. 99 | GINSDGTTNY ADPVKG SEQ ID NO. 160 | RFTISRDNAKNTIYL HMDMLKPEDTAVY YCAS SEQ ID NO. 119 | GKY SEQ ID NO. 180 | RGQGTQV TVSS SEQ ID NO. 132 |
| 127D01 | EVQLVESGGGLVQA GESLRLSCAASGSTFD SEQ ID NO. 79 | FKVMG SEQ ID NO. 141 | WYRQPPGK QREGVA SEQ ID NO. 100 | AIRLSGNMHY AESVKG SEQ ID NO. 161 | RFTISKANAKNTVYL QMNSLRPEDTAVYY CKV SEQ ID NO. 120 | NIRGQDY SEQ ID NO. 181 | WGQGTQ VTVSS SEQ ID NO. 131 |
| 126B11 | EVQLVESGGGLVQA GGSLTLSCAVSGSSFR SEQ ID NO. 80 | INTMG SEQ ID NO. 142 | WYRRAPGK QRELVA SEQ ID NO. 101 | ARDRGGYINY VDSVKG SEQ ID NO. 162 | RFTVSRDNAKPTMY LQMNSLKPEDTAVY YCHA SEQ ID NO. 121 | GTQDRTGRNFDH SEQ ID NO. 182 | WGQGTQ VTVSS SEQ ID NO. 131 |
| 097A09 | EVQLVESGGGLVQP GGSLRLSCVASGSIVR SEQ ID NO. 81. | INTMG SEQ ID NO. 143 | WYRQTPGK QRELVA SEQ ID NO. 102 | DITSGGNINYI DAVKG SEQ ID NO. 163 | RFTISRDNTKNTVYL QMNSLKPEDTAVYY CNA SEQ ID NO. 122 | EIVVLVGVWTQR ARTGNY SEQ ID NO. 183 | WGQGTQ VTVSS SEQ ID NO. 133 |
| 159B10 | EVQLVESGGGLVQP GGSLRLSCAASGRTFS SEQ ID NO. 82 | SLSMG SEQ ID NO. 144 | WFRQAPGK ERAFVA SEQ ID NO. 103 | ALTRNGGYR YYADSVKG SEQ ID NO. 164 | RFTISRDVAKKTLYL QMNSLKPEDTAVYY CAA SEQ ID NO. 123 | DSLSGSDYLGTNL DY SEQ ID NO. 184 | WGQGTQ VTVSS SEQ ID NO. 131 |
| 163D02 | EVQLVESGGGLVQA GGSLRLSCAASGRTFS SEQ ID NO. 83 | DYAMG SEQ ID NO. 145 | WFRQAPGK EREFVA SEQ ID NO. 104 | AITWNGGRVF YTASVKG SEQ ID NO. 165 | RFTISRDNAKNTMY LQMNSLKPEDTAVY YCAA SEQ ID NO. 124 | DKDRRTDYLGHP VAY SEQ ID NO. 185 | WGQGTQ VTVSS SEQ ID NO. 131 |
| 163E03 | EVQLVESGGGLVQP GGSLRLSCVASGRIFS SEQ ID NO. 84 | SNAMG SEQ ID NO. 146 | WFRQAPGK EREFVA SEQ ID NO. 105 | AITWRSGGSA YYADSAKG SEQ ID NO. 166 | RFTISRDNAKNTVYL QMNSLKPEDTAVYY CAA SEQ ID NO. 125 | GGSSWLSFPPDY SEQ ID NO. 186 | WGQGTQ VTVSS SEQ ID NO. 131 |
| 002B02 | EVQLVESGGELVQP GGSLRLSCAASGSILT SEQ ID NO. 85 | INAMG SEQ ID NO. 147 | WYRQAPGK QRELVV SEQ ID NO. 106 | RRTRGGSTTY QDSVKG SEQ ID NO. 167 | RFTISADIAKKTMYL QMNSLKPEDTAVYY CML SEQ ID NO. 126 | DDRGGVY SEQ ID NO. 187 | WGQGTQ VTVSS SEQ ID NO. 131 |

TABLE 19-continued

| | Framework 1 | CDR1 | Framework 2 | CDR2 | Framework 3 | CDR3 | Framework 4 |
|---|---|---|---|---|---|---|---|
| 146A06 | EVQLVESGGGLVQA GGSLRLTCAASGRIGT SEQ ID NO. 86 | INAMG SEQ ID NO. 148 | WYRQAPGK QRELVA SEQ ID NO. 107 | VITSGGRIDY ADSVKG SEQ ID NO. 168 | RFTISRDNAKNTVYL QMNSLKPEDTAVYY YNV SEQ ID NO. 127 | ETVVGAVY SEQ ID NO. 188 | WGQGTQ VTVSS SEQ ID NO. 131 |
| 147A01 | EVQLVESGGGLVQA GGSLRLSCAASGRM GN SEQ ID NO. 87 | INAMG SEQ ID NO. 149 | WYRQAPGK ERELVA SEQ ID NO. 108 | KITRGGAITY ADSVKG SEQ ID NO. 169 | RFTIARDNILNTAYL QMNDLKPEDTAVY YYNV SEQ ID NO. 128 | DGGPSQNY SEQ ID NO. 189 | WGQGTQ VTVSS SEQ ID NO. 131 |
| 144D01 | EVQLVESGGGLVQA GGSLRLSCAASGTIGT SEQ ID NO. 88 | IRAMG SEQ ID NO. 150 | WYRQAPGK QRELVA SEQ ID NO. 109 | LITSTGRINYA DSVKG SEQ ID NO. 170 | RFTIGRDNAKNTAY LQMNNLKPEDTAVY YYNI SEQ ID NO. 129 | ETLRRNY SEQ ID NO. 190 | WGQGTQ VTVSS SEQ ID NO. 131 |
| 054B12 | EVQLVESGGGLVQA GGSLTLSCAVSGSTFR SEQ ID NO. 89 | INTMG SEQ ID NO. 151 | WYRRAPGK QRELVA SEQ ID NO. 110 | ARDRGGYINY VDSVKG SEQ ID NO. 171 | RFTVSRDNAKPTMY LQMNSLKPEDTAVY YCHA SEQ ID NO. 130 | GTQDRTGRNFDR SEQ ID NO. 191 | WGQGTQ VTVSS SEQ ID NO. 131 |

21. Sequence Optimisation—CXCR2 Antagonist Polypeptides

Thermal Shift Assay (TSA):

5 μl of purified monovalent Nanobody (80 mg/ml) was mixed with 5 μl of the fluorescent probe Sypro Orange (Invitrogen, Carlsbad, Calif., catalogue # S6551) (final concentration 10×) in 10 μl of buffer (100 mM phosphate, 100 mM borate, 100 mM citrate, 115 mM NaCl, buffered at different pH's ranging from 3.5 to 9). The samples were then heated in a LightCycler 480II machine (Roche, Basel, Switzerland), from 37 to 90° C. at 4.4° C./s, after which they were cooled down to 37° C. at 2.2° C./s. Upon heat-induced unfolding, hydrophobic patches of the proteins are exposed to which the Sypro Orange binds resulting in an increase in fluorescence intensity. The inflection point of the first derivative of the fluorescence intensity curve serves as a measure of the melting temperature (Tm). (Ericsson et al. 2006 (Annals of Biochemistry, 357: 289-298).

Differential Scanning Calometry (DSC):

Experiments were performed on an Auto-Cap VP-DSC (MicroCal—GE Healthcare) according to the manufacturer's instructions. Melting temperature determinations of Nanobodies (0.25 mg/mL) were performed at a heating rate of 1° C./min over a temperature range from 30° C. to 95° C. Final thermograms were obtained after proper baseline subtraction. Software-driven (Origin 7.0) peak detection yielded the corresponding melting temperatures.

Forced Oxidation:

Nanobody samples (1 mg/mL) were subjected for four hours at RT and in the dark to 10 mM $H_2O_2$ in PBS, in parallel with control samples without $H_2O_2$, followed by buffer switch to PBS using Zeba desalting spin columns (0.5 mL) (Thermo Scientific). Stressed and control samples were then analyzed by means of RPC on a Series 1200 machine (Agilent Technologies) over a Zorbax 300SB-C3 column (Agilent Technologies) at 70° C. Oxidation of Nanobodies was quantified by determination of % peak area of pre-peaks occurring as a result of oxidative stress, compared to the main protein peak.

2B2 Sequence Optimisation

The protein sequence of parental 2B2 was aligned to the human VH3-23 (DP-47) and JH5 germlines (Table 20, page 147). Amino acid differences relative to the human germline sequence are represented by letters, identical amino acids by dots. Amino acid differences that are underlined were selected for conversion into the human counterpart whereas the others were left untouched.

Purified, monovalent material was produced from 2B2, CXCR20059 and CXCR20063, which was then characterized in a FACS ligand competition assay and an agonist-induced release of intracellular calcium (FLIPR) assay on both human and cynomolgus CXCR2. In addition, the melting temperature of the variants was determined in the thermal shift assay (TSA) or by means of differential scanning calometry (DSC) (Table 21). The M93L mutation in CXCR20059 and CXCR20063 abolishes the sensitivity of parental 2B2 to forced oxidation.

TABLE 21

Functional characterisation of monovalent 2B2 and sequence-optimised variants

| | Tm | FACS hGro-competition IC50 (M) | | FLIPR hGro-IC50 (M) | |
|---|---|---|---|---|---|
| | (° C.) | hCXCR2 | cCXCR2 | hCXCR2 | cCXCR2 |
| 2B2 | 73.7 | $1.3 \times 10^{-09}$ | $3.5 \times 10^{-08}$ | $6.5 \times 10^{-07}$ | $2.4 \times 10^{-05}$ |
| CXCR20059 | 73.4 | $1.5 \times 10^{-09}$ | $1.9 \times 10^{-08}$ | $3.9 \times 10^{-07}$ | $1.9 \times 10^{-05}$ |
| CXCR20063 | 71.9 | nd | $5.4 \times 10^{-08}$ | $6.1 \times 10^{-06}$ | $2.4 \times 10^{-05}$ |

97A9 Sequence Optimisation

The protein sequence of parental 97A9 was aligned to the human VH3-23 (DP-47) and JH5 germlines (Table 22, page 147). Amino acid differences relative to the human germline sequence are represented by letters, identical amino acids by dots. Amino acid differences that are underlined were selected for conversion into the human counterpart whereas the others were left untouched.

Purified, monovalent material was produced from 97A9 and CXCR20061, which was then characterized in a FACS ligand competition assay and an agonist-induced release of intracellular calcium (FLIPR) assay on both human and cynomolgus CXCR2. In addition, the melting temperature of the variants was determined in the thermal shift assay (TSA) (Table 23).

TABLE 23

Functional characterisation of monovalent 979A9 and sequence-optimised variant

| | | FACS hGro-competition IC50 (M) | | FLIPR hGro-IC50 (M) | |
|---|---|---|---|---|---|
| ID | Tm (° C.) | hCXCR2 ctrl | cCXCR2 ctrl | hCXCR2 | cCXCR2 |
| 97A9 | 76.5 | $1.2 \times 10^{-08}$ | $6.3 \times 10^{-08}$ | $9.4 \times 10^{-08}$ | $8.0 \times 10^{-07}$ |
| CXCR20061 | 80.2 | $1.5 \times 10^{-08}$ | $6.2 \times 10^{-08}$ | $6.6 \times 10^{-08}$ | $3.5 \times 10^{-07}$ |

163E3 Sequence Optimisation

The protein sequence of parental 163E3 was aligned to the human VH3-23 (DP-47) and JH5 germlines (Table 24, page 147). Amino acid differences relative to the human germline sequence are represented by letters, identical amino acids by dots. Amino acid differences that are underlined were selected for conversion into the human counterpart whereas the others were left untouched.

Purified, monovalent material was produced from 163E3 and CXCR20076, which was then characterized in a FACS ligand competition assay and an agonist-induced release of intracellular calcium (FLIPR) assay on both human and cynomolgus CXCR2. In addition, the melting temperature of the variants was determined in the thermal shift assay (TSA) (Table 25).

TABLE 25

Functional characterisation of monovalent 163E3 and sequence-optimised variant

| | | FACS hGro-competition IC50 (M) | | FLIPR hGro-IC50 (M) | |
|---|---|---|---|---|---|
| | Tm (° C.) | hCXCR2 | cCXCR2 | hCXCR2 | cCXCR2 |
| 163E3 | 74.4 | $1.0 \times 10^{-08}$ | $2.2 \times 10^{-08}$ | $3.5 \times 10^{-08}$ | $1.5 \times 10^{-07}$ |
| CXCR20076 | 77.3 | $1.6 \times 10^{-08}$ | $2.5 \times 10^{-08}$ | $3.1 \times 10^{-08}$ | $1.0 \times 10^{-07}$ |

127D1 Sequence Optimisation

The protein sequence of parental 127D1 was aligned to the human VH3-23 (DP-47) and JH5 germlines (Table 26, page 147). Amino acid differences relative to the human germline sequence are represented by letters, identical amino acids by dots. Amino acid differences that are underlined were selected for conversion into the human counterpart whereas the others were left untouched.

Purified, monovalent material was produced from 127D1 and CXCR20079, which was then characterized in a FACS ligand competition assay and an agonist-induced release of intracellular calcium (FLIPR) assay on both human and cynomolgus CXCR2. In addition, the melting temperature of the variants was determined in the thermal shift assay (TSA) (Table 27). The M57R mutation in CXCR20079 abolishes the sensitivity of parental 127D1 to forced oxidation.

TABLE 27

Functional characterisation of monovalent 127D1 and sequence-optimised variant

| | | FACS hGro-competition IC50 (M) | | FLIPR hGro-IC50 (M) | |
|---|---|---|---|---|---|
| | Tm (° C.) | hCXCR2 | cCXCR2 | hCXCR2 | cCXCR2 |
| 127D1 | 67.2 | $5.5 \times 10^{-10}$ | $6.1 \times 10^{-09}$ | $1.5 \times 10^{-08}$ | $1.1 \times 10^{-06}$ |
| CXCR20079 | 68.6 | $8.0 \times 10^{-10}$ | $2.8 \times 10^{-09}$ | $1.0 \times 10^{-08}$ | $4.5 \times 10^{-07}$ |

163D2 Sequence Optimisation

The protein sequence of parental 163D2 was aligned to the human VH3-23 (DP-47) and JH5 germlines (Table 28, page 148). Amino acid differences relative to the human germline sequence are represented by letters, identical amino acids by dots. Amino acid differences that are underlined were selected for conversion into the human counterpart whereas the others were left untouched.

Purified, monovalent material was produced from 163D2 and CXCR20086, which was then characterized in a FACS ligand competition assay and an agonist-induced release of intracellular calcium (FLIPR) assay on both human and cynomolgus CXCR2. In addition, the melting temperature of the variants was determined in the thermal shift assay (TSA) (Table 29).

TABLE 29

Functional characterisation of monovalent 163D2 and sequence-optimised variant

| | | FACS hGro-competition IC50 (M) | | FLIPR hGro-IC50 (M) | |
|---|---|---|---|---|---|
| | Tm (° C.) | hCXCR2 | cCXCR2 | hCXCR2 | cCXCR2 |
| 163D2 | 70.7 | $2.8 \times 10^{-09}$ | $7.1 \times 10^{-09}$ | $6.6 \times 10^{-08}$ | $9.2 \times 10^{-08}$ |
| CXCR20086 | 72.3 | $2.0 \times 10^{-09}$ | $4.8 \times 10^{-09}$ | $7.3 \times 10^{-08}$ | $8.5 \times 10^{-08}$ |

54B12 Sequence Optimisation

The protein sequence of parental 54B12 was aligned to the human VH3-23 (DP-47) and JH5 germlines (Table 30, page 148). Amino acid differences relative to the human germline sequence are represented by letters, identical amino acids by dots. Amino acid differences that are underlined were selected for conversion into the human counterpart whereas the others were left untouched.

Purified, monovalent material was produced from 54B12, CXCR20103 and CXCR2104, which was then characterized in a FACS ligand competition assay and an agonist-induced release of intracellular calcium (FLIPR) assay on both human and cynomolgus CXCR2. In addition, the melting temperature of the variants was determined in the thermal shift assay (TSA) (Table 31).

TABLE 31

Functional characterisation of monovalent 54B12 and sequence-optimised variant

| | | FACS hGro-competition IC50 (M) | | FLIPR hGro-IC50 (M) | |
|---|---|---|---|---|---|
| ID | Tm (° C.) | hCXCR2 ctrl | cCXCR2 ctrl | hCXCR2 | cCXCR2 |
| 54B12 | 64.4 | nf* | $3.3 \times 10^{-08}$ | $1.5 \times 10^{-07}$ | $1.1 \times 10^{-06}$ |
| CXCR20104 | tbd | nf* | $1.3 \times 10^{-08}$ | $5.9 \times 10^{-8}$ | $3.5 \times 15^{-6}$ |

TABLE 20

Alignment of 2B2 and sequence-optimised variants

```
             10      20       30       40       50       60        70       80         90       101   110
Kabat#:  .......|.......|.......|.......|.......|..a.....|.......|.......|..abc.....|.......|......|...

VH3-23/JH5:

EVQLLESGGGLVQPGGSLRLSCAASGFTFSSYAMSWVRQAPGKGLEWVSAISGSGGSTYYADSVKGRFTISRDNSKNTLYLQMNSL
RAEDTAVYYCAK-------WGQGTLVTVSS

CXCR22B2: ....V....E................SILTIN..G.Y......QR.L.VRRT-R....T.Q..........A.IA.K.M.......
          KP........MLDDRGGVY.....Q.....

CXCR20059: ..........................SILTIN..G.Y......QR.L.VRRT-R....T.Q..........A.I..K.M........
           P........LLDDRGGVY...........

CXCR20063: ..........................SILTIN..G.Y......QR.L.VRRT-R....T.Q..........A.I....M........
           P........LLDDRGGVY...........

VH3-23/JHS-SEQ ID NO. 212
```

TABLE 22

Alignment of 97A9 and sequence-optimised variant

```
             10     20      30      40      50       60       70     80       90         100          110
Kabat#:  ......|......|......|......|......|..a....|......|......|..abc....|......|abcdefghij......|...

VH3-23/JH5:

EVQLLESGGGLVQPGGSLRLSCAASGFTFSSYAMSWVRQAPGKGLEWVSAISGSGGSTYYADSVKGRFTISRDNSKNTLYLQMNSL
RAEDTAVYYCAK-----------------WGQGTLVTVSS

CXCR297A9: ....V.................V...SIVRINT.G.Y..T...QR.L.LAD.T-...NIN.I.A...........T...V......
           KP........NAEIVVLVGVWTQRARTGNY.....Q.....

CXCR20061: ..........................SIVRINT.G.Y......QR.L.AD.T-...NIN...................V........
           P........NAEIVVLVGVWTQRARTGNY...........
```

TABLE 24

Alignment of 163E3 and sequence-optimised variant

```
           10      20      30      40      50         60      70      80         90      100         110
Kabat#: .......|.......|.......|.......|.......|..ab....|.......|.......|..abc....|.......|abcd.......|...

VH3-23/JH5:

EVQLLESGGGLVQPGGSLRLSCAASGFTFSSYAMSWVRQAPGKGLEWVSAISGSGGSTYYADSVKGRFTISRDNSKNTLYLQMNSL
RAEDTAVYYCAK------------------WGQGTLVTVSS

CXCR2163E3: ....V.................V...RI...N..G.F......ER.F.A..TWR....A.....A..........A...V........
            KP.........AGGSSWLSFPPDY.....Q.....

CXCR20076: ..........................RI...N..G.F......ER.F.A..TWR....A....................V........
           P.........AGGSSWLSFPPDY...........
```

TABLE 26 alignment of 127D1 and sequence-optimised variant

```
           10      20      30      40      50        60      70      80         90      101     110
Kabat#: .......|.......|.......|.......|.......|..a.....|.......|.......|..abc.....|.......|......|...

VH3-23/JH5:

EVQLLESGGGLVQPGGSLRLSCAASGFTFSSYAMSWVRQAPGKGLEWVSAISGSGGSTYYADSVKGRFTISRDNSKNTLYLQMNSL
RAEDTAVYYCAK-------WGQGTLVTVSS

CXCR2127D1: ....V........A.E..........S..DFKV.G.Y..P...QR.G.A..R-LS.NMH..E.........KA.A...V........
            P........KVNIRGQDY.....Q.....

CXCR20079: ..........................S..DFKV.G.Y......QR.G.A..R-LS.NRH..E..........A.....V........
           P........KVNIRGQDY...........
```

TABLE 28

Alignment of 163D2 and sequence-optimised variant

```
            10     20     30     40     50        60     70     80        90     100              110
Kabat#: ......|......|......|......|......|..a....|......|......|..abc....|......|abcdefg......|...

VH3-23/JH5:

EVQLLESGGGLVQPGGSLRLSCAASGFTFSSYAMSWVRQAPGKGLEWVSAISGSGGSTYYADSVKGRFTISRDNSKNTLYLQMNSLRAED
RAEDTAVYYCAK---------------WGQGTLVTVSS

CXCR2163D2: ....V........A............R...D...G.F......ER.F.A..TWN..RVF.TA............A...M.......
            KP.........ADKDRRTDYLGHPVAY.....Q.....

CXCR20086: ..........................R...D...G.F......ER.F.A..TWN..RVF.TA.........................
           P.........ADKDRRTDYLGHPVAY...........
```

TABLE 30

| alignment of 54B12 and sequence-optimised variants | |
|---|---|
| | 10 20 30 40 50 60 70 80 90 100 110 |
| Kabat#: | ......\|......\|......\|......\|......\|..a....\|......\|......\|..abc....\|......\|abcd......\|... |
| VH3-23/JH5: | EVQLLESGGGLVQPGGSLRLSCAASGFTFSSYAMSWVRQAPGKGLEWVSAISGSGGSTYYADSVKGRFTISRDNSKNTLYLQMNSL<br>RAEDTAVYYCAK------------WGQGTLVTVSS |
| CXCR254B12: | ....V........A....T....V..S..RINT.G.Y.R....QR.L.A.RD-R..YIN.V........V....A.P.M.......<br>KP........HAGTQDRTGRNFDR.....Q..... |
| CXCR20103: | .......................V..S..RINT.G.Y......QR.L.A.RD-R..YIN.................P.M........<br>P........HAGTQDRTGRNFDR........... |
| CXCR20104: | .......................V..S..RINT.G.Y......QR.L.A.RD-R..YIN.V...............P.M........<br>P........HAGTQDRTGRNFDR........... |

TABLE 32

| Amino acid sequences of sequence-optimised variants | | |
|---|---|---|
| CXCR20059 | EVQLLESGGGLVQPGGSLRLSCAASGSILTINAMGWYRQAPGKQRELVVRRTR GGSTTYQDSVKGRFTISADISKKTMYLQMNSLRPEDTAVYYCLLDDRGGVYW GQGTLVTVSS | SEQ ID NO. 213 |
| CXCR20063 | EVQLLESGGGLVQPGGSLRLSCAASGSILTINAMGWYRQAPGKQRELVVRRTR GGSTTYQDSVKGRFTISADISKNTMYLQMNSLRPEDTAVYYCLLDDRGGVYW GQGTLVTVSS | SEQ ID NO. 214 |
| CXCR20061 | EVQLLESGGGLVQPGGSLRLSCAASGSIVRINTMGWYRQAPGKQRELVADITSG GNINYADSVKGRFTISRDNSKNTVYLQMNSLRPEDTAVYYCNAEIVVLVGVWT QRARTGNYWGQGTLVTVSS | SEQ ID NO. 215 |
| CXCR20079 | EVQLLESGGGLVQPGGSLRLSCAASGSTFDFKVMGWYRQAPGKQREGVAAIRL SGNRHYAESVKGRFTISRANSKNTVYLQMNSLRPEDTAVYYCKVNIRGQDYW GQGTLVTVSS | SEQ ID NO. 216 |
| CXCR20076 | EVQLLESGGGLVQPGGSLRLSCAASGRIFSSNAMGWFRQAPGKEREFVAAITW RSGGSAYYADSVKGRFTISRDNSKNTVYLQMNSLRPEDTAVYYCAAGGSSWLS FPPDYWGQGTLVTVSS | SEQ ID NO. 217 |
| CXCR20086 | EVQLLESGGGLVQPGGSLRLSCAASGRTFSDYAMGWFRQAPGKEREFVAAITW NGGRVFYTASVKGRFTISRDNSKNTLYLQMNSLRPEDTAVYYCAADKDRRTD YLGHPVAYWGQGTLVTVSS | SEQ ID NO. 218 |
| CXCR20104 | EVQLLESGGGLVQPGGSLRLSCAVSGSTFRINTMGWYRQAPGKQRELVAARDR GGYINYVDSVKGRFTISRDNSKPTMYLQMNSLRPEDTAVYYCHAGTQDRTGR NFDRWGQGTLVTVSS | SEQ ID NO. 219 |

TABLE 33

| amino acid sequences of sequenceoptimised biparatopic (including HLE with Alb8): | | |
|---|---|---|
| CXCR20079-35GS-CXCR20076 | SEQ ID NO. 221 | EVQLLESGGGLVQPGGSLRLSCAASGSTFDFKVMGWYRQAPGKQREGVAAIRLSGNRHYAESV KGRFTISRANSKNTVYLQMNSLRPEDTAVYYCKVNIRGQDYWGQGTLVTVSSGGGGSGGGGSG GGGSGGGGSGGGGSGGGGSGGGGSEVQLLESGGGLVQPGGSLRLSCAASGRIFSSNAMGWFRQ APGKEREFVAAITWRSGGSAYYADSVKGRFTISRDNSKNTVYLQMNSLRPEDTAVYYCAAGGS SWLSFPPDYWGQGTLVTVSS |
| CXCR20079-35GS-CXCR20086 | SEQ ID NO. 222 | EVQLLESGGGLVQPGGSLRLSCAASGSTFDFKVMGWYRQAPGKQREGVAAIRLSGNRHYAESV KGRFTISRANSKNTVYLQMNSLRPEDTAVYYCKVNIRGQDYWGQGTLVTVSSGGGGSGGGGSG GGGSGGGGSGGGGSGGGGSGGGGS EVQLLESGGGLVQPGGSLRLSCAASGRTFSDYAMGWFRQAPGKEREFVAAITWNGGRVFYTAS VKGRFTISRDNSKNTLYLQMNSLRPEDTAVYYCAADKDRRTDYLGHPVAYWGQGTLVTVSS |
| CXCR20104-35GS- | SEQ ID NO. 223 | EVQLLESGGGLVQPGGSLRLSCAVSGSTFRINTMGWYRQAPGKQRELVAARDRGGYINYVDSV KGRFTISRDNSKPTMYLQMNSLRPEDTAVYYCHAGTQDRTGRNFDRWGQGTLVTVSSGGGGS |

TABLE 33-continued

| amino acid sequences of sequenceoptimised biparatopic (including HLE with Alb8): | | |
|---|---|---|
| CXCR20076 | | GGGGSGGGGSGGGGSGGGGSGGGGSGGGGSEVQLLESGGGLVQPGGSLRLSCAASGRIFSSNA<br>MGWFRQAPGKEREFVAAITWRSGGSAYYADSVKGRFTISRDNSKNTVYLQMNSLRPEDTAVYY<br>CAAGGSSWLSFPPDYWGQGTLVTVSS |
| CXCR20104-<br>35GS-<br>CXCR20086 | SEQ ID<br>NO. 224 | EVQLLESGGGLVQPGGSLRLSCAVSGSTFRINTMGWYRQAPGKQRELVAARDRGGYINYVDSV<br>KGRFTISRDNSKPTMYLQMNSLRPEDTAVYYCHAGTQDRTGRNFDRWGQGTLVTVSSGGGGS<br>GGGGSGGGGSGGGGSGGGGSGGGGSGGGGSEVQLLESGGGLVQPGGSLRLSCAASGRTFSDYA<br>MGWFRQAPGKEREFVAAITWNGGRVFYTASVKGRFTISRDNSKNTLYLQMNSLRPEDTAVYYC<br>AADKDRRTDYLGHPVAYWGQGTLVTVSS |
| CXCR20079-<br>35GS-<br>CXCR20076-<br>35GS-Alb8 | SEQ ID<br>NO. 225 | EVQLLESGGGLVQPGGSLRLSCAASGSTFDFKVMGWYRQAPGKQREGVAAIRLSGNRHYAESV<br>KGRFTISRANSKNTVYLQMNSLRPEDTAVYYCKVNIRGQDYWGQGTLVTVSSGGGGSGGGGSG<br>GGGSGGGGSGGGGSGGGGSGGGGSEVQLLESGGGLVQPGGSLRLSCAASGRIFSSNAMGWFRQ<br>APGKEREFVAAITWRSGGSAYYADSVKGRFTISRDNSKNTVYLQMNSLRPEDTAVYYCAAGGS<br>SWLSFPPDYWGQGTLVTVSSGGGGSGGGGSGGGGSGGGGSGGGGSGGGGSGGGGSEVQLVES<br>GGGLVQPGNSLRLSCAASGFTFSSFGMSWVRQAPGKGLEWVSSISGSGSDTLYADSVKGRFTISR<br>DNAKTTLYLQMNSLRPEDTAVYYCTIGGSLSRSSQGTLVTVSS |
| CXCR20079-<br>35GS-<br>CXCR20061-<br>35GS-Alb8 | SEQ ID<br>NO. 226 | EVQLLESGGGLVQPGGSLRLSCAASGSTFDFKVMGWYRQAPGKQREGVAAIRLSGNRHYAESV<br>KGRFTISRANSKNTVYLQMNSLRPEDTAVYYCKVNIRGQDYWGQGTLVTVSSGGGGSGGGGSG<br>GGGSGGGGSGGGGSGGGGSGGGGS<br>EVQLLESGGGLVQPGGSLRLSCAASGSIVRINTMGWYRQAPGKQRELVADITSGGNINYADSVK<br>GRFTISRDNSKNTVYLQMNSLRPEDTAVYYCNAEIVVLVGVWTQRARTGNYWGQGTLVTVSS<br>GGGGSGGGGSGGGGSGGGGSGGGGSGGGGSGGGGSEVQLVESGGGLVQPGNSLRLSCAASGF<br>TFSSFGMSWVRQAPGKGLEWVSSISGSGSDTLYADSVKGRFTISRDNAKTTLYLQMNSLRPEDT<br>AVYYCTIGGSLSRSSQGTLVTVSS |
| CXCR20079-<br>35GS-<br>CXCR20086-<br>35GS-Alb8 | SEQ ID<br>NO. 227 | EVQLLESGGGLVQPGGSLRLSCAASGSTFDFKVMGWYRQAPGKQREGVAAIRLSGNRHYAESVK<br>GRFTISRANSKNTVYLQMNSLRPEDTAVYYCKVNIRGQDYWGQGTLVTVSSGGGGSGGGGSGG<br>GGSGGGGSGGGGSGGGGSGGGGS<br>EVQLLESGGGLVQPGGSLRLSCAASGRTFSDYAMGWFRQAPGKEREFVAAITWNGGRVFYTASV<br>KGRFTISRDNSKNTLYLQMNSLRPEDTAVYYCAADKDRRTDYLGHPVAYWGQGTLVTVSSGGG<br>GSGGGGSGGGGSGGGGSGGGGSGGGGSGGGGSEVQLVESGGGLVQPGNSLRLSCAASGFTFSSF<br>GMSWVRQAPGKGLEWVSSISGSGSDTLYADSVKGRFTISRDNAKTTLYLQMNSLRPEDTAVYYC<br>TIGGSLSRSSQGTLVTVSS |
| ALB8 | SEQ ID<br>NO. 228 | EVQLVESGGGLVQPGNSLRLSCAASGFTFSSFGMSWVRQAPGKGLEWVSSISGSGSDTLYADSVK<br>GRFTISRDNAKTTLYLQMNSLRPEDTAVYYCTIGGSLSRSSQGTLVTVSS |

TABLE 34 amino acid sequences of sequence optimised variants and parentals including annotations of CDRs (Kabat) and framework regions:

| | Framework 1 | CDR1 | Framework 2 | CDR2 | Framework 3 | CDR3 | Framework 4 |
|---|---|---|---|---|---|---|---|
| CXCR20059 | EVQLLESGGGLVQPGGSLR<br>LSCAASGSILT<br>SEQ ID NO. 229 | INAMG<br>SEQ ID<br>NO. 147 | WYRQAPGKQ<br>RELVV<br>SEQ ID NO.<br>106 | RRTRGGSTTYQD<br>SVKG<br>SEQ ID NO. 167 | RFTISADISKKTMY<br>LQMNSLRPEDTAV<br>YYCLL<br>SEQ ID NO. 238 | DDRGGVY<br>SEQ ID<br>NO. 187 | WGQGTLV<br>TVSS<br>SEQ ID NO.<br>245 |
| CXCR20063 | EVQLLESGGGLVQPGGSLR<br>LSCAASGSILT<br>SEQ ID NO. 229 | INAMG<br>SEQ ID<br>NO. 147 | WYRQAPGKQ<br>RELVV<br>SEQ ID NO.<br>106 | RRTRGGSTTYQD<br>SVKG<br>SEQ ID NO. 167 | RFTISADISKNTMY<br>LQMNSLRPEDTAV<br>YYCLL<br>SEQ ID NO. 239 | DDRGGVY<br>SEQ ID<br>NO. 187 | WGQGTLV<br>TVSS<br>SEQ ID NO.<br>245 |
| 002B02 | EVQLVESGGELVQPGGSLR<br>LSCAASGSILT<br>SEQ ID NO. 85 | INAMG<br>SEQ ID<br>NO. 147 | WYRQAPGKQ<br>RELVV<br>SEQ ID NO.<br>106 | RRTRGGSTTYQD<br>SVKG<br>SEQ ID NO. 167 | RFTISADIAKKTM<br>YLQMNSLKPEDTA<br>VYYCML<br>SEQ ID NO. 126 | DDRGGVY<br>SEQ ID<br>NO. 187 | WGQGTQV<br>TVSS<br>SEQ ID NO.<br>131 |
| CXCR20061 | EVQLLESGGGLVQPGGSLR<br>LSCAASGSIVR<br>SEQ ID NO. 230 | INTMG<br>SEQ ID<br>NO. 143 | WYRQAPGKQ<br>RELVA<br>SEQ ID NO.<br>234 | DITSGGNINYADS<br>VKG<br>SEQ ID NO. 235 | RFTISRDNSKNTV<br>YLQMNSLRPEDTA<br>VYYCNA<br>SEQ ID NO. 240 | EIVVLVGVWTQR<br>ARTGNY<br>SEQ ID<br>NO. 183 | WGQGTLV<br>TVSS<br>SEQ ID NO.<br>245 |
| 097A09 | EVQLVESGGGLVQPGGSLR<br>LSCVASGSIVR<br>SEQ ID NO. 81. | INTMG<br>SEQ ID<br>NO. 143 | WYRQTPGKQ<br>RELVA<br>SEQ ID NO.<br>102 | DITSGGNINYIDA<br>VKG<br>SEQ ID NO. 163 | RFTISRDNTKNTV<br>YLQMNSLKPEDTA<br>VYYCNA<br>SEQ ID NO. 122 | EIVVLVGVWTQR<br>ARTGNY<br>SEQ ID<br>NO. 183 | WGQGTQV<br>TVSS<br>SEQ ID NO.<br>133 |
| CXCR20079 | EVQLLESGGGLVQPGGSLR<br>LSCAASGSTFD<br>SEQ ID NO. 231 | FKVMG<br>SEQ ID<br>NO. 141 | WYRQAPGKQ<br>REGVA<br>SEQ ID NO.<br>235 | AIRLSGNRHYAE<br>SVKG<br>SEQ ID NO. 236 | RFTISRANSKNTV<br>YLQMNSLRPEDTA<br>VYYCKV<br>SEQ ID NO. 241 | NIRGQDY<br>SEQ ID<br>NO. 181 | WGQGTLV<br>TVSS<br>SEQ ID NO.<br>245 |

TABLE 34-continued amino acid sequences of sequence optimised variants and parentals including annotations of CDRs (Kabat) and framework regions:

| | Framework 1 | CDR1 | Framework 2 | CDR2 | Framework 3 | CDR3 | Framework 4 |
|---|---|---|---|---|---|---|---|
| 127D01 | EVQLVESGGGLVQAGESLR<br>LSCAASGSTFD<br>SEQ ID NO. 79 | FKVMG<br>SEQ ID<br>NO. 141 | WYRQPPGKQ<br>REGVA<br>SEQ ID NO.<br>100 | AIRLSGNMHYAE<br>SVKG<br>SEQ ID NO. 161 | RFTISKANAKNTV<br>YLQMNSLRPEDTA<br>VYYCKV<br>SEQ ID NO. 120 | NIRGQDY<br>SEQ ID<br>NO. 181 | WGQGTQV<br>TVSS<br>SEQ ID NO.<br>131 |
| CXCR20076 | EVQLLESGGGLVQPGGSLR<br>LSCAASGRIFS<br>SEQ ID NO. 232 | SNAMG<br>SEQ ID<br>NO. 146 | WFRQAPGKE<br>REFVA<br>SEQ ID NO.<br>105 | AITWRSGGSAYY<br>ADSVKG<br>SEQ ID NO. 237 | RFTISRDNSKNTV<br>YLQMNSLRPEDTA<br>VYYCAA<br>SEQ ID NO. 242 | GGSSWLSFPPDY<br>SEQ ID<br>NO. 186 | WGQGTLV<br>TVSS<br>SEQ ID NO.<br>245 |
| 163E03 | EVQLVESGGGLVQPGGSLR<br>LSCVASGRIFS<br>SEQ ID NO. 84 | SNAMG<br>SEQ ID<br>NO. 146 | WFRQAPGKE<br>REFVA<br>SEQ ID NO.<br>105 | AITWRSGGSAYY<br>ADSAKG<br>SEQ ID NO. 166 | RFTISRDNAKNTV<br>YLQMNSLKPEDTA<br>VYYCAA<br>SEQ ID NO. 125 | GGSSWLSFPPDY<br>SEQ ID<br>NO. 186 | WGQGTQV<br>TVSS<br>SEQ ID NO.<br>131 |
| CXCR20086 | EVQLLESGGGLVQPGGSLR<br>LSCAASGRTFS<br>SEQ ID NO. 233 | DYAMG<br>SEQ ID<br>NO. 145 | WFRQAPGKE<br>REFVA<br>SEQ ID NO.<br>104 | AITWNGGRVFYT<br>ASVKG<br>SEQ ID NO. 165 | RFTISRDNSKNTLY<br>LQMNSLRPEDTAV<br>YYCAA<br>SEQ ID NO. 243 | DKDRRTDYLGHP<br>VAY<br>SEQ ID<br>NO. 185 | WGQGTLV<br>TVSS<br>SEQ ID NO.<br>245 |
| 163D02 | EVQLVESGGGLVQAGGSLR<br>LSCAASGRTFS<br>SEQ ID NO. 83 | DYAMG<br>SEQ ID<br>NO. 145 | WFRQAPGKE<br>REFVA<br>SEQ ID NO.<br>104 | AITWNGGRVFYT<br>ASVKG<br>SEQ ID NO. 165 | RFTISRDNAKNTM<br>YLQMNSLKPEDTA<br>VYYCAA<br>SEQ ID NO. 124 | DKDRRTDYLGHP<br>VAY<br>SEQ ID<br>NO. 185 | WGQGTQV<br>TVSS<br>SEQ ID NO.<br>131 |
| CXCR20104 | EVQLLESGGGLVQPGGSLR<br>LSCAVSGSTFR<br>SEQ ID NO. 234 | INTMG<br>SEQ ID<br>NO. 151 | WYRQAPGKQ<br>RELVA<br>SEQ ID NO.<br>234 | ARDRGGYINYVD<br>SVKG<br>SEQ ID NO. 171 | RFTISRDNSKPTM<br>YLQMNSLRPEDTA<br>VYYCHA<br>SEQ ID NO. 244 | GTQDRTGRNFDR<br>SEQ ID<br>NO. 191 | WGQGTLV<br>TVSS<br>SEQ ID NO.<br>245 |
| 054B12 | EVQLVESGGGLVQAGGSLT<br>LSCAVSGSTFR<br>SEQ ID NO. 89 | INTMG<br>SEQ ID<br>NO. 151 | WYRRAPGKQ<br>RELVA<br>SEQ ID NO.<br>110 | ARDRGGYINYVD<br>SVKG<br>SEQ ID NO. 171 | RFTVSRDNAKPTM<br>YLQMNSLKPEDTA<br>VYYCHA<br>SEQ ID NO. 130 | GTQDRTGRNFDR<br>SEQ ID<br>NO. 191 | WGQGTQV<br>TVSS<br>SEQ ID NO.<br>131 |

TABLE 35

Chotia CDR annotations of sequence optimised variants

| | HCDR1 | HCDR2 | HCDR3 |
|---|---|---|---|
| CXCR20059 | GSILTIN | TRGGS | DDRGGVY |
| CXCR20063 | GSILTIN | TRGGS | DDRGGVY |
| CXCR20061 | GSIVRIN | TSGGN | EIVVLVGVWTQRARTGNY |
| CXCR20079 | GSTFDFK | RLSGN | NIRGQDY |
| CXCR20076 | GRIFSSN | TWRSGGS | GGSSWLSFPPDY |
| CXCR20086 | GRTFSDY | TWNGGR | DKDRRTDYLGHPVAY |
| CXCR20104 | GSTFRIN | DRGGY | GTQDRTGRNFDR |

22. Epitope Mapping

Epitope mapping of nanobodies was carried out by Integral Molecular Inc., 3711 Market street, Suite 900, Philadelphia, Pa., USA, www.integralmolecular.com using their Shotgun Mutagenesis Technology.

Shotgun Mutagenesis Technology Summary

Shotgun Mutagenesis uses a proprietary high throughput cellular expression technology that enables the expression and analysis of large libraries of mutated target proteins within eukaryotic cells. Every residue in a protein is individually mutated, usually to multiple other amino acids, in order to assay changes in function. Proteins are expressed within standard mammalian cell lines, so even difficult proteins that require eukaryotic translational or post-translational processing can be mapped.

The nomenclature for the epitope mapping is as follows:

RDHBC 792=CXCR20079

RDHBC 793=CXCR20061

RDHBC 792=CXCR20076

The epitopes of anti-CXCR2 antibodies RD-HBC792 (CXCR20079), RD-HBC793 (CXCR220061) and RD-HBC794 (CXCR20076) were mapped at single amino acid resolution using shotgun Mutagenesis as follows.

Parental construct: The untagged parental gene was cloned into a high-expression vector, sequenced and validated for expression by immunodetection. Nanobody optimization:detection of nanobodies was optimized in the Shotgun Mutageneisis format by assaying a panel of nanobody dilutions in 394-well microplates. An optimal concentration of each nanobody was selected for screening the mutation library. The mutation library was completed and each amino acid position was mutated to a conserved and non-conserved change, including mutation of every residue to an Ala substitution. The library was tested for surface expression and screened, in triplicate, for nanobody binding by immunodetection. Analysis of the library for loss of nanobody binding was performed, critical residues were identified and mapped.

Parental Construct Expression Immunodetection of transiently expressed wild type parental construct was carried out in 384 well format by immunoluminescence and immunofluorescence. For all experiments, liquid handling steps involved in cell transfection and immunostaining were performed using liquid handling robots to ensure precision and high experimental reproducibility.

TABLE 36

| Experimental parameters used to test parental plasmid. | | |
|---|---|---|
| Experimental Parameter | Immunoluminescence | Immunofluorescence |
| Cells | HEK-293T | HEK-293T |
| Fixative | 4% PFA | 4% PFA |
| Blocking Buffer | 10% Goat Serum | 10% Goat Serum |
| 1°MAb Target Conc Incubation Manufacturer Catalog # | α-CXCR2 2 ug/ml 1 hour R&D Systems MAB331 | α-CXCR2 3 ug/ml 1 hour R&D Systems MAB331 |
| 2°MAb Target Conc Manufacturer Catalog # | α-mouse HRP 0.8 ug/ml Jackson Immunoresearch 115-035-003 | α-mouse Dyelight 549 3.75 ug/ml Jackson Immunoresearch 115-505-003 |
| Washes | PBS++ | PBS++ |
| Signal:Background | 29:1 | 2.2:1 |
| % CV of Parental | 4.7% | 12% |

TABLE 37

| Experimental parameters used for polyclonal immunodetection. | |
|---|---|
| Detection of total receptor cell surface expression using polyclonal serum. Polyclonal serum (capable of reacting with all mutants) is used to quantify total expression so that each clone in the mutation library can be detected. Experimental Parameter | Polyclonal Immunodetection |
| Cells | HEK-293T |
| Fixative | 4% PFA |
| Blocking Buffer | 10% Goat Serum |
| 1°PAb Target Conc Incubation Manufacturer Catalog # | α-CXCR2 1:1,000 dilution 1 hour Novus NBP1-49218 |
| 2°MAb Target Conc Manufacturer Catalog # | α-rabbit HRP 0.8 ug/ml Southern Biotech 4050-05 |
| Washes | PBS++ |
| Signal:Background | 17:1 |
| % CV | 10% |

Conclusion: Robust surface expression and total expression is detected for the wild type parental construct using a control MAb and a polyclonal serum, so the wild type parental construct can be used for Shotgun Mutagenesis. The immunoluminescence assay shows high signal: background and low variability and will be used for mapping studies.

Immunodetection was optimized using mapping nanobodies. Immunodetection was done in a 384-well format, using cells transiently transfected with wild type receptor or vector only plasmid. The concentrations chosen for further mapping studies was based upon a near-maximal signal with high signal:background and low variability.

Final Assay Conditions for Screening Mutation Library

TABLE 38

| Experimental parameters used for optimized assay detection in Shotgun Mutagenesis 384-well format. | | | |
|---|---|---|---|
| Experimental Parameter | RD-HBC792 | RD-HBC793 | RD-HBC794 |
| Cells | HEK-293T | HEK-293T | HEK-293T |
| Fixative | 4% PFA | 4% PFA | 4% PFA |
| Blocking Buffer | 10% Goat Serum | 10% Goat Serum | 10% Goat Serum |
| 1°MAb Target Optimal Conc Incubation | α-CXCR2 1.0 ug/ml 1 hour | α-CXCR2 1.0 ug/ml 1 hour | α-CXCR2 2.0 ug/ml 1 hour |
| 2°MAb Target Conc Incubation Manufacturer Antibody name | α-myc 2 ug/ml 1 hour in-house hybridoma 9E10 | α-myc 2 ug/ml 1 hour in-house hybridoma 9E10 | α-myc 2 ug/ml 1 hour in-house hybridoma 9E10 |
| 3°MAb Target Conc Manufacturer Catalog # | α-mouse HRP 0.8 ug/ml Jackson Immunoresearch 115-035-003 | α-mouse HRP 0.8 ug/ml Jackson Immunoresearch 115-035-003 | α-mouse HRP 0.8 ug/ml Jackson Immunoresearch 115-035-003 |
| Washes | PBS++ | PBS++ | PBS++ |
| Signal:Background | 13:1 | 6.9:1 | 20:1 |
| % CV | 7.9% | 22% | 13% |

Optimized assay conditions defined here was used for mapping the CXCR2 mutation library in a 384-well format. Each clone in the library was expressed in cells by transient transfection and was assayed for nanobody reactivity approximately 18 hours post-transfection. The CXCR2 nanobodies RD-HBC792, RDHBC793 and RD-HBC794 lack Fc regions but contain a myc-tag, so a multi-step detection strategy was used in which an intermediate mouse anti-myc antibody (9E10) was used, followed by detection with an anti-mouse HRP antibody.

Conclusion:

Final conditions for immunodetection and epitope mapping of 3 CXCR2 nanobodies were determined. Optimized conditions resulted in high signal:background and low variability in the Shotgun Mutagenesis format, and could thus be used for epitope mapping with high confidence. Epitope mapping involved applying the same assay conditions determined here, but with a mutation library of receptor variants.

Identification of Critical Residues for Nanobody Epitopes

TABLE 39

Identification of critical residues.

| Residue ID | Mutations | Clone_ID | Polyclonal Mean | Polyclonal St Dev | RD HBC 792 Mean | RD HBC 792 St Dev | RD HBC 793 Mean | RD HBC 793 St Dev | RD HBC 794 Mean | RD HBC 794 St Dev |
|---|---|---|---|---|---|---|---|---|---|---|
| 11 | F11A | 10 | 39.9 | 17.0 | 7.1 | 2.1 | 81.1 | 13.7 | 81.6 | 20.6 |
| | F11Y | 975 | 70.5 | 6.2 | 26.7 | 14.7 | 113.9 | 5.4 | 100.2 | 29.1 |
| 14 | F14A | 486 | 35.4 | 5.4 | 9.4 | 3.9 | 98.6 | 8.7 | 110.3 | 5.5 |
| | F14Y | 1170 | 100.2 | 16.7 | 53.0 | 10.0 | 117.7 | 46.6 | 124.9 | 4.6 |
| 15 | W15A | 116 | 69.2 | 2.8 | 6.4 | 1.4 | 125.4 | 18.6 | 114.5 | 13.1 |
| | W15Y | 1075 | 92.3 | 6.2 | 14.9 | 6.4 | 112.2 | 27.9 | 110.8 | 11.4 |
| 39 | C39A | 95 | 86.2 | 6.0 | 65.0 | 6.7 | 7.6 | 7.1 | 10.1 | 0.7 |
| | C39N | 1099 | 108.7 | 8.8 | 94.4 | 34.9 | 4.7 | 6.7 | 9.2 | 4.4 |
| 112 | W112A | 318 | 88.2 | 12.9 | 102.8 | 28.7 | 15.5 | 7.4 | 25.4 | 6.6 |
| | W112Y | 1462 | 109.9 | 13.6 | 106.1 | 25.1 | 37.1 | 6.2 | 39.9 | 16.1 |
| 114 | F114A | 211 | 88.9 | 5.8 | 73.1 | 10.6 | 26.3 | 8.4 | 33.4 | 10.2 |
| | F114Y | 1560 | 122.3 | 14.6 | 87.4 | 21.0 | 102.2 | 25.4 | 116.8 | 37.2 |
| 115 | G115A | 320 | 82.7 | 7.7 | 70.4 | 14.1 | 13.2 | 5.2 | 18.3 | 2.2 |
| | G115T | 1561 | 82.4 | 40.6 | 89.7 | 9.8 | 61.7 | 14.8 | 55.6 | 6.6 |
| 188 | Y188A | 765 | 89.6 | 21.2 | 100.0 | 37.7 | 102.8 | 12.4 | 20.1 | 6.3 |
| | Y188F | 1634 | 133.8 | 16.2 | 106.8 | 14.2 | 87.1 | 31.1 | 107.2 | 11.7 |
| 196 | C196A | 963 | 86.9 | 16.4 | 99.9 | 17.2 | 1.2 | 7.0 | 8.8 | 2.4 |
| | C196N | 1836 | 97.9 | 8.1 | 90.9 | 14.3 | 7.3 | 2.1 | 9.3 | 3.3 |
| 274 | D274A | 889 | 101.4 | 14.9 | 102.2 | 1.9 | 21.4 | 7.0 | 29.4 | 9.2 |
| | D274E | 1955 | 80.3 | 20.3 | 97.5 | 6.6 | 52.1 | 13.2 | 60.4 | 14.3 |
| 282 | I282A | 669 | 79.6 | 10.7 | 66.8 | 17.7 | 25.5 | 12.2 | 24.6 | 8.8 |
| | I282N | 1989 | 58.8 | 9.2 | 78.5 | 13.7 | 6.9 | 18.0 | 10.3 | 3.1 |
| 285 | T285A | 770 | 64.8 | 14.3 | 53.1 | 2.4 | 17.1 | 9.7 | 28.8 | 13.6 |
| | T285S | 2215 | 154.4 | 65.9 | 91.8 | 23.2 | 116.4 | 37.0 | 121.5 | 27.0 |
| 286 | C286A | 771 | 87.3 | 19.6 | 57.4 | 9.6 | 5.6 | 6.5 | 6.2 | 2.0 |
| | C286N | 2024 | 92.0 | 20.9 | 58.0 | 13.5 | 1.3 | 9.3 | 11.7 | 8.2 |
| 293 | D293A | 778 | 131.5 | 4.9 | 100.8 | 49.9 | 15.9 | 8.2 | 44.9 | 17.6 |
| | D293E | 2127 | 150.3 | 23.4 | 138.9 | 24.6 | 73.3 | 26.5 | 141.9 | 19.4 |

Critical residues for the MAb were identified by comparing the nanobody reactivities of the clones against polyclonal reactivity (surface expression). Residues involved in the antibody epitope were identified as those that were negative for nanobody binding but positive for polyclonal binding, included an Ala residue substitution (i.e. removal of the residue's side chain), and were located in the extracellular loops. Mean reactivities and standard deviation for MAb binding and polyclonal antibody binding are shown. Critical residues identified for each MAb are shaded grey. Data for RD HBC792 was also compared to RD HBC793, since the binding profile for RD HBC792 was found to be similar to the commercial polyclonal serum (which was derived from the N-terminal extracellular domain of human CXCR2, likely explaining the lowered reactivity of the serum against the F11, F14, and W15 mutations).

Further Analysis of Epitope Information

The critical amino acids identified by Shotgun Mutagenesis Mapping define the binding site(s) for the 3 CXCR2 MAbs. MAb RD HBC792 maps to N-terminal region of CXCR2, and the close proximity of the critical residues suggests that the epitope is linear in nature. MAbs RD HBC793 and RD HBC794 appear to bind a conformationally-complex epitope formed primarily by ECL1 and ECL3 of CXCR2. Mutation of the extracellular Cys residues, known to form two disulfide bridges that hold the extracellular loops in place in chemokine receptors, also eliminates binding of MAbs 793 and 794 so are not believed to be directly involved in the epitope interaction. The epitopes of 793 and 794 significantly overlap, although subtle differences between the two are apparent.

EMBODIMENTS

1. A polypeptide comprising at least two immunoglobulin antigen binding domains, which polypeptide is directed against or binds to chemokine receptor CXCR2 wherein said polypeptide includes a first antigen binding domain recognising a first epitope on CXCR2 and a second antigen binding domain recognising a second epitope on CXCR2.

2. The polypeptide of embodiment 1 wherein said first antigen binding domain is capable of binding to a linear peptide consisting of the sequence of amino acids set forth in SEQ ID No. 7 and said second antigen binding domain is either not capable of binding or binds with lower affinity to said linear peptide.

3. The polypeptide of embodiment 1 or embodiment 2 wherein said first antigen binding domain is comprised within a first immunoglobulin single variable domain and said second antigen binding domain is comprised within a second immunoglobulin single variable domain of an antibody.

4. The polypeptide of embodiment 3 wherein at least one of said first and second antigen binding domains is comprised within an antibody $V_L$ domain or a fragment thereof.

5. The polypeptide of embodiment 3 wherein at least one of said first and second antigen binding domains is comprised within an antibody $V_H$ domain or a fragment thereof.

6. The polypeptide of embodiment 4 or 5 wherein said first antigen binding domain is comprised in a $V_L$ domain or a fragment thereof and said second antigen binding domain is comprised in a $V_H$ domain or a fragment thereof.

7. The polypeptide of embodiment 4 or 5 wherein said first antigen binding domain is comprised in a $V_H$ domain or fragment thereof and said second antibody binding domain is comprised in a $V_L$ domain or a fragment thereof.

8. The polypeptide of any one of embodiments 3 to 7 wherein said first and second antigen binding domains are comprised within first and second domain antibodies (dAbs).

9. The polypeptide of embodiment 3 or embodiment 5 wherein at least one of said first and second antigen binding domains is comprised within a $V_{HH}$ domain or fragment thereof from a single heavy chain of a heavy chain antibody obtainable from a Camelid or is a sequence-optimised, including humanised, variant thereof.

10. The polypeptide of embodiment 9 wherein each of said antigen binding domains is comprised within a $V_{HH}$ domain or fragment thereof from a single heavy chain of a heavy chain antibody derived from a Camelid or is a sequence-optimised, including humanised, variant thereof.

11. The polypeptide of embodiment 9 or 10 wherein each $V_{HH}$ sequence or fragment thereof includes one, two or three CDRs.

12. The polypeptide of any one of embodiments 9 to 11 wherein each $V_{HH}$ sequence has the structure: FR-CDR-FR-CDR-FR-CDR-FR.

13. The polypeptide of any one of the preceding embodiments wherein said at least two antigen binding domains are joined by a linker.

14. The polypeptide of any one of embodiments 3 to 13 which has the structure:

FR1-CDR1-FR2-CDR2-FR3-CDR3-FR4--LINKER--FR5-CDR4-FR6-CDR5-FR7-CDR6-FR8 wherein if FR1-CDR1-FR2-CDR2-FR3-CDR3-FR4 comprises the first antigen binding domain then FR5-CDR4-FR6-CDR5-FR7-CDR6-FR8 comprises the second antigen domain and if FR1-CDR1-FR2-CDR2-FR3-CDR3-FR4 comprises the second antigen domain then FR5-CDR4-FR6-CDR5-FR7-CDR6-FR8 comprises the first antigen binding domain.

15. The polypeptide of embodiments 1 or 2 wherein each of said first and second antigen binding domains is comprised within a heavy chain antibody.

16. The polypeptide of embodiment 1 or 2 wherein said first antigen binding domain is comprised within a single chain of a first heavy chain antibody and said second antigen binding domain is comprised within a single chain of a second heavy chain antibody wherein said first and second heavy single chain antibodies are joined by a linker.

17. The polypeptide of embodiments 1 or 2 wherein each of said first and second antigen binding domains is comprised within an antibody consisting of two heavy chains and two light chains.

18. The polypeptide of embodiment 1 or 2 wherein said first and second antigen binding domains are comprised in first and second antibodies respectively each comprising two heavy and two light chains wherein said first and second antibodies are joined by a linker.

19. The polypeptide of embodiment 1 or 2 wherein said first and second antigen binding domains are comprised within first and second antibody Fab or F(ab)2 fragments respectively and wherein said first and second Fab or F(ab)2 fragments are joined by a linker.

20. The polypeptide of embodiment 19 wherein said first antigen binding domain is comprised within an antibody Fab fragment and said second antigen binding domain is comprised within a F(ab)2 fragment or visa versa.

21. The polypeptide of embodiment 1 or 2 wherein said first and second antigen binding domains are comprised within first and second antibody single chain Fv (scFvs) or fragments thereof respectively and wherein said first and second scFvs are joined by a linker 22. The polypeptide of any one of embodiments 13, 14, 16, 18, 19, 20, or 21 wherein the linker joins the C-terminal of one immunoglobulin comprising an antigen binding domain to the N-terminal of a second immunoglobulin comprising an antigen binding domain.

23. The polypeptide of any one of embodiments 13, 14, 16, or 18 to 22 wherein the linker is a peptide comprising an amino acid sequence not of immunoglobulin origin.

24. The polypeptide of embodiment 23 wherein the peptide linker is between 3 and 50 amino acids long 25. The polypeptide of embodiment 24 wherein the number of amino acids in the linker is selected from 3 to 9, 10 to 15, 16 to 20, 21 to 25, 26 to 35, 36 to 40, 41 to 45 or 46 to 50.

26. The polypeptide of embodiment 24 wherein the linker is 35 amino acids long.

27. The polypeptide of embodiment 24 wherein the linker which is constituted solely from two different amino acids.

28. The polypeptide of embodiment 27 wherein the linker is constituted from amino acids glycine and serine.

29. The polypeptide of embodiment 27 wherein the linker is constituted from amino acids proline and serine and optionally alanine 30. The polypeptide of any one of embodiments 23 to 26 wherein the linker is constituted solely of alanine 31. The polypeptide of embodiment 26 wherein the peptide linker consists of the amino acid sequence set forth in SEQ ID No 220.

32. The polypeptide of any one of the preceding embodiments which includes CDR amino acid sequences derived from or characteristic of camelid single heavy chain antibodies.

33. The polypeptide of any one of embodiments 9 to 14 wherein the amino acid sequences of the framework regions are derived from or characteristic of camelid single heavy chain antibodies.

34. The polypeptide of any one of embodiments 9 to 14 wherein the amino acid sequences of the framework regions are sequence-optimised, including humanised, variants thereof.

35. The polypeptide of any one of the preceding embodiments which specifically binds to CXCR2.

36. The polypeptide of any preceding embodiment which is directed against or binds to human CXCR2.

37. The polypeptide of any preceding embodiment including a least one further antigen binding domain which is directed against or specifically binds to a serum protein.

38. The polypeptide of any preceding embodiment wherein the serum protein is human serum albumin.

39. A molecule comprising at least two polypeptides, which molecule is directed against or binds to chemokine receptor CXCR2, wherein a first polypeptide comprises a first immunoglobulin antigen binding domain and a second polypeptide comprises a second immunoglobulin antigen binding domain, wherein said first and second antigen binding domains recognise first and second epitopes on CXCR2 and wherein said at least two polypeptides are joined by a non-peptide linker.

40. A molecule as embodimented in embodiment 38 wherein said first antigen binding domain is capable of binding to a linear peptide consisting of the sequence of amino acids set forth in SEQ ID No. 7 and said second antigen binding domain is either not capable of binding or binds with low affinity to said linear peptide.

41. A molecule as embodimented in embodiment 39 or 40 having the feature defined in any one of embodiments 3 to 22 and 32 to 38.

42. The polypeptide of any one of embodiments 3 to 14 or embodiments 22 to 39 wherein said second immunoglobulin single variable domain includes at least one CDR comprising an amino acid sequence selected from the group consisting of SEQ ID Nos 145, 165 and 185 or an amino acid sequence having at least 80% amino acid sequence identity with the amino acid sequences of SEQ ID Nos 145, 165 or 185 and wherein said first immunoglobulin of a single variable domain includes at least one CDR comprising an amino acid sequence selected from the group consisting of SEQ ID Nos 141, 161 and 181 or an amino acid sequence having at least 80% amino acid identity with the amino acid sequences of SEQ ID Nos 141, 161 or 181. (163D2/127D1)

43. The polypeptide of embodiment 42 comprising the structure as embodimented in embodiment 14 wherein in said second immunoglobulin of a single variable domain CDR1 comprises an amino acid sequence as set forth in SEQ ID No 145, CDR2 comprises the amino acid sequence set forth in SEQ ID No 165 and CDR3 comprises the amino acid sequence set forth in SEQ ID No 185 and wherein in said first immunoglobulin of a single variable domain CDR4 comprises an amino acid sequence as set forth in SEQ ID No 141, CDR5 comprises the amino acid sequence set forth in SEQ ID No 161 and CDR6 comprises the amino acid sequence set forth in SEQ ID No 181.

44. The polypeptide of embodiment 43 in which the amino acid sequences of CDR1, CDR2, CDR3, CDR4, CDR5 or CDR6 have at least 80% amino acid identity with the any one of the amino acid sequences set forth in SEQ ID Nos 145, 165, 185, 141, 161 or 181.

45 The polypeptide of embodiments 43 or 44 wherein the amino acid sequences differ from those set forth in SEQ ID Nos 145, 165, 185, 141, 161 or 181 only in conservative amino acid changes.

46. The polypeptide of any one of embodiments 43 to 45 wherein the framework regions in each monomer of a single variable domain comprise one or more hallmark residues at amino acid positions 11, 37, 44, 46, 47, 83, 84, 103, 104 and 108 according to Kabat numbering.

47. The polypeptide of any one of embodiments 43 to 46 wherein FR1 comprises an amino acid sequence as set forth in SEQ ID No 83, FR2 comprises an amino acid sequence as set forth in SEQ ID No 104, FR3 comprises an amino acid sequence as set forth in SEQ ID No 124, FR4 comprises an amino acid sequence set forth in SEQ ID No 131, FR5 comprises an amino acid sequence as set forth in SEQ ID No 79, FR6 comprises an amino acid sequence as set forth in SEQ ID No 100, FR7 comprises an amino acid sequence as set forth in SEQ ID No 120 and/or FR8 comprises an amino acid sequence as set forth in SEQ ID No 131.

48. The polypeptide of embodiment 47, which is modified such that FR1, FR2, FR3, FR4, FR5, FR6, FR7 and FR8 have amino acid sequences with at least 80% amino acid identity with amino acid sequences set forth in any of SEQ ID Nos 83, 104, 124, 131, 79, 100, or 120.

49. The polypeptide of any of embodiments 41 to 48 comprising the amino acid sequence set forth in SEQ ID No 58 or a polypeptide having at least 80% amino acid identity with the amino acid sequence of SEQ ID No 58.

50. The polypeptide of any one of embodiments 42 to 46, wherein said second immunoglobulin single variable domain comprises the amino acid sequence set forth in SEQ ID No. 218 or an amino acid sequence having at least 80% amino acid identity to SEQ ID NO. 218 and said first immunoglobulin single variable domain comprises the amino acid sequence set forth in SEQ ID NO. 216 or an amino acid sequence having at least 80% amino acid identity to SEQ ID NO. 216.

51. The polypeptide of any one of embodiments 3 to 14 or embodiment 22 to 39 wherein said second immunoglobulin single variable domain includes at least one CDR comprising an amino acid sequence selected from the group consisting of SEQ ID Nos 146, 166 and 186 or an amino acid sequence having at least 80% amino acid sequence identity with the amino acid sequences of SEQ ID Nos 146, 166 or 188 and wherein said first immunoglobulin single variable domain includes at least one CDR selected from the group consisting of SEQ ID Nos 141, 161 and 181 or an amino acid sequence having at least 80% amino acid identity with the amino acid sequences of SEQ ID Nos 141, 161 or 181. (163E3/127D1)

52. The polypeptide of embodiment 51 comprising the structure as embodimented in embodiment 14 wherein in said second immunoglobulin of a single variable domain CDR1 comprises an amino acid sequence as set forth in SEQ ID No 146, CDR2 comprises the amino acid sequence set forth in SEQ ID No 166 and CDR3 comprises the amino acid sequence set forth in SEQ ID No 186 and wherein in said first immunoglobulin of a single variable domain CDR4 comprises an amino acid sequence as set forth in SEQ ID No 141, CDR5 comprises the amino acid sequence set forth in SEQ ID No 161 and CDR6 comprises the amino acid sequence set forth in SEQ ID No 181.

53. The polypeptide of embodiment 52 in which the amino acid sequences of CDR1, CDR2, CDR3, CDR4, CDR5 or CDR6 have at least 80% amino acid identity with the any one of the amino acid sequences set forth in SEQ ID Nos 176, 166, 186, 141, 161 or 181.

54. The polypeptide of embodiments 52 or 53 wherein the amino acid sequences differ from those set forth in SEQ ID Nos 146, 166, 186, 141, 161 or 181 only in conservative amino acid changes.

55. The polypeptide of any one of embodiments 52 to 54 wherein the framework regions in each monomer of a single variable domain comprise one or more hallmark residues at amino acid positions 11, 37, 44, 45, 47, 83, 84, 103, 104 and 108.

56. The polypeptide of any one of embodiments 52 to 55 wherein FR1 comprises an amino acid sequence as set forth in SEQ ID No 84, FR2 comprises an amino acid sequence as set forth in SEQ ID No 105, FR3 comprises an amino acid sequence as set forth in SEQ ID No 125, FR4 comprises an amino acid sequence set forth in SEQ ID No 131, FR5 comprises an amino acid sequence as set forth in SEQ ID No 79, FR6 comprises an amino acid sequence as set forth in SEQ ID No 100, FR7 comprises an amino acid sequence as set forth in SEQ ID No 120 and/or FR8 comprises an amino acid sequence as set forth in SEQ ID No 131.

57. The polypeptide of embodiment 56 which is modified such that FR1, FR2, FR3, FR4, FR5, FR6, FR7 and FR8 have amino acid sequences with at least 80% amino acid identity with amino acid sequences set forth in any of SEQ ID Nos 84, 105, 125, 131, 79, 100, or 120.

58. The polypeptide of any of embodiments 51 to 57 comprising the amino acid sequence set forth in SEQ ID No 59 or a polypeptide having at least 80% amino acid identity with the amino acid sequence of SEQ ID No 59.

59. The polypeptide of any one of embodiments 51 to 58 wherein said second immunoglobulin single variable domain comprises the amino acid sequence set forth in SEQ ID No 217 or an amino acid sequence having at least 80% amino acid identity with SEQ ID No 217 and wherein said first immunoglobulin single variable domain comprises the amino acid sequences set forth in SEQ ID No 216 or an amino acid sequence having at least 80% amino acid identity with SEQ ID No. 216.

60. The polypeptide of any one of embodiments 3 to 14 or embodiments 22 to 39 wherein said second immunoglobulin single variable domain includes at least one CDR comprising an amino acid sequence selected from the group consisting of SEQ ID Nos 146, 166 and 186 or an amino acid sequence having at least 80% amino acid sequence identity with the amino acid sequences of SEQ ID Nos 146, 166 or 186 and wherein said first immunoglobulin single variable domain includes at least one CDR selected from the group consisting of SEQ ID Nos 151, 171 and 191 or an amino acid sequence having at least 80% amino acid identity with the amino acid sequences of SEQ ID Nos 151, 171 or 191. (163E3/54B12)

61. The polypeptide of embodiment 60 comprising the structure as embodimented in embodiment 14 wherein in said second immunoglobulin single variable domain CDR1 comprises an amino acid sequence as set forth in SEQ ID No 146, CDR2 comprises the amino acid sequence set forth in SEQ ID No 166 and CDR3 comprises the amino acid sequence set forth in SEQ ID No 186 and wherein in said first immunoglobulin single variable domain CDR4 comprises an amino acid sequence as set forth in SEQ ID No 151, CDR5 comprises the amino acid sequence set forth in SEQ ID No 171 and CDR6 comprises the amino acid sequence set forth in SEQ ID No 191

62. The polypeptide of embodiment 61 in which the amino acid sequences of CDR1, CDR2, CDR3, CDR4, CDR5 or CDR6 have at least 80% amino acid identity with the any one of the amino acid sequences set forth in SEQ ID Nos 146, 166, 186, 151, 171 or 191.

63. The polypeptide of embodiments 61 or 62 wherein the amino acid sequences differ from those set forth in SEQ ID Nos 146, 166, 186, 151, 171 or 191 only in conservative amino acid changes.

64. The polypeptide of any one of embodiments 61 to 63 wherein the framework regions in each monomer of a single variable domain comprise one or more hallmark residues at amino acid positions 11, 37, 44, 45, 47, 83, 84, 103, 104 and 108 according to Kabat numbering.

65. The polypeptide of any one of embodiments 61 to 64 wherein FR1 comprises an amino acid sequence as set forth in SEQ ID No 84, FR2 comprises an amino acid sequence as set forth in SEQ ID No 105, FR3 comprises an amino acid sequence as set forth in SEQ ID No 125, FR4 comprises an amino acid sequence set forth in SEQ ID No 131, FR5 comprises an amino acid sequence as set forth in SEQ ID No 89, FR6 comprises an amino acid sequence as set forth in SEQ ID No 110, FR7 comprises an amino acid sequence as set forth in SEQ ID No 130 and/or FR8 comprises an amino acid sequence as set forth in SEQ ID No 131.

66. The polypeptide of embodiment 65, which is modified such that FR1, FR2, FR3, FR4, FR5, FR6, FR7 and FR8 have amino acid sequences with at least 80% amino acid identity with amino acid sequences set forth in any of SEQ ID Nos 84, 105, 125, 131, 89, 110, or 130.

67. The polypeptide of any of embodiments 60 to 66 comprising the amino acid sequence set forth in SEQ ID No 62 or a polypeptide having at least 80% amino acid identity with the amino acid sequence of SEQ ID No 62.

68. The polypeptide of any one of embodiments 60 to 64 wherein said second immunoglobulin single variable domain comprises the amino acid sequence set forth in SEQ ID No 217 or an amino acid sequence having at least 80% amino acid identity with SEQ ID No. 217 and wherein said first immunoglobulin single variable domain comprises the amino acid sequence set forth in SEQ ID No 219 or an amino acid sequence having at least 80% amino acid identity with SEQ ID No. 219.

69. The polypeptide of any one of embodiments 3 to 14 or embodiments 22 to 39 wherein said second immunoglobulin single variable domain includes at least one CDR comprising an amino acid sequence selected from the group consisting of SEQ ID Nos 145, 165 and 185 or an amino acid sequence having at least 80% amino acid sequence identity with the amino acid sequences of SEQ ID Nos 145, 165 or 185 and wherein said first immunoglobulin single variable domain includes at least one CDR selected from the group consisting of SEQ ID Nos 151, 171 and 191 or an amino acid sequence having at least 80% amino acid identity with the amino acid sequences of SEQ ID Nos 151, 171 or 191. (163D2/54B12)

70. The polypeptide of embodiment 69 comprising the structure as embodimented in embodiment 14 wherein in said second immunoglobulin single variable domain CDR1 comprises an amino acid sequence as set forth in SEQ ID No 145, CDR2 comprises the amino acid sequence set forth in SEQ ID No 165 and CDR3 comprises the amino acid sequence set forth in SEQ ID No 185 and wherein in said first immunoglobulin single variable domain CDR4 comprises an amino acid sequence as set forth in SEQ ID No 151, CDR5 comprises the amino acid sequence set forth in SEQ ID No 171 and CDR6 comprises the amino acid sequence set forth in SEQ ID No 191.

71. The polypeptide of embodiment 70 in which the amino acid sequences of CDR1, CDR2, CDR3, CDR4, CDR5 or CDR6 have at least 80% amino acid identity with the any one of the amino acid sequences set forth in SEQ ID Nos 145, 165, 185, 151, 171, or 191.

72. The polypeptide of embodiments 70 or 71 wherein the amino acid sequences differ from those set forth in SEQ ID Nos 145, 165, 185, 151, 171 or 191 by only in conservative amino acid changes.

73. The polypeptide of any one of embodiments 70 to 72 wherein the framework regions in each monomer of a single variable domain comprise one or more hallmark residues at amino acid positions 11, 37, 44, 45, 47, 83, 84, 103, 104 and 108 according to Kabat numbering.

74. The polypeptide of any one of embodiments 70 to 73 wherein FR1 comprises an amino acid sequence as set forth in SEQ ID No 83, FR2 comprises an amino acid sequence as set forth in SEQ ID No 104, FR3 comprises an amino acid sequence as set forth in SEQ ID No 124, FR4 comprises an amino acid sequence set forth in SEQ ID No 131, FR5 comprises an amino acid sequence as set forth in SEQ ID No 89, FR6 comprises an amino acid sequence as set forth in SEQ ID No 110, FR7 comprises an amino acid sequence as set forth in SEQ ID No 130 and/or FR8 comprises an amino acid sequence as set forth in SEQ ID No 131.

75. The polypeptide of embodiment 74, which is modified such that FR1, FR2, FR3, FR4, FR5, FR6, FR7 and FR8 have amino acid sequences with at least 80% amino acid identity with amino acid sequences set forth in any of SEQ ID Nos 83, 104, 124, 131, 89, 110 or 130.

76. The polypeptide of any of embodiments 69 to 75 comprising the amino acid sequence set forth in SEQ ID No 63 or a polypeptide having at least 80% amino acid identity with the amino acid sequence of SEQ ID No 63.

77. The polypeptide of any one of embodiments 69 to 73 wherein said second immunoglobulin single variable domain comprises the amino acid sequence set forth in SEQ ID No 218 or an amino acid sequence having at least 80% amino acid identity with SEQ ID No 218 and wherein said first immunoglobulin single variable domain comprises the amino acid sequence set forth in SEQ ID No 219 or an amino acid sequence having at least 80% amino acid identity with either SEQ ID No 219.

78. The polypeptide of any one of embodiments 3 to 14 or embodiments 22 to 39 wherein said first immunoglobulin single variable domain includes at least one CDR comprising an amino acid sequence selected from the group consisting of SEQ ID Nos 147, 167 and 187 or an amino acid sequence having at least 80% amino acid sequence identity with the amino acid sequences of SEQ ID Nos 147, 167 or 187 and wherein said second immunoglobulin single variable domain includes at least one CDR selected from the group consisting of SEQ ID Nos 146, 166 and 186 or an amino acid sequence having at least 80% amino acid identity with the amino acid sequences of SEQ ID Nos 146, 166 or 186. (2B2/163E3)

79. The polypeptide of embodiment 78 comprising the structure as embodimented in embodiment 14 wherein in said first immunoglobulin single variable domain CDR1 comprises an amino acid sequence as set forth in SEQ ID No 147, CDR2 comprises the amino acid sequence set forth in SEQ ID No 167 and CDR3 comprises the amino acid sequence set forth in SEQ ID No 187 and wherein in said second immunoglobulin single variable domain CDR4 comprises an amino acid sequence as set forth in SEQ ID No 146, CDR5 comprises the amino acid sequence set forth in SEQ ID No 166 and CDR6 comprises the amino acid sequence set forth in SEQ ID No 186.

80. The polypeptide of embodiment 79 in which the amino acid sequences of CDR1, CDR2, CDR3, CDR4, CDR5 or CDR6 have at least 80% amino acid identity with the any one of the amino acid sequences set forth in SEQ ID Nos 147, 167, 187, 146, 166 or 186.

81. The polypeptide of embodiments 79 or 80 wherein the amino acid sequences differ from those set forth in SEQ ID Nos 147, 167, 187, 146, 166 or 186 only in conservative amino acid changes.

82. The polypeptide of any one of embodiments 79 to 81 wherein the framework regions in each monomer of a single variable domain comprise one or more hallmark residues at amino acid positions 11, 37, 44, 45, 47, 83, 84, 103, 104 and 108 according to Kabat numbering.

83. The polypeptide of any one of embodiments 79 to 82 wherein FR1 comprises an amino acid sequence as set forth in SEQ ID No 85, FR2 comprises an amino acid sequence as set forth in SEQ ID No 106, FR3 comprises an amino acid sequence as set forth in SEQ ID No 126, FR4 comprises an amino acid sequence set forth in SEQ ID No 131, FR5 comprises an amino acid sequence as set forth in SEQ ID No 84, FR6 comprises an amino acid sequence as set forth in SEQ ID No 105, FR7 comprises an amino acid sequence as set forth in SEQ ID No 125 and/or FR8 comprises an amino acid sequence as set forth in SEQ ID No 131.

84. The polypeptide of embodiment 83, which is modified such that FR1, FR2, FR3, FR4, FR5, FR6, FR7 and FR8 have amino acid sequences with at least 80% amino acid identity with amino acid sequences set forth in any of SEQ ID Nos 85, 106, 126, 131, 84, 105 or 125.

85. The polypeptide of any of embodiments 78 to 84 comprising the amino acid sequence set forth in SEQ ID No 64 or a polypeptide having at least 80% amino acid identity with the amino acid sequence of SEQ ID No 64.

86. The polypeptide of any one of embodiments 78 to 82 wherein said first immunoglobulin single variable domain comprises the amino acid sequence set forth in SEQ ID No 213 or 214 or an amino acid sequence having at least 80% amino acid identity with either SEQ ID No 213 or 214 and wherein said second immunoglobulin single variable domain comprises the amino acid sequence set forth in SEQ ID No 217 or an amino acid sequence having at least 80% amino acid sequence identity with SEQ ID No 217.

87. The polypeptide of any one of embodiments 3 to 14 or embodiments 22 to 39 wherein said first immunoglobulin single variable domain includes at least one CDR comprising an amino acid sequence selected from the group consisting of SEQ ID Nos 147, 167 and 187 or an amino acid sequence having at least 80% amino acid sequence identity with the amino acid sequences of SEQ ID Nos 147, 167 or 187 and wherein said second immunoglobulin variable domain includes at least one CDR selected from the group consisting of SEQ ID Nos 145, 165 and 185 or an amino acid sequence having at least 80% amino acid identity with the amino acid sequences of SEQ ID Nos 145, 165 or 185. (2B2/163D2)

88. The polypeptide of embodiment 87 comprising the structure as embodimented in embodiment 14 wherein in said first immunoglobulin single variable domain CDR1 comprises an amino acid sequence as set forth in SEQ ID No 147, CDR2 comprises the amino acid sequence set forth in SEQ ID No 167 and CDR3 comprises the amino acid sequence set forth in SEQ ID No 187 and wherein in said second immunoglobulin single variable domain CDR4 comprises an amino acid sequence as set forth in SEQ ID No 145, CDR5 comprises the amino acid sequence set forth in SEQ ID No 165 and CDR6 comprises the amino acid sequence set forth in SEQ ID No 185.

89. The polypeptide of embodiment 88 in which the amino acid sequences of CDR1, CDR2, CDR3, CDR4, CDR5 or CDR6 have at least 80% amino acid identity with the any one of the amino acid sequences set forth in SEQ ID Nos 147, 167, 187, 145, 165 or 185.

90. The polypeptide of embodiments 88 or 89 wherein the amino acid sequences differ from those set forth in SEQ ID Nos 147, 167, 187, 145, 165 or 185 only in conservative amino acid changes.

91. The polypeptide of any one of embodiments 88 to 90 wherein the framework regions in each monomer of a single variable domain comprise one or more hallmark residues at amino acid positions 11, 37, 44, 45, 47, 83, 84, 103, 104 and 108 according to Kabat numbering.

92. The polypeptide of any one of embodiments 88 to 91 wherein FR1 comprises an amino acid sequence as set forth in SEQ ID No 85, FR2 comprises an amino acid sequence as set forth in SEQ ID No 106, FR3 comprises an amino acid sequence as set forth in SEQ ID No 126, FR4 comprises an amino acid sequence set forth in SEQ ID No 131, FR5 comprises an amino acid sequence as set forth in SEQ ID No 83, FR6 comprises an amino acid sequence as set forth in SEQ ID No 104, FR7 comprises an amino acid sequence as set forth in SEQ ID No 124 and/or FR8 comprises an amino acid sequence as set forth in SEQ ID No 131.

93. The polypeptide of embodiment 94, which is modified such that FR1, FR2, FR3, FR4, FR5, FR6, FR7 and FR8 have amino acid sequences with at least 80% amino acid identity with amino acid sequences set forth in any of SEQ ID Nos 85, 106, 126, 131, 83, 104 or 124.

94. The polypeptide of any of embodiments 87 to 93 comprising the amino acid sequence set forth in SEQ ID No 65 or a polypeptide having at least 80% amino acid identity with the amino acid sequence of SEQ ID No 65.

95. The polypeptide of any one of embodiments 87 to 91 wherein said first immunoglobulin single variable domain comprises the amino acid sequence set forth in SEQ ID No. 213 or 214 or an amino acid sequence having at least 80% amino acid identity with either SEQ ID No 213 or 214 and wherein said second immunoglobulin single variable domain comprises the amino acid sequence set forth in SEQ ID No. 218 or an amino acid sequence having at least 80% identity with SEQ ID No. 218.

96. The polypeptide of any one of embodiments 3 to 14 or embodiments 22 to 39 wherein said second immunoglobulin single variable domain includes at least one CDR comprising an amino acid sequence selected from the group consisting of SEQ ID Nos 143, 163 and 183 or an amino acid sequence having at least 80% amino acid sequence identity with the amino acid sequences of SEQ ID Nos 143, 163 or 183 and wherein said first immunoglobulin single variable domain includes at least one CDR selected from the group consisting of SEQ ID Nos 147, 167 and 187 or an amino acid sequence having at least 80% amino acid identity with the amino acid sequences of SEQ ID Nos 147, 167 or 187. (97A9/2B2)

97. The polypeptide of embodiment 96 comprising the structure as embodimented in embodiment 14 wherein in said second immunoglobulin single variable domain CDR1 comprises an amino acid sequence as set forth in SEQ ID No 143, CDR2 comprises the amino acid sequence set forth in SEQ ID No 163 and CDR3 comprises the amino acid sequence set forth in SEQ ID No 183 and wherein in said first immunoglobulin single variable domain CDR4 comprises an amino acid sequence as set forth in SEQ ID No 147, CDR5 comprises the amino acid sequence set forth in SEQ ID No 167 and CDR6 comprises the amino acid sequence set forth in SEQ ID No 187.

98. The polypeptide of embodiment 97 in which the amino acid sequences of CDR1, CDR2, CDR3, CDR4, CDR5 or CDR6 have at least 80% amino acid identity with the any one of the amino acid sequences set forth in SEQ ID Nos 143, 163, 183, 147, 167 or 187.

99. The polypeptide of embodiments 97 or 98 wherein the amino acid sequences differ from those set forth in SEQ ID Nos 143, 163, 183, 147, 167 or 187 only in conservative amino acid changes.

100. The polypeptide of any one of embodiments 97 to 99 wherein the framework regions in each monomer of a single variable domain comprise one or more hallmark residues at amino acid positions 11, 37, 44, 45, 47, 83, 84, 103, 104 and 108 according to Kabat numbering.

101. The polypeptide of any one of embodiments 97 to 100 wherein FR1 comprises an amino acid sequence as set forth in SEQ ID No 81, FR2 comprises an amino acid sequence as set forth in SEQ ID No 102, FR3 comprises an amino acid sequence as set forth in SEQ ID No 122, FR4 comprises an amino acid sequence set forth in SEQ ID No 133, FR5 comprises an amino acid sequence as set forth in SEQ ID No 85, FR6 comprises an amino acid sequence as set forth in SEQ ID No 106, FR7 comprises an amino acid sequence as set forth in SEQ ID No 126 and/or FR8 comprises an amino acid sequence as set forth in SEQ ID No 131.

102. The polypeptide of embodiment 101, which is modified such that FR1, FR2, FR3, FR4, FR5, FR6, FR7 and FR8 have amino acid sequences with at least 80% amino acid identity with amino acid sequences set forth in any of SEQ ID Nos 81, 102, 122, 133, 85, 106, 126 or 131.

103. The polypeptide of any of embodiments 96 to 102 comprising the amino acid sequence set forth in SEQ ID No 47 or a polypeptide having at least 80% amino acid identity with the amino acid sequence of SEQ ID No 47.

104. A polypeptide as embodimented in any one of embodiments 96 to 100 wherein said second immunoglobulin single variable domain comprises the sequence of amino acids set forth in SEQ ID No 215 or an amino acid sequence having at least 80% amino acid identity with SEQ ID No 215 and wherein said first immunoglobulin single variable domain comprises the sequence of amino acids set forth in SEQ ID No. 213 and 214 or a sequence of amino acids having at least 80% identity with SEQ ID No. 213 or 214.

105. The polypeptide of any one of embodiments 3 to 14 or embodiments 22 to 39 wherein said second immunoglobulin single variable domain includes at least one CDR comprising an amino acid sequence selected from the group consisting of SEQ ID Nos 143, 163 and 183 or an amino acid sequence having at least 80% amino acid sequence identity with the amino acid sequences of SEQ ID Nos 143, 163 or 183 and wherein said first immunoglobulin single variable domain includes at least one CDR selected from the group consisting of SEQ ID Nos 151, 171 and 191 or an amino acid sequence having at least 80% amino acid identity with the amino acid sequences of SEQ ID Nos 151, 171 or 191. (97A9/54B12)

106. The polypeptide of embodiment 105 comprising the structure as embodimented in embodiment 14 wherein in said second immunoglobulin single variable domain CDR1 comprises an amino acid sequence as set forth in SEQ ID No 143, CDR2 comprises the amino acid sequence set forth in SEQ ID No 163 and CDR3 comprises the amino acid sequence set forth in SEQ ID No 183 and wherein in said first immunoglobulin single variable domain CDR4 comprises an amino acid sequence as set forth in SEQ ID No 151, CDR5 comprises the amino acid sequence set forth in SEQ ID No 171 and CDR6 comprises the amino acid sequence set forth in SEQ ID No 191.

107. The polypeptide of embodiment 106 in which the amino acid sequences of CDR1, CDR2, CDR3, CDR4, CDR5 or CDR6 have at least 80% amino acid identity with the any one of the amino acid sequences set forth in SEQ ID Nos 143, 163, 183, 151, 171 or 191.

108. The polypeptide of embodiments 106 or 107 wherein the amino acid sequences differ from those set forth in SEQ ID Nos 143, 163, 183, 151, 171 or 191 only in conservative amino acid changes.

109. The polypeptide of any one of embodiments 106 to 108 wherein the framework regions in each monomer of a single variable domain comprise one or more hallmark residues at amino acid positions 11, 37, 44, 45, 47, 83, 84, 103, 104 and 108 according to Kabat numbering.

110. The polypeptide of any one of embodiments 106 to 109 wherein FR1 comprises an amino acid sequence as set forth in SEQ ID No 81, FR2 comprises an amino acid sequence as set forth in SEQ ID No 102, FR3 comprises an amino acid sequence as set forth in SEQ ID No 122, FR4 comprises an amino acid sequence 133, FR5 comprises an amino acid sequence set forth in SEA ID No 89, FR6 comprises an amino acid sequence as set forth in SEQ ID No 110, FR7 comprises an amino acid sequence as set forth in SEQ ID No 130 and/or FR8 comprises an amino acid sequence as set forth in SEQ ID No 131.

111. The polypeptide of embodiment 110, which is modified such that FR1, FR2, FR3, FR4, FR5, FR6, FR7 and FR8 have amino acid sequences with at least 80% amino acid identity with amino acid sequences set forth in any of SEQ ID Nos 81, 102, 122, 133, 89, 110, 130 or 131.

112. The polypeptide of any of embodiments 105 to 111 comprising the amino acid sequence set forth in SEQ ID No 61 or a polypeptide having at least 80% amino acid identity with the amino acid sequence of SEQ ID No 61.

113. The polypeptide as embodimented in any one of embodiments 105 to 109 wherein said second immunoglobulin single variable domain comprises the sequence of amino acids set forth in SEQ ID No 215 or sequence of amino acids having at least 80% amino acid identity with SEQ ID No 215 and wherein said first immunoglobulin single variable domain comprises the sequence of amino acids set forth in SEQ ID No 219 or an amino acid sequence having at least 80% amino acid identity with SEQ ID No 219.

114. The polypeptide of any one of embodiments 1 to 38 or 42 to 113 comprising sequence-optimised framework regions, including partially or fully humanised framework regions.

115. The polypeptide of any one of embodiment 1 to 38 of 42 to 114 which cross-reacts with non-human primate CXCR2.

116. The polypeptide of embodiment 115 wherein the primate is Cynomolgus monkey

117. The polypeptide of any one of embodiments 1 to 38 or 42 to 116 which does not cross-react with CXCR2 from non-primate species.

118. The polypeptide of any one of embodiments 1 to 38 or 42 to 117 which does not cross-react with other receptors of the CXC chemokine family.

119. The polypeptide of any one of embodiments 1 to 38 and 114 to 118 wherein said second antigen binding domain recognises a CXCR2 epitope comprising or within the amino acid sequences selected from the group consisting of amino acid sequences set forth in SEQ ID No 8, 9, 10, 11 and 12.

120. The polypeptide of embodiment 119 wherein said first antigen binding domain recognises an epitope comprising or within the amino acid sequence set forth in SEQ ID No 7.

121. The polypeptide of embodiment 119 or 120 wherein said first antigen binding domain recognises an epitope comprising or within the amino acid sequence set forth in SEQ ID No 4.

122. The polypeptide of any of embodiments 119 to 121 wherein said second antigen binding domain recognises an epitope comprising or within the amino acid sequence set forth in SEQ ID No 5 or 6.

123. The polypeptide of any one of embodiments 1 to 38 or embodiments 42 to 122 which can specifically bind to human CXCR2 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

124. The polypeptide of any one of embodiments 1 to 38 or embodiments 42 to 123 which can specifically bind to human CXCR2 with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

125. The polypeptide of any one of embodiments 1 to 38 or embodiments 42 to 124 which can specifically bind to human CXCR2 with a rate of dissociation ($k_{off}$ rate) between 1 $s^{-1}$ and $10^{-6}$ $s^{-1}$, preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

126. The polypeptide of any one of embodiments 1 to 38 or embodiment 42 to 125 which can specifically bind to human CXCR2 with an affinity less than 500 nM, preferably less than 200 nM, more preferably less than 10 nM, such as less than 500 pM.

127. The polypeptide of any one of embodiments 1 to 38 or embodiments 42 to 126 capable of inhibiting binding of Gro-α to human CXCR2 with an IC50 of less than 20 nM.

128. The polypeptide of any one of embodiments 1 to 38 or 42 to 127 capable of inhibiting Gro-α-induced calcium release from RBL cells expressing human CXCR2 with an IC50 of less than 100 nM.

129. The polypeptide of any one of embodiments 1 to 38 or 42 to 128 capable of inhibiting Gro-α-induced accumulation of [$^{35}$S]GTPγS in human CHO-CXCR2 membranes with an IC50 of less than 50 nM.

130. The polypeptide of any one of embodiments 1 to 38 or 42 to 129 wherein said polypeptide is in substantially isolated form.

131. The polypeptide of any one embodiments 1 to 38 and 42 to 130 which is a multiparatopic construct.

132. The polypeptide according to any one of embodiments 1 to 38 or 42 to 131 which is modified to have an increased in vivo half-life, compared to the corresponding unmodified amino acid sequence.

133. The polypeptide according to embodiment 132 wherein said increased half-life is provided by one or more binding units chosen from the group consisting of serum proteins or fragments thereof, binding units that can bind to serum proteins, an Fc portion, and small proteins or peptides that can bind to serum proteins.

134. The polypeptide according to embodiment 133 wherein said one or more other binding units that provide the polypeptide with increased half-life is chosen from the group consisting of human serum albumin or fragments thereof.

135. The polypeptide according to 133, wherein said one or more other binding units that provide the polypeptide with increased half-life are chosen from the group consisting of binding units that can bind to serum albumin (such as human serum albumin) or a serum immunoglobulin (such as IgG).

136. The polypeptide according to embodiment 132 wherein said increased half-life is provided by one or more other binding units chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum albumin (such as human serum albumin) or a serum immunoglobulin (such as IgG).

137. The polypeptide according to embodiment 134 which is an immunoglobulin single variable domain that can bind to serum albumin (such as human serum albumin) or a serum immunoglobulin (such as IgG).

138. The polypeptide according to any of embodiments 132 to 137 that has a serum half-life that is at least 1.5 times, preferably at least 2 times, such as at least 5 times, for example at least 10 times or more than 20 times, greater than the half-life of the corresponding unmodified polypeptide.

139. A polypeptide according to any of embodiments 132 to 138 that has a serum half-life that is increased by more than 1 hour, preferably more than 2 hours, more preferably more than 6 hours, such as more than 12 hours, or even more than 24, 48 or 72 hours, compared to the corresponding unmodified polypeptide.

140. A polypeptide according to any of embodiments 132 to 139 that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

141. A polypeptide according to any of embodiments 1 to 38 or 42 to 140 which is pegylated.

142. A polypeptide according to any one of embodiments 1 to 38 or 42 to 140 which is pasylated 143. A polypeptide according to any one of embodiments 1 to 38 or 42 of 140 which is hesylated.

144. The polypeptide of embodiment 36 or 37 or anyone of embodiments 42 to 143 wherein said further antigen binding domain binds a serum protein with an affinity of less than 500 nM, preferably less than 200 nM, more preferably less than 10 nM, such as less than 500 nM.

145. A nucleic acid molecule which encodes a polypeptide according to any one of embodiments 1 to 38 or 42 to 144.

146. A nucleic acid molecule encoding an immunoglobulin single variable domain comprising an amino acid sequence selected from the group consisting of the amino acid sequences set forth in SEQ ID Nos 25 to 43, 90 and 213 to 219.

147. The nucleic acid molecule of embodiment 146 comprising a nucleotide sequence selected from the group consisting of the nucleic acid sequences set forth in SEQ ID Nos 192 to 211.

148. A nucleic acid molecule encoding a polypeptide comprising an amino acid sequence selected from the group consisting of the amino acid sequences set forth in SEQ ID Nos 44 to 69.

149. An expression vector comprising a nucleic acid molecule as embodimented in any one of embodiments 145 to 148.

150. A host cell capable of expressing a polypeptide according to any one of embodiments 1 to 38 or 42 to 149 from a nucleic acid sequence according to any one of embodiments 145 to 148.

151. A monovalent, bivalent, multivalent, biparatopic or multiparatopic Nanobody obtainable by culturing the host cell of embodiment 150.

152. A pharmaceutical composition comprising the polypeptide of any one of embodiments 1 to 38 or 42 to 144 and a pharmaceutically acceptable carrier or diluent.

153. The polypeptide of any one of embodiments 1 to 38 or 42 to 144 for use as a medicament.

154. The polypeptide of any one of embodiments 1 to 38 or 42 to 144 for use in the treatment of chronic obstructive pulmonary disease (COPD) and exacerbations of COPD.

155. The polypeptide of any one of embodiments 1 to 38 or 42 to 144 for use in the treatment of Cystic Fibrosis, Asthma, severe Asthma, exacerbations of Asthma, allergic Asthma, Acute lung injury, Acute respiratory distress syndrome, Idiopathic pulmonary fibrosis, Airway remodeling, Bronchiolitis obliterans syndrome or Bronchopulmonary dysplasia.

156. The polypeptide of any one of embodiments 1 to 38 or 42 to 144 for use in the treatment of Atherosclerosis, Glomerulonephritis, Inflammatory Bowl Disease (Crohn's), Angiogenesis and diseases characterised by new blood vessel development including Macular degeneration, Diabetic retinopathy and Diabetic neuropathy, Multiple sclerosis, Psoriasis, Age-related Macula degenerative disease, Ocular Behcet Disease, Uveitis, Pulmonary Arterial Hypertension (PAH) including idiopathic PAH, familial PAH and associated PAH, Chronic inflammatory diseases, Rhenumatoid arthritis, Osteoarthritis, non-small cell carcinoma, Colon cancer, Pancreatic cancer, Esophageal cancer, Ovarian cancer, Breast cancer, Solid tumors and Metasases, Melanoma, Hepatocellular carcinoma or Ischaemia reperfusion injury.

157. A method of treating chronic obstructive pulmonary disease (COPD) or exacerbations of (COPD) comprising administering to a subject an effective amount of a polypeptide according to any one of embodiments 1 to 38 or 42 to 144.

158. A method of treating a condition selected from the group consisting of Cystic Fibrosis, Asthma, severe Asthma, exacerbations of Asthma, allergic Asthma, Acute lung injury, Acute respiratory distress syndrome, Idiopathic pulmonary fibrosis, Airway remodeling, Bronchiolitis obliterans syndrome or Bronchopulmonary dysplasia comprising administering to a subject an effective amount of a polypeptide according to any one of embodiments 1 to 37 or 41 to 143.

159. A method of treating a condition selected from the group consisting of Atherosclerosis, Glomerulonephritis, Inflammatory Bowl Disease (Crohn's), Angiogenesis and diseases characterised by new blood vessel development including Macular degeneration, Diabetic retinopathy and Diabetic neuropathy, Multiple sclerosis, Psoriasis, Age-related Macula degenerative disease, Ocular Behcet Disease, Uveitis, Pulmonary Arterial Hypertension (PAH) including idiopathic PAH, familial PAH and associated PAH, Chronic inflammatory diseases, Rhenumatoid arthritis, Osteoarthritis, non-small cell carcinoma, Colon cancer, Pancreatic cancer, Esophageal cancer, Ovarian cancer, Breast cancer, Solid tumors and Metasases, Melanoma, Hepatocellular carcinoma and Ischaemia perfusion injury by administering to a subject an effective amount of a polypeptide according to any one of embodiments 1 to 38 or 42 to 144.

160. Use of the polypeptide of any one of embodiments 1 to 38 or 42 to 144 in the manufacture of a medicament for the treatment of chronic obstructive pulmonary disease (COPD) or exacerbations of COPD.

161. Use of the polypeptide of any one of embodiments 1 to 38 or 42 to 144 in the manufacture of a medicament for the treatment of Asthma, severe Asthma, exacerbations of Asthma, allergic Asthma, Acute lung injury, Acute respiratory distress syndrome, Idiopathic pulmonary fibrosis, Airway remodeling, Bronchiolitis obliterans syndrome or Bronchopulmonary dysplasis.

162. Use of the polypeptide of any one of embodiments 1 to 38 or 42 to 144 in the manufacture of a medicament for the treatment of Atherosclerosis, Glomerulonephritis, Inflammatory Bowl Disease (Crohn's), Angiogenesis and diseases characterised by new blood vessel development including Macular degeneration, Diabetic retinopathy and Diabetic neuropathy, Multiple sclerosis, Psoriasis, Age-related Macula degenerative disease, Ocular Behcet Disease, Uveitis, Pulmonary Arterial Hypertension (PAH) including idiopathic PAH, familial PAH and associated PAH, Chronic inflammatory diseases, Rhenumatoid arthritis, Osteoarthritis, non-small cell carcinoma, Colon cancer, Pancreatic cancer, Esophageal cancer, Ovarian cancer, Breast cancer, Solid tumors and Metasases, Melanoma, Hepatocellular carcinoma or Ischaemia reperfusion injury.

163. A polypeptide according to any one of embodiments 1 to 38 which is capable of cross-blocking binding to CXCR2 with a polypeptide of any one of embodiments 49, 58, 67, 76, 85, 94, 103 or 112.

164. The molecule of any one of embodiments 39 to 41 wherein said first and second antigen binding domains comprise any of the features set forth for said domains in any one of embodiments 1 to 22, 32 to 38 or 42 to 144.

165. The molecule of embodiment 164 which exhibits any of the features of embodiments 106 to 135.

166. A polypeptide comprising at least one immunoglobulin single variable domain which is directed against or binds to CXCR2 which is capable of cross-blocking binding to CXCR2, with a polypeptide of any one of embodiments 49, 58, 67, 76, 85, 94, 103 or 112.

167. The polypeptide of embodiments 3 to 14 and 22 to 39 comprising the structure as embodimented in embodiment 14 wherein said second immunoglobulin single variable domain comprises CDR amino acid sequences according to Kabat numbering encoded by deposited plasmid DSM 23727 and wherein said first immunoglobulin single variable domain comprises CDR amino acid sequences according to Kabat numbering encoded by deposited plasmid DSM 23726.

168. The polypeptide of embodiment 167 further comprising in said second immunoglobulin single variable domain FR regions with amino acid sequences according to Kabat numbering encoded by deposited plasmid DSM 23727 and in said first immunoglobulin single variable domain FR regions with amino acid sequences according to Kabat numbering encoded by deposited plasmid DSM 23726.

169. The polypeptide of embodiment 168 wherein said second immunoglobulin single variable domain is joined to said first immunoglobulin single variable domain by a peptide linker with amino sequence set forth in SEQ ID No 220.

170. The polypeptide of embodiments 3 to 14 and 22 to 39 comprising the structure as embodimented in embodiment 14 wherein said second immunoglobulin single variable domain comprises CDR amino acid sequences according to Kabat numbering encoded by deposited plasmid DSM 23725 and wherein said first immunoglobulin single variable domain comprises CDR amino acid sequences according to Kabat numbering encoded by deposited plasmid DSM 23726.

171. The polypeptide of embodiment 170 further comprising in said second immunoglobulin single variable domain FR regions with amino acid sequences according to Kabat numbering encoded by deposited plasmid DSM 23725 and in said first immunoglobulin single variable domain FR regions with amino acid sequences according to Kabat numbering encoded by deposited plasmid DSM 23726.

172. The polypeptide of embodiment 171 wherein said second immunoglobulin single variable domain is joined to said first immunoglobulin single variable domain by a peptide linker with amino sequence set forth in SEQ ID No 220.

173. The polypeptide of embodiments 3 to 14 and 22 to 39 comprising the structure as embodimented in embodiment 14 wherein said second immunoglobulin single variable domain comprises CDR amino acid sequences according to Kabat numbering encoded by deposited plasmid DSM 23725 and wherein said first immunoglobulin single variable domain comprises CDR amino acid sequences according to Kabat numbering encoded by deposited plasmid DSM 23728.

174. The polypeptide of embodiment 173 further comprising in said second immunoglobulin single variable domain FR regions with amino acid sequences according to Kabat numbering encoded by deposited plasmid DSM 23725 and in said first immunoglobulin single variable domain FR regions with amino acid sequences according to Kabat numbering encoded by deposited plasmid DSM 23728.

175. The polypeptide of embodiment 174 wherein said second immunoglobulin single variable domain is joined to said first immunoglobulin single variable domain by a peptide linker with amino sequence set forth in SEQ ID No 220.

176. The polypeptide of embodiments 3 to 14 and 22 to 39 comprising the structure as embodimented in embodiment 14 wherein said second immunoglobulin single variable domain comprises CDR amino acid sequences according to Kabat numbering encoded by deposited plasmid DSM 23727 and wherein said first immunoglobulin single variable domain comprises CDR amino acid sequences according to Kabat numbering encoded by deposited plasmid DSM 23728.

177. The polypeptide of embodiment 176 further comprising in said second immunoglobulin single variable domain FR regions with amino acid sequences according to Kabat numbering encoded by deposited plasmid DSM 23727 and in said first immunoglobulin single variable domain FR regions with amino acid sequences according to Kabat numbering encoded by deposited plasmid DSM 23728.

178. The polypeptide of embodiment 177 wherein said second immunoglobulin single variable domain is joined to said first immunoglobulin single variable domain by a peptide linker with amino sequence set forth in SEQ ID No 220.

179. The polypeptide of embodiments 3 to 14 and 22 to 39 comprising the structure as embodimented in embodiment 14 wherein said first immunoglobulin single variable domain comprises CDR amino acid sequences according to Kabat numbering encoded by deposited plasmid DSM 23723 and wherein said second immunoglobulin single variable domain comprises CDR amino acid sequences according to Kabat numbering encoded by deposited plasmid DSM 23725.

180. The polypeptide of embodiment 179 further comprising in said first immunoglobulin single variable domain FR regions with amino acid sequences according to Kabat numbering encoded by deposited plasmid DSM 23723 and in said second immunoglobulin single variable domain FR regions with amino acid sequences according to Kabat numbering encoded by deposited plasmid DSM 23725.

181. The polypeptide of embodiment 180 wherein said second immunoglobulin single variable domain is joined to said first immunoglobulin single variable domain by a peptide linker with amino sequence set forth in SEQ ID No 220.

182. The polypeptide of embodiments 3 to 14 and 22 to 39 comprising the structure as embodimented in embodiment 14 wherein said first immunoglobulin single variable domain comprises CDR amino acid sequences according to Kabat numbering encoded by deposited plasmid DSM 23723 and wherein said second immunoglobulin single variable domain comprises CDR amino acid sequences according to Kabat numbering encoded by deposited plasmid DSM 23727.

183. The polypeptide of embodiment 182 further comprising in said first immunoglobulin single variable domain FR regions with amino acid sequences according to Kabat numbering encoded by deposited plasmid DSM 23723 and in said second immunoglobulin single variable domain FR regions with amino acid sequences according to Kabat numbering encoded by deposited plasmid DSM 23727.

184. The polypeptide of embodiment 183 wherein said second immunoglobulin single variable domain is joined to said first immunoglobulin single variable domain by a peptide linker with amino sequence set forth in SEQ ID No 220.

185. The polypeptide of embodiments 3 to 14 and 22 to 39 comprising the structure as embodimented in embodiment 14 wherein said second immunoglobulin single variable domain comprises CDR amino acid sequences according to Kabat numbering encoded by deposited plasmid DSM 23724 and wherein said first immunoglobulin single variable domain comprises CDR amino acid sequences according to Kabat numbering encoded by deposited plasmid DSM 23723.

186. The polypeptide of embodiment 185 further comprising in said second immunoglobulin single variable domain FR regions with amino acid sequences according to Kabat numbering encoded by deposited plasmid DSM 23724 and in said first immunoglobulin single variable domain FR regions with amino acid sequences according to Kabat numbering encoded by deposited plasmid DSM 23723.

187. The polypeptide of embodiment 186 wherein said second immunoglobulin single variable domain is joined to said first immunoglobulin single variable domain by a peptide linker with amino sequence set forth in SEQ ID No 220.

188. The polypeptide of embodiments 3 to 14 and 22 to 39 comprising the structure as embodimented in embodiment 14 wherein said second immunoglobulin single variable domain comprises CDR amino acid sequences according to Kabat numbering encoded by deposited plasmid DSM 23724 and wherein said first immunoglobulin single variable domain comprises CDR amino acid sequences according to Kabat numbering encoded by deposited plasmid DSM 23728.

189. The polypeptide of embodiment 188 further comprising in said second immunoglobulin single variable domain FR regions with amino acid sequences according to Kabat numbering encoded by deposited plasmid DSM 23724 and in said first immunoglobulin single variable domain FR regions with amino acid sequences according to Kabat numbering encoded by deposited plasmid DSM 23728.

190. The polypeptide of embodiment 189 wherein said second immunoglobulin single variable domain is joined to said first immunoglobulin single variable domain by a peptide linker with amino sequence set forth in SEQ ID No 220.

The invention claimed is:

1. A method of treating respiratory diseases with aberrant CXCR2 signaling comprising administering to a subject an effective amount of an isolated polypeptide comprising a first immunoglobulin single variable domain and a second immunoglobulin single variable domain, wherein each domain binds to the chemokine receptor CXCR2, and wherein the first immunoglobulin single variable domain binds a linear peptide consisting of the sequence of amino acids set forth in SEQ ID NO: 7 and the second immunoglobulin single variable domain does not bind to said linear peptide, wherein said isolated polypeptide has one of the following structures:

a. FR1-CDR1-FR2-CDR2-FR3-CDR3-FR4--LINKER--FR5-CDR4-FR6-CDR5-FR7-CDR6-FR8;
b. FR1-CDR1-FR2-CDR2-FR3-CDR3-FR4--LINKER--FR5-CDR4-FR6-CDR5-FR7-CDR6-FR8--LINKER--HLE; or
c. FR1-CDR1-FR2-CDR2-FR3-CDR3-FR4--LINKER--HLE--LINKER--FR5-CDR4-FR6-CDR5-FR7-CDR6-FR8;

wherein if the first immunoglobulin single variable domain comprises FR1-CDR1-FR2-CDR2-FR3-CDR3-FR4 then the second immunoglobulin single variable domain comprises FR5-CDR4-FR6-CDR5-FR7-CDR6-FR8; and if the second immunoglobulin single variable domain comprises FR1-CDR1-FR2-CDR2-FR3-CDR3-FR4 then the first immunoglobulin single variable domain comprises FR5-CDR4-FR6-CDR5-FR7-CDR6-FR8; and the HLE is a binding unit providing an increased in vivo half-life; and wherein said second immunoglobulin single variable domain comprises 3 CDRs having the amino acid sequences set forth in SEQ ID NOs: 141, 236 and 181 and said first immunoglobulin single variable domain comprises 3 CDRs having the amino acid sequence set forth in SEQ ID NO: 146, 237 and 186.

2. The method of claim 1 wherein the respiratory disease is chronic obstructive pulmonary disease (COPD) or exacerbations of (COPD).

3. The method of claim 1 wherein the respiratory disease is selected from the group consisting of Cystic Fibrosis, Asthma, severe Asthma, exacerbations of Asthma, allergic Asthma, Acute lung injury, Acute respiratory distress syndrome, Idiopathic pulmonary fibrosis, Airway remodeling, Bronchiolitis obliterans syndrome or Bronchopulmonary dysplasia.

4. The method of claim 1, wherein said first immunoglobulin single variable domain has the amino acid sequence of SEQ ID NO: 216 and said second immunoglobulin single variable domain has the amino acid sequence of SEQ ID NO: 217.

5. The method of claim 1, wherein the isolated polypeptide comprises the amino acid sequence as set forth in SEQ ID NO: 221.

6. The method of claim 5 wherein the isolated polypeptide further comprises an HLE binding unit having the amino acid sequence of SEQ ID NO: 228.

7. The method of claim 6 wherein the isolated polypeptide comprises the amino acid sequence set forth in SEQ ID NO: 225.

* * * * *